United States Patent
Cui et al.

(10) Patent No.: US 11,572,389 B2
(45) Date of Patent: Feb. 7, 2023

(54) VACCINE COMPOSITIONS OF HERPESVIRUS ENVELOPE PROTEIN COMBINATIONS TO INDUCE IMMUNE RESPONSE

(71) Applicant: THE HENRY M. JACKSON FOUNDATION FOR THE ADVANCEMENT OF MILITARY MEDICINE, INC., Bethesda, MD (US)

(72) Inventors: Xinle Cui, Gaithersburg, MD (US); Clifford M. Snapper, Potomac, MD (US)

(73) Assignee: THE HENRY M. JACKSON FOUNDATION FOR THE ADVANCEMENT OF MILITARY MEDICINE, INC., Bethesda, MD (US)

( * ) Notice: Subject to any disclaimer, the term of this patent is extended or adjusted under 35 U.S.C. 154(b) by 0 days.

(21) Appl. No.: 16/480,098

(22) PCT Filed: Jan. 26, 2018

(86) PCT No.: PCT/US2018/015459
§ 371 (c)(1),
(2) Date: Jul. 23, 2019

(87) PCT Pub. No.: WO2018/140733
PCT Pub. Date: Aug. 2, 2018

(65) Prior Publication Data
US 2019/0367561 A1 Dec. 5, 2019

Related U.S. Application Data

(60) Provisional application No. 62/451,396, filed on Jan. 27, 2017.

(51) Int. Cl.
| | |
|---|---|
| *C07K 14/005* | (2006.01) |
| *A61P 31/22* | (2006.01) |
| *A61K 39/245* | (2006.01) |
| *A61K 39/25* | (2006.01) |
| *C12N 7/00* | (2006.01) |

(52) U.S. Cl.
CPC .......... *C07K 14/005* (2013.01); *A61K 39/245* (2013.01); *A61K 39/25* (2013.01); *A61P 31/22* (2018.01); *C12N 7/00* (2013.01); *C12N 2710/16034* (2013.01); *C12N 2710/16071* (2013.01); *C12N 2710/16134* (2013.01); *C12N 2710/16171* (2013.01); *C12N 2710/16234* (2013.01); *C12N 2710/16271* (2013.01); *C12N 2710/16334* (2013.01); *C12N 2710/16371* (2013.01); *C12N 2710/16634* (2013.01); *C12N 2710/16671* (2013.01); *C12N 2710/16734* (2013.01); *C12N 2710/16771* (2013.01)

(58) Field of Classification Search
CPC .... C07K 14/005; A61K 39/245; A61K 39/25; A61K 45/06; A61K 2039/505; A61K 2039/507; A61K 39/12; A61P 31/22; A61P 37/04; C12N 7/00; C12N 2710/16034; C12N 2710/16071; C12N 2710/16134; C12N 2710/16171; C12N 2710/16234; C12N 2710/16271; C12N 2710/16334; C12N 2710/16371; C12N 2710/16634; C12N 2710/16671; C12N 2710/16734; C12N 2710/16771
See application file for complete search history.

(56) References Cited

U.S. PATENT DOCUMENTS

| | | |
|---|---|---|
| 4,617,379 A | 10/1986 | Dobkin et al. |
| 2009/0270268 A1 | 10/2009 | Funaro et al. |
| 2013/0171234 A1* | 7/2013 | Fairman ............ A61K 39/12 424/450 |
| 2014/0023673 A1* | 1/2014 | Weiner ............. A61P 31/22 424/186.1 |

(Continued)

FOREIGN PATENT DOCUMENTS

| | | |
|---|---|---|
| WO | 2014/018858 A2 | 1/2014 |
| WO | WO-2015054639 A1 * | 4/2015 ........... A61K 39/12 |

(Continued)

OTHER PUBLICATIONS

Xu F, Schillinger JA, Sternberg MR, et al. Seroprevalence and coinfection with herpes simplex virus type 1 and type 2 in the United States, 1988-1994. J Infect Dis. 2002;185(8):1019-1024.*

(Continued)

*Primary Examiner* — Rachel B Gill
(74) *Attorney, Agent, or Firm* — Baker Donelson

(57) ABSTRACT

Provided are antigenic compositions and uses thereof that include at least two human herpesvirus (HHV) polypeptides involved in mediating HHV binding, fusion, and entry into host cells, such as gp350, gH, gL, and gB, or nucleic acids encoding the polypeptides. The two HHV polypeptides comprise any combination of: a gB polypeptide; a gp350 polypeptide; a gL polypeptide; and a gH polypeptide, and optionally any one or more of the following polypeptides: gp42, gM, gN, gI, gC, gE, gD, ORF68, BMRF-2, BDLF2, UL128, UL130, UL131A, and gpK8.1. Also disclosed are methods of inducing an immune response or treating or preventing an HHV infection in a subject by administering to the subject at least two of the HHV polypeptides or nucleic acid(s) encoding the same. Methods of passively transferring immunity using high-titer anti-HHV antibodies or immune cells are also disclosed.

Figure 1:
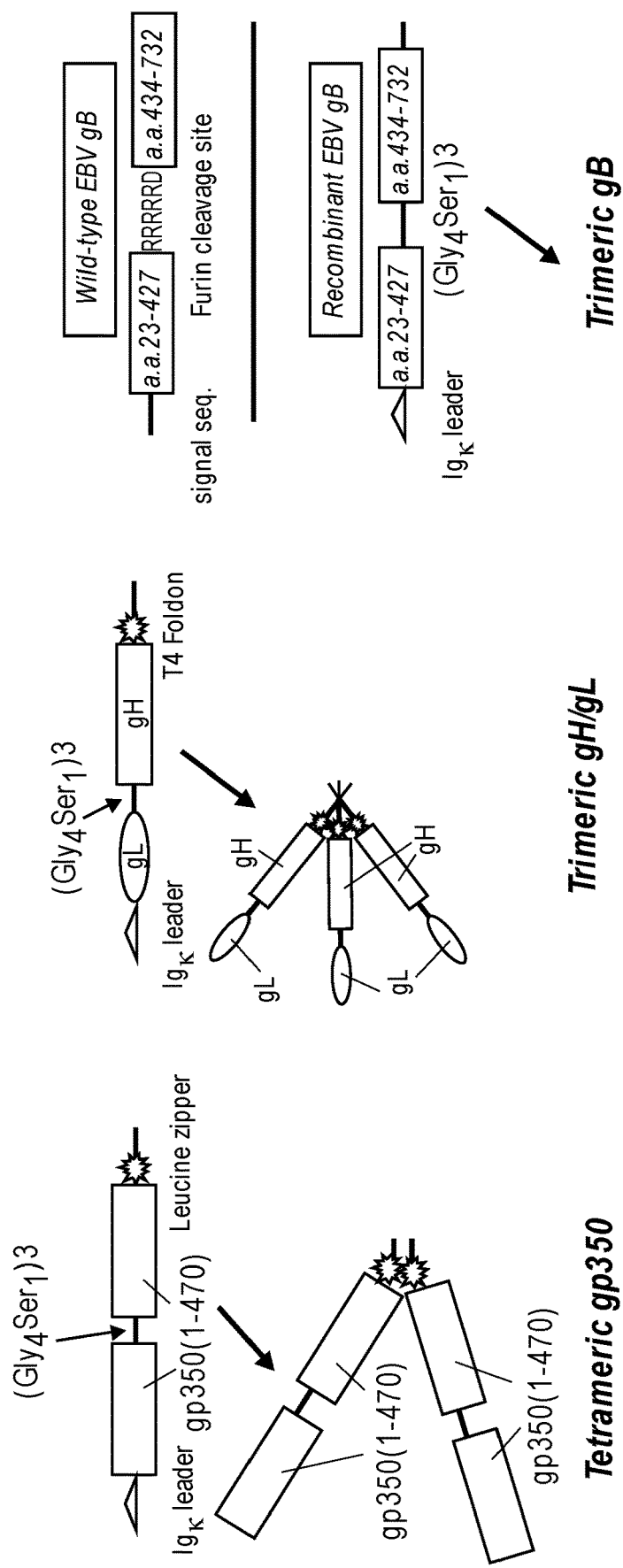

24 Claims, 19 Drawing Sheets
Specification includes a Sequence Listing.

(56) References Cited

U.S. PATENT DOCUMENTS

| | | | | |
|---|---|---|---|---|
| 2014/0030292 | A1* | 1/2014 | Franti | A61P 31/22 424/229.1 |
| 2014/0127247 | A1* | 5/2014 | Dubensky, Jr. | A61K 39/245 424/186.1 |
| 2014/0370026 | A1* | 12/2014 | Shenk | C07K 16/088 424/139.1 |
| 2015/0093413 | A1* | 4/2015 | Thess | A61P 31/12 424/210.1 |
| 2016/0303225 | A1 | 10/2016 | Cui et al. | |
| 2018/0311343 | A1* | 11/2018 | Huang | A61K 39/0011 |
| 2020/0163878 | A1* | 5/2020 | Baumhof | A61K 39/12 |

FOREIGN PATENT DOCUMENTS

| | | | | |
|---|---|---|---|---|
| WO | 2015/089340 | A1 | 6/2015 | |
| WO | WO-2015089340 | A1 * | 6/2015 | C07K 7/08 |
| WO | 2019/055887 | A1 | 3/2019 | |

OTHER PUBLICATIONS

Mocarski Jr. ES. Comparative analysis of herpesvirus-common proteins. In: Arvin A, Campadelli-Fiume G, Mocarski E, et al., editors. Human Herpesviruses: Biology, Therapy, and Immunoprophylaxis. Cambridge: Cambridge University Press; 2007. Chapter 4. Available from: https://www.ncbi.nlm.nih.gov/books/NBK47403/.*

Backovic M, Longnecker R, Jardetzky TS. Structure of a trimeric variant of the Epstein-Barr virus glycoprotein B. Proc Natl Acad Sci USA. 2009; 106(8):2880-2885.*

International Search Report and Written Opinion dated Apr. 13, 2018 from International Application No. PCT/US2018/015459 (Authorized Officer, Blaine R. Copenheaver), 21 Pages.

Fouts et al., "Antibodies against the gH/gL/UL128/UL130/UL131 Complex Comprise the Majority of the Anti-Cytomegalovirus (Anti-CMV) Neutralizing Antibody Response in CMV Hyperimmune Globulin", Journal of Virology, Jul. 2012, vol. 86, No. 13, pp. 7444-7447.

Wille et al., "A Human Cytomegalovirus gO-Null Mutant Fails To Incorporate gH/gL into the Virion Envelope and Is Unable To Enter Fibroblasts and Epithelial and Endothelial Cells", Journal of Virology, Mar. 2010, vol. 84, No. 5, pp. 2585-2596.

Wussow et al., "A Vaccine Based on the Rhesus Cytomegalovirus UL128 Complex Induces Broadly Neutralizing Antibodies in Rhesus Macaques", Journal of Virology, Feb. 2013, vol. 87, No. 3, pp. 1322-1332.

Achour et al., "Human herpesvirus-6 (HHV-6) DNA in plasma reflects the presence of infected blood cells rather than circulating viral particles"; Journal of Clinical Virology, 2007, vol. 38, pp. 280-285.

Akter et al., "Two novel spliced genes in human cytomegalovirus", Journal of General Virology, 2003, vol. 84, pp. 1117-1122.

PrabhuDas et al., "Challenges in infant immunity: implications for responses to infection and vaccines", Nature Immunology, Mar. 2011, vol. 12, No. 3, pp. 189-194.

Cui et al., "Rabbits immunized with Epstein-Barr virus gH/gL or GB recombinant proteins elicit higher serum virus neutralizing activity than gp350", Vaccine, 2016, vol. 34, pp. 4050-4055.

Amy W Hudson, "Roseoloviruses and their modulation of host defenses", Current Opinion in Virology, 2014, vol. 9, p. 178-187.

Ellinger et al., "The glycoprotein B homologue of human herpesvirus 6", Journal of General Virology, 1993, vol. 74, pp. 495-500.

Chandran et al., "Chapter 23 Gammaherpesviruses entry and early events during infection", Gammaherpesviruses entry and early events during infection—Human Herpesviruses—NCBI Bookshelf, 2007, https://www.ncbi.nlm.nih.gov/30oks/NBK47405/?report=printable, 55 Pages.

Gilden et al., "The neurobiology of varicella zoster virus infection", Neuropathol Appl Neurobiol., Aug. 2011, vol. 37, No. 5, pp. 441-463.

Peeters et al., "Effect of Carrier Priming on Immunogenicity of Saccharide-Protein Conjugate Vaccines", Infection and Immunity, Oct. 1991, vol. 59, No. 10, pp. 3504-3510.

Santoro et al., "Interaction of Glycoprotein H of Human Herpesvirus 6 with the Cellular Receptor CD46", The Journal of Biological Chemistry, Jul. 11, 2003, vol. 278, No. 28, pp. 25964-25969.

Patrone et al., "Human Cytomegalovirus UL130 Protein Promotes Endothelial Cell Infection through a Producer Cell Modification of the Virion", Journal of Virology, Jul. 2005, vol. 79, No. 13, pp. 8361-8373.

Ryckman et al., "Characterization of the Human Cytomegalovirus gH/gL/UL128-131 Complex That Mediates Entry into Epithelial and Endothelial Cells", Journal of Virology, Jan. 2008, vol. 82, No. 1, pp. 60-70.

Yang et al., "A role for the αV integrin subunit in Varicella Zoster Virus-mediated fusion and infection", Journal of Virology, 2016, 45 Pages.

Flamand et al., "Activation of the Epstein-Barr Virus Replicative Cycle by Human Herpesvirus 6", Journal of Virology, Nov. 1993, vol. 67, No. 11, pp. 6768-6777.

P. J. Klasse, "Neutralization of Virus Infectivity by Antibodies: Old Problems in New Perspectives", Advances in Biology 2014, vol. 2014, Article ID 157895, 24 Pages.

Magdalena Anna Krzyzaniak, "Role of The gM/gN Glycoprotein Complex in the Final Assembly and Egress of the Human Cytomegalovirus (HCMV)", A Dissertation Submitted to the graduate faculty of the University of Alabama at Birmingham, in partial fulfillment of the requirements for the degree of Doctor of Philosophy, Birmingham, Alabama, 2008, 160 pages.

Edward S. Mocarski, Jr., "Immune escape and exploitation strategies of cytomegaloviruses: impact on and imitation of the major histocompatibility system", Cellular Microbiology, 2004, vol. 6, No. 8, pp. 707-717.

Martin I. Muggeridge, "Characterization of cell-cell fusion mediated by herpes simplex virus 2 glycoproteins gB, gD, gH and gL in transfected cells", Journal of General Virology, 2000, vol. 81, pp. 2017-2027.

Ciferri et al., "Structural and biochemical studies of HCMV gH/gL/gO and Pentamer reveal mutually exclusive cell entry complexes", PNAS, Feb. 10, 2015, vol. 112, No. 6, p. 1767-1772.

Laurie T Krug, "Editorial overview: Roseoloviruses: Stopping to smell the roses—the Roseoloviruses have come of age as human pathogens". Current Opinion in Virology, 2014, vol. 9, pp. vi-vii.

Krug et al., "Roseolovirus molecular biology: recent advances", Current Opinion in Virology, 2014, vol. 9, pp. 170-177.

Caserta et al., "Roseoloviruses: unmet needs and research priorities Perspective", Current Opinion in Virology, 2014, vol. 9, pp. 167-169.

Frenkel et al., "Roseoloviruses manipulate host cell cycle", Current Opinion in Virology, 2014, vol. 9, pp. 162-166.

Becerra et al., "Immune response to HHV-6 and implications for immunotherapy", Current Opinion in Environmental Sustainability, 2014, vol. 9, pp. 154-161.

Prichard et al.,"The development of new therapies for human herpesvirus 6", Current Opinion in Virology, 2014, vol. 9, pp. 148-153.

Leibovitch et al., "Evidence linking HHV-6 with multiple sclerosis: an update", Current Opinion in Virology, 2014, vol. 9, pp. 127-133.

Kaufer et al., "Chromosomally integrated HHV-6: impact on virus, cell and organismal biology", Current Opinion in Virology, 2014, vol. 9, pp. 111-118.

Horvat et al., "Recent developments in animal models for human herpesvirus 6A and 6B", Current Opinion in Virology, 2014, vol. 9, pp. 97-103.

Tesini et al.,"Clinical impact of primary infection with roseoloviruses", Current Opinion in Virology, 2014, vol. 9, pp. 91-96.

Hill et al., "Past, present, and future perspectives on the diagnosis of Roseolovirus infections", Current Opinion in Virology, 2014, vol. 9, pp. 84-90.

Moorman et al., "Roseomics: a blank slate", Current Opinion in Virology, 2014, vol. 9, pp. 188-193.

Tang et al., "Human Herpesvirus 6 Glycoprotein Complex Formation Is Required for Folding and Trafficking of the gH/gL/gQ1/gQ2

(56) References Cited

OTHER PUBLICATIONS

Complex and Its Cellular Receptor Binding", Journal of Virology, Nov. 2011, vol. 85, No. 21, pp. 11121-11130.
Torrisi et al., "Intracellular Transport and Maturation Pathway of Human Herpesvirus 6", Virology, 1999, vol. 257, pp. 460-471.
Wills et al., "Vaccines against persistent DNA virus infections", British Medical Bulletin, 2002, vol. 62, pp. 125-138.
Extended Search Report dated Dec. 1, 2020 for corresponding European Application No. 18744000.3, 7 pages.
Office Action dated Aug. 17, 2021 for corresponding Japanese Patent Application No. 2019-540440, 6 pages with English translation.
McVoy et al., "A cytomegalovirus DNA vaccine induces antibodies that block viral entry into fibroblasts and epithelial cells", Vaccine, 2015, vol. 33, pp. 7328-7336.
Perez et al., "Novel Epstein-Barr virus-like particles incorporating gH/gl-EBNA1 or gB-LMP2 induce high neutralizing antibody titers and EBV-specific T-cell responses in immunized mice", Oncotarget, 2017, vol. 8, No. 12, pp. 19255-19273.

\* cited by examiner

Trimeric HCMV gB + Monmomeric gH/gL immune pooled sera

SEQUENCE LISTING

```
<160> NUMBER OF SEQ ID NOS: 55

<210> SEQ ID NO 1
<211> LENGTH: 907
<212> TYPE: PRT
<213> ORGANISM: Epstein-Barr virus

<400> SEQUENCE: 1

Met Glu Ala Ala Leu Leu Val Cys Gln Tyr Thr Ile Gln Ser Leu Ile
1               5                   10                  15

His Leu Thr Gly Glu Asp Pro Gly Phe Phe Asn Val Glu Ile Pro Glu
            20                  25                  30

Phe Pro Phe Tyr Pro Thr Cys Asn Val Cys Thr Ala Asp Val Asn Val
        35                  40                  45

Thr Ile Asn Phe Asp Val Gly Gly Lys Lys His Gln Leu Asp Leu Asp
    50                  55                  60

Phe Gly Gln Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
        115                 120                 125
```

```
Asp Val Tyr Phe Gln Asp Val Phe Gly Thr Met Trp Cys His His Ala
    130                 135                 140
Glu Met Gln Asn Pro Val Tyr Leu Ile Pro Glu Thr Val Pro Tyr Ile
145                 150                 155                 160
Lys Trp Asp Asn Cys Asn Ser Thr Asn Ile Thr Ala Val Val Arg Ala
                165                 170                 175
Gln Gly Leu Asp Val Thr Leu Pro Leu Ser Leu Pro Thr Ser Ala Gln
            180                 185                 190
Asp Ser Asn Phe Ser Val Lys Thr Glu Met Leu Gly Asn Glu Ile Asp
        195                 200                 205
Ile Glu Cys Ile Met Glu Asp Gly Glu Ile Ser Gln Val Leu Pro Gly
210                 215                 220
Asp Asn Lys Phe Asn Ile Thr Cys Ser Gly Tyr Glu Ser His Val Pro
225                 230                 235                 240
Ser Gly Gly Ile Leu Thr Ser Thr Ser Pro Val Ala Thr Pro Ile Pro
                245                 250                 255
Gly Thr Gly Tyr Ala Tyr Ser Leu Arg Leu Thr Pro Arg Pro Val Ser
            260                 265                 270
Arg Phe Leu Gly Asn Asn Ser Ile Leu Tyr Val Phe Tyr Ser Gly Asn
        275                 280                 285
Gly Pro Lys Ala Ser Gly Gly Asp Tyr Cys Ile Gln Ser Asn Ile Val
290                 295                 300
Phe Ser Asp Glu Ile Pro Ala Ser Gln Asp Met Pro Thr Asn Thr Thr
305                 310                 315                 320
Asp Ile Thr Tyr Val Gly Asp Asn Ala Thr Tyr Ser Val Pro Met Val
                325                 330                 335
Thr Ser Glu Asp Ala Asn Ser Pro Asn Val Thr Val Thr Ala Phe Trp
            340                 345                 350
Ala Trp Pro Asn Asn Thr Glu Thr Asp Phe Lys Cys Lys Trp Thr Leu
        355                 360                 365
Thr Ser Gly Thr Pro Ser Gly Cys Glu Asn Ile Ser Gly Ala Phe Ala
370                 375                 380
Ser Asn Arg Thr Phe Asp Ile Thr Val Ser Gly Leu Gly Thr Ala Pro
385                 390                 395                 400
Lys Thr Leu Ile Ile Thr Arg Thr Ala Thr Asn Ala Thr Thr Thr Thr
                405                 410                 415
His Lys Val Ile Phe Ser Lys Ala Pro Glu Ser Thr Thr Ser Pro
            420                 425                 430
Thr Leu Asn Thr Gly Phe Ala Asp Pro Asn Thr Thr Thr Gly Leu
        435                 440                 445
Pro Ser Ser Thr His Val Pro Thr Asn Leu Thr Ala Pro Ala Ser Thr
450                 455                 460
Gly Pro Thr Val Ser Thr Ala Asp Val Thr Ser Pro Thr Pro Ala Gly
465                 470                 475                 480
Thr Thr Ser Gly Ala Ser Pro Val Thr Pro Ser Pro Ser Pro Trp Asp
                485                 490                 495
Asn Gly Thr Glu Ser Lys Ala Pro Asp Met Thr Ser Ser Thr Ser Pro
            500                 505                 510
Val Thr Thr Pro Thr Pro Asn Ala Thr Ser Pro Thr Pro Ala Val Thr
        515                 520                 525
Thr Pro Thr Pro Asn Ala Thr Ser Pro Thr Pro Ala Val Thr Thr Pro
530                 535                 540
Thr Pro Asn Ala Thr Ser Pro Thr Leu Gly Lys Thr Ser Pro Thr Ser
```

```
            545                 550                 555                 560
Ala Val Thr Thr Pro Thr Pro Asn Ala Thr Ser Pro Thr Leu Gly Lys
                    565                 570                 575

Thr Ser Pro Thr Ser Ala Val Thr Thr Pro Thr Pro Asn Ala Thr Ser
            580                 585                 590

Pro Thr Leu Gly Lys Thr Ser Pro Thr Ser Ala Val Thr Thr Pro Thr
        595                 600                 605

Pro Asn Ala Thr Gly Pro Thr Val Gly Glu Thr Ser Pro Gln Ala Asn
    610                 615                 620

Ala Thr Asn His Thr Leu Gly Gly Thr Ser Pro Thr Pro Val Val Thr
625                 630                 635                 640

Ser Gln Pro Lys Asn Ala Thr Ser Ala Val Thr Thr Gly Gln His Asn
                    645                 650                 655

Ile Thr Ser Ser Ser Thr Ser Ser Met Ser Leu Arg Pro Ser Ser Asn
                660                 665                 670

Pro Glu Thr Leu Ser Pro Ser Thr Ser Asp Asn Ser Thr Ser His Met
            675                 680                 685

Pro Leu Leu Thr Ser Ala His Pro Thr Gly Gly Glu Asn Ile Thr Gln
        690                 695                 700

Val Thr Pro Ala Ser Ile Ser Thr His His Val Ser Thr Ser Ser Pro
705                 710                 715                 720

Glu Pro Arg Pro Gly Thr Thr Ser Gln Ala Ser Gly Pro Gly Asn Ser
                    725                 730                 735

Ser Thr Ser Thr Lys Pro Gly Glu Val Asn Val Thr Lys Gly Thr Pro
                740                 745                 750

Pro Gln Asn Ala Thr Ser Pro Gln Ala Pro Ser Gly Gln Lys Thr Ala
            755                 760                 765

Val Pro Thr Val Thr Ser Thr Gly Gly Lys Ala Asn Ser Thr Thr Gly
        770                 775                 780

Gly Lys His Thr Thr Gly His Gly Ala Arg Thr Ser Thr Glu Pro Thr
785                 790                 795                 800

Thr Asp Tyr Gly Gly Asp Ser Thr Thr Pro Arg Pro Arg Tyr Asn Ala
                    805                 810                 815

Thr Thr Tyr Leu Pro Pro Ser Thr Ser Ser Lys Leu Arg Pro Arg Trp
                820                 825                 830

Thr Phe Thr Ser Pro Pro Val Thr Thr Ala Gln Ala Thr Val Pro Val
            835                 840                 845

Pro Pro Thr Ser Gln Pro Arg Phe Ser Asn Leu Ser Met Leu Val Leu
        850                 855                 860

Gln Trp Ala Ser Leu Ala Val Leu Thr Leu Leu Leu Leu Leu Val Met
865                 870                 875                 880

Ala Asp Cys Ala Phe Arg Arg Asn Leu Ser Thr Ser His Thr Tyr Thr
                    885                 890                 895

Thr Pro Pro Tyr Asp Asp Ala Glu Thr Tyr Val
                900                 905

<210> SEQ ID NO 2
<211> LENGTH: 658
<212> TYPE: PRT
<213> ORGANISM: Epstein-Barr virus

<400> SEQUENCE: 2

Met Glu Ala Ala Leu Leu Val Cys Gln Tyr Thr Ile Gln Ser Leu Ile
1               5                   10                  15
```

```
His Leu Thr Gly Glu Asp Pro Gly Phe Asn Val Glu Ile Pro Glu
             20                  25                  30

Phe Pro Phe Tyr Pro Thr Cys Asn Val Cys Thr Ala Asp Val Asn Val
         35                  40                  45

Thr Ile Asn Phe Asp Val Gly Gly Lys Lys His Gln Leu Asp Leu Asp
 50                  55                  60

Phe Gly Gln Leu Thr Pro His Thr Lys Ala Val Tyr Gln Pro Arg Gly
 65                  70                  75                  80

Ala Phe Gly Gly Ser Glu Asn Ala Thr Asn Leu Phe Leu Leu Glu Leu
                 85                  90                  95

Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
            115                 120                 125

Asp Val Tyr Phe Gln Asp Val Phe Gly Thr Met Trp Cys His His Ala
130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
            195                 200                 205

Ile Glu Cys Ile Met Glu Asp Gly Glu Ile Ser Gln Val Leu Pro Gly
210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
            275                 280                 285

Gly Pro Lys Ala Ser Gly Gly Asp Tyr Cys Ile Gln Ser Asn Ile Val
290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
            355                 360                 365

Thr Ser Gly Thr Pro Ser Gly Cys Glu Asn Ile Ser Gly Ala Phe Ala
            370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Leu Asn Thr Thr Gly Phe Ala Asp Pro Asn Thr Thr Thr Gly Leu
```

```
                435                 440                 445
Pro Ser Ser Thr His Val Pro Thr Asn Leu Thr Ala Pro Ala Ser Thr
450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Trp Asp
                485                 490                 495

Asn Gly Thr Glu Ser Thr Pro Pro Gln Asn Ala Thr Ser Pro Gln Ala
                500                 505                 510

Pro Ser Gly Gln Lys Thr Ala Val Pro Thr Val Thr Ser Thr Gly Gly
                515                 520                 525

Lys Ala Asn Ser Thr Thr Gly Gly Lys His Thr Thr Gly His Gly Ala
530                 535                 540

Arg Thr Ser Thr Glu Pro Thr Thr Asp Tyr Gly Gly Asp Ser Thr Thr
545                 550                 555                 560

Pro Arg Pro Arg Tyr Asn Ala Thr Thr Tyr Leu Pro Pro Ser Thr Ser
                565                 570                 575

Ser Lys Leu Arg Pro Arg Trp Thr Phe Thr Ser Pro Pro Val Thr Thr
                580                 585                 590

Ala Gln Ala Thr Val Pro Val Pro Pro Thr Ser Gln Pro Arg Phe Ser
                595                 600                 605

Asn Leu Ser Met Leu Val Leu Gln Trp Ala Ser Leu Ala Val Leu Thr
610                 615                 620

Leu Leu Leu Leu Leu Val Met Ala Asp Cys Ala Phe Arg Arg Asn Leu
625                 630                 635                 640

Ser Thr Ser His Thr Tyr Thr Thr Pro Pro Tyr Asp Asp Ala Glu Thr
                645                 650                 655

Tyr Val

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 706
<212> TYPE: PRT
<213> ORGANISM: Epstein-Barr virus

<400> SEQUENCE: 4

Met Gln Leu Leu Cys Val Phe Cys Leu Val Leu Leu Trp Glu Val Gly
1               5                   10                  15

Ala Ala Ser Leu Ser Glu Val Lys Leu His Leu Asp Ile Glu Gly His
                20                  25                  30

Ala Ser His Tyr Thr Ile Pro Trp Thr Glu Leu Met Ala Lys Val Pro
                35                  40                  45

Gly Leu Ser Pro Glu Ala Leu Trp Arg Glu Ala Asn Val Thr Glu Asp
                50                  55                  60

Leu Ala Ser Met Leu Asn Arg Tyr Lys Leu Ile Tyr Lys Thr Ser Gly
65                  70                  75                  80
```

```
Thr Leu Gly Ile Ala Leu Ala Glu Pro Val Asp Ile Pro Ala Val Ser
                    85                  90                  95

Glu Gly Ser Met Gln Val Asp Ala Ser Lys Val His Pro Gly Val Ile
                100                 105                 110

Ser Gly Leu Asn Ser Pro Ala Cys Met Leu Ser Ala Pro Leu Glu Lys
                115                 120                 125

Gln Leu Phe Tyr Tyr Ile Gly Thr Met Leu Pro Asn Thr Arg Pro His
130                 135                 140

Ser Tyr Val Phe Tyr Gln Leu Arg Cys His Leu Ser Tyr Val Ala Leu
145                 150                 155                 160

Ser Ile Asn Gly Asp Lys Phe Gln Tyr Thr Gly Ala Met Thr Ser Lys
                165                 170                 175

Phe Leu Met Gly Thr Tyr Lys Arg Val Thr Glu Lys Gly Asp Glu His
                180                 185                 190

Val Leu Ser Leu Ile Phe Gly Lys Thr Lys Asp Leu Pro Asp Leu Arg
                195                 200                 205

Gly Pro Phe Ser Tyr Pro Ser Leu Thr Ser Ala Gln Ser Gly Asp Tyr
                210                 215                 220

Ser Leu Val Ile Val Thr Thr Phe Val His Tyr Ala Asn Phe His Asn
225                 230                 235                 240

Tyr Phe Val Pro Asn Leu Lys Asp Met Phe Ser Arg Ala Val Thr Met
                245                 250                 255

Thr Ala Ala Ser Tyr Ala Arg Tyr Val Leu Gln Lys Leu Val Leu Leu
                260                 265                 270

Glu Met Lys Gly Gly Cys Arg Glu Pro Glu Leu Asp Thr Glu Thr Leu
                275                 280                 285

Thr Thr Met Phe Glu Val Ser Val Ala Phe Phe Lys Val Gly His Ala
                290                 295                 300

Val Gly Glu Thr Gly Asn Gly Cys Val Asp Leu Arg Trp Leu Ala Lys
305                 310                 315                 320

Ser Phe Phe Glu Leu Thr Val Leu Lys Asp Ile Ile Gly Ile Cys Tyr
                325                 330                 335

Gly Ala Thr Val Lys Gly Met Gln Ser Tyr Gly Leu Glu Arg Leu Ala
                340                 345                 350

Ala Val Leu Met Ala Thr Val Lys Met Glu Glu Leu Gly His Leu Thr
                355                 360                 365

Thr Glu Lys Gln Glu Tyr Ala Leu Arg Leu Ala Thr Val Gly Tyr Pro
                370                 375                 380

Lys Ala Gly Val Tyr Ser Gly Leu Ile Gly Gly Ala Thr Ser Val Leu
385                 390                 395                 400

Leu Ser Ala Tyr Asn Arg His Pro Leu Phe Gln Pro Leu His Thr Val
                405                 410                 415

Met Arg Glu Thr Leu Phe Ile Gly Ser His Val Val Leu Arg Glu Leu
                420                 425                 430

Arg Leu Asn Val Thr Thr Gln Gly Pro Asn Leu Ala Leu Tyr Gln Leu
                435                 440                 445

Leu Ser Thr Ala Leu Cys Ser Ala Leu Glu Ile Gly Glu Val Leu Arg
450                 455                 460

Gly Leu Ala Leu Gly Thr Glu Ser Gly Leu Phe Ser Pro Cys Tyr Leu
465                 470                 475                 480

Ser Leu Arg Phe Asp Leu Thr Arg Asp Lys Leu Leu Ser Met Ala Pro
                485                 490                 495
```

```
Gln Glu Ala Met Leu Asp Gln Ala Ala Val Ser Asn Ala Val Asp Gly
                500                 505                 510

Phe Leu Gly Arg Leu Ser Leu Glu Arg Glu Asp Arg Asp Ala Trp His
            515                 520                 525

Leu Pro Ala Tyr Lys Cys Val Asp Arg Leu Asp Lys Val Leu Met Ile
        530                 535                 540

Ile Pro Leu Ile Asn Val Thr Phe Ile Ile Ser Ser Asp Arg Glu Val
545                 550                 555                 560

Arg Gly Ser Ala Leu Tyr Glu Ala Ser Thr Thr Tyr Leu Ser Ser Ser
                565                 570                 575

Leu Phe Leu Ser Pro Val Ile Met Asn Lys Cys Ser Gln Gly Ala Val
            580                 585                 590

Ala Gly Glu Pro Arg Gln Ile Pro Lys Ile Gln Asn Phe Thr Arg Thr
        595                 600                 605

Gln Lys Ser Cys Ile Phe Cys Gly Phe Ala Leu Leu Ser Tyr Asp Glu
610                 615                 620

Lys Glu Gly Leu Glu Thr Thr Thr Tyr Ile Thr Ser Gln Glu Val Gln
625                 630                 635                 640

Asn Ser Ile Leu Ser Ser Asn Tyr Phe Asp Phe Asp Asn Leu His Val
                645                 650                 655

His Tyr Leu Leu Leu Thr Thr Asn Gly Thr Val Met Glu Ile Ala Gly
            660                 665                 670

Leu Tyr Glu Glu Arg Ala His Val Val Leu Ala Ile Ile Leu Tyr Phe
        675                 680                 685

Ile Ala Phe Ala Leu Gly Ile Phe Leu Val His His Lys Ile Val Met Phe
690                 695                 700

Phe Leu
705

<210> SEQ ID NO 5
<211> LENGTH: 137
<212> TYPE: PRT
<213> ORGANISM: Epstein-Barr virus

<400> SEQUENCE: 5

Met Arg Thr Val Gly Val Phe Leu Ala Thr Cys Leu Val Thr Ile Phe
1               5                   10                  15

Val Leu Pro Thr Trp Gly Asn Trp Ala Tyr Pro Cys Cys His Val Thr
            20                  25                  30

Gln Leu Arg Ala Gln His Leu Leu Ala Leu Glu Asn Ile Ser Asp Ile
        35                  40                  45

Tyr Leu Val Ser Asn Gln Thr Cys Asp Gly Phe Ser Leu Ala Ser Leu
50                  55                  60

Asn Ser Pro Lys Asn Gly Ser Asn Gln Leu Val Ile Ser Arg Cys Ala
65                  70                  75                  80

Asn Gly Leu Asn Val Val Ser Phe Phe Ile Ser Ile Leu Lys Arg Ser
                85                  90                  95

Ser Ser Ala Leu Thr Gly His Leu Arg Glu Leu Leu Thr Thr Leu Glu
            100                 105                 110

Thr Leu Tyr Gly Ser Phe Ser Val Glu Asp Leu Phe Gly Ala Asn Leu
        115                 120                 125

Asn Arg Tyr Ala Trp His Arg Gly Gly
    130                 135

<210> SEQ ID NO 6
```

<211> LENGTH: 857
<212> TYPE: PRT
<213> ORGANISM: Epstein-Barr virus

<400> SEQUENCE: 6

```
Met Thr Arg Arg Arg Val Leu Ser Val Val Leu Leu Ala Ala Leu
1               5                   10                  15

Ala Cys Arg Leu Gly Ala Gln Thr Pro Glu Gln Pro Ala Pro Ala
                20                  25                  30

Thr Thr Val Gln Pro Thr Ala Thr Arg Gln Gln Thr Ser Phe Pro Phe
            35                  40                  45

Arg Val Cys Glu Leu Ser Ser His Gly Asp Leu Phe Arg Phe Ser Ser
        50                  55                  60

Asp Ile Gln Cys Pro Ser Phe Gly Thr Arg Glu Asn His Thr Glu Gly
65                  70                  75                  80

Leu Leu Met Val Phe Lys Asp Asn Ile Ile Pro Tyr Ser Phe Lys Val
                85                  90                  95

Arg Ser Tyr Thr Lys Ile Val Thr Asn Ile Leu Ile Tyr Asn Gly Trp
            100                 105                 110

Tyr Ala Asp Ser Val Thr Asn Arg His Glu Glu Lys Phe Ser Val Asp
        115                 120                 125

Ser Tyr Glu Thr Asp Gln Met Asp Thr Ile Tyr Gln Cys Tyr Asn Ala
    130                 135                 140

Val Lys Met Thr Lys Asp Gly Leu Thr Arg Val Tyr Val Asp Arg Asp
145                 150                 155                 160

Gly Val Asn Ile Thr Val Asn Leu Lys Pro Thr Gly Gly Leu Ala Asn
                165                 170                 175

Gly Val Arg Arg Tyr Ala Ser Gln Thr Glu Leu Tyr Asp Ala Pro Gly
            180                 185                 190

Trp Leu Ile Trp Thr Tyr Arg Thr Arg Thr Thr Val Asn Cys Leu Ile
        195                 200                 205

Thr Asp Met Met Ala Lys Ser Asn Ser Pro Phe Asp Phe Phe Val Thr
    210                 215                 220

Thr Thr Gly Gln Thr Val Glu Met Ser Pro Phe Tyr Asp Gly Lys Asn
225                 230                 235                 240

Lys Glu Thr Phe His Glu Arg Ala Asp Ser Phe His Val Arg Thr Asn
                245                 250                 255

Tyr Lys Ile Val Asp Tyr Asp Asn Arg Gly Thr Asn Pro Gln Gly Glu
            260                 265                 270

Arg Arg Ala Phe Leu Asp Lys Gly Thr Tyr Thr Leu Ser Trp Lys Leu
        275                 280                 285

Glu Asn Arg Thr Ala Tyr Cys Pro Leu Gln His Trp Gln Thr Phe Asp
    290                 295                 300

Ser Thr Ile Ala Thr Glu Thr Gly Lys Ser Ile His Phe Val Thr Asp
305                 310                 315                 320

Glu Gly Thr Ser Ser Phe Val Thr Asn Thr Thr Val Gly Ile Glu Leu
                325                 330                 335

Pro Asp Ala Phe Lys Cys Ile Glu Glu Gln Val Asn Lys Thr Met His
            340                 345                 350

Glu Lys Tyr Glu Ala Val Gln Asp Arg Tyr Thr Lys Gly Gln Glu Ala
        355                 360                 365

Ile Thr Tyr Phe Ile Thr Ser Gly Gly Leu Leu Leu Ala Trp Leu Pro
    370                 375                 380

Leu Thr Pro Arg Ser Leu Ala Thr Val Lys Asn Leu Thr Glu Leu Thr
```

```
            385                 390                 395                 400
        Thr Pro Thr Ser Ser Pro Pro Ser Ser Pro Ser Pro Pro Ala Pro Pro
                        405                 410                 415

Ala Ala Arg Gly Ser Thr Ser Ala Ala Val Leu Arg Arg Arg Arg Arg
                        420                 425                 430

Asp Ala Gly Asn Ala Thr Thr Pro Val Pro Pro Ala Ala Pro Gly Lys
                        435                 440                 445

Ser Leu Gly Thr Leu Asn Asn Pro Ala Thr Val Gln Ile Gln Phe Ala
                        450                 455                 460

Tyr Asp Ser Leu Arg Arg Gln Ile Asn Arg Met Leu Gly Asp Leu Ala
        465                 470                 475                 480

Arg Ala Trp Cys Leu Glu Gln Lys Arg Gln Asn Met Val Leu Arg Glu
                        485                 490                 495

Leu Thr Lys Ile Asn Pro Thr Thr Val Met Ser Ser Ile Tyr Gly Lys
                        500                 505                 510

Ala Val Ala Ala Lys Arg Leu Gly Asp Val Ile Ser Val Ser Gln Cys
                        515                 520                 525

Val Pro Val Asn Gln Ala Thr Val Thr Leu Arg Lys Ser Met Arg Val
                        530                 535                 540

Pro Gly Ser Glu Thr Met Cys Tyr Ser Arg Pro Leu Val Ser Phe Ser
        545                 550                 555                 560

Phe Ile Asn Asp Thr Lys Thr Tyr Glu Gly Gln Leu Gly Thr Asp Asn
                        565                 570                 575

Glu Ile Phe Leu Thr Lys Lys Met Thr Glu Val Cys Gln Ala Thr Ser
                        580                 585                 590

Gln Tyr Tyr Phe Gln Ser Gly Asn Glu Ile His Val Tyr Asn Asp Tyr
                        595                 600                 605

His His Phe Lys Thr Ile Glu Leu Asp Gly Ile Ala Thr Leu Gln Thr
                        610                 615                 620

Phe Ile Ser Leu Asn Thr Ser Leu Ile Glu Asn Ile Asp Phe Ala Ser
        625                 630                 635                 640

Leu Glu Leu Tyr Ser Arg Asp Glu Gln Arg Ala Ser Asn Val Phe Asp
                        645                 650                 655

Leu Glu Gly Ile Phe Arg Glu Tyr Asn Phe Gln Ala Gln Asn Ile Ala
                        660                 665                 670

Gly Leu Arg Lys Asp Leu Asp Asn Ala Val Ser Asn Gly Arg Asn Gln
                        675                 680                 685

Phe Val Asp Gly Leu Gly Glu Leu Met Asp Ser Leu Gly Ser Val Gly
                        690                 695                 700

Gln Ser Ile Thr Asn Leu Val Ser Thr Val Gly Gly Leu Phe Ser Ser
        705                 710                 715                 720

Leu Val Ser Gly Phe Ile Ser Phe Phe Lys Asn Pro Phe Gly Gly Met
                        725                 730                 735

Leu Ile Leu Val Leu Val Ala Gly Val Val Ile Leu Val Ile Ser Leu
                        740                 745                 750

Thr Arg Arg Thr Arg Gln Met Ser Gln Gln Pro Val Gln Met Leu Tyr
                        755                 760                 765

Pro Gly Ile Asp Glu Leu Ala Gln Gln His Ala Ser Gly Glu Gly Pro
                        770                 775                 780

Gly Ile Asn Pro Ile Ser Lys Thr Glu Leu Gln Ala Ile Met Leu Ala
        785                 790                 795                 800

Leu His Glu Gln Asn Gln Glu Gln Lys Arg Ala Ala Gln Arg Ala Ala
                        805                 810                 815
```

Gly Pro Ser Val Ala Ser Arg Ala Leu Gln Ala Ala Arg Asp Arg Phe
            820                 825                 830

Pro Gly Leu Arg Arg Arg Tyr His Asp Pro Glu Thr Ala Ala Ala
        835                 840                 845

Leu Leu Gly Glu Ala Glu Thr Glu Phe
    850                 855

<210> SEQ ID NO 7
<211> LENGTH: 223
<212> TYPE: PRT
<213> ORGANISM: Epstein-Barr virus

<400> SEQUENCE: 7

Met Val Ser Phe Lys Gln Val Arg Val Pro Leu Phe Thr Ala Ile Ala
1               5                   10                  15

Leu Val Ile Val Leu Leu Ala Tyr Phe Leu Pro Pro Arg Val Arg
            20                  25                  30

Gly Gly Gly Arg Val Ser Ala Ala Ile Thr Trp Val Pro Lys Pro
        35                  40                  45

Asn Val Glu Val Trp Pro Val Asp Pro Pro Pro Val Asn Phe Asn
50                  55                  60

Lys Thr Ala Glu Gln Glu Tyr Gly Asp Lys Glu Ile Lys Leu Pro His
65                  70                  75                  80

Trp Thr Pro Thr Leu His Thr Phe Gln Val Pro Lys Asn Tyr Thr Lys
                85                  90                  95

Ala Asn Cys Thr Tyr Cys Asn Thr Arg Glu Tyr Thr Phe Ser Tyr Lys
            100                 105                 110

Glu Arg Cys Phe Tyr Phe Thr Lys Lys Lys His Thr Trp Asn Gly Cys
        115                 120                 125

Phe Gln Ala Cys Ala Glu Leu Tyr Pro Cys Thr Tyr Phe Tyr Gly Pro
130                 135                 140

Thr Pro Asp Ile Leu Pro Val Val Thr Arg Asn Leu Asn Ala Ile Glu
145                 150                 155                 160

Ser Leu Trp Val Gly Val Tyr Arg Val Gly Glu Gly Asn Trp Thr Ser
                165                 170                 175

Leu Asp Gly Gly Thr Phe Lys Val Tyr Gln Ile Phe Gly Ser His Cys
            180                 185                 190

Thr Tyr Val Ser Lys Phe Ser Thr Val Pro Val Ser His His Glu Cys
        195                 200                 205

Ser Phe Leu Lys Pro Cys Leu Cys Val Ser Gln Arg Ser Asn Ser
210                 215                 220

<210> SEQ ID NO 8
<211> LENGTH: 357
<212> TYPE: PRT
<213> ORGANISM: Epstein-Barr virus

<400> SEQUENCE: 8

Met Phe Ser Cys Lys Gln His Leu Ser Leu Gly Ala Cys Val Phe Cys
1               5                   10                  15

Leu Gly Leu Leu Ala Ser Thr Pro Phe Ile Trp Cys Phe Val Phe Ala
            20                  25                  30

Asn Leu Leu Ser Leu Glu Ile Phe Ser Pro Trp Gln Thr His Val Tyr
        35                  40                  45

Arg Leu Gly Phe Pro Thr Ala Cys Leu Met Ala Val Leu Trp Thr Leu
50                  55                  60

```
Val Pro Ala Lys His Ala Val Arg Ala Val Thr Pro Ala Ile Met Leu
 65                  70                  75                  80

Asn Ile Ala Ser Ala Leu Ile Phe Phe Ser Leu Arg Val Tyr Ser Thr
                 85                  90                  95

Ser Thr Trp Val Ser Ala Pro Cys Leu Phe Leu Ala Asn Leu Pro Leu
            100                 105                 110

Leu Cys Leu Trp Pro Arg Leu Ala Ile Glu Ile Val Tyr Ile Cys Pro
        115                 120                 125

Ala Ile His Gln Arg Phe Phe Glu Leu Gly Leu Leu Leu Ala Cys Thr
    130                 135                 140

Ile Phe Ala Leu Ser Val Val Ser Arg Ala Leu Glu Val Ser Ala Val
145                 150                 155                 160

Phe Met Ser Pro Phe Phe Ile Phe Leu Ala Leu Gly Ser Gly Ser Leu
                165                 170                 175

Ala Gly Ala Arg Arg Asn Gln Ile Tyr Thr Ser Gly Leu Glu Arg Arg
            180                 185                 190

Arg Ser Ile Phe Cys Ala Arg Gly Asp His Ser Val Ala Ser Leu Lys
        195                 200                 205

Glu Thr Leu His Lys Cys Pro Trp Asp Leu Leu Ala Ile Ser Ala Leu
    210                 215                 220

Thr Val Leu Val Val Cys Val Met Ile Val Leu His Val His Ala Glu
225                 230                 235                 240

Val Phe Phe Gly Leu Ser Arg Tyr Leu Pro Leu Phe Leu Cys Gly Ala
                245                 250                 255

Met Ala Ser Gly Gly Leu Tyr Leu Gly His Ser Ser Ile Ile Ala Cys
            260                 265                 270

Val Met Ala Thr Leu Cys Thr Leu Thr Ser Val Val Tyr Phe Leu
        275                 280                 285

His Glu Thr Leu Gly Pro Leu Gly Lys Thr Val Leu Phe Ile Ser Ile
    290                 295                 300

Phe Val Tyr Tyr Phe Ser Gly Val Ala Ala Leu Ser Ala Ala Met Arg
305                 310                 315                 320

Tyr Lys Leu Lys Lys Phe Val Asn Gly Pro Leu Val His Leu Arg Val
                325                 330                 335

Val Tyr Met Cys Cys Phe Val Phe Thr Phe Cys Glu Tyr Leu Leu Val
            340                 345                 350

Thr Phe Ile Lys Ser
        355

<210> SEQ ID NO 9
<211> LENGTH: 420
<212> TYPE: PRT
<213> ORGANISM: Epstein-Barr virus

<400> SEQUENCE: 9

Met Val Asp Glu Gln Val Ala Val Glu His Gly Thr Val Ser His Thr
1               5                   10                  15

Ile Ser Arg Glu Glu Asp Gly Val Val His Glu Arg Arg Val Leu Ala
                20                  25                  30

Ser Gly Glu Arg Val Glu Val Phe Tyr Lys Ala Pro Ala Pro Arg Pro
            35                  40                  45

Arg Glu Gly Arg Ala Ser Thr Phe His Asp Phe Thr Val Pro Ala Ala
        50                  55                  60

Ala Ala Val Pro Gly Pro Glu Pro Glu Pro Glu Pro His Pro Pro Met
```

-continued

```
                65                  70                  75                  80
        Pro Ile His Ala Asn Gly Gly Glu Thr Lys Thr Asn Thr Gln Asp
                            85                  90                  95
        Gln Asn Gln Asn Gln Thr Thr Arg Thr Arg Thr Asn Ala Lys Ala Glu
                           100                 105                 110
        Glu Arg Thr Ala Glu Met Asp Asp Thr Met Ala Ser Ser Gly Gly Gln
                       115                 120                 125
        Arg Gly Ala Pro Ile Ser Ala Asp Leu Leu Ser Leu Ser Ser Leu Thr
                   130                 135                 140
        Gly Arg Met Ala Ala Met Ala Pro Ser Trp Met Lys Ser Glu Val Cys
        145                 150                 155                 160
        Gly Glu Arg Met Arg Phe Lys Glu Asp Val Tyr Asp Gly Glu Ala Glu
                           165                 170                 175
        Thr Leu Ala Glu Pro Pro Arg Cys Phe Met Leu Ser Phe Val Phe Ile
                       180                 185                 190
        Tyr Tyr Cys Cys Tyr Leu Ala Phe Leu Ala Leu Leu Ala Phe Gly Phe
                       195                 200                 205
        Asn Pro Leu Phe Leu Pro Ser Phe Met Pro Val Gly Ala Lys Val Leu
                   210                 215                 220
        Arg Gly Lys Gly Arg Asp Phe Gly Val Pro Leu Ser Tyr Gly Cys Pro
        225                 230                 235                 240
        Thr Asn Pro Phe Cys Lys Val Tyr Thr Leu Ile Pro Ala Val Val Ile
                           245                 250                 255
        Asn Asn Val Thr Tyr Tyr Pro Asn Asn Thr Asp Ser His Gly Gly His
                       260                 265                 270
        Gly Gly Phe Glu Ala Ala Ala Leu His Val Ala Ala Leu Phe Glu Ser
                       275                 280                 285
        Gly Cys Pro Asn Leu Gln Ala Val Thr Asn Arg Asn Arg Thr Phe Asn
                   290                 295                 300
        Val Thr Arg Ala Ser Gly Arg Val Glu Arg Arg Leu Val Gln Asp Met
        305                 310                 315                 320
        Gln Arg Val Leu Ala Ser Ala Val Val Met His His His Cys His
                       325                 330                 335
        Tyr Glu Thr Tyr Tyr Val Phe Asp Gly Val Pro Glu Phe Gly Thr
                       340                 345                 350
        Ile Pro Thr Pro Cys Phe Lys Asp Val Leu Ala Phe Arg Pro Ser Leu
                   355                 360                 365
        Val Thr Asn Cys Thr Ala Pro Leu Lys Thr Ser Val Lys Gly Pro Asn
                   370                 375                 380
        Trp Ser Gly Ala Ala Gly Gly Met Lys Arg Lys Gln Cys Arg Val Asp
        385                 390                 395                 400
        Arg Leu Thr Asp Arg Ser Phe Pro Ala Tyr Leu Glu Glu Val Met Tyr
                           405                 410                 415
        Val Met Val Gln
                       420

<210> SEQ ID NO 10
<211> LENGTH: 228
<212> TYPE: PRT
<213> ORGANISM: Kaposi's sarcoma-associated herpesvirus

<400> SEQUENCE: 10

Met Ser Ser Thr Gln Ile Arg Thr Glu Ile Pro Val Ala Leu Leu Ile
1               5                   10                  15
```

```
Leu Cys Leu Cys Leu Val Ala Cys His Ala Asn Cys Pro Thr Tyr Arg
            20                  25                  30

Ser His Leu Gly Phe Trp Gln Glu Gly Trp Ser Gly Gln Val Tyr Gln
            35                  40                  45

Asp Trp Leu Gly Arg Met Asn Cys Ser Tyr Glu Asn Met Thr Ala Leu
 50                  55                  60

Glu Ala Val Ser Leu Asn Gly Thr Arg Leu Ala Ala Gly Ser Pro Ser
 65                  70                  75                  80

Ser Glu Tyr Pro Asn Val Ser Val Ser Val Glu Asp Thr Ser Ala Ser
                85                  90                  95

Gly Ser Gly Glu Asp Ala Ile Asp Glu Ser Gly Ser Gly Glu Glu Glu
            100                 105                 110

Arg Pro Val Thr Ser His Val Thr Phe Met Thr Gln Ser Val Gln Ala
            115                 120                 125

Thr Thr Glu Leu Thr Asp Ala Leu Ile Ser Ala Phe Ser Gly Ser Tyr
130                 135                 140

Ser Ser Gly Glu Pro Ser Arg Thr Thr Arg Ile Arg Val Ser Pro Val
145                 150                 155                 160

Ala Glu Asn Gly Arg Asn Ser Gly Ala Ser Asn Arg Val Pro Phe Ser
                165                 170                 175

Ala Thr Thr Thr Thr Arg Gly Arg Asp Ala His Tyr Asn Ala Glu
            180                 185                 190

Ile Arg Thr His Leu Tyr Ile Leu Trp Ala Val Gly Leu Leu Leu Gly
            195                 200                 205

Leu Val Leu Ile Leu Tyr Leu Cys Val Pro Arg Cys Arg Arg Lys Lys
210                 215                 220

Pro Tyr Ile Val
225

<210> SEQ ID NO 11
<211> LENGTH: 167
<212> TYPE: PRT
<213> ORGANISM: Kaposi's sarcoma-associated herpesvirus

<400> SEQUENCE: 11

Met Ser Ser Thr Gln Ile Arg Thr Glu Ile Pro Val Ala Leu Leu Ile
 1               5                  10                  15

Leu Cys Leu Cys Leu Val Ala Cys His Ala Asn Cys Pro Thr Tyr Arg
            20                  25                  30

Ser His Leu Gly Phe Trp Gln Glu Gly Trp Ser Gly Gln Val Tyr Gln
            35                  40                  45

Asp Trp Leu Gly Arg Met Asn Cys Ser Tyr Glu Asn Met Thr Ala Leu
 50                  55                  60

Glu Ala Val Ser Leu Asn Gly Thr Arg Leu Ala Ala Gly Ser Pro Ser
 65                  70                  75                  80

Arg Ser Tyr Ser Ser Gly Glu Pro Ser Arg Thr Thr Arg Ile Arg Val
                85                  90                  95

Ser Pro Val Ala Glu Asn Gly Arg Asn Ser Gly Ala Ser Asn Arg Val
            100                 105                 110

Pro Phe Ser Ala Thr Thr Thr Thr Thr Arg Gly Arg Asp Ala His Tyr
            115                 120                 125

Asn Ala Glu Ile Arg Thr His Leu Tyr Ile Leu Trp Ala Val Gly Leu
130                 135                 140

Leu Leu Gly Leu Val Leu Ile Leu Tyr Leu Cys Val Pro Arg Cys Arg
145                 150                 155                 160
```

```
Arg Lys Lys Pro Tyr Ile Val
                165

<210> SEQ ID NO 12
<211> LENGTH: 730
<212> TYPE: PRT
<213> ORGANISM: Kaposi's sarcoma-associated herpesvirus

<400> SEQUENCE: 12

Met Gln Gly Leu Ala Phe Leu Ala Ala Leu Ala Cys Trp Arg Cys Ile
1               5                   10                  15

Ser Leu Thr Cys Gly Ala Thr Gly Ala Leu Pro Thr Thr Ala Thr Thr
            20                  25                  30

Ile Thr Arg Ser Ala Thr Gln Leu Ile Asn Gly Arg Thr Asn Leu Ser
        35                  40                  45

Ile Glu Leu Glu Phe Asn Gly Thr Ser Phe Phe Leu Asn Trp Gln Asn
    50                  55                  60

Leu Leu Asn Val Ile Thr Glu Pro Ala Leu Thr Glu Leu Trp Thr Ser
65                  70                  75                  80

Ala Glu Val Ala Glu Asp Leu Arg Val Thr Leu Lys Lys Arg Gln Ser
                85                  90                  95

Leu Phe Phe Pro Asn Lys Thr Val Val Ile Ser Gly Asp Gly His Arg
            100                 105                 110

Tyr Thr Cys Glu Val Pro Thr Ser Ser Gln Thr Tyr Asn Ile Thr Lys
        115                 120                 125

Gly Phe Asn Tyr Ser Ala Leu Pro Gly His Leu Gly Gly Phe Gly Ile
    130                 135                 140

Asn Ala Arg Leu Val Leu Gly Asp Ile Phe Ala Ser Lys Trp Ser Leu
145                 150                 155                 160

Phe Ala Arg Asp Thr Pro Glu Tyr Arg Val Phe Tyr Pro Met Asn Val
                165                 170                 175

Met Ala Val Lys Phe Ser Ile Ser Ile Gly Asn Asn Glu Ser Gly Val
            180                 185                 190

Ala Leu Tyr Gly Val Val Ser Glu Asp Phe Val Val Thr Leu His
        195                 200                 205

Asn Arg Ser Lys Glu Ala Asn Glu Thr Ala Ser His Leu Leu Phe Gly
    210                 215                 220

Leu Pro Asp Ser Leu Pro Ser Leu Lys Gly His Ala Thr Tyr Asp Glu
225                 230                 235                 240

Leu Thr Phe Ala Arg Asn Ala Lys Tyr Ala Leu Val Ala Ile Leu Pro
                245                 250                 255

Lys Asp Ser Tyr Gln Thr Leu Leu Thr Glu Asn Tyr Thr Arg Ile Phe
            260                 265                 270

Leu Asn Met Thr Glu Ser Thr Pro Leu Glu Phe Thr Arg Thr Ile Gln
        275                 280                 285

Thr Arg Ile Val Ser Ile Glu Ala Arg Arg Ala Cys Ala Ala Gln Glu
    290                 295                 300

Ala Ala Pro Asp Ile Phe Leu Val Leu Phe Gln Met Leu Val Ala His
305                 310                 315                 320

Phe Leu Val Ala Arg Gly Ile Ala Glu His Arg Phe Val Glu Val Asp
                325                 330                 335

Cys Val Cys Arg Gln Tyr Ala Glu Leu Tyr Phe Leu Arg Arg Ile Ser
            340                 345                 350

Arg Leu Cys Met Pro Thr Phe Thr Thr Val Gly Tyr Asn His Thr Thr
```

```
                    355                 360                 365
Leu Gly Ala Val Ala Ala Thr Gln Ile Ala Arg Val Ser Ala Thr Lys
    370                 375                 380

Leu Ala Ser Leu Pro Arg Ser Ser Gln Glu Thr Val Leu Ala Met Val
385                 390                 395                 400

Gln Leu Gly Ala Arg Asp Gly Ala Val Pro Ser Ser Ile Leu Glu Gly
                405                 410                 415

Ile Ala Met Val Val Glu His Met Tyr Thr Ala Tyr Thr Tyr Val Tyr
            420                 425                 430

Thr Leu Gly Asp Thr Glu Arg Lys Leu Met Leu Asp Ile His Thr Val
        435                 440                 445

Leu Thr Asp Ser Cys Pro Pro Lys Asp Ser Gly Val Ser Glu Lys Leu
    450                 455                 460

Leu Arg Thr Tyr Leu Met Phe Thr Ser Met Cys Thr Asn Ile Glu Leu
465                 470                 475                 480

Gly Glu Met Ile Ala Arg Phe Ser Lys Pro Asp Ser Leu Asn Ile Tyr
                485                 490                 495

Arg Ala Phe Ser Pro Cys Phe Leu Gly Leu Arg Tyr Asp Leu His Pro
            500                 505                 510

Ala Lys Leu Arg Ala Glu Ala Pro Gln Ser Ser Ala Leu Thr Arg Thr
        515                 520                 525

Ala Val Ala Arg Gly Thr Ser Gly Phe Ala Glu Leu Leu His Ala Leu
    530                 535                 540

His Leu Asp Ser Leu Asn Leu Ile Pro Ala Ile Asn Cys Ser Lys Ile
545                 550                 555                 560

Thr Ala Asp Lys Ile Ile Ala Thr Val Pro Leu Pro His Val Thr Tyr
                565                 570                 575

Ile Ile Ser Ser Glu Ala Leu Ser Asn Ala Val Val Tyr Glu Val Ser
            580                 585                 590

Glu Ile Phe Leu Lys Ser Ala Met Phe Ile Ser Ala Ile Lys Pro Asp
        595                 600                 605

Cys Ser Gly Phe Asn Phe Ser Gln Ile Asp Arg His Ile Pro Ile Val
    610                 615                 620

Tyr Asn Ile Ser Thr Pro Arg Arg Gly Cys Pro Leu Cys Asp Ser Val
625                 630                 635                 640

Ile Met Ser Tyr Asp Glu Ser Asp Gly Leu Gln Ser Leu Met Tyr Val
                645                 650                 655

Thr Asn Glu Arg Val Gln Thr Asn Leu Phe Leu Asp Lys Ser Pro Phe
            660                 665                 670

Phe Asp Asn Asn Asn Leu His Ile His Tyr Leu Trp Leu Arg Asp Asn
        675                 680                 685

Gly Thr Val Val Glu Ile Arg Gly Met Tyr Arg Arg Arg Ala Ala Ser
    690                 695                 700

Ala Leu Phe Leu Ile Leu Ser Phe Ile Gly Phe Ser Gly Val Ile Tyr
705                 710                 715                 720

Phe Leu Tyr Arg Leu Phe Ser Ile Leu Tyr
                725                 730

<210> SEQ ID NO 13
<211> LENGTH: 167
<212> TYPE: PRT
<213> ORGANISM: Kaposi's sarcoma-associated herpesvirus

<400> SEQUENCE: 13
```

```
Met Gly Ile Phe Ala Leu Phe Ala Val Leu Trp Thr Thr Leu Leu Val
1               5                   10                  15

Thr Ser His Ala Tyr Val Ala Leu Pro Cys Cys Ala Ile Gln Ala Ser
            20                  25                  30

Ala Ala Ser Thr Leu Pro Leu Phe Phe Ala Val His Ser Ile His Phe
        35                  40                  45

Ala Asp Pro Asn His Cys Asn Gly Val Cys Ile Ala Lys Leu Arg Ser
    50                  55                  60

Lys Thr Gly Asp Ile Thr Val Glu Thr Cys Val Asn Gly Phe Asn Leu
65                  70                  75                  80

Arg Ser Phe Leu Val Ala Val Val Arg Arg Leu Gly Ser Trp Ala Ser
                85                  90                  95

Gln Glu Asn Leu Arg Leu Leu Trp Tyr Leu Gln Arg Ser Leu Thr Ala
            100                 105                 110

Tyr Thr Val Gly Phe Asn Ala Thr Thr Ala Asp Ser Ser Ile His Asn
        115                 120                 125

Val Asn Ile Ile Ile Ser Val Gly Lys Ala Met Asn Arg Thr Gly
    130                 135                 140

Ser Val Ser Gly Ser Gln Thr Arg Ala Lys Ser Ser Arg Arg Ala
145                 150                 155                 160

His Ala Gly Gln Lys Gly Lys
                165
```

```
<210> SEQ ID NO 14
<211> LENGTH: 110
<212> TYPE: PRT
<213> ORGANISM: Kaposi's sarcoma-associated herpesvirus

<400> SEQUENCE: 14

Met Thr Ala Ser Thr Val Ala Leu Ala Leu Phe Val Ala Ser Ile Leu
1               5                   10                  15

Gly His Cys Trp Val Thr Ala Asn Ser Thr Gly Val Ala Ser Ser Thr
            20                  25                  30

Glu Arg Ser Ser Pro Ser Thr Ala Gly Leu Ser Ala Arg Pro Ser Pro
        35                  40                  45

Gly Pro Thr Ser Val Thr Thr Pro Gly Phe Tyr Asp Val Ala Cys Ser
    50                  55                  60

Ala Asp Ser Phe Ser Pro Ser Leu Ser Ser Phe Ser Ser Val Trp Ala
65                  70                  75                  80

Leu Ile Asn Ala Leu Leu Val Val Val Ala Thr Phe Phe Tyr Leu Val
                85                  90                  95

Tyr Leu Cys Phe Phe Lys Phe Val Asp Glu Val Val His Ala
            100                 105                 110
```

```
<210> SEQ ID NO 15
<211> LENGTH: 400
<212> TYPE: PRT
<213> ORGANISM: Kaposi's sarcoma-associated herpesvirus

<400> SEQUENCE: 15

Met Arg Ala Ser Lys Ser Asp Arg Phe Leu Met Ser Ser Trp Val Lys
1               5                   10                  15

Leu Leu Phe Val Ala Val Ile Met Tyr Ile Cys Ser Ala Val Val Pro
            20                  25                  30

Met Ala Ala Thr Tyr Glu Gly Leu Gly Phe Pro Cys Tyr Phe Asn Asn
        35                  40                  45
```

```
Leu Val Asn Tyr Ser Ala Leu Asn Leu Thr Val Arg Asn Ser Ala Lys
 50                  55                  60

His Leu Thr Pro Thr Leu Phe Leu Glu Lys Pro Glu Met Leu Val Tyr
 65                  70                  75                  80

Ile Phe Trp Thr Phe Ile Val Asp Gly Ile Ala Ile Val Tyr Tyr Cys
                 85                  90                  95

Leu Ala Ala Val Ala Val Tyr Arg Ala Lys His Val His Ala Thr Thr
            100                 105                 110

Met Met Ser Met Gln Ser Trp Ile Ala Leu Leu Gly Ser His Ser Val
        115                 120                 125

Leu Tyr Val Ala Ile Leu Arg Met Trp Ser Met Gln Leu Phe Ile His
130                 135                 140

Val Leu Ser Tyr Lys His Val Leu Met Ala Ala Phe Val Tyr Cys Ile
145                 150                 155                 160

His Phe Cys Ile Ser Phe Ala His Ile Gln Ser Leu Ile Thr Cys Asn
                165                 170                 175

Ser Ala Gln Trp Glu Ile Pro Leu Leu Glu Gln His Val Pro Asp Asn
            180                 185                 190

Thr Met Met Glu Ser Leu Leu Thr Arg Trp Lys Pro Val Cys Val Asn
        195                 200                 205

Leu Tyr Leu Ser Thr Thr Ala Leu Glu Met Leu Leu Phe Ser Leu Ser
210                 215                 220

Thr Met Met Ala Val Gly Asn Ser Phe Tyr Val Leu Val Ser Asp Ala
225                 230                 235                 240

Ile Phe Gly Ala Val Asn Met Phe Leu Ala Leu Thr Val Trp Tyr
                245                 250                 255

Ile Asn Thr Glu Phe Phe Leu Val Lys Phe Met Arg Arg Gln Val Gly
            260                 265                 270

Phe Tyr Val Gly Val Phe Val Gly Tyr Leu Ile Leu Leu Pro Val
        275                 280                 285

Ile Arg Tyr Glu Asn Ala Phe Val Gln Ala Asn Leu His Tyr Ile Val
290                 295                 300

Ala Ile Asn Ile Ser Cys Ile Pro Ile Leu Cys Ile Leu Ala Ile Val
305                 310                 315                 320

Ile Arg Val Ile Arg Ser Asp Trp Gly Leu Cys Thr Pro Ser Ala Ala
                325                 330                 335

Tyr Met Pro Leu Ala Thr Ser Ala Pro Thr Val Asp Arg Thr Pro Thr
            340                 345                 350

Val His Gln Lys Pro Pro Pro Leu Pro Ala Lys Thr Arg Ala Arg Ala
        355                 360                 365

Lys Val Lys Asp Ile Ser Thr Pro Ala Pro Arg Thr Gln Tyr Gln Ser
370                 375                 380

Asp His Glu Ser Asp Ser Glu Ile Asp Glu Thr Gln Met Ile Phe Ile
385                 390                 395                 400

<210> SEQ ID NO 16
<211> LENGTH: 467
<212> TYPE: PRT
<213> ORGANISM: Kaposi's sarcoma-associated herpesvirus

<400> SEQUENCE: 16

Met Phe Val Pro Trp Gln Leu Gly Thr Ile Thr Arg His Arg Asp Glu
  1               5                  10                  15

Leu Gln Lys Leu Leu Ala Ala Ser Leu Leu Pro Glu His Pro Glu Glu
                 20                  25                  30
```

-continued

```
Ser Leu Gly Asn Pro Ile Met Thr Gln Ile His Gln Ser Leu Gln Pro
         35                  40                  45

Ser Ser Pro Cys Arg Val Cys Gln Leu Leu Phe Ser Leu Val Arg Asp
50              55                  60

Ser Ser Thr Pro Met Gly Phe Phe Glu Asp Tyr Ala Cys Leu Cys Phe
65              70                  75                  80

Phe Cys Leu Tyr Ala Pro His Cys Trp Thr Ser Thr Met Ala Ala Ala
                85                  90                  95

Ala Asp Leu Cys Glu Ile Met His Leu His Phe Pro Glu Glu Glu Ala
                100                 105                 110

Thr Tyr Gly Leu Phe Gly Pro Gly Arg Leu Met Gly Ile Asp Leu Gln
            115                 120                 125

Leu His Phe Phe Val Gln Lys Cys Phe Lys Thr Thr Ala Ala Glu Lys
            130                 135                 140

Ile Leu Gly Ile Ser Asn Leu Gln Phe Leu Lys Ser Glu Phe Ile Arg
145                 150                 155                 160

Gly Met Leu Thr Gly Thr Ile Thr Cys Asn Phe Cys Phe Lys Thr Ser
                165                 170                 175

Trp Pro Arg Thr Asp Lys Glu Glu Ala Thr Gly Pro Thr Pro Cys Cys
            180                 185                 190

Gln Ile Thr Asp Thr Thr Thr Ala Pro Ala Ser Gly Ile Pro Glu Leu
            195                 200                 205

Ala Arg Ala Thr Phe Cys Gly Ala Ser Arg Pro Thr Lys Pro Ser Leu
            210                 215                 220

Leu Pro Ala Leu Ile Asp Ile Trp Ser Thr Ser Ser Glu Leu Leu Asp
225                 230                 235                 240

Glu Pro Arg Pro Arg Leu Ile Ala Ser Asp Met Ser Glu Leu Lys Ser
                245                 250                 255

Val Val Ala Ser His Asp Pro Phe Phe Ser Pro Pro Leu Gln Ala Asp
                260                 265                 270

Thr Ser Gln Gly Pro Cys Leu Met His Pro Thr Leu Gly Leu Arg Tyr
            275                 280                 285

Lys Asn Gly Thr Ala Ser Val Cys Leu Leu Cys Glu Cys Leu Ala Ala
            290                 295                 300

His Pro Glu Ala Pro Lys Ala Leu Gln Thr Leu Gln Cys Glu Val Met
305                 310                 315                 320

Gly His Ile Glu Asn Asn Val Lys Leu Val Asp Arg Ile Ala Phe Val
                325                 330                 335

Leu Asp Asn Pro Phe Ala Met Pro Tyr Val Ser Asp Pro Leu Leu Arg
            340                 345                 350

Glu Leu Ile Arg Gly Cys Thr Pro Gln Glu Ile His Lys His Leu Phe
            355                 360                 365

Cys Asp Pro Leu Cys Ala Leu Asn Ala Lys Val Val Ser Glu Asp Val
            370                 375                 380

Leu Phe Arg Leu Pro Arg Glu Gln Glu Tyr Lys Lys Leu Arg Ala Ser
385                 390                 395                 400

Ala Ala Ala Gly Gln Leu Leu Asp Ala Asn Thr Leu Phe Asp Cys Glu
                405                 410                 415

Val Val Gln Thr Leu Val Phe Leu Phe Lys Gly Leu Gln Asn Ala Arg
            420                 425                 430

Val Gly Lys Thr Thr Ser Leu Asp Ile Ile Arg Glu Leu Thr Ala Gln
            435                 440                 445
```

```
Leu Lys Arg His Arg Leu Asp Leu Ala His Pro Ser Gln Thr Ser His
    450                 455                 460

Leu Tyr Ala
465

<210> SEQ ID NO 17
<211> LENGTH: 743
<212> TYPE: PRT
<213> ORGANISM: Human cytomegalovirus

<400> SEQUENCE: 17

Met Arg Pro Gly Leu Pro Pro Tyr Leu Thr Val Phe Thr Val Tyr Leu
1               5                  10                  15

Leu Ser His Leu Pro Ser Gln Arg Tyr Gly Ala Asp Ala Ala Ser Glu
            20                  25                  30

Ala Leu Asp Pro His Ala Phe His Leu Leu Asn Thr Tyr Gly Arg
        35                  40                  45

Pro Ile Arg Phe Leu Arg Glu Asn Thr Thr Gln Cys Thr Tyr Asn Ser
50                  55                  60

Ser Leu Arg Asn Ser Thr Val Val Arg Glu Asn Ala Ile Ser Phe Asn
65                  70                  75                  80

Phe Phe Gln Ser Tyr Asn Gln Tyr Tyr Val Phe His Met Pro Arg Cys
                85                  90                  95

Leu Phe Ala Gly Pro Leu Ala Glu Gln Phe Leu Asn Gln Val Asp Leu
            100                 105                 110

Thr Glu Thr Leu Glu Arg Tyr Gln Gln Arg Leu Asn Thr Tyr Ala Leu
        115                 120                 125

Val Ser Lys Asp Leu Ala Ser Tyr Arg Ser Phe Ser Gln Gln Leu Lys
130                 135                 140

Ala Gln Asp Ser Leu Gly Gln Gln Pro Thr Thr Val Pro Pro Pro Ile
145                 150                 155                 160

Asp Leu Ser Ile Pro His Val Trp Met Pro Pro Gln Thr Thr Pro His
                165                 170                 175

Asp Trp Lys Gly Ser His Thr Thr Ser Gly Leu His Arg Pro His Phe
            180                 185                 190

Asn Gln Thr Cys Ile Leu Phe Asp Gly His Asp Leu Leu Phe Ser Thr
        195                 200                 205

Val Thr Pro Cys Leu His Gln Gly Phe Tyr Leu Met Asp Glu Leu Arg
210                 215                 220

Tyr Val Lys Ile Thr Leu Thr Glu Asp Phe Phe Val Val Thr Val Ser
225                 230                 235                 240

Ile Asp Asp Asp Thr Pro Met Leu Leu Ile Phe Gly His Leu Pro Arg
                245                 250                 255

Val Leu Phe Lys Ala Pro Tyr Gln Arg Asp Asn Phe Ile Leu Arg Gln
            260                 265                 270

Thr Glu Lys His Glu Leu Leu Val Leu Val Lys Lys Ala Gln Leu Asn
        275                 280                 285

Arg His Ser Tyr Leu Lys Asp Ser Asp Phe Leu Asp Ala Ala Leu Asp
290                 295                 300

Phe Asn Tyr Leu Asp Leu Ser Ala Leu Leu Arg Asn Ser Phe His Arg
305                 310                 315                 320

Tyr Ala Val Asp Val Leu Lys Ser Gly Arg Cys Gln Met Leu Asp Arg
                325                 330                 335

Arg Thr Val Glu Met Ala Phe Ala Tyr Ala Leu Ala Leu Phe Ala Ala
            340                 345                 350
```

Ala Arg Gln Glu Glu Ala Gly Thr Glu Ile Ser Ile Pro Arg Ala Leu
            355                 360                 365

Asp Arg Gln Ala Ala Leu Leu Gln Ile Gln Glu Phe Met Ile Thr Cys
    370                 375                 380

Leu Ser Gln Thr Pro Pro Arg Thr Thr Leu Leu Leu Tyr Pro Thr Ala
385                 390                 395                 400

Val Asp Leu Ala Lys Arg Ala Leu Trp Thr Pro Asp Gln Ile Thr Asp
                405                 410                 415

Ile Thr Ser Leu Val Arg Leu Val Tyr Ile Leu Ser Lys Gln Asn Gln
                420                 425                 430

Gln His Leu Ile Pro Gln Trp Ala Leu Arg Gln Ile Ala Asp Phe Ala
            435                 440                 445

Leu Gln Leu His Lys Thr His Leu Ala Ser Phe Leu Ser Ala Phe Ala
        450                 455                 460

Arg Gln Glu Leu Tyr Leu Met Gly Ser Leu Val His Ser Met Leu Val
465                 470                 475                 480

His Thr Thr Glu Arg Arg Glu Ile Phe Ile Val Glu Thr Gly Leu Cys
                485                 490                 495

Ser Leu Ala Glu Leu Ser His Phe Thr Gln Leu Leu Ala His Pro His
            500                 505                 510

His Glu Tyr Leu Ser Asp Leu Tyr Thr Pro Cys Ser Ser Ser Gly Arg
        515                 520                 525

Arg Asp His Ser Leu Glu Arg Leu Thr Arg Leu Phe Pro Asp Ala Thr
    530                 535                 540

Val Pro Ala Thr Val Pro Ala Ala Leu Ser Ile Leu Ser Thr Met Gln
545                 550                 555                 560

Pro Ser Thr Leu Glu Thr Phe Pro Asp Leu Phe Cys Leu Pro Leu Gly
                565                 570                 575

Glu Ser Phe Ser Ala Leu Thr Val Ser Glu His Val Ser Tyr Val Val
            580                 585                 590

Thr Asn Gln Tyr Leu Ile Lys Gly Ile Ser Tyr Pro Val Ser Thr Thr
        595                 600                 605

Val Val Gly Gln Ser Leu Ile Ile Thr Gln Thr Asp Ser Gln Thr Lys
    610                 615                 620

Cys Glu Leu Thr Arg Asn Met His Thr His Ser Ile Thr Ala Ala
625                 630                 635                 640

Leu Asn Ile Ser Leu Glu Asn Cys Ala Phe Cys Gln Ser Ala Leu Leu
                645                 650                 655

Glu Tyr Asp Asp Thr Gln Gly Val Ile Asn Ile Met Tyr Met His Asp
            660                 665                 670

Ser Asp Asp Val Leu Phe Ala Leu Asp Pro Tyr Asn Glu Val Val Val
        675                 680                 685

Ser Ser Pro Arg Thr His Tyr Leu Met Leu Lys Asn Gly Thr Val
    690                 695                 700

Leu Glu Val Thr Asp Val Val Asp Ala Thr Asp Ser Arg Leu Leu
705                 710                 715                 720

Met Met Ser Val Tyr Ala Leu Ser Ala Ile Ile Gly Ile Tyr Leu Leu
                725                 730                 735

Tyr Arg Met Leu Lys Thr Cys
            740

<210> SEQ ID NO 18
<211> LENGTH: 278

```
<212> TYPE: PRT
<213> ORGANISM: Human cytomegalovirus

<400> SEQUENCE: 18

Met Cys Arg Arg Pro Asp Cys Gly Phe Ser Phe Ser Pro Gly Pro Val
1               5                   10                  15

Ile Leu Leu Trp Cys Cys Leu Leu Pro Ile Val Ser Ser Ala Ala
            20                  25                  30

Val Ser Val Ala Pro Thr Ala Ala Glu Lys Val Pro Ala Glu Cys Pro
            35                  40                  45

Glu Leu Thr Arg Arg Cys Leu Leu Gly Glu Val Phe Glu Gly Asp Lys
        50                  55                  60

Tyr Glu Ser Trp Leu Arg Pro Leu Val Asn Val Thr Gly Arg Asp Gly
65              70                  75                  80

Pro Leu Ser Gln Leu Ile Arg Tyr Arg Pro Val Thr Pro Glu Ala Ala
                    85                  90                  95

Asn Ser Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                    165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                    245                 250                 255

Leu Lys Gln Thr Arg Val Asn Leu Pro Ala His Ser Arg Tyr Gly Pro
            260                 265                 270

Gln Ala Val Asp Ala Arg
        275

<210> SEQ ID NO 19
<211> LENGTH: 906
<212> TYPE: PRT
<213> ORGANISM: Human cytomegalovirus

<400> SEQUENCE: 19

Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Ser Glu Ala Val Ser
    50                  55                  60
```

```
His Arg Ala Asn Glu Thr Ile Tyr Asn Thr Thr Leu Lys Tyr Gly Asp
 65                  70                  75                  80

Val Val Gly Val Asn Thr Thr Lys Tyr Pro Tyr Arg Val Cys Ser Met
                 85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Ile Thr His Arg Thr Arg Ser Thr Ser Asp Asn
    450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
```

```
            485                 490                 495
Ala Leu Ala Gln Ile Ala Glu Ala Trp Cys Val Asp Gln Arg Arg Thr
            500                 505                 510

Leu Glu Val Phe Lys Glu Leu Ser Lys Ile Asn Pro Ser Ala Ile Leu
            515                 520                 525

Ser Ala Ile Tyr Asn Lys Pro Ile Ala Arg Phe Met Gly Asp Val
            530                 535             540

Leu Gly Leu Ala Ser Cys Val Thr Ile Asn Gln Thr Ser Val Lys Val
545             550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
            580                 585                 590

Gln Leu Gly Glu Asp Asn Glu Ile Leu Leu Gly Asn His Arg Thr Glu
            595                 600                 605

Glu Cys Gln Leu Pro Ser Leu Lys Ile Phe Ile Ala Gly Asn Ser Ala
            610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
            660                 665                 670

Ser Ser Asn Val Phe Asp Leu Glu Glu Ile Met Arg Glu Phe Asn Ser
            675                 680                 685

Tyr Lys Gln Arg Val Lys Tyr Val Glu Asp Lys Val Val Asp Pro Leu
            690                 695                 700

Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
                725                 730                 735

Ala Ser Val Val Glu Gly Val Ala Thr Phe Leu Lys Asn Pro Phe Gly
            740                 745                 750

Ala Phe Thr Ile Ile Leu Val Ala Ile Ala Val Val Ile Ile Thr Tyr
            755                 760                 765

Leu Ile Tyr Thr Arg Gln Arg Arg Leu Cys Thr Gln Pro Leu Gln Asn
            770                 775                 780

Leu Phe Pro Tyr Leu Val Ser Ala Asp Gly Thr Thr Val Thr Ser Gly
785                 790                 795                 800

Ser Thr Lys Asp Thr Ser Leu Gln Ala Pro Pro Ser Tyr Glu Glu Ser
                805                 810                 815

Val Tyr Asn Ser Gly Arg Lys Gly Pro Gly Pro Pro Ser Ser Asp Ala
            820                 825                 830

Ser Thr Ala Ala Pro Pro Tyr Thr Asn Glu Gln Ala Tyr Gln Met Leu
            835                 840                 845

Leu Ala Leu Ala Arg Leu Asp Ala Glu Gln Arg Ala Gln Gln Asn Gly
            850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                885                 890                 895

Leu Lys Asp Ser Asp Glu Glu Asn Val
            900                 905
```

<210> SEQ ID NO 20
<211> LENGTH: 138
<212> TYPE: PRT
<213> ORGANISM: Human cytomegalovirus

<400> SEQUENCE: 20

Met Glu Trp Asn Thr Leu Val Leu Gly Leu Val Leu Ser Val Val
1               5                   10                  15

Ala Glu Ser Ser Gly Asn Asn Ser Ser Thr Ser Thr Ser Ala Thr Thr
            20                  25                  30

Ser Lys Ser Ser Ala Ser Val Ser Thr Thr Lys Leu Thr Thr Val Ala
        35                  40                  45

Thr Thr Ser Ala Thr Thr Thr Thr Thr Thr Leu Ser Thr Thr Ser
    50                  55                  60

Thr Lys Leu Ser Ser Thr Thr His Asp Pro Asn Val Met Arg Arg His
65                  70                  75                  80

Ala Asn Asp Asp Phe Tyr Lys Ala His Cys Thr Ser His Met Tyr Glu
                85                  90                  95

Leu Ser Leu Ser Ser Phe Ala Ala Trp Trp Thr Met Leu Asn Ala Leu
            100                 105                 110

Ile Leu Met Gly Ala Phe Cys Ile Val Leu Arg His Cys Cys Phe Gln
        115                 120                 125

Asn Phe Thr Ala Thr Thr Thr Lys Gly Tyr
    130                 135

<210> SEQ ID NO 21
<211> LENGTH: 372
<212> TYPE: PRT
<213> ORGANISM: Human cytomegalovirus

<400> SEQUENCE: 21

Met Ala Pro Ser His Val Asp Lys Val Asn Thr Arg Thr Trp Ser Ala
1               5                   10                  15

Ser Ile Val Phe Met Val Leu Thr Phe Val Asn Val Ser Val His Leu
            20                  25                  30

Val Leu Ser Asn Phe Pro His Leu Gly Tyr Pro Cys Val Tyr His
        35                  40                  45

Val Val Asp Phe Glu Arg Leu Asn Met Ser Ala Tyr Asn Val Met His
    50                  55                  60

Leu His Thr Pro Met Leu Phe Leu Asp Ser Val Gln Leu Val Cys Tyr
65                  70                  75                  80

Ala Val Phe Met Gln Leu Val Phe Leu Ala Val Thr Ile Tyr Tyr Leu
                85                  90                  95

Val Cys Trp Ile Lys Ile Ser Met Arg Lys Asp Lys Gly Met Ser Leu
            100                 105                 110

Asn Gln Ser Thr Arg Asp Ile Ser Tyr Met Gly Asp Ser Leu Thr Ala
        115                 120                 125

Phe Leu Phe Ile Leu Ser Met Asp Thr Phe Gln Leu Phe Thr Leu Thr
    130                 135                 140

Met Ser Phe Arg Leu Pro Ser Met Ile Ala Phe Met Ala Ala Val His
145                 150                 155                 160

Phe Phe Cys Leu Thr Ile Phe Asn Val Ser Met Val Thr Gln Tyr Arg
                165                 170                 175

Ser Tyr Lys Arg Ser Leu Phe Phe Ser Arg Leu His Pro Lys Leu
            180                 185                 190

```
Lys Gly Thr Val Gln Phe Arg Thr Leu Ile Val Asn Leu Val Glu Val
        195                 200                 205

Ala Leu Gly Phe Asn Thr Thr Val Val Ala Met Ala Leu Cys Tyr Gly
210                 215                 220

Phe Gly Asn Asn Phe Phe Val Arg Thr Gly His Met Val Leu Ala Val
225                 230                 235                 240

Phe Val Val Tyr Ala Ile Ile Ser Ile Ile Tyr Phe Leu Leu Ile Glu
                245                 250                 255

Ala Val Phe Phe Gln Tyr Val Lys Val Gln Phe Gly Tyr His Leu Gly
            260                 265                 270

Ala Phe Phe Gly Leu Cys Gly Leu Ile Tyr Pro Ile Val Gln Tyr Asp
            275                 280                 285

Thr Phe Leu Ser Asn Glu Tyr Arg Thr Gly Ile Ser Trp Ser Phe Gly
        290                 295                 300

Met Leu Phe Phe Ile Trp Ala Met Phe Thr Thr Cys Arg Ala Val Arg
305                 310                 315                 320

Tyr Phe Arg Gly Arg Gly Ser Gly Ser Val Lys Tyr Gln Ala Leu Ala
                325                 330                 335

Thr Ala Ser Gly Glu Glu Val Ala Val Leu Ser His His Asp Ser Leu
            340                 345                 350

Glu Ser Arg Arg Leu Arg Glu Glu Asp Asp Asp Asp Asp Glu Asp
        355                 360                 365

Phe Glu Asp Ala
        370

<210> SEQ ID NO 22
<211> LENGTH: 466
<212> TYPE: PRT
<213> ORGANISM: Human cytomegalovirus

<400> SEQUENCE: 22

Met Gly Arg Lys Glu Met Met Val Arg Asp Val Pro Lys Met Val Phe
1               5                   10                  15

Leu Ile Ser Ile Ser Phe Leu Leu Val Ser Phe Ile Asn Cys Lys Val
            20                  25                  30

Met Ser Lys Ala Leu Tyr Asn Arg Pro Trp Arg Gly Leu Val Leu Ser
        35                  40                  45

Lys Ile Gly Lys Tyr Lys Leu Asp Gln Leu Lys Leu Glu Ile Leu Arg
    50                  55                  60

Gln Leu Glu Thr Thr Ile Ser Thr Lys Tyr Asn Val Ser Lys Gln Pro
65                  70                  75                  80

Val Lys Asn Leu Thr Met Asn Met Thr Glu Phe Pro Gln Tyr Tyr Ile
                85                  90                  95

Leu Ala Gly Pro Ile Gln Asn Tyr Ser Ile Thr Tyr Leu Trp Phe Asp
            100                 105                 110

Phe Tyr Ser Thr Gln Leu Arg Lys Pro Ala Lys Tyr Val Tyr Ser Gln
        115                 120                 125

Tyr Asn His Thr Ala Lys Thr Ile Thr Phe Arg Pro Pro Cys Gly
    130                 135                 140

Thr Val Pro Ser Met Thr Cys Leu Ser Glu Met Leu Asn Val Ser Lys
145                 150                 155                 160

Arg Asn Asp Thr Gly Glu Gln Gly Cys Gly Asn Phe Thr Thr Phe Asn
                165                 170                 175

Pro Met Phe Phe Asn Val Pro Arg Trp Asn Thr Lys Leu Tyr Val Gly
```

```
            180                 185                 190
Pro Thr Lys Val Asn Val Asp Ser Gln Thr Ile Tyr Phe Leu Gly Leu
        195                 200                 205

Thr Ala Leu Leu Leu Arg Tyr Ala Gln Arg Asn Cys Thr His Ser Phe
        210                 215                 220

Tyr Leu Val Asn Ala Met Ser Arg Asn Leu Phe Arg Val Pro Lys Tyr
225                 230                 235                 240

Ile Asn Gly Thr Lys Leu Lys Asn Thr Met Arg Lys Leu Lys Arg Lys
                245                 250                 255

Gln Ala Pro Val Lys Glu Gln Phe Glu Lys Ala Lys Lys Thr Gln
                260                 265                 270

Ser Thr Thr Thr Pro Tyr Phe Ser Tyr Thr Thr Ser Ala Ala Leu Asn
            275                 280                 285

Val Thr Thr Asn Val Thr Tyr Ser Ile Thr Thr Ala Ala Arg Arg Val
            290                 295                 300

Ser Thr Ser Thr Ile Ala Tyr Arg Pro Asp Ser Ser Phe Met Lys Ser
305                 310                 315                 320

Ile Met Ala Thr Gln Leu Arg Asp Leu Ala Thr Trp Val Tyr Thr Thr
                325                 330                 335

Leu Arg Tyr Arg Gln Asn Pro Phe Cys Glu Pro Ser Arg Asn Arg Thr
                340                 345                 350

Ala Val Ser Glu Phe Met Lys Asn Thr His Val Leu Ile Arg Asn Glu
                355                 360                 365

Thr Pro Tyr Thr Ile Tyr Gly Thr Leu Asp Met Ser Ser Leu Tyr Tyr
            370                 375                 380

Asn Glu Thr Met Phe Val Glu Asn Lys Thr Ala Ser Asp Ser Asn Lys
385                 390                 395                 400

Thr Thr Pro Thr Ser Pro Ser Met Gly Phe Gln Arg Thr Phe Ile Asp
                405                 410                 415

Pro Leu Trp Asp Tyr Leu Asp Ser Leu Leu Phe Leu Asp Glu Ile Arg
                420                 425                 430

Asn Phe Ser Leu Arg Ser Pro Thr Tyr Val Asn Leu Thr Pro Pro Glu
                435                 440                 445

His Arg Arg Ala Val Asn Leu Ser Thr Leu Asn Ser Leu Trp Trp Trp
        450                 455                 460

Leu Gln
465

<210> SEQ ID NO 23
<211> LENGTH: 171
<212> TYPE: PRT
<213> ORGANISM: Human cytomegalovirus

<400> SEQUENCE: 23

Met Ser Pro Lys Asn Leu Thr Pro Phe Leu Thr Ala Leu Trp Leu Leu
1               5                   10                  15

Leu Gly His Ser Arg Val Pro Arg Val Arg Ala Glu Glu Cys Cys Glu
                20                  25                  30

Phe Ile Asn Val Asn His Pro Pro Glu Arg Cys Tyr Asp Phe Lys Met
            35                  40                  45

Cys Asn Arg Phe Thr Val Ala Leu Arg Cys Pro Asp Gly Glu Val Cys
        50                  55                  60

Tyr Ser Pro Glu Lys Thr Ala Glu Ile Arg Gly Ile Val Thr Thr Met
65                  70                  75                  80
```

```
Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170
```

<210> SEQ ID NO 24
<211> LENGTH: 214
<212> TYPE: PRT
<213> ORGANISM: Human cytomegalovirus

<400> SEQUENCE: 24

```
Met Leu Arg Leu Leu Arg His Tyr Phe His Cys Leu Leu Leu Cys
1               5                   10                  15

Ala Val Trp Ala Thr Pro Cys Leu Ala Ser Ser Trp Ser Thr Leu Thr
                20                  25                  30

Ala Asn Gln Asn Pro Ser Pro Pro Trp Ser Lys Leu Thr Tyr Ser Lys
            35                  40                  45

Pro His Asp Ala Ala Thr Phe Tyr Cys Pro Phe Leu Tyr Pro Ser Pro
        50                  55                  60

Pro Arg Ser Pro Ser Gln Phe Ser Gly Phe Gln Arg Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
        115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Val
    210
```

<210> SEQ ID NO 25
<211> LENGTH: 129
<212> TYPE: PRT
<213> ORGANISM: Human cytomegalovirus

<400> SEQUENCE: 25

```
Met Arg Leu Cys Arg Val Trp Leu Ser Val Cys Leu Cys Ala Val Val
1               5                   10                  15
```

```
Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn

<210> SEQ ID NO 26
<211> LENGTH: 694
<212> TYPE: PRT
<213> ORGANISM: Human herpes virus 6a

<400> SEQUENCE: 26

Met Leu Leu Arg Leu Trp Val Phe Val Leu Leu Thr Pro Cys Tyr Gly
1               5                   10                  15

Trp Arg Pro Leu Asn Ile Ser Asn Ser Ser His Cys Arg Asn Gly Asn
            20                  25                  30

Phe Glu Asn Pro Ile Val Arg Pro Gly Phe Ile Thr Phe Asn Phe Tyr
        35                  40                  45

Thr Lys Asn Asp Thr Arg Ile Tyr Gln Val Pro Lys Cys Leu Leu Gly
    50                  55                  60

Ser Asp Ile Thr Tyr His Leu Phe Asp Ala Ile Asn Thr Thr Glu Ser
65                  70                  75                  80

Leu Thr Asn Tyr Glu Lys Arg Val Thr Arg Phe Tyr Glu Pro Pro Met
                85                  90                  95

Asn Asp Ile Leu Arg Leu Ser Pro Val Pro Ser Val Lys Gln Phe Asn
            100                 105                 110

Leu Asp Arg Ser Ile Gln Pro Gln Val Val Tyr Ser Leu Asn Met Tyr
        115                 120                 125

Pro Ser Gln Gly Ile Tyr Tyr Val Arg Val Val Glu Val Arg Gln Met
    130                 135                 140

Gln Tyr Asp Asn Val Ser Cys Lys Leu Pro Asn Ser Leu Lys Glu Leu
145                 150                 155                 160

Ile Phe Pro Val Gln Val Arg Cys Ala Lys Ile Thr Arg Tyr Val Gly
                165                 170                 175

Glu Asp Ile Tyr Thr His Phe Phe Thr Pro Asp Phe Met Ile Leu Tyr
            180                 185                 190

Ile Gln Asn Pro Ala Gly Asp Leu Thr Met Met Tyr Gly Asn Thr Thr
        195                 200                 205

Ser Ile Asn Phe Lys Ala Pro Tyr Lys Lys Ser Ser Phe Ile Phe Lys
    210                 215                 220

Gln Thr Leu Thr Asp Asp Leu Leu Ile Val Glu Lys Asp Val Ile
225                 230                 235                 240

Asp Val Gln Tyr Arg Phe Ile Ser Asp Ala Thr Phe Val Asp Glu Thr
                245                 250                 255
```

```
Leu Asn Asp Val Asp Glu Val Glu Ala Leu Leu Lys Phe Asn Asn
            260                 265                 270

Leu Gly Ile Gln Thr Leu Leu Arg Gly Asp Cys Lys Lys Pro Asn Tyr
        275                 280                 285

Ala Gly Ile Pro Gln Met Met Phe Leu Tyr Gly Ile Val His Phe Ser
        290                 295                 300

Tyr Ser Thr Lys Asn Thr Gly Pro Met Pro Val Leu Arg Val Leu Lys
305                 310                 315                 320

Thr His Glu Asn Leu Leu Ser Ile Asp Ser Phe Val Asn Arg Cys Val
            325                 330                 335

Asn Val Ser Glu Gly Thr Leu Gln Tyr Pro Lys Met Lys Glu Phe Leu
            340                 345                 350

Lys Tyr Glu Pro Ser Asp Tyr Ser Tyr Ile Thr Lys Asn Lys Ser Ile
            355                 360                 365

Ser Val Ser Thr Leu Leu Thr Tyr Leu Ala Thr Ala Tyr Glu Ser Asn
            370                 375                 380

Val Thr Ile Ser Lys Tyr Lys Trp Thr Asp Ile Ala Asn Thr Leu Gln
385                 390                 395                 400

Asn Ile Tyr Glu Lys His Met Phe Phe Thr Asn Leu Thr Phe Ser Asp
            405                 410                 415

Arg Glu Thr Leu Phe Met Leu Ala Glu Ile Ala Asn Ile Ile Pro Thr
            420                 425                 430

Asp Glu Arg Met Gln Arg His Met Gln Leu Leu Ile Gly Asn Leu Cys
            435                 440                 445

Asn Pro Val Glu Ile Val Ser Trp Ala Arg Met Leu Thr Ala Asp Arg
450                 455                 460

Ala Pro Asn Leu Glu Asn Ile Tyr Ser Pro Cys Ala Ser Pro Val Arg
465                 470                 475                 480

Arg Asp Val Thr Asn Ser Phe Leu Lys Thr Val Leu Thr Tyr Ala Ser
                485                 490                 495

Leu Asp Arg Tyr Arg Ser Asp Met Met Glu Met Leu Ser Val Tyr Arg
            500                 505                 510

Pro Pro Asn Met Glu Arg Val Ala Ala Ile Gln Cys Leu Ser Pro Ser
            515                 520                 525

Glu Pro Ala Ala Ser Leu Thr Leu Pro Asn Val Thr Phe Val Ile Ser
530                 535                 540

Pro Ser Tyr Val Ile Lys Gly Val Ser Leu Thr Ile Thr Thr Thr Ile
545                 550                 555                 560

Val Ala Thr Ser Ile Ile Thr Ala Ile Pro Leu Asn Ser Thr Cys
            565                 570                 575

Val Ser Thr Asn Tyr Lys Tyr Ala Gly Gln Asp Leu Leu Val Leu Arg
            580                 585                 590

Asn Ile Ser Ser Gln Thr Cys Glu Phe Cys Gln Ser Val Val Met Glu
            595                 600                 605

Tyr Asp Asp Ile Asp Gly Pro Leu Gln Tyr Ile Tyr Ile Lys Asn Ile
610                 615                 620

Asp Glu Leu Lys Thr Leu Thr Asp Pro Asn Asn Leu Leu Val Pro
625                 630                 635                 640

Asn Thr Arg Thr His Tyr Leu Leu Leu Ala Lys Asn Gly Ser Val Phe
            645                 650                 655

Glu Met Ser Glu Val Gly Ile Asp Ile Asp Gln Val Ser Ile Ile Leu
            660                 665                 670

Val Ile Ile Tyr Ile Leu Ile Ala Ile Ile Ala Leu Phe Gly Leu Tyr
```

```
                675                 680                 685

Arg Leu Ile Arg Leu Cys
    690

<210> SEQ ID NO 27
<211> LENGTH: 694
<212> TYPE: PRT
<213> ORGANISM: Human herpes Virus 6b

<400> SEQUENCE: 27

Met Leu Phe Arg Leu Trp Val Phe Val Leu Thr Pro Cys Tyr Ser
1               5                   10                  15

Trp Arg Pro Trp Thr Ile Ser Asp Glu Ser His Cys Lys Asn Gly Asn
            20                  25                  30

Ser Glu Asn Pro Ile Val Arg Pro Gly Phe Ile Thr Phe Asn Phe Tyr
        35                  40                  45

Thr Lys Asn Asp Thr Arg Ile Tyr Gln Val Pro Lys Cys Leu Leu Gly
    50                  55                  60

Ser Asp Ile Thr Tyr His Leu Phe Asp Ala Ile Asn Thr Thr Glu Ser
65                  70                  75                  80

Leu Thr Asn Tyr Glu Lys Arg Val Thr Arg Phe Tyr Glu Pro Pro Met
                85                  90                  95

Asn Asp Ile Leu Arg Leu Ser Thr Val Pro Ala Val Lys Gln Phe Asn
            100                 105                 110

Leu Asp His Ser Ile Gln Pro Gln Ile Val Tyr Ser Leu Asn Leu Tyr
        115                 120                 125

Pro Ser His Gly Ile Tyr Tyr Ile Arg Val Val Glu Val Arg Gln Met
    130                 135                 140

Gln Tyr Asp Asn Val Ser Cys Lys Leu Pro Asn Ser Leu Asn Glu Leu
145                 150                 155                 160

Ile Phe Pro Val Gln Val Arg Cys Ala Lys Ile Thr Arg Tyr Ala Gly
                165                 170                 175

Glu Asn Ile Tyr Thr His Phe Phe Thr Pro Asp Phe Met Ile Leu Tyr
            180                 185                 190

Ile Gln Asn Pro Ala Gly Asp Leu Thr Met Met Tyr Gly Asn Thr Thr
        195                 200                 205

Asp Ile Asn Phe Lys Ala Pro Tyr Arg Lys Ser Ser Phe Ile Phe Lys
    210                 215                 220

Gln Thr Leu Thr Asp Asp Leu Leu Ile Val Glu Lys Asp Val Val
225                 230                 235                 240

Asp Glu Glu Tyr Arg Phe Ile Ser Asp Ala Thr Phe Val Asp Glu Thr
                245                 250                 255

Leu Asp Asp Val Asp Glu Val Glu Ala Leu Leu Leu Lys Phe Asn Asn
            260                 265                 270

Leu Gly Ile Gln Thr Leu Leu Arg Gly Asp Cys Lys Lys Pro Asp Tyr
        275                 280                 285

Ala Gly Ile Pro Gln Met Met Phe Leu Tyr Gly Ile Val His Phe Ser
    290                 295                 300

Tyr Ser Thr Lys Asn Thr Gly Pro Met Pro Val Leu Arg Val Leu Lys
305                 310                 315                 320

Thr His Glu Asn Leu Leu Ser Ile Asp Ser Phe Val Asn Arg Cys Val
                325                 330                 335

Asn Val Ser Glu Gly Thr Ile Gln Tyr Pro Lys Met Lys Glu Phe Leu
            340                 345                 350
```

```
Lys Tyr Glu Pro Ser Asp Tyr Ser Tyr Ile Thr Lys Asn Lys Ser Ile
            355                 360                 365

Pro Val Ser Thr Leu Leu Thr Tyr Leu Ala Thr Ala Tyr Glu Thr Asn
        370                 375                 380

Val Thr Ile Ser Arg Tyr Lys Trp Ser Asp Ile Ala Asn Thr Leu Gln
385                 390                 395                 400

Lys Ile Tyr Glu Lys His Met Phe Phe Thr Asn Leu Thr Phe Ser Asp
            405                 410                 415

Arg Glu Thr Leu Phe Met Leu Ala Glu Ile Ala Asn Phe Ile Pro Ala
                420                 425                 430

Asp Glu Arg Met Gln Arg His Met Gln Leu Leu Ile Gly Asn Leu Cys
            435                 440                 445

Asn Pro Val Glu Ile Val Ser Trp Ala His Met Leu Thr Ala Asp Lys
        450                 455                 460

Ala Pro Asn Leu Glu Asn Ile Tyr Ser Pro Cys Ala Ser Pro Val Arg
465                 470                 475                 480

Arg Asp Val Thr Asn Ser Phe Val Lys Thr Val Leu Thr Tyr Ala Ser
            485                 490                 495

Leu Asp Arg Tyr Arg Ser Asp Met Met Glu Met Leu Ser Val Tyr Arg
                500                 505                 510

Pro Pro Asp Met Ala Arg Val Ala Ala Ile Gln Cys Leu Ser Pro Ser
            515                 520                 525

Glu Pro Ala Ala Ser Leu Pro Leu Pro Asn Val Thr Phe Val Ile Ser
        530                 535                 540

Pro Ser Tyr Val Ile Lys Gly Val Ser Leu Thr Ile Thr Thr Thr Ile
545                 550                 555                 560

Val Ala Thr Ser Ile Ile Ile Thr Ala Ile Pro Leu Asn Ser Thr Cys
            565                 570                 575

Val Ser Thr Asn Tyr Lys Tyr Ala Gly Gln Asp Leu Leu Val Leu Arg
                580                 585                 590

Asn Ile Ser Ser Gln Thr Cys Glu Phe Cys Gln Ser Val Val Met Glu
            595                 600                 605

Tyr Asp Asp Ile Asp Gly Pro Leu Gln Tyr Ile Tyr Ile Lys Asn Ile
        610                 615                 620

Asp Glu Leu Lys Thr Leu Thr Asp Pro Asn Asn Asn Leu Leu Val Pro
625                 630                 635                 640

Asn Thr Arg Thr His Tyr Leu Leu Leu Ala Lys Asn Gly Ser Val Phe
            645                 650                 655

Glu Met Ser Glu Val Gly Ile Asp Ile Asp Gln Val Ser Ile Ile Leu
                660                 665                 670

Val Ile Ile Tyr Val Leu Ile Ala Ile Ala Leu Phe Gly Leu Tyr
            675                 680                 685

Arg Leu Ile Arg Leu Cys
690

<210> SEQ ID NO 28
<211> LENGTH: 250
<212> TYPE: PRT
<213> ORGANISM: Human herpes virus 6a

<400> SEQUENCE: 28

Met Glu Leu Leu Leu Phe Val Met Ser Leu Ile Leu Leu Thr Phe Ser
1               5                   10                  15

Lys Ala Ile Pro Leu Phe Asn His Asn Ser Phe Tyr Phe Glu Lys Leu
            20                  25                  30
```

```
Asp Asp Cys Ile Ala Ala Val Ile Asn Cys Thr Lys Ser Glu Val Pro
        35                  40                  45

Leu Leu Leu Glu Pro Ile Tyr Gln Pro Pro Ala Tyr Asn Glu Asp Val
 50                  55                  60

Met Ser Ile Leu Leu Gln Pro Pro Thr Lys Lys Lys Pro Phe Ser Arg
 65                  70                  75                  80

Ile Met Val Thr Asp Glu Phe Leu Ser Asp Phe Leu Leu Gln Asp
                 85                  90                  95

Asn Pro Glu Gln Leu Arg Thr Leu Phe Ala Leu Ile Arg Asp Pro Glu
                100                 105                 110

Ser Arg Asp Asn Trp Leu Asn Phe Phe Asn Gly Phe Gln Thr Cys Ser
                115                 120                 125

Pro Ser Val Gly Ile Thr Thr Cys Ile Arg Asp Asn Cys Arg Lys Tyr
            130                 135                 140

Ser Pro Glu Lys Ile Thr Tyr Val Asn Asn Phe Phe Val Asp Asn Ile
145                 150                 155                 160

Ala Gly Leu Glu Phe Asn Ile Ser Glu Asn Thr Asp Ser Phe Tyr Ser
                    165                 170                 175

Asn Ile Gly Phe Leu Leu Tyr Leu Glu Asn Pro Ala Lys Gly Val Thr
                180                 185                 190

Lys Ile Ile Arg Phe Pro Phe Asn Ser Leu Thr Leu Phe Asp Thr Ile
                195                 200                 205

Leu Asn Cys Leu Lys Tyr Phe His Leu Lys Thr Gly Val Glu Leu Asp
            210                 215                 220

Leu Leu Lys His Met Glu Thr Tyr Asn Ser Lys Leu Pro Phe Arg Ser
225                 230                 235                 240

Ser Arg Pro Thr Ile Leu Ile Arg Asn Thr
                245                 250

<210> SEQ ID NO 29
<211> LENGTH: 250
<212> TYPE: PRT
<213> ORGANISM: Human herpes Virus 6b

<400> SEQUENCE: 29

Met Glu Leu Leu Leu Phe Val Met Ser Leu Ile Leu Leu Thr Phe Ser
 1               5                  10                  15

Lys Ala Met Pro Leu Phe Asp His Asn Ser Phe Tyr Phe Glu Lys Leu
                20                  25                  30

Asp Asp Cys Ile Ala Ala Val Ile Asn Cys Thr Arg Ser Glu Val Pro
        35                  40                  45

Leu Leu Leu Glu Pro Ile Tyr Gln Pro Pro Val Tyr Asn Glu Asp Val
 50                  55                  60

Met Ser Ile Leu Leu Lys Pro Pro Thr Lys Lys Lys Pro Phe Ser Arg
 65                  70                  75                  80

Ile Met Val Thr Asn Glu Phe Leu Ser Asp Phe Leu Leu Leu Gln Asp
                 85                  90                  95

Asn Pro Glu Gln Leu Arg Thr Leu Phe Ala Leu Ile Gly Asp Pro Glu
                100                 105                 110

Ser Arg Asp Asn Trp Leu Asn Phe Phe Asn Gly Phe Gln Thr Cys Ser
                115                 120                 125

Pro Ser Val Gly Ile Thr Thr Cys Ile Ser Asp Asn Cys Arg Lys Tyr
            130                 135                 140

Leu Pro Glu Arg Ile Thr Tyr Val Asn Asn Phe Phe Val Asp Asn Ile
```

```
 145                 150                 155                 160
Ala Gly Leu Glu Phe Asn Ile Ser Glu Asn Thr Asp Ser Phe Tyr Ser
                165                 170                 175

Asn Ile Gly Phe Leu Leu Tyr Leu Glu Asn Pro Ala Thr Gly Ile Thr
                180                 185                 190

Lys Ile Ile Arg Phe Pro Phe Asn Ser Leu Thr Leu Phe Asp Thr Ile
                195                 200                 205

Leu Asn Cys Leu Lys Tyr Phe His Leu Lys Thr Gly Val Glu Phe Asp
            210                 215                 220

Leu Leu Lys Gln Met Glu Ala Tyr Asn Ser Lys Leu Pro Phe Arg Ser
225                 230                 235                 240

Ser Arg Pro Thr Ile Leu Ile Arg Asn Thr
                245                 250

<210> SEQ ID NO 30
<211> LENGTH: 830
<212> TYPE: PRT
<213> ORGANISM: Human herpes virus 6a

<400> SEQUENCE: 30

Met Ser Lys Met Ala Val Leu Phe Leu Ala Val Phe Leu Met Asn Ser
1               5                   10                  15

Val Leu Met Ile Tyr Cys Asp Pro Asp His Tyr Ile Arg Ala Gly Tyr
            20                  25                  30

Asn His Lys Tyr Pro Phe Arg Ile Cys Ser Ile Ala Lys Gly Thr Asp
            35                  40                  45

Leu Met Arg Phe Asp Arg Asp Ile Ser Cys Ser Pro Tyr Lys Ser Asn
    50                  55                  60

Ala Lys Met Ser Glu Gly Phe Phe Ile Ile Tyr Lys Thr Asn Ile Glu
65                  70                  75                  80

Thr Tyr Thr Phe Pro Val Arg Thr Tyr Lys Lys Glu Leu Thr Phe Gln
                85                  90                  95

Ser Ser Tyr Arg Asp Val Gly Val Val Tyr Phe Leu Asp Arg Thr Val
                100                 105                 110

Met Gly Leu Ala Met Pro Val Tyr Glu Ala Asn Leu Val Asn Ser His
            115                 120                 125

Ala Gln Cys Tyr Ser Ala Val Ala Met Lys Arg Pro Asp Gly Thr Val
    130                 135                 140

Phe Ser Ala Phe His Glu Asp Asn Lys Asn Asn Thr Leu Asn Leu
145                 150                 155                 160

Phe Pro Leu Asn Phe Lys Ser Ile Thr Asn Lys Arg Phe Ile Thr Thr
                165                 170                 175

Lys Glu Pro Tyr Phe Ala Arg Gly Pro Leu Trp Leu Tyr Ser Thr Ser
                180                 185                 190

Thr Ser Leu Asn Cys Ile Val Thr Glu Ala Thr Ala Lys Ala Lys Tyr
            195                 200                 205

Pro Phe Ser Tyr Phe Ala Leu Thr Thr Gly Glu Ile Val Glu Gly Ser
    210                 215                 220

Pro Phe Phe Asn Gly Ser Asn Gly Lys His Phe Ala Glu Pro Leu Glu
225                 230                 235                 240

Lys Leu Thr Ile Leu Glu Asn Tyr Thr Met Ile Glu Asp Leu Met Asn
                245                 250                 255

Gly Met Asn Gly Ala Thr Thr Leu Val Arg Lys Ile Ala Phe Leu Glu
            260                 265                 270
```

```
Lys Ala Asp Thr Leu Phe Ser Trp Glu Ile Lys Glu Asn Glu Ser
            275                 280                 285

Val Cys Met Leu Lys His Trp Thr Thr Val Thr His Gly Leu Arg Ala
290                 295                 300

Glu Thr Asn Glu Thr Tyr His Phe Ile Ser Lys Glu Leu Thr Ala Ala
305                 310                 315                 320

Phe Val Ala Pro Lys Glu Ser Leu Asn Leu Thr Asp Pro Lys Gln Thr
                325                 330                 335

Cys Ile Lys Asn Glu Phe Glu Lys Ile Asn Glu Val Tyr Met Ser
            340                 345                 350

Asp Tyr Asn Asp Thr Tyr Ser Met Asn Gly Ser Tyr Gln Ile Phe Lys
            355                 360                 365

Thr Thr Gly Asp Leu Ile Leu Ile Trp Gln Pro Leu Val Gln Lys Ser
            370                 375                 380

Leu Met Phe Leu Glu Gln Gly Ser Glu Lys Ile Arg Arg Arg Arg Asp
385                 390                 395                 400

Val Gly Asp Val Lys Ser Arg His Asp Ile Leu Tyr Val Gln Leu Gln
                405                 410                 415

Tyr Leu Tyr Asp Thr Leu Lys Asp Tyr Ile Asn Asp Ala Leu Gly Asn
            420                 425                 430

Leu Ala Glu Ser Trp Cys Leu Asp Gln Lys Arg Thr Ile Thr Met Leu
435                 440                 445

His Glu Leu Ser Lys Ile Ser Pro Ser Ser Ile Val Ser Glu Val Tyr
            450                 455                 460

Gly Arg Pro Ile Ser Ala Gln Leu His Gly Asp Val Leu Ala Ile Ser
465                 470                 475                 480

Lys Cys Ile Glu Val Asn Gln Ser Ser Val Gln Leu His Lys Ser Met
                485                 490                 495

Arg Val Val Asp Ala Lys Gly Val Arg Ser Glu Thr Met Cys Tyr Asn
            500                 505                 510

Arg Pro Leu Val Thr Phe Ser Phe Val Asn Ser Thr Pro Glu Val Val
            515                 520                 525

Pro Gly Gln Leu Gly Leu Asp Asn Glu Ile Leu Leu Gly Asp His Arg
530                 535                 540

Thr Glu Glu Cys Glu Ile Pro Ser Thr Lys Ile Phe Leu Ser Gly Asn
545                 550                 555                 560

His Ala His Val Tyr Thr Asp Tyr Thr His Thr Asn Ser Thr Pro Ile
                565                 570                 575

Glu Asp Ile Glu Val Leu Asp Ala Phe Ile Arg Leu Lys Ile Asp Pro
            580                 585                 590

Leu Glu Asn Ala Asp Phe Lys Val Leu Asp Leu Tyr Ser Pro Asp Glu
            595                 600                 605

Leu Ser Arg Ala Asn Val Phe Asp Leu Glu Asn Ile Leu Arg Glu Tyr
610                 615                 620

Asn Ser Tyr Lys Ser Ala Leu Tyr Thr Ile Glu Ala Lys Ile Ala Thr
625                 630                 635                 640

Asn Thr Pro Ser Tyr Val Asn Gly Ile Asn Ser Phe Leu Gln Gly Leu
                645                 650                 655

Gly Ala Ile Gly Thr Gly Leu Gly Ser Val Ile Ser Val Thr Ala Gly
            660                 665                 670

Ala Leu Gly Asp Ile Val Gly Val Ser Phe Leu Lys Asn Pro
            675                 680                 685

Phe Gly Gly Gly Leu Met Leu Ile Leu Ala Ile Val Val Val Val Ile
```

```
                690             695             700
Ile Ile Val Val Phe Val Arg Gln Arg His Val Leu Ser Lys Pro Ile
705             710             715             720

Asp Met Met Phe Pro Tyr Ala Thr Asn Pro Val Thr Thr Val Ser Ser
                725             730             735

Val Thr Gly Thr Thr Val Val Lys Thr Pro Ser Val Lys Asp Val Asp
            740             745             750

Gly Gly Thr Ser Val Ala Val Ser Glu Lys Glu Gly Met Ala Asp
            755             760             765

Val Ser Gly Gln Val Ser Asp Asp Glu Tyr Ser Gln Glu Asp Ala Leu
            770             775             780

Lys Met Leu Lys Ala Ile Lys Ser Leu Asp Glu Ser Tyr Arg Arg Lys
785             790             795             800

Pro Ser Ser Ser Glu Ser His Ala Ser Lys Pro Ser Leu Ile Asp Arg
            805             810             815

Ile Arg Tyr Arg Gly Tyr Lys Ser Val Asn Val Glu Glu Ala
            820             825             830

<210> SEQ ID NO 31
<211> LENGTH: 830
<212> TYPE: PRT
<213> ORGANISM: Human herpes Virus 7

<400> SEQUENCE: 31

Met Ser Lys Met Arg Val Leu Phe Leu Ala Val Phe Leu Met Asn Ser
1               5               10              15

Val Leu Met Ile Tyr Cys Asp Ser Asp Asp Tyr Ile Arg Ala Gly Tyr
                20              25              30

Asn His Lys Tyr Pro Phe Arg Ile Cys Ser Ile Ala Lys Gly Thr Asp
            35              40              45

Leu Met Arg Phe Asp Arg Asp Ile Ser Cys Ser Pro Tyr Lys Ser Asn
50              55              60

Ala Lys Met Ser Glu Gly Phe Phe Ile Ile Tyr Lys Thr Asn Ile Glu
65              70              75              80

Thr Tyr Thr Phe Pro Val Arg Thr Tyr Lys Asn Glu Leu Thr Phe Pro
                85              90              95

Thr Ser Tyr Arg Asp Val Gly Val Val Tyr Phe Leu Asp Arg Thr Val
            100             105             110

Met Gly Leu Ala Met Pro Val Tyr Glu Ala Asn Leu Val Asn Ser Arg
            115             120             125

Ala Gln Cys Tyr Ser Ala Val Ala Ile Lys Arg Pro Asp Gly Thr Val
130             135             140

Phe Ser Ala Tyr His Glu Asp Asn Lys Asn Glu Thr Leu Glu Leu
145             150             155             160

Phe Pro Leu Asn Phe Lys Ser Val Thr Asn Lys Arg Phe Ile Thr Thr
                165             170             175

Lys Glu Pro Tyr Phe Ala Arg Gly Pro Leu Trp Leu Tyr Ser Thr Ser
            180             185             190

Thr Ser Leu Asn Cys Ile Val Thr Glu Ala Thr Ala Lys Ala Lys Tyr
            195             200             205

Pro Phe Ser Tyr Phe Ala Leu Thr Thr Gly Glu Ile Val Glu Gly Ser
210             215             220

Pro Phe Phe Asp Gly Ser Asn Gly Lys His Phe Ala Glu Pro Leu Glu
225             230             235             240
```

```
Lys Leu Thr Ile Leu Glu Asn Tyr Thr Met Ile Glu Asp Leu Met Asn
            245                 250                 255

Gly Met Asn Gly Ala Thr Thr Leu Val Arg Lys Ile Ala Phe Leu Glu
        260                 265                 270

Lys Gly Asp Thr Leu Phe Ser Trp Glu Ile Lys Glu Glu Asn Glu Ser
    275                 280                 285

Val Cys Met Leu Lys His Trp Thr Thr Val Thr His Gly Leu Arg Ala
290                 295                 300

Glu Thr Asp Glu Thr Tyr His Phe Ile Ser Lys Glu Leu Thr Ala Ala
305                 310                 315                 320

Phe Val Ala Ser Lys Glu Ser Leu Asn Leu Thr Asp Pro Lys Gln Thr
                325                 330                 335

Cys Ile Lys Asn Glu Phe Glu Lys Ile Ile Thr Asp Val Tyr Met Ser
            340                 345                 350

Asp Tyr Asn Asp Ala Tyr Ser Met Asn Gly Ser Tyr Gln Ile Phe Lys
        355                 360                 365

Thr Thr Gly Asp Leu Ile Leu Ile Trp Gln Pro Leu Val Gln Lys Ser
    370                 375                 380

Leu Met Val Leu Glu Gln Gly Ser Val Asn Leu Arg Arg Arg Arg Asp
385                 390                 395                 400

Leu Val Asp Val Lys Ser Arg His Asp Ile Leu Tyr Val Gln Leu Gln
                405                 410                 415

Tyr Leu Tyr Asp Thr Leu Lys Asp Tyr Ile Asn Asp Ala Leu Gly Asn
            420                 425                 430

Leu Ala Glu Ser Trp Cys Leu Asp Gln Lys Arg Thr Ile Thr Met Leu
        435                 440                 445

His Glu Leu Ser Lys Ile Ser Pro Ser Ser Ile Val Ser Glu Val Tyr
    450                 455                 460

Gly Arg Pro Ile Ser Ala Gln Leu His Gly Asp Val Leu Ala Ile Ser
465                 470                 475                 480

Lys Cys Ile Glu Val Asn Gln Ser Ser Val Gln Leu Tyr Lys Ser Met
                485                 490                 495

Arg Val Val Asp Ala Lys Gly Val Arg Ser Glu Thr Met Cys Tyr Asn
            500                 505                 510

Arg Pro Leu Val Thr Phe Ser Phe Val Asn Ser Thr Pro Glu Val Val
        515                 520                 525

Leu Gly Gln Leu Gly Leu Asp Asn Glu Ile Leu Leu Gly Asp His Arg
    530                 535                 540

Thr Glu Glu Cys Glu Ile Pro Ser Thr Lys Ile Phe Leu Ser Gly Asn
545                 550                 555                 560

His Ala His Val Tyr Thr Asp Tyr Thr His Thr Asn Ser Thr Pro Ile
                565                 570                 575

Glu Asp Ile Glu Val Leu Asp Ala Phe Ile Arg Leu Lys Ile Asp Pro
            580                 585                 590

Leu Glu Asn Ala Asp Phe Lys Leu Leu Asp Leu Tyr Ser Pro Asp Glu
        595                 600                 605

Leu Ser Arg Ala Asn Val Phe Asp Leu Glu Asn Ile Leu Arg Glu Tyr
    610                 615                 620

Asn Ser Tyr Lys Ser Ala Leu Tyr Thr Ile Glu Ala Lys Ile Ala Thr
625                 630                 635                 640

Asn Thr Pro Ser Tyr Val Asn Gly Ile Asn Ser Phe Leu Gln Gly Leu
                645                 650                 655

Gly Ala Ile Gly Thr Gly Leu Gly Ser Val Ile Ser Val Thr Ala Gly
```

```
                660             665             670
Ala Leu Gly Asp Ile Val Gly Val Val Ser Phe Leu Lys Asn Pro
            675             680             685

Phe Gly Gly Gly Leu Met Leu Ile Leu Ala Ile Val Val Val Ile
            690             695             700

Ile Ile Val Val Phe Val Arg Gln Lys His Val Leu Ser Lys Pro Ile
705             710             715             720

Asp Met Met Phe Pro Tyr Ala Thr Asn Pro Val Thr Thr Val Ser Ser
            725             730             735

Val Thr Gly Thr Thr Val Val Lys Thr Pro Ser Val Lys Asp Ala Asp
            740             745             750

Gly Gly Thr Ser Val Ala Val Ser Glu Lys Glu Gly Met Ala Asp
            755             760             765

Val Ser Gly Gln Ile Ser Gly Asp Glu Tyr Ser Gln Glu Asp Ala Leu
            770             775             780

Lys Met Leu Lys Ala Ile Lys Ser Leu Asp Glu Ser Tyr Arg Arg Lys
785             790             795             800

Pro Ser Ser Ser Glu Ser His Ala Ser Lys Pro Ser Leu Ile Asp Arg
            805             810             815

Ile Arg Tyr Arg Gly Tyr Lys Ser Val Asn Val Glu Glu Ala
            820             825             830

<210> SEQ ID NO 32
<211> LENGTH: 690
<212> TYPE: PRT
<213> ORGANISM: Human herpes Virus 7

<400> SEQUENCE: 32

Met Tyr Phe Tyr Ile Asn Ser Leu Leu Leu Ile Val Ser Ile Asn Gly
1               5               10              15

Trp Lys His Trp Asn Ile Leu Asn Ser Ser Ile Cys Val Asn Glu Lys
            20              25              30

Thr Asn Gln Thr Ile Ile Gln Pro Gly Leu Ile Thr Phe Asn Phe His
            35              40              45

Asp Tyr Asn Glu Thr Arg Val Tyr Gln Ile Pro Lys Cys Leu Phe Gly
50              55              60

Tyr Thr Phe Val Ser Asn Leu Phe Asp Ser Val Asn Phe Asp Glu Ser
65              70              75              80

Phe Asp Gln Tyr Lys His Arg Ile Thr Arg Phe Phe Asn Pro Ser Thr
            85              90              95

Glu Lys Ala Val Lys Ile Tyr Ala Gln Lys Phe Gln Thr Asn Ile Lys
            100             105             110

Pro Val Ser His Thr Lys Thr Ile Thr Val Ser Phe Leu Pro Leu Phe
            115             120             125

Tyr Glu Lys Asp Val Tyr Phe Ala Asn Val Ser Glu Ile Arg Lys Leu
            130             135             140

Tyr Tyr Asn Gln Tyr Ile Cys Thr Leu Ser Asn Gly Leu Thr Asp Tyr
145             150             155             160

Leu Phe Pro Ile Thr Glu Arg Cys Val Met Arg His Tyr Asn Tyr Leu
            165             170             175

Asn Thr Val Phe Met Leu Ala Leu Thr Pro Ser Phe Ile Ile Ser
            180             185             190

Val Glu Thr Gly Met Asp Asp Val Val Phe Ile Phe Gly Asn Val Ser
            195             200             205
```

-continued

```
Arg Ile Phe Phe Lys Ala Pro Phe Arg Lys Ser Ser Phe Ile Tyr Arg
210                 215                 220

Gln Thr Val Ser Asp Asp Leu Leu Ile Thr Lys Lys Thr Thr Ile
225                 230                 235                 240

Glu Arg Phe Tyr Pro Phe Leu Lys Ile Asp Phe Leu Asp Asp Ile Trp
                245                 250                 255

Lys Gln Asn Tyr Asp Ile Ser Phe Leu Ile Ala Lys Phe Asn Lys Leu
            260                 265                 270

Ala Thr Val Tyr Ile Met Glu Gly Phe Cys Gly Lys Pro Val Asn Lys
        275                 280                 285

Asp Thr Phe His Leu Met Phe Leu Phe Gly Leu Thr His Phe Leu Tyr
290                 295                 300

Ser Thr Arg Gly Asp Gly Leu Leu Pro Leu Leu Glu Ile Leu Asn Thr
305                 310                 315                 320

His Gln Ser Ile Ile Thr Met Gly Arg Phe Leu Glu Lys Cys Phe Lys
                325                 330                 335

Met Thr Lys Ser His Leu Leu Tyr Pro Glu Met Glu Lys Leu Gln Asn
            340                 345                 350

Phe Gln Leu Val Asp Tyr Ser Tyr Ile Thr Ser Asp Leu Thr Ile Pro
        355                 360                 365

Ile Ser Ala Lys Leu Ala Phe Leu Ser Leu Ala Asp Gly Arg Ile Val
370                 375                 380

Thr Val Pro Gln Asn Lys Trp Lys Glu Ile Glu Asn Asn Ile Glu Thr
385                 390                 395                 400

Leu Tyr Glu Lys His Lys Leu Phe Thr Asn Leu Thr Gln Pro Glu Arg
                405                 410                 415

Ala Asn Leu Phe Leu Leu Ser Glu Ile Gly Asn Ser Leu Val Phe Gln
            420                 425                 430

Glu Lys Ile Lys Arg Lys Ile His Val Leu Leu Ala Ser Leu Cys Asn
        435                 440                 445

Pro Leu Glu Met Tyr Phe Trp Thr His Met Leu Asp Asn Val Met Asp
450                 455                 460

Ile Glu Thr Met Phe Ser Pro Cys Ala Thr Ala Thr Arg Lys Asp Leu
465                 470                 475                 480

Thr Gln Arg Val Val Asn Asn Ile Leu Ser Tyr Lys Asn Leu Asp Ala
                485                 490                 495

Tyr Thr Asn Lys Val Met Asn Thr Leu Ser Val Tyr Arg Lys Lys Arg
            500                 505                 510

Leu Asp Met Phe Lys Ser Ile Ser Cys Val Ser Asn Glu Gln Ala Ala
        515                 520                 525

Phe Leu Thr Leu Pro Asn Ile Thr Tyr Thr Ile Ser Ser Lys Tyr Ile
530                 535                 540

Leu Ala Gly Thr Ser Phe Ser Val Thr Ser Val Ile Ser Thr Thr
545                 550                 555                 560

Ile Ile Ile Thr Val Val Pro Leu Asn Ser Thr Cys Thr Pro Thr Asn
                565                 570                 575

Tyr Lys Tyr Ser Val Lys Asn Ile Lys Pro Ile Tyr Asn Ile Ser Ser
            580                 585                 590

His Asp Cys Val Phe Cys Glu Ser Leu Val Val Glu Tyr Asp Asp Ile
        595                 600                 605

Asp Gly Ile Ile Gln Phe Val Tyr Ile Met Asp Asp Lys Gln Leu Leu
610                 615                 620

Lys Leu Ile Asp Pro Asp Thr Asn Phe Ile Asp Val Asn Pro Arg Thr
```

```
                625                 630                 635                 640
His Tyr Leu Leu Phe Leu Arg Asn Gly Ser Val Phe Glu Ile Thr Ala
                        645                 650                 655

Leu Asp Leu Lys Ser Ser Gln Val Ser Ile Met Leu Val Leu Leu Tyr
                660                 665                 670

Leu Ile Ile Ile Ile Val Leu Phe Gly Ile Tyr His Val Phe Arg
                675                 680                 685

Leu Phe
    690

<210> SEQ ID NO 33
<211> LENGTH: 246
<212> TYPE: PRT
<213> ORGANISM: Human herpes Virus 7

<400> SEQUENCE: 33

Met Lys Thr Asn Ile Phe Phe Ile Phe Leu Ile Ser Ile Leu Asn Gln
1               5                   10                  15

Ile Tyr Ala Leu Phe Asn Asn Ser Tyr Tyr Ser Asn Leu Glu Gln Glu
            20                  25                  30

Cys Ile Lys Asn Ile Leu Asn Cys Thr Gln Ser Lys Thr Leu Ser Leu
        35                  40                  45

Leu Glu Pro Ile Asp Gln Ala Pro Ile Pro Lys Ser Asp Ile Ile Ser
    50                  55                  60

Arg Leu Leu Tyr His Thr Pro Tyr Ile Ser Arg Arg Asp Gln Val Leu
65                  70                  75                  80

Ile Asp Glu Asp Phe Leu Glu Thr Phe Tyr Leu Leu Tyr Asn Asn Pro
                85                  90                  95

Asn Gln Leu His Thr Leu Leu Ser Leu Ile Lys Asp Ser Glu Ser Gly
            100                 105                 110

His Asn Trp Leu Gly Phe Leu Asn Asn Phe Glu Arg Cys Leu Ser Asp
        115                 120                 125

Asn Thr Leu Leu Thr Cys Arg Asp Asn Val Cys Lys Ser Tyr Ser Tyr
    130                 135                 140

Glu Lys Leu Lys Phe Thr Gly Asn Ile Phe Val Glu Asn Ile Ile Gly
145                 150                 155                 160

Phe Glu Phe Asn Ile Pro Ser Asn Met Ile Asn Phe Asn Met Ser Ile
                165                 170                 175

Leu Ile Tyr Leu Glu Asn Glu Glu Thr Arg Thr Gln Arg Ile Val Arg
            180                 185                 190

Ile Asp His His Gly Ile Asn Val Phe Asp Ala Leu Leu Asn Cys Leu
        195                 200                 205

Arg Tyr Phe Ser Arg Tyr Tyr Asn Phe Ser Phe Pro Leu Ile Gln Glu
    210                 215                 220

Met Glu Lys Tyr Asn Glu Val Leu Pro Phe Arg Ser Glu Phe Ser Asn
225                 230                 235                 240

Leu Leu Ile Arg Thr Tyr
                245

<210> SEQ ID NO 34
<211> LENGTH: 822
<212> TYPE: PRT
<213> ORGANISM: Human herpes Virus 7

<400> SEQUENCE: 34

Met Lys Ile Leu Phe Leu Ser Val Phe Ile Thr Phe Ser Leu Gln Leu
```

-continued

```
1               5                   10                  15
Ser Leu Gln Thr Glu Ala Asp Phe Val Met Thr Gly His Asn Gln His
                20                  25                  30
Leu Pro Phe Arg Ile Cys Ser Ile Ala Thr Gly Thr Asp Leu Val Arg
                35                  40                  45
Phe Asp Arg Glu Val Ser Cys Ala Ser Tyr Gly Ser Asn Ile Lys Thr
 50                  55                  60
Thr Glu Gly Ile Leu Ile Ile Tyr Lys Thr Lys Ile Glu Ala His Thr
 65                  70                  75                  80
Phe Ser Val Arg Thr Phe Lys Lys Glu Leu Thr Phe Gln Thr Thr Tyr
                85                  90                  95
Arg Asp Val Gly Thr Val Tyr Phe Leu Asp Arg Thr Val Thr Thr Leu
                100                 105                 110
Pro Met Pro Ile Glu Glu Val His Met Val Asn Thr Glu Ala Arg Cys
                115                 120                 125
Leu Ser Ser Ile Ser Val Lys Arg Ser Glu Glu Glu Tyr Val Ala
                130                 135                 140
Tyr His Lys Asp Glu Tyr Val Asn Lys Thr Leu Asp Leu Ile Pro Leu
145                 150                 155                 160
Asn Phe Lys Ser Asp Thr Val Arg Arg Tyr Ile Thr Thr Lys Glu Pro
                165                 170                 175
Phe Leu Arg Asn Gly Pro Leu Trp Phe Tyr Ser Thr Ser Thr Ser Ile
                180                 185                 190
Asn Cys Ile Val Thr Asp Cys Ile Ala Lys Thr Lys Tyr Pro Phe Asp
                195                 200                 205
Phe Phe Ala Leu Ser Thr Gly Glu Thr Val Glu Gly Ser Pro Phe Tyr
 210                 215                 220
Asn Gly Ile Asn Ser Lys Thr Phe Asn Glu Pro Thr Glu Lys Ile Leu
225                 230                 235                 240
Phe Arg Asn Asn Tyr Thr Met Leu Lys Thr Phe Asp Asp Gly Ser Lys
                245                 250                 255
Gly Asn Phe Val Thr Leu Thr Lys Met Ala Phe Leu Glu Lys Gly Asn
                260                 265                 270
Thr Ile Phe Ser Trp Glu Val Gln Asn Glu Glu Ser Ser Ile Cys Leu
                275                 280                 285
Leu Lys His Trp Met Thr Ile Pro His Ala Leu Arg Ala Glu Asn Ala
                290                 295                 300
Asn Ser Phe His Phe Ile Ala Gln Glu Leu Thr Ala Ser Phe Val Thr
305                 310                 315                 320
Gly Lys Ser Asn Tyr Thr Leu Ser Asp Ser Lys Tyr Asn Cys Ile Asn
                325                 330                 335
Ser Asn Tyr Thr Ser Ile Leu Asp Glu Ile Tyr Gln Thr Gln Tyr Asn
                340                 345                 350
Asn Ser His Asp Lys Asn Gly Ser Tyr Glu Ile Phe Lys Thr Glu Gly
                355                 360                 365
Asp Leu Ile Leu Ile Trp Gln Pro Leu Ile Gln Arg Lys Leu Thr Val
                370                 375                 380
Leu Glu Asn Phe Ser Asn Ala Ser Arg Lys Arg Arg Lys Arg Glu Leu
385                 390                 395                 400
Glu Thr Asn Lys Asp Ile Val Tyr Val Gln Leu Gln Tyr Leu Tyr Asp
                405                 410                 415
Thr Leu Lys Asp Tyr Ile Asn Thr Ala Leu Gly Lys Leu Ala Glu Ala
                420                 425                 430
```

Trp Cys Leu Asn Gln Lys Arg Thr Ile Thr Val Leu His Glu Leu Ser
            435                 440                 445

Lys Ile Ser Pro Ser Gly Ile Ile Ser Ala Val Tyr Gly Lys Pro Met
    450                 455                 460

Ser Ala Lys Leu Ile Gly Asp Val Leu Ala Val Ser Lys Cys Ile Glu
465                 470                 475                 480

Val Asn Gln Thr Ser Val Gln Leu His Lys Ser Met Arg Leu Thr Lys
                485                 490                 495

Asp Ser Ser Tyr Asp Ala Leu Arg Cys Tyr Ser Arg Pro Leu Leu Thr
            500                 505                 510

Tyr Ser Phe Ala Asn Ser Ser Lys Glu Thr Tyr Leu Gly Gln Leu Gly
        515                 520                 525

Leu Asp Asn Glu Ile Leu Leu Gly Asn His Arg Thr Glu Glu Cys Glu
    530                 535                 540

Gln Ser Asn Thr Lys Ile Phe Leu Ser Gly Lys Phe Ala His Ile Phe
545                 550                 555                 560

Lys Asp Tyr Thr Tyr Val Asn Ser Ser Leu Ile Thr Glu Ile Glu Ala
                565                 570                 575

Leu Asp Ala Phe Val Asp Leu Asn Ile Asp Pro Leu Glu Asn Ala Asp
            580                 585                 590

Phe Thr Leu Leu Glu Leu Tyr Thr Lys Asp Glu Leu Ser Lys Ala Asn
        595                 600                 605

Val Phe Asp Leu Glu Thr Ile Leu Arg Glu Tyr Asn Ser Tyr Lys Ser
    610                 615                 620

Ala Leu His His Ile Glu Thr Lys Ile Ala Thr Val Thr Pro Thr Tyr
625                 630                 635                 640

Ile Gly Gly Ile Asp Thr Phe Phe Lys Gly Leu Gly Ala Leu Gly Leu
                645                 650                 655

Gly Leu Gly Ala Val Leu Gly Val Thr Ala Gly Ala Leu Gly Asp Val
            660                 665                 670

Val Asn Gly Val Phe Ser Phe Leu Lys Asn Pro Phe Gly Gly Ala Leu
        675                 680                 685

Thr Ile Leu Leu Thr Leu Gly Val Ile Gly Leu Val Ile Phe Leu Phe
    690                 695                 700

Leu Arg His Lys Arg Leu Ala Gln Thr Pro Ile Asp Ile Leu Phe Pro
705                 710                 715                 720

Tyr Thr Ser Lys Ser Thr Asn Ser Val Leu Gln Ala Thr Gln Ser Val
                725                 730                 735

Gln Ala Gln Val Lys Glu Pro Leu Asp Ser Ser Pro Pro Tyr Leu Lys
            740                 745                 750

Thr Asn Lys Asp Thr Glu Pro Gln Gly Asp Asp Ile Thr His Thr Asn
        755                 760                 765

Glu Tyr Ser Gln Val Glu Ala Leu Lys Met Leu Lys Ala Ile Lys Leu
    770                 775                 780

Leu Asp Glu Ser Tyr Lys Lys Ala Glu Ile Ala Glu Ala Lys Lys Ser
785                 790                 795                 800

Gln Arg Pro Ser Leu Leu Glu Arg Ile Gln Tyr Arg Gly Tyr Gln Lys
                805                 810                 815

Leu Ser Thr Glu Glu Leu
            820

<210> SEQ ID NO 35
<211> LENGTH: 841

<212> TYPE: PRT
<213> ORGANISM: Varicella-zoster virus

<400> SEQUENCE: 35

```
Met Phe Ala Leu Val Leu Ala Val Val Ile Leu Pro Leu Trp Thr Thr
1               5                   10                  15

Ala Asn Lys Ser Tyr Val Thr Pro Thr Pro Ala Thr Arg Ser Ile Gly
            20                  25                  30

His Met Ser Ala Leu Leu Arg Glu Tyr Ser Asp Arg Asn Met Ser Leu
        35                  40                  45

Lys Leu Glu Ala Phe Tyr Pro Thr Gly Phe Asp Glu Glu Leu Ile Lys
    50                  55                  60

Ser Leu His Trp Gly Asn Asp Arg Lys His Val Phe Leu Val Ile Val
65                  70                  75                  80

Lys Val Asn Pro Thr Thr His Glu Gly Asp Val Gly Leu Val Ile Phe
                85                  90                  95

Pro Lys Tyr Leu Leu Ser Pro Tyr His Phe Lys Ala Glu His Arg Ala
            100                 105                 110

Pro Phe Pro Ala Gly Arg Phe Gly Phe Leu Ser His Pro Val Thr Pro
        115                 120                 125

Asp Val Ser Phe Phe Asp Ser Ser Phe Ala Pro Tyr Leu Thr Thr Gln
    130                 135                 140

His Leu Val Ala Phe Thr Thr Phe Pro Pro Asn Pro Leu Val Trp His
145                 150                 155                 160

Leu Glu Arg Ala Glu Thr Ala Ala Thr Ala Glu Arg Pro Phe Gly Val
                165                 170                 175

Ser Leu Leu Pro Ala Arg Pro Thr Val Pro Lys Asn Thr Ile Leu Glu
            180                 185                 190

His Lys Ala His Phe Ala Thr Trp Asp Ala Leu Ala Arg His Thr Phe
        195                 200                 205

Phe Ser Ala Glu Ala Ile Ile Thr Asn Ser Thr Leu Arg Ile His Val
    210                 215                 220

Pro Leu Phe Gly Ser Val Trp Pro Ile Arg Tyr Trp Ala Thr Gly Ser
225                 230                 235                 240

Val Leu Leu Thr Ser Asp Ser Gly Arg Val Glu Val Asn Ile Gly Val
                245                 250                 255

Gly Phe Met Ser Ser Leu Ile Ser Leu Ser Ser Gly Pro Pro Ile Glu
            260                 265                 270

Leu Ile Val Val Pro His Thr Val Lys Leu Asn Ala Val Thr Ser Asp
        275                 280                 285

Thr Thr Trp Phe Gln Leu Asn Pro Pro Gly Pro Asp Pro Gly Pro Ser
    290                 295                 300

Tyr Arg Val Tyr Leu Leu Gly Arg Gly Leu Asp Met Asn Phe Ser Lys
305                 310                 315                 320

His Ala Thr Val Asp Ile Cys Ala Tyr Pro Glu Glu Ser Leu Asp Tyr
                325                 330                 335

Arg Tyr His Leu Ser Met Ala His Thr Glu Ala Leu Arg Met Thr Thr
            340                 345                 350

Lys Ala Asp Gln His Asp Ile Asn Glu Glu Ser Tyr Tyr His Ile Ala
        355                 360                 365

Ala Arg Ile Ala Thr Ser Ile Phe Ala Leu Ser Glu Met Gly Arg Thr
    370                 375                 380

Thr Glu Tyr Phe Leu Leu Asp Glu Ile Val Asp Val Gln Tyr Gln Leu
385                 390                 395                 400
```

```
Lys Phe Leu Asn Tyr Ile Leu Met Arg Ile Gly Ala Gly Ala His Pro
                405                 410                 415

Asn Thr Ile Ser Gly Thr Ser Asp Leu Ile Phe Ala Asp Pro Ser Gln
            420                 425                 430

Leu His Asp Glu Leu Ser Leu Leu Phe Gly Gln Val Lys Pro Ala Asn
        435                 440                 445

Val Asp Tyr Phe Ile Ser Tyr Asp Glu Ala Arg Asp Gln Leu Lys Thr
    450                 455                 460

Ala Tyr Ala Leu Ser Arg Gly Gln Asp His Val Asn Ala Leu Ser Leu
465                 470                 475                 480

Ala Arg Arg Val Ile Met Ser Ile Tyr Lys Gly Leu Leu Val Lys Gln
                485                 490                 495

Asn Leu Asn Ala Thr Glu Arg Gln Ala Leu Phe Phe Ala Ser Met Ile
            500                 505                 510

Leu Leu Asn Phe Arg Glu Gly Leu Glu Asn Ser Ser Arg Val Leu Asp
        515                 520                 525

Gly Arg Thr Thr Leu Leu Met Thr Ser Met Cys Thr Ala Ala His
    530                 535                 540

Ala Thr Gln Ala Ala Leu Asn Ile Gln Glu Gly Leu Ala Tyr Leu Asn
545                 550                 555                 560

Pro Ser Lys His Met Phe Thr Ile Pro Asn Val Tyr Ser Pro Cys Met
                565                 570                 575

Gly Ser Leu Arg Thr Asp Leu Thr Glu Glu Ile His Val Met Asn Leu
            580                 585                 590

Leu Ser Ala Ile Pro Thr Arg Pro Gly Leu Asn Glu Val Leu His Thr
        595                 600                 605

Gln Leu Asp Glu Ser Glu Ile Phe Asp Ala Ala Phe Lys Thr Met Met
    610                 615                 620

Ile Phe Thr Thr Trp Thr Ala Lys Asp Leu His Ile Leu His Thr His
625                 630                 635                 640

Val Pro Glu Val Phe Thr Cys Gln Asp Ala Ala Ala Arg Asn Gly Glu
                645                 650                 655

Tyr Val Leu Ile Leu Pro Ala Val Gln Gly His Ser Tyr Val Ile Thr
            660                 665                 670

Arg Asn Lys Pro Gln Arg Gly Leu Val Tyr Ser Leu Ala Asp Val Asp
        675                 680                 685

Val Tyr Asn Pro Ile Ser Val Val Tyr Leu Ser Arg Asp Thr Cys Val
    690                 695                 700

Ser Glu His Gly Val Ile Glu Thr Val Ala Leu Pro His Pro Asp Asn
705                 710                 715                 720

Leu Lys Glu Cys Leu Tyr Cys Gly Ser Val Phe Leu Arg Tyr Leu Thr
                725                 730                 735

Thr Gly Ala Ile Met Asp Ile Ile Ile Asp Ser Lys Asp Thr Glu
            740                 745                 750

Arg Gln Leu Ala Ala Met Gly Asn Ser Thr Ile Pro Pro Phe Asn Pro
        755                 760                 765

Asp Met His Gly Asp Asp Ser Lys Ala Val Leu Leu Phe Pro Asn Gly
    770                 775                 780

Thr Val Val Thr Leu Leu Gly Phe Glu Arg Arg Gln Ala Ile Arg Met
785                 790                 795                 800

Ser Gly Gln Tyr Leu Gly Ala Ser Leu Gly Gly Ala Phe Leu Ala Val
                805                 810                 815
```

```
Val Gly Phe Gly Ile Ile Gly Trp Met Leu Cys Gly Asn Ser Arg Leu
            820                 825                 830

Arg Glu Tyr Asn Lys Ile Pro Leu Thr
            835                 840

<210> SEQ ID NO 36
<211> LENGTH: 159
<212> TYPE: PRT
<213> ORGANISM: Varicella-zoster virus

<400> SEQUENCE: 36

Met Ala Ser His Lys Trp Leu Leu Gln Ile Val Phe Leu Lys Thr Ile
1               5                   10                  15

Thr Ile Ala Tyr Cys Leu His Leu Gln Asp Asp Thr Pro Leu Phe Phe
            20                  25                  30

Gly Ala Lys Pro Leu Ser Asp Val Ser Leu Ile Ile Thr Glu Pro Cys
        35                  40                  45

Val Ser Ser Val Tyr Glu Ala Trp Asp Tyr Ala Ala Pro Pro Val Ser
    50                  55                  60

Asn Leu Ser Glu Ala Leu Ser Gly Ile Val Val Lys Thr Lys Cys Pro
65                  70                  75                  80

Val Pro Glu Val Ile Leu Trp Phe Lys Asp Lys Gln Met Ala Tyr Trp
                85                  90                  95

Thr Asn Pro Tyr Val Thr Leu Lys Gly Leu Ala Gln Ser Val Gly Glu
            100                 105                 110

Glu His Lys Ser Gly Asp Ile Arg Asp Ala Leu Leu Asp Ala Leu Ser
        115                 120                 125

Gly Val Trp Val Asp Ser Thr Pro Ser Ser Thr Asn Ile Pro Glu Asn
    130                 135                 140

Gly Cys Val Trp Gly Ala Asp Arg Leu Phe Gln Arg Val Cys Gln
145                 150                 155

<210> SEQ ID NO 37
<211> LENGTH: 931
<212> TYPE: PRT
<213> ORGANISM: Varicella-zoster virus

<400> SEQUENCE: 37

Met Ser Pro Cys Gly Tyr Tyr Ser Lys Trp Arg Asn Arg Asp Arg Pro
1               5                   10                  15

Glu Tyr Arg Arg Asn Leu Arg Phe Arg Arg Phe Phe Ser Ser Ile His
            20                  25                  30

Pro Asn Ala Ala Ala Gly Ser Gly Phe Asn Gly Pro Gly Val Phe Ile
        35                  40                  45

Thr Ser Val Thr Gly Val Trp Leu Cys Phe Leu Cys Ile Phe Ser Met
    50                  55                  60

Phe Val Thr Ala Val Val Ser Val Ser Pro Ser Ser Phe Tyr Glu Ser
65                  70                  75                  80

Leu Gln Val Glu Pro Thr Gln Ser Glu Asp Ile Thr Arg Ser Ala His
                85                  90                  95

Leu Gly Asp Gly Asp Glu Ile Arg Glu Ala Ile His Lys Ser Gln Asp
            100                 105                 110

Ala Glu Thr Lys Pro Thr Phe Tyr Val Cys Pro Pro Thr Gly Ser
        115                 120                 125

Thr Ile Val Arg Leu Glu Pro Thr Arg Thr Cys Pro Asp Tyr His Leu
    130                 135                 140
```

```
Gly Lys Asn Phe Thr Glu Gly Ile Ala Val Val Tyr Lys Glu Asn Ile
145                 150                 155                 160

Ala Ala Tyr Lys Phe Lys Ala Thr Val Tyr Tyr Lys Asp Val Ile Val
                165                 170                 175

Ser Thr Ala Trp Ala Gly Ser Ser Tyr Thr Gln Ile Thr Asn Arg Tyr
                180                 185                 190

Ala Asp Arg Val Pro Ile Pro Val Ser Glu Ile Thr Asp Thr Ile Asp
            195                 200                 205

Lys Phe Gly Lys Cys Ser Ser Lys Ala Thr Tyr Val Arg Asn Asn His
    210                 215                 220

Lys Val Glu Ala Phe Asn Glu Asp Lys Asn Pro Gln Asp Met Pro Leu
225                 230                 235                 240

Ile Ala Ser Lys Tyr Asn Ser Val Gly Ser Lys Ala Trp His Thr Thr
                245                 250                 255

Asn Asp Thr Tyr Met Val Ala Gly Thr Pro Gly Thr Tyr Arg Thr Gly
                260                 265                 270

Thr Ser Val Asn Cys Ile Ile Glu Glu Val Glu Ala Arg Ser Ile Phe
            275                 280                 285

Pro Tyr Asp Ser Phe Gly Leu Ser Thr Gly Asp Ile Ile Tyr Met Ser
    290                 295                 300

Pro Phe Phe Gly Leu Arg Asp Gly Ala Tyr Arg Glu His Ser Asn Tyr
305                 310                 315                 320

Ala Met Asp Arg Phe His Gln Phe Glu Gly Tyr Arg Gln Arg Asp Leu
                325                 330                 335

Asp Thr Arg Ala Leu Leu Glu Pro Ala Ala Arg Asn Phe Leu Val Thr
            340                 345                 350

Pro His Leu Thr Val Gly Trp Asn Trp Lys Pro Lys Arg Thr Glu Val
    355                 360                 365

Cys Ser Leu Val Lys Trp Arg Glu Val Glu Asp Val Val Arg Asp Glu
370                 375                 380

Tyr Ala His Asn Phe Arg Phe Thr Met Lys Thr Leu Ser Thr Thr Phe
385                 390                 395                 400

Ile Ser Glu Thr Asn Glu Phe Asn Leu Asn Gln Ile His Leu Ser Gln
                405                 410                 415

Cys Val Lys Glu Glu Ala Arg Ala Ile Ile Asn Arg Ile Tyr Thr Thr
            420                 425                 430

Arg Tyr Asn Ser Ser His Val Arg Thr Gly Asp Ile Gln Thr Tyr Leu
        435                 440                 445

Ala Arg Gly Gly Phe Val Val Phe Gln Pro Leu Leu Ser Asn Ser
450                 455                 460

Leu Ala Arg Leu Tyr Leu Gln Glu Leu Val Arg Glu Asn Thr Asn His
465                 470                 475                 480

Ser Pro Gln Lys His Pro Thr Arg Asn Thr Arg Ser Arg Ser Val
                485                 490                 495

Pro Val Glu Leu Arg Ala Asn Arg Thr Ile Thr Thr Ser Ser Val
            500                 505                 510

Glu Phe Ala Met Leu Gln Phe Thr Tyr Asp His Ile Gln Glu His Val
    515                 520                 525

Asn Glu Met Leu Ala Arg Ile Ser Ser Trp Cys Gln Leu Gln Asn
                530                 535                 540

Arg Glu Arg Ala Leu Trp Ser Gly Leu Phe Pro Ile Asn Pro Ser Ala
545                 550                 555                 560

Leu Ala Ser Thr Ile Leu Asp Gln Arg Val Lys Ala Arg Ile Leu Gly
```

```
                565                 570                 575
Asp Val Ile Ser Val Ser Asn Cys Pro Glu Leu Gly Ser Asp Thr Arg
            580                 585                 590

Ile Ile Leu Gln Asn Ser Met Arg Val Ser Gly Ser Thr Thr Arg Cys
            595                 600                 605

Tyr Ser Arg Pro Leu Ile Ser Ile Val Ser Leu Asn Gly Ser Gly Thr
            610                 615                 620

Val Glu Gly Gln Leu Gly Thr Asp Asn Glu Leu Ile Met Ser Arg Asp
625                 630                 635                 640

Leu Leu Glu Pro Cys Val Ala Asn His Lys Arg Tyr Phe Leu Phe Gly
                645                 650                 655

His His Tyr Val Tyr Tyr Glu Asp Tyr Arg Tyr Val Arg Glu Ile Ala
            660                 665                 670

Val His Asp Val Gly Met Ile Ser Thr Tyr Val Asp Leu Asn Leu Thr
            675                 680                 685

Leu Leu Lys Asp Arg Glu Phe Met Pro Leu Gln Val Tyr Thr Arg Asp
            690                 695                 700

Glu Leu Arg Asp Thr Gly Leu Leu Asp Tyr Ser Glu Ile Gln Arg Arg
705                 710                 715                 720

Asn Gln Met His Ser Leu Arg Phe Tyr Asp Ile Asp Lys Val Val Gln
                725                 730                 735

Tyr Asp Ser Gly Thr Ala Ile Met Gln Gly Met Ala Gln Phe Phe Gln
            740                 745                 750

Gly Leu Gly Thr Ala Gly Gln Ala Val Gly His Val Val Leu Gly Ala
            755                 760                 765

Thr Gly Ala Leu Leu Ser Thr Val His Gly Phe Thr Thr Phe Leu Ser
770                 775                 780

Asn Pro Phe Gly Ala Leu Ala Val Gly Leu Leu Val Leu Ala Gly Leu
785                 790                 795                 800

Val Ala Ala Phe Phe Ala Tyr Arg Tyr Val Leu Lys Leu Lys Thr Ser
                805                 810                 815

Pro Met Lys Ala Leu Tyr Pro Leu Thr Thr Lys Gly Leu Lys Gln Leu
            820                 825                 830

Pro Glu Gly Met Asp Pro Phe Ala Glu Lys Pro Asn Ala Thr Asp Thr
            835                 840                 845

Pro Ile Glu Glu Ile Gly Asp Ser Gln Asn Thr Glu Pro Ser Val Asn
850                 855                 860

Ser Gly Phe Asp Pro Asp Lys Phe Arg Glu Ala Gln Glu Met Ile Lys
865                 870                 875                 880

Tyr Met Thr Leu Val Ser Ala Ala Glu Arg Gln Glu Ser Lys Ala Arg
                885                 890                 895

Lys Lys Asn Lys Thr Ser Ala Leu Leu Thr Ser Arg Leu Thr Gly Leu
            900                 905                 910

Ala Leu Arg Asn Arg Arg Gly Tyr Ser Arg Val Arg Thr Glu Asn Val
            915                 920                 925

Thr Gly Val
    930

<210> SEQ ID NO 38
<211> LENGTH: 354
<212> TYPE: PRT
<213> ORGANISM: Varicella-zoster virus

<400> SEQUENCE: 38
```

```
Met Phe Leu Ile Gln Cys Leu Ile Ser Ala Val Ile Phe Tyr Ile Gln
1               5                   10                  15

Val Thr Asn Ala Leu Ile Phe Lys Gly Asp His Val Ser Leu Gln Val
            20                  25                  30

Asn Ser Ser Leu Thr Ser Ile Leu Ile Pro Met Gln Asn Asp Asn Tyr
        35                  40                  45

Thr Glu Ile Lys Gly Gln Leu Val Phe Ile Gly Gln Leu Pro Thr
    50                  55                  60

Gly Thr Asn Tyr Ser Gly Thr Leu Glu Leu Leu Tyr Ala Asp Thr Val
65                  70                  75                  80

Ala Phe Cys Phe Arg Ser Val Gln Val Ile Arg Tyr Asp Gly Cys Pro
                85                  90                  95

Arg Ile Arg Thr Ser Ala Phe Ile Ser Cys Arg Tyr Lys His Ser Trp
            100                 105                 110

His Tyr Gly Asn Ser Thr Asp Arg Ile Ser Thr Glu Pro Asp Ala Gly
        115                 120                 125

Val Met Leu Lys Ile Thr Lys Pro Gly Ile Asn Asp Ala Gly Val Tyr
    130                 135                 140

Val Leu Leu Val Arg Leu Asp His Ser Arg Ser Thr Asp Gly Phe Ile
145                 150                 155                 160

Leu Gly Val Asn Val Tyr Thr Ala Gly Ser His His Asn Ile His Gly
                165                 170                 175

Val Ile Tyr Thr Ser Pro Ser Leu Gln Asn Gly Tyr Ser Thr Arg Ala
            180                 185                 190

Leu Phe Gln Gln Ala Arg Leu Cys Asp Leu Pro Ala Thr Pro Lys Gly
        195                 200                 205

Ser Gly Thr Ser Leu Phe Gln His Met Leu Asp Leu Arg Ala Gly Lys
    210                 215                 220

Ser Leu Glu Asp Asn Pro Trp Leu His Glu Asp Val Val Thr Thr Glu
225                 230                 235                 240

Thr Lys Ser Val Val Lys Glu Gly Ile Glu Asn His Val Tyr Pro Thr
                245                 250                 255

Asp Met Ser Thr Leu Pro Glu Lys Ser Leu Asn Asp Pro Pro Glu Asn
            260                 265                 270

Leu Leu Ile Ile Ile Pro Ile Val Ala Ser Val Met Ile Leu Thr Ala
        275                 280                 285

Met Val Ile Val Ile Val Ile Ser Val Lys Arg Arg Arg Ile Lys Lys
    290                 295                 300

His Pro Ile Tyr Arg Pro Asn Thr Lys Thr Arg Arg Gly Ile Gln Asn
305                 310                 315                 320

Ala Thr Pro Glu Ser Asp Val Met Leu Glu Ala Ala Ile Ala Gln Leu
                325                 330                 335

Ala Thr Ile Arg Glu Glu Ser Pro Pro His Ser Val Val Asn Pro Phe
            340                 345                 350

Val Lys

<210> SEQ ID NO 39
<211> LENGTH: 560
<212> TYPE: PRT
<213> ORGANISM: Varicella-zoster virus

<400> SEQUENCE: 39

Met Lys Arg Ile Gln Ile Asn Leu Ile Leu Thr Ile Ala Cys Ile Gln
1               5                   10                  15
```

Leu Ser Thr Glu Ser Gln Pro Thr Pro Val Ser Ile Thr Glu Leu Tyr
            20                      25                      30

Thr Ser Ala Ala Thr Arg Lys Pro Asp Pro Ala Val Ala Pro Thr Ser
        35                      40                      45

Ala Ala Ser Arg Lys Pro Asp Pro Ala Val Ala Pro Thr Ser Ala Ala
    50                      55                      60

Ser Arg Lys Pro Asp Pro Ala Val Ala Pro Thr Ser Ala Ala Ser Arg
65                      70                      75                      80

Lys Pro Asp Pro Ala Val Ala Pro Thr Ser Ala Ala Thr Arg Lys Pro
                85                      90                      95

Asp Pro Ala Val Ala Pro Thr Ser Ala Ala Ser Arg Lys Pro Asp Pro
            100                     105                     110

Ala Val Ala Pro Thr Ser Ala Ala Thr Arg Lys Pro Asp Pro Ala Val
        115                     120                     125

Ala Pro Thr Ser Ala Ala Ser Arg Lys Pro Asp Pro Ala Ala Asn Thr
    130                     135                     140

Gln His Ser Gln Pro Pro Phe Leu Tyr Glu Asn Ile Gln Cys Val His
145                     150                     155                     160

Gly Gly Ile Gln Ser Ile Pro Tyr Phe His Thr Phe Ile Met Pro Cys
                165                     170                     175

Tyr Met Arg Leu Thr Thr Gly Gln Gln Ala Ala Phe Lys Gln Gln Gln
            180                     185                     190

Lys Thr Tyr Glu Gln Tyr Ser Leu Asp Pro Glu Gly Ser Asn Ile Thr
        195                     200                     205

Arg Trp Lys Ser Leu Ile Arg Pro Asp Leu His Ile Glu Val Trp Phe
    210                     215                     220

Thr Arg His Leu Ile Asp Pro His Arg Gln Leu Gly Asn Ala Leu Ile
225                     230                     235                     240

Arg Met Pro Asp Leu Pro Val Met Leu Tyr Ser Asn Ser Ala Asp Leu
                245                     250                     255

Asn Leu Ile Asn Asn Pro Glu Ile Phe Thr His Ala Lys Glu Asn Tyr
            260                     265                     270

Val Ile Pro Asp Val Lys Thr Thr Ser Asp Phe Ser Val Thr Ile Leu
        275                     280                     285

Ser Met Asp Ala Thr Thr Glu Gly Thr Tyr Ile Trp Arg Val Val Asn
    290                     295                     300

Thr Lys Thr Lys Asn Val Ile Ser Glu His Ser Ile Thr Val Thr Thr
305                     310                     315                     320

Tyr Tyr Arg Pro Asn Ile Thr Val Val Gly Asp Pro Val Leu Thr Gly
                325                     330                     335

Gln Thr Tyr Ala Ala Tyr Cys Asn Val Ser Lys Tyr Tyr Pro Pro His
            340                     345                     350

Ser Val Arg Val Arg Trp Thr Ser Arg Phe Gly Asn Ile Gly Lys Asn
        355                     360                     365

Phe Ile Thr Asp Ala Ile Gln Glu Tyr Ala Asn Gly Leu Phe Ser Tyr
    370                     375                     380

Val Ser Ala Val Arg Ile Pro Gln Gln Lys Gln Met Asp Tyr Pro Pro
385                     390                     395                     400

Pro Ala Ile Gln Cys Asn Val Leu Trp Ile Arg Asp Gly Val Ser Asn
                405                     410                     415

Met Lys Tyr Ser Ala Val Val Thr Pro Asp Val Tyr Pro Phe Pro Asn
            420                     425                     430

Val Ser Ile Gly Ile Ile Asp Gly His Ile Val Cys Thr Ala Lys Cys

```
            435                 440                 445
Val Pro Arg Gly Val Val His Phe Val Trp Val Asn Asp Ser Pro
450                 455                 460

Ile Asn His Glu Asn Ser Glu Ile Thr Gly Val Cys Asp Gln Asn Lys
465                 470                 475                 480

Arg Phe Val Asn Met Gln Ser Ser Cys Pro Thr Ser Glu Leu Asp Gly
                485                 490                 495

Pro Ile Thr Tyr Ser Cys His Leu Asp Gly Tyr Pro Lys Lys Phe Pro
                500                 505                 510

Pro Phe Ser Ala Val Tyr Thr Tyr Asp Ala Ser Thr Tyr Ala Thr Thr
                515                 520                 525

Phe Ser Val Val Ala Val Ile Ile Gly Val Ile Ser Ile Leu Gly Thr
                530                 535                 540

Leu Gly Leu Ile Ala Val Ile Ala Thr Leu Cys Ile Arg Cys Cys Ser
545                 550                 555                 560

<210> SEQ ID NO 40
<211> LENGTH: 623
<212> TYPE: PRT
<213> ORGANISM: Varicella-zoster virus

<400> SEQUENCE: 40

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
                20                  25                  30

Leu Arg Tyr Asp Asp Phe His Thr Asp Glu Asp Lys Leu Asp Thr Asn
                35                  40                  45

Ser Val Tyr Glu Pro Tyr Tyr His Ser Asp His Ala Glu Ser Ser Trp
            50                  55                  60

Val Asn Arg Gly Glu Ser Ser Arg Lys Ala Tyr Asp His Asn Ser Pro
65              70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
                100                 105                 110

Arg Leu Met Gln Pro Thr Gln Met Ser Ala Gln Glu Asp Leu Gly Asp
                115                 120                 125

Asp Thr Gly Ile His Val Ile Pro Thr Leu Asn Gly Asp Asp Arg His
130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
                180                 185                 190

Gly Val Arg Tyr Thr Glu Thr Trp Ser Phe Leu Pro Ser Leu Thr Cys
                195                 200                 205

Thr Gly Asp Ala Ala Pro Ala Ile Gln His Ile Cys Leu Lys His Thr
                210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255
```

-continued

```
Glu Ala Asp Gln Pro Trp Ile Val Val Asn Thr Ser Thr Leu Phe Asp
                260                 265                 270

Glu Leu Glu Leu Asp Pro Pro Glu Ile Glu Pro Gly Val Leu Lys Val
            275                 280                 285

Leu Arg Thr Glu Lys Gln Tyr Leu Gly Val Tyr Ile Trp Asn Met Arg
        290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
530                 535                 540

Leu Ala Ala Val Val Leu Leu Cys Leu Val Ile Phe Leu Ile Cys Thr
545                 550                 555                 560

Ala Lys Arg Met Arg Val Lys Ala Tyr Arg Val Asp Lys Ser Pro Tyr
                565                 570                 575

Asn Gln Ser Met Tyr Tyr Ala Gly Leu Pro Val Asp Asp Phe Glu Asp
            580                 585                 590

Ser Glu Ser Thr Asp Thr Glu Glu Phe Gly Asn Ala Ile Gly Gly
        595                 600                 605

Ser His Gly Gly Ser Ser Tyr Thr Val Tyr Ile Asp Lys Thr Arg
610                 615                 620
```

<210> SEQ ID NO 41
<211> LENGTH: 838
<212> TYPE: PRT
<213> ORGANISM: Herpes simplex virus-1

<400> SEQUENCE: 41

```
Met Gly Asn Gly Leu Trp Phe Val Gly Val Ile Ile Leu Gly Ala Ala
1               5                   10                  15
```

-continued

Trp Gly Gln Val His Asp Trp Thr Glu Gln Thr Asp Pro Trp Phe Leu
            20                  25                  30

Asp Gly Leu Gly Met Asp Arg Met Tyr Trp Arg Asp Thr Asn Thr Gly
        35                  40                  45

Arg Leu Trp Leu Pro Asn Thr Pro Asp Pro Gln Lys Pro Pro Arg Gly
50                  55                  60

Phe Leu Ala Pro Pro Asp Glu Leu Asn Leu Thr Thr Ala Ser Leu Pro
65                  70                  75                  80

Leu Leu Arg Trp Tyr Glu Arg Phe Cys Phe Val Leu Val Thr Thr
                85                  90                  95

Ala Glu Phe Pro Arg Asp Pro Gly Gln Leu Leu Tyr Ile Pro Lys Thr
                100                 105                 110

Tyr Leu Leu Gly Arg Pro Pro Asn Ala Ser Leu Pro Ala Pro Thr Thr
            115                 120                 125

Val Glu Pro Thr Ala Gln Pro Pro Ala Val Ala Pro Leu Lys Gly
        130                 135                 140

Leu Leu His Asn Pro Thr Ala Ser Val Leu Leu Arg Ser Arg Ala Trp
145                 150                 155                 160

Val Thr Phe Ser Ala Val Pro Asp Pro Glu Ala Leu Thr Phe Pro Arg
                165                 170                 175

Gly Asp Asn Val Ala Thr Ala Ser His Pro Ser Gly Pro Arg Asp Thr
                180                 185                 190

Pro Pro Pro Arg Pro Pro Val Gly Ala Arg Arg His Pro Thr Thr Glu
            195                 200                 205

Leu Asp Ile Thr His Leu His Asn Ala Ser Thr Thr Trp Leu Ala Thr
        210                 215                 220

Arg Gly Leu Leu Arg Ser Pro Gly Arg Tyr Val Tyr Phe Ser Pro Ser
225                 230                 235                 240

Ala Ser Thr Trp Pro Val Gly Ile Trp Thr Thr Gly Glu Leu Val Leu
                245                 250                 255

Gly Cys Asp Ala Ala Leu Val Arg Ala Arg Tyr Gly Arg Glu Phe Met
                260                 265                 270

Gly Leu Val Ile Ser Met His Asp Ser Pro Pro Ala Glu Val Met Val
            275                 280                 285

Val Pro Ala Gly Gln Thr Leu Asp Arg Val Gly Asp Pro Ala Asp Glu
        290                 295                 300

Asn Pro Pro Gly Ala Leu Pro Gly Pro Pro Gly Gly Pro Arg Tyr Arg
305                 310                 315                 320

Val Phe Val Leu Gly Ser Leu Thr Arg Ala Asp Asn Gly Ser Ala Leu
                325                 330                 335

Asp Ala Leu Arg Arg Val Gly Tyr Pro Glu Glu Gly Thr Asn Tyr
            340                 345                 350

Ala Gln Phe Leu Ser Arg Ala Tyr Ala Glu Phe Phe Ser Gly Asp Ala
        355                 360                 365

Gly Ala Glu Gln Gly Pro Arg Pro Pro Leu Phe Trp Arg Leu Thr Gly
        370                 375                 380

Leu Leu Ala Thr Ser Gly Phe Ala Phe Val Asn Ala Ala His Ala Asn
385                 390                 395                 400

Gly Ala Val Cys Leu Ser Asp Leu Leu Gly Phe Leu Ala His Ser Arg
                405                 410                 415

Ala Leu Ala Gly Leu Ala Ala Arg Gly Ala Ala Gly Cys Ala Ala Asp
            420                 425                 430

```
Ser Val Phe Phe Asn Val Ser Val Leu Asp Pro Thr Ala Arg Leu Gln
            435                 440                 445

Leu Glu Ala Arg Leu Gln His Leu Val Ala Glu Ile Leu Glu Arg Glu
    450                 455                 460

Gln Ser Leu Ala Leu His Ala Leu Gly Tyr Gln Leu Ala Phe Val Leu
465                 470                 475                 480

Asp Ser Pro Ser Ala Tyr Asp Ala Val Ala Pro Ser Ala Ala His Leu
                485                 490                 495

Ile Asp Ala Leu Tyr Ala Glu Phe Leu Gly Gly Arg Val Val Thr Thr
                500                 505                 510

Pro Val Val His Arg Ala Leu Phe Tyr Ala Ser Ala Val Leu Arg Gln
            515                 520                 525

Pro Phe Leu Ala Gly Val Pro Ser Ala Val Gln Arg Glu Arg Ala Arg
        530                 535                 540

Arg Ser Leu Leu Ile Ala Ser Ala Leu Cys Thr Ser Asp Val Ala Ala
545                 550                 555                 560

Ala Thr Asn Ala Asp Leu Arg Thr Ala Leu Ala Arg Ala Asp His Gln
                565                 570                 575

Lys Thr Leu Phe Trp Leu Pro Asp His Phe Ser Pro Cys Ala Ala Ser
            580                 585                 590

Leu Arg Phe Asp Leu Asp Glu Ser Val Phe Ile Leu Asp Ala Leu Ala
        595                 600                 605

Gln Ala Thr Arg Ser Glu Thr Pro Val Glu Val Leu Ala Gln Gln Thr
        610                 615                 620

His Gly Leu Ala Ser Thr Leu Thr Arg Trp Ala His Tyr Asn Ala Leu
625                 630                 635                 640

Ile Arg Ala Phe Val Pro Glu Ala Ser His Arg Cys Gly Gly Gln Ser
                645                 650                 655

Ala Asn Val Glu Pro Arg Ile Leu Val Pro Ile Thr His Asn Ala Ser
                660                 665                 670

Tyr Val Val Thr His Ser Pro Leu Pro Arg Gly Ile Gly Tyr Lys Leu
            675                 680                 685

Thr Gly Val Asp Val Arg Arg Pro Leu Phe Leu Thr Tyr Leu Thr Ala
    690                 695                 700

Thr Cys Glu Gly Ser Thr Arg Asp Ile Glu Ser Lys Arg Leu Val Arg
705                 710                 715                 720

Thr Gln Asn Gln Arg Asp Leu Gly Leu Val Gly Ala Val Phe Met Arg
                725                 730                 735

Tyr Thr Pro Ala Gly Glu Val Met Ser Val Leu Leu Val Asp Thr Asp
            740                 745                 750

Asn Thr Gln Gln Gln Ile Ala Ala Gly Pro Thr Glu Gly Ala Pro Ser
        755                 760                 765

Val Phe Ser Ser Asp Val Pro Ser Thr Ala Leu Leu Leu Phe Pro Asn
        770                 775                 780

Gly Thr Val Ile His Leu Leu Ala Phe Asp Thr Gln Pro Val Ala Ala
785                 790                 795                 800

Ile Ala Pro Gly Phe Leu Ala Ala Ser Ala Leu Gly Val Val Met Ile
                805                 810                 815

Thr Ala Ala Leu Ala Gly Ile Leu Lys Val Leu Arg Thr Ser Val Pro
            820                 825                 830

Phe Phe Trp Arg Arg Glu
            835
```

```
<210> SEQ ID NO 42
<211> LENGTH: 224
<212> TYPE: PRT
<213> ORGANISM: Herpes simplex virus-1

<400> SEQUENCE: 42

Met Gly Ile Leu Gly Trp Val Gly Leu Ile Ala Val Gly Val Leu Cys
 1               5                  10                  15

Val Arg Gly Gly Leu Pro Ser Thr Glu Tyr Val Ile Arg Ser Arg Val
                20                  25                  30

Ala Arg Glu Val Gly Asp Ile Leu Lys Val Pro Cys Val Pro Leu Pro
            35                  40                  45

Ser Asp Asp Leu Asp Trp Arg Tyr Glu Thr Pro Ser Ala Ile Asn Tyr
        50                  55                  60

Ala Leu Ile Asp Gly Ile Phe Leu Arg Tyr His Cys Pro Gly Leu Asp
65                  70                  75                  80

Thr Val Leu Trp Asp Arg His Ala Gln Lys Ala Tyr Trp Val Asn Pro
                85                  90                  95

Phe Leu Phe Val Ala Gly Phe Leu Glu Asp Leu Ser Tyr Pro Ala Phe
               100                 105                 110

Pro Ala Asn Thr Gln Glu Thr Glu Thr Arg Leu Ala Leu Tyr Lys Glu
           115                 120                 125

Ile Arg Gln Ala Leu Asp Ser Arg Lys Gln Ala Ala Ser His Thr Pro
       130                 135                 140

Val Lys Ala Gly Cys Val Asn Phe Asp Tyr Ser Arg Thr Arg Arg Cys
145                 150                 155                 160

Val Gly Arg Gln Asp Leu Gly Pro Thr Asn Gly Thr Ser Gly Arg Thr
                165                 170                 175

Pro Val Leu Pro Pro Asp Asp Glu Ala Gly Leu Gln Pro Lys Pro Leu
            180                 185                 190

Thr Thr Pro Pro Pro Ile Ile Ala Thr Ser Asp Pro Thr Pro Arg Arg
        195                 200                 205

Asp Ala Ala Thr Lys Ser Arg Arg Arg Pro His Ser Arg Arg Leu
    210                 215                 220

<210> SEQ ID NO 43
<211> LENGTH: 904
<212> TYPE: PRT
<213> ORGANISM: Herpes simplex virus-1

<400> SEQUENCE: 43

Met His Gln Gly Ala Pro Ser Trp Gly Arg Arg Trp Phe Val Val Trp
 1               5                  10                  15

Ala Leu Leu Gly Leu Thr Leu Gly Val Leu Val Ala Ser Ala Ala Pro
                20                  25                  30

Thr Ser Pro Gly Thr Pro Gly Val Ala Ala Thr Gln Ala Ala Asn
            35                  40                  45

Gly Gly Pro Ala Thr Pro Ala Pro Pro Leu Gly Ala Ala Pro Thr
        50                  55                  60

Gly Asp Pro Lys Pro Lys Lys Asn Lys Lys Pro Lys Asn Pro Thr Pro
65                  70                  75                  80

Pro Arg Pro Ala Gly Asp Asn Ala Thr Val Ala Ala Gly His Ala Thr
                85                  90                  95

Leu Arg Glu His Leu Arg Asp Ile Lys Ala Glu Asn Thr Asp Ala Asn
               100                 105                 110

Phe Tyr Val Cys Pro Pro Pro Thr Gly Ala Thr Val Val Gln Phe Glu
```

```
            115                 120                 125
Gln Pro Arg Arg Cys Pro Thr Arg Pro Glu Gly Gln Asn Tyr Thr Glu
130                 135                 140

Gly Ile Ala Val Val Phe Lys Glu Asn Ile Ala Pro Tyr Lys Phe Lys
145                 150                 155                 160

Ala Thr Met Tyr Tyr Lys Asp Val Thr Val Ser Gln Val Trp Phe Gly
                165                 170                 175

His Arg Tyr Ser Gln Phe Met Gly Ile Phe Glu Asp Arg Ala Pro Val
            180                 185                 190

Pro Phe Glu Glu Val Ile Asp Lys Ile Asn Ala Lys Gly Val Cys Arg
        195                 200                 205

Ser Thr Ala Lys Tyr Val Arg Asn Asn Leu Glu Thr Thr Ala Phe His
    210                 215                 220

Arg Asp Asp His Glu Thr Asp Met Glu Leu Lys Pro Ala Asn Ala Ala
225                 230                 235                 240

Thr Arg Thr Ser Arg Gly Trp His Thr Thr Asp Leu Lys Tyr Asn Pro
                245                 250                 255

Ser Arg Val Glu Ala Phe His Arg Tyr Gly Thr Thr Val Asn Cys Ile
            260                 265                 270

Val Glu Glu Val Asp Ala Arg Ser Val Tyr Pro Tyr Asp Glu Phe Val
        275                 280                 285

Leu Ala Thr Gly Asp Phe Val Tyr Met Ser Pro Phe Tyr Gly Tyr Arg
    290                 295                 300

Glu Gly Ser His Thr Glu His Thr Thr Tyr Ala Ala Asp Arg Phe Lys
305                 310                 315                 320

Gln Val Asp Gly Phe Tyr Ala Arg Asp Leu Thr Thr Lys Ala Arg Ala
                325                 330                 335

Thr Ala Pro Thr Thr Arg Asn Leu Leu Thr Thr Pro Lys Phe Thr Val
            340                 345                 350

Ala Trp Asp Trp Val Pro Lys Arg Pro Ser Val Cys Thr Met Thr Lys
        355                 360                 365

Trp Gln Glu Val Asp Glu Met Leu Arg Ser Glu Tyr Gly Gly Ser Phe
    370                 375                 380

Arg Phe Ser Ser Asp Ala Ile Ser Thr Thr Phe Thr Thr Asn Leu Thr
385                 390                 395                 400

Glu Tyr Pro Leu Ser Arg Val Asp Leu Gly Asp Cys Ile Gly Lys Asp
                405                 410                 415

Ala Arg Asp Ala Met Asp Arg Ile Phe Ala Arg Arg Tyr Asn Ala Thr
            420                 425                 430

His Ile Lys Val Gly Gln Pro Gln Tyr Tyr Gln Ala Asn Gly Gly Phe
        435                 440                 445

Leu Ile Ala Tyr Gln Pro Leu Leu Ser Asn Thr Leu Ala Glu Leu Tyr
    450                 455                 460

Val Arg Glu His Leu Arg Glu Gln Ser Arg Lys Pro Pro Asn Pro Thr
465                 470                 475                 480

Pro Pro Pro Pro Gly Ala Ser Ala Asn Ala Ser Val Glu Arg Ile Lys
                485                 490                 495

Thr Thr Ser Ser Ile Glu Phe Ala Arg Leu Gln Phe Thr Tyr Asn His
            500                 505                 510

Ile Gln Arg His Val Asn Asp Met Leu Gly Arg Val Ala Ile Ala Trp
        515                 520                 525

Cys Glu Leu Gln Asn His Glu Leu Thr Leu Trp Asn Glu Ala Arg Lys
    530                 535                 540
```

Leu Asn Pro Asn Ala Ile Ala Ser Val Thr Val Gly Arg Arg Val Ser
545                 550                 555                 560

Ala Arg Met Leu Gly Asp Val Met Ala Val Ser Thr Cys Val Pro Val
                565                 570                 575

Ala Ala Asp Asn Val Ile Val Gln Asn Ser Met Arg Ile Ser Ser Arg
            580                 585                 590

Pro Gly Ala Cys Tyr Ser Arg Pro Leu Val Ser Phe Arg Tyr Glu Asp
        595                 600                 605

Gln Gly Pro Leu Val Glu Gly Gln Leu Gly Glu Asn Asn Glu Leu Arg
    610                 615                 620

Leu Thr Arg Asp Ala Ile Glu Pro Cys Thr Val Gly His Arg Arg Tyr
625                 630                 635                 640

Phe Thr Phe Gly Gly Gly Tyr Val Tyr Phe Glu Glu Tyr Ala Tyr Ser
                645                 650                 655

His Gln Leu Ser Arg Ala Asp Ile Thr Thr Val Ser Thr Phe Ile Asp
            660                 665                 670

Leu Asn Ile Thr Met Leu Glu Asp His Glu Phe Val Pro Leu Glu Val
        675                 680                 685

Tyr Thr Arg His Glu Ile Lys Asp Ser Gly Leu Leu Asp Tyr Thr Glu
    690                 695                 700

Val Gln Arg Arg Asn Gln Leu His Asp Leu Arg Phe Ala Asp Ile Asp
705                 710                 715                 720

Thr Val Ile His Ala Asp Ala Asn Ala Ala Met Phe Ala Gly Leu Gly
                725                 730                 735

Ala Phe Phe Glu Gly Met Gly Asp Leu Gly Arg Ala Val Gly Lys Val
            740                 745                 750

Val Met Gly Ile Val Gly Gly Val Val Ser Ala Val Ser Gly Val Ser
        755                 760                 765

Ser Phe Met Ser Asn Pro Phe Gly Ala Leu Ala Val Gly Leu Leu Val
    770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
                805                 810                 815

Leu Lys Asn Pro Thr Asn Pro Asp Ala Ser Gly Glu Gly Glu Glu Gly
            820                 825                 830

Gly Asp Phe Asp Glu Ala Lys Leu Ala Glu Ala Arg Glu Met Ile Arg
        835                 840                 845

Tyr Met Ala Leu Val Ser Ala Met Glu Arg Thr Glu His Lys Ala Lys
    850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                885                 890                 895

Gly Asp Ala Asp Glu Asp Asp Leu
            900

<210> SEQ ID NO 44
<211> LENGTH: 394
<212> TYPE: PRT
<213> ORGANISM: Herpes simplex virus-1

<400> SEQUENCE: 44

Met Gly Gly Ala Ala Ala Arg Leu Gly Ala Val Ile Leu Phe Val Val

```
            1               5                  10                 15
          Ile Val Gly Leu His Gly Val Arg Gly Lys Tyr Ala Leu Ala Asp Ala
                           20                 25                 30

Ser Leu Lys Met Ala Asp Pro Asn Arg Phe Arg Gly Lys Asp Leu Pro
                           35                 40                 45

Val Pro Asp Arg Leu Thr Asp Pro Pro Gly Val Arg Val Tyr His
                           50                 55                 60

Ile Gln Ala Gly Leu Pro Asp Pro Phe Gln Pro Ser Leu Pro Ile
          65                70                 75                 80

Thr Val Tyr Tyr Ala Val Leu Glu Arg Ala Cys Arg Ser Val Leu Leu
                           85                 90                 95

Asn Ala Pro Ser Glu Ala Pro Gln Ile Val Arg Gly Gly Ser Glu Asp
                           100                105                110

Val Arg Lys Gln Pro Tyr Asn Leu Thr Ile Ala Trp Phe Arg Met Gly
                           115                120                125

Gly Asn Cys Ala Ile Pro Ile Thr Val Met Glu Tyr Thr Glu Cys Ser
                           130                135                140

Tyr Asn Lys Ser Leu Gly Ala Cys Pro Ile Arg Thr Gln Pro Arg Trp
          145               150                155                160

Asn Tyr Tyr Asp Ser Phe Ser Ala Val Ser Glu Asp Asn Leu Gly Phe
                           165                170                175

Leu Met His Ala Pro Ala Phe Glu Thr Ala Gly Thr Tyr Leu Arg Leu
                           180                185                190

Val Lys Ile Asn Asp Trp Thr Glu Ile Thr Gln Phe Ile Leu Glu His
                           195                200                205

Arg Ala Lys Gly Ser Cys Lys Tyr Ala Leu Pro Leu Arg Ile Pro Pro
                           210                215                220

Ser Ala Cys Leu Ser Pro Gln Ala Tyr Gln Gln Gly Val Thr Val Asp
          225               230                235                240

Ser Ile Gly Met Leu Pro Arg Phe Ile Pro Glu Asn Gln Arg Ile Val
                           245                250                255

Ala Val Tyr Ser Leu Lys Ile Ala Gly Trp His Gly Pro Lys Ala Pro
                           260                265                270

Tyr Thr Ser Thr Leu Leu Pro Pro Glu Leu Ser Glu Thr Pro Asn Ala
                           275                280                285

Thr Gln Pro Glu Leu Ala Pro Glu Asp Pro Glu Asp Ser Ala Leu Leu
                           290                295                300

Glu Asp Pro Val Gly Thr Val Ala Pro Gln Ile Pro Asn Trp His
          305               310                315                320

Ile Pro Ser Ile Gln Asp Ala Ala Thr Pro Tyr His Pro Pro Ala Thr
                           325                330                335

Pro Asn Asn Met Gly Leu Ile Ala Gly Ala Val Gly Gly Ser Leu Leu
                           340                345                350

Ala Ala Leu Val Ile Cys Gly Ile Val Tyr Trp Met Arg Arg Arg Thr
                           355                360                365

Gln Lys Gly Pro Lys Arg Ile Arg Leu Pro His Ile Arg Glu Asp Asp
                           370                375                380

Gln Pro Ser Ser His Gln Pro Leu Phe Tyr
          385               390

<210> SEQ ID NO 45
<211> LENGTH: 838
<212> TYPE: PRT
<213> ORGANISM: Herpes simplex virus-2
```

<400> SEQUENCE: 45

```
Met Gly Pro Gly Leu Trp Val Val Met Gly Val Leu Val Gly Val Ala
1               5                   10                  15

Gly Gly His Asp Thr Tyr Trp Thr Glu Gln Ile Asp Pro Trp Phe Leu
            20                  25                  30

His Gly Leu Gly Leu Ala Arg Thr Tyr Trp Arg Asp Thr Asn Thr Gly
        35                  40                  45

Arg Leu Trp Leu Pro Asn Thr Pro Asp Ala Ser Asp Pro Gln Arg Gly
    50                  55                  60

Arg Leu Ala Pro Pro Gly Glu Leu Asn Leu Thr Thr Ala Ser Val Pro
65                  70                  75                  80

Met Leu Arg Trp Tyr Ala Glu Arg Phe Cys Phe Val Leu Val Thr Thr
                85                  90                  95

Ala Glu Phe Pro Arg Asp Pro Gly Gln Leu Leu Tyr Ile Pro Lys Thr
            100                 105                 110

Tyr Leu Leu Gly Arg Pro Arg Asn Ala Ser Leu Pro Glu Leu Pro Glu
        115                 120                 125

Ala Gly Pro Thr Ser Arg Pro Ala Glu Val Thr Gln Leu Lys Gly
    130                 135                 140

Leu Ser His Asn Pro Gly Ala Ser Ala Leu Leu Arg Ser Arg Ala Trp
145                 150                 155                 160

Val Thr Phe Ala Ala Pro Asp Arg Glu Gly Leu Thr Phe Pro Arg
                165                 170                 175

Gly Asp Asp Gly Ala Thr Glu Arg His Pro Asp Gly Arg Arg Asn Ala
            180                 185                 190

Pro Pro Pro Gly Pro Pro Ala Gly Ala Pro Arg His Pro Thr Thr Asn
        195                 200                 205

Leu Ser Ile Ala His Leu His Asn Ala Ser Val Thr Trp Leu Ala Ala
    210                 215                 220

Arg Gly Leu Leu Arg Thr Pro Gly Arg Tyr Val Tyr Leu Ser Pro Ser
225                 230                 235                 240

Ala Ser Thr Trp Pro Val Gly Val Trp Thr Thr Gly Gly Leu Ala Phe
                245                 250                 255

Gly Cys Asp Ala Ala Leu Val Arg Ala Arg Tyr Gly Lys Gly Phe Met
            260                 265                 270

Gly Leu Val Ile Ser Met Arg Asp Ser Pro Ala Glu Ile Ile Val
        275                 280                 285

Val Pro Ala Asp Lys Thr Leu Ala Arg Val Gly Asn Pro Thr Asp Glu
    290                 295                 300

Asn Ala Pro Ala Val Leu Pro Gly Pro Ala Gly Pro Arg Tyr Arg
305                 310                 315                 320

Val Phe Val Leu Gly Ala Pro Thr Pro Ala Asp Asn Gly Ser Ala Leu
                325                 330                 335

Asp Ala Leu Arg Arg Val Ala Gly Tyr Pro Glu Glu Ser Thr Asn Tyr
            340                 345                 350

Ala Gln Tyr Met Ser Arg Ala Tyr Ala Glu Phe Leu Gly Glu Asp Pro
        355                 360                 365

Gly Ser Gly Thr Asp Ala Arg Pro Ser Leu Phe Trp Arg Leu Ala Gly
    370                 375                 380

Leu Leu Ala Ser Ser Gly Phe Ala Phe Ile Asn Ala Ala His Ala His
385                 390                 395                 400

Asp Ala Ile Arg Leu Ser Asp Leu Leu Gly Phe Leu Ala His Ser Arg
```

```
            405                 410                 415
Val Leu Ala Gly Leu Ala Ala Arg Gly Ala Ala Gly Cys Ala Ala Asp
            420                 425                 430

Ser Val Phe Leu Asn Val Ser Val Leu Asp Pro Ala Ala Arg Leu Arg
            435                 440                 445

Leu Glu Ala Arg Leu Gly His Leu Val Ala Ala Ile Leu Glu Arg Glu
            450                 455                 460

Gln Ser Leu Ala Ala His Ala Leu Gly Tyr Gln Leu Ala Phe Val Leu
465                 470                 475                 480

Asp Ser Pro Ala Ala Tyr Gly Ala Val Ala Pro Ser Ala Ala Arg Leu
            485                 490                 495

Ile Asp Ala Leu Tyr Ala Glu Phe Leu Gly Gly Arg Ala Leu Thr Ala
            500                 505                 510

Pro Met Val Arg Arg Ala Leu Phe Tyr Ala Thr Ala Val Leu Arg Ala
            515                 520                 525

Pro Phe Leu Ala Gly Ala Pro Ser Ala Glu Gln Arg Glu Arg Ala Arg
            530                 535                 540

Arg Gly Leu Leu Ile Thr Thr Ala Leu Cys Thr Ser Asp Val Ala Ala
545                 550                 555                 560

Ala Thr His Ala Asp Leu Arg Ala Ala Leu Ala Arg Thr Asp His Gln
            565                 570                 575

Lys Asn Leu Phe Trp Leu Pro Asp His Phe Ser Pro Cys Ala Ala Ser
            580                 585                 590

Leu Arg Phe Asp Leu Ala Glu Gly Gly Phe Ile Leu Asp Ala Leu Ala
            595                 600                 605

Met Ala Thr Arg Ser Asp Ile Pro Ala Asp Val Met Ala Gln Gln Thr
            610                 615                 620

Arg Gly Val Ala Ser Ala Leu Thr Arg Trp Ala His Tyr Asn Ala Leu
625                 630                 635                 640

Ile Arg Ala Phe Val Pro Glu Ala Thr His Gln Cys Ser Gly Pro Ser
            645                 650                 655

His Asn Ala Glu Pro Arg Ile Leu Val Pro Ile Thr His Asn Ala Ser
            660                 665                 670

Tyr Val Val Thr His Thr Pro Leu Pro Arg Gly Ile Gly Tyr Lys Leu
            675                 680                 685

Thr Gly Val Asp Val Arg Arg Pro Leu Phe Ile Thr Tyr Leu Thr Ala
            690                 695                 700

Thr Cys Glu Gly His Ala Arg Glu Ile Glu Pro Lys Arg Leu Val Arg
705                 710                 715                 720

Thr Glu Asn Arg Arg Asp Leu Gly Leu Val Gly Ala Val Phe Leu Arg
            725                 730                 735

Tyr Thr Pro Ala Gly Glu Val Met Ser Val Leu Leu Val Asp Thr Asp
            740                 745                 750

Ala Thr Gln Gln Gln Leu Ala Gln Gly Pro Val Ala Gly Thr Pro Asn
            755                 760                 765

Val Phe Ser Ser Asp Val Pro Ser Val Ala Leu Leu Leu Phe Pro Asn
            770                 775                 780

Gly Thr Val Ile His Leu Leu Ala Phe Asp Thr Leu Pro Ile Ala Thr
785                 790                 795                 800

Ile Ala Pro Gly Phe Leu Ala Ala Ser Ala Leu Gly Val Val Met Ile
            805                 810                 815

Thr Ala Ala Leu Ala Gly Ile Leu Arg Val Val Arg Thr Cys Val Pro
            820                 825                 830
```

```
Phe Leu Trp Arg Arg Glu
        835

<210> SEQ ID NO 46
<211> LENGTH: 516
<212> TYPE: PRT
<213> ORGANISM: Herpes simplex virus-2

<400> SEQUENCE: 46

Met Gly Phe Val Cys Leu Phe Gly Leu Val Val Met Gly Ala Trp Gly
1               5                   10                  15

Ala Trp Gly Gly Ser Gln Ala Thr Glu Tyr Val Leu Arg Ser Val Ile
            20                  25                  30

Ala Lys Glu Val Gly Asp Ile Leu Arg Val Pro Cys Met Arg Thr Pro
        35                  40                  45

Ala Asp Asp Val Ser Trp Arg Tyr Glu Ala Pro Ser Val Ile Asp Tyr
    50                  55                  60

Ala Arg Ile Asp Gly Ile Phe Leu Arg Tyr His Cys Pro Gly Leu Asp
65                  70                  75                  80

Thr Phe Leu Trp Asp Arg His Ala Gln Arg Ala Tyr Leu Val Asn Pro
                85                  90                  95

Phe Leu Phe Ala Ala Gly Phe Leu Glu Asp Leu Ser His Ser Val Phe
            100                 105                 110

Pro Ala Asp Thr Gln Glu Thr Thr Thr Arg Arg Ala Leu Tyr Lys Glu
        115                 120                 125

Ile Arg Asp Ala Leu Gly Ser Arg Lys Gln Ala Val Ser His Ala Pro
    130                 135                 140

Val Arg Ala Gly Cys Val Asn Phe Asp Tyr Ser Arg Thr Arg Arg Cys
145                 150                 155                 160

Val Gly Arg Arg Asp Leu Arg Pro Ala Asn Thr Thr Ser Thr Trp Glu
                165                 170                 175

Pro Pro Val Ser Ser Asp Asp Glu Ala Ser Ser Gln Ser Lys Pro Leu
            180                 185                 190

Ala Thr Gln Pro Pro Val Leu Ala Leu Ser Asn Ala Pro His Gly Gly
        195                 200                 205

Ser Pro Arg Arg Glu Val Gly Ala Gly Ile Leu Ala Ser Asp Ala Thr
    210                 215                 220

Ser His Val Cys Ile Ala Ser His Pro Gly Ser Gly Ala Gly Gln Pro
225                 230                 235                 240

Thr Arg Leu Ala Ala Gly Ser Ala Val Gln Arg Arg Pro Arg Gly
                245                 250                 255

Cys Pro Pro Gly Val Met Phe Ser Ala Ser Thr Thr Pro Glu Gln Pro
            260                 265                 270

Leu Gly Leu Ser Gly Asp Ala Thr Pro Pro Leu Pro Thr Ser Val Pro
        275                 280                 285

Leu Asp Trp Ala Ala Phe Arg Arg Ala Phe Leu Ile Asp Asp Ala Trp
    290                 295                 300

Arg Pro Leu Leu Glu Pro Glu Leu Ala Asn Pro Leu Thr Ala Arg Leu
305                 310                 315                 320

Leu Ala Glu Tyr Asp Arg Arg Cys Gln Thr Glu Val Leu Pro Pro
                325                 330                 335

Arg Glu Asp Val Phe Ser Trp Thr Arg Tyr Cys Thr Pro Asp Asp Val
            340                 345                 350

Arg Val Val Ile Ile Gly Gln Asp Pro Tyr His His Pro Gly Gln Ala
```

```
            355                 360                 365
His Gly Leu Ala Phe Ser Val Arg Ala Asp Val Pro Val Pro Ser
    370                 375                 380

Leu Arg Asn Val Leu Ala Val Lys Asn Cys Tyr Pro Asp Ala Arg
385                 390                 395                 400

Met Ser Gly Arg Gly Cys Leu Glu Lys Trp Ala Arg Asp Gly Val Leu
                405                 410                 415

Leu Leu Asn Thr Thr Leu Thr Val Lys Arg Gly Ala Ala Ser His
                420                 425                 430

Ser Lys Leu Gly Trp Asp Arg Phe Val Gly Val Val Arg Arg Leu
            435                 440                 445

Ala Ala Arg Arg Pro Gly Leu Val Phe Met Leu Trp Gly Ala His Ala
        450                 455                 460

Gln Asn Ala Ile Arg Pro Asp Pro Arg Gln His Tyr Val Leu Lys Phe
465                 470                 475                 480

Ser His Pro Ser Pro Leu Ser Lys Val Pro Phe Gly Thr Cys Gln His
                485                 490                 495

Phe Leu Ala Ala Asn Arg Tyr Leu Glu Thr Arg Asp Ile Met Pro Ile
                500                 505                 510

Asp Trp Ser Val
            515

<210> SEQ ID NO 47
<211> LENGTH: 904
<212> TYPE: PRT
<213> ORGANISM: Herpes simplex virus-2

<400> SEQUENCE: 47

Met Arg Gly Gly Gly Leu Ile Cys Ala Leu Val Val Gly Ala Leu Val
1               5                   10                  15

Ala Val Ala Ser Ala Ala Pro Ala Ala Pro Ala Pro Arg Ala
            20                  25                  30

Ser Gly Gly Val Ala Ala Thr Val Ala Ala Asn Gly Gly Pro Ala Ser
        35                  40                  45

Arg Pro Pro Pro Val Pro Ser Pro Ala Thr Thr Lys Ala Arg Lys Arg
    50                  55                  60

Lys Thr Lys Lys Pro Pro Lys Arg Pro Glu Ala Thr Pro Pro Asp
65                  70                  75                  80

Ala Asn Ala Thr Val Ala Ala Gly His Ala Thr Leu Arg Ala His Leu
                85                  90                  95

Arg Glu Ile Lys Val Glu Asn Ala Asp Ala Gln Phe Tyr Val Cys Pro
                100                 105                 110

Pro Pro Thr Gly Ala Thr Val Val Gln Phe Glu Gln Pro Arg Arg Cys
            115                 120                 125

Pro Thr Arg Pro Glu Gly Gln Asn Tyr Thr Glu Gly Ile Ala Val Val
        130                 135                 140

Phe Lys Glu Asn Ile Ala Pro Tyr Lys Phe Lys Ala Thr Met Tyr Tyr
145                 150                 155                 160

Lys Asp Val Thr Val Ser Gln Val Trp Phe Gly His Arg Tyr Ser Gln
                165                 170                 175

Phe Met Gly Ile Phe Glu Asp Arg Ala Pro Val Pro Phe Glu Glu Val
                180                 185                 190

Ile Asp Lys Ile Asn Thr Lys Gly Val Cys Arg Ser Thr Ala Lys Tyr
            195                 200                 205
```

-continued

Val Arg Asn Asn Met Glu Thr Thr Ala Phe His Arg Asp Asp His Glu
210                 215                 220

Thr Asp Met Glu Leu Lys Pro Ala Lys Val Ala Thr Arg Thr Ser Arg
225                 230                 235                 240

Gly Trp His Thr Thr Asp Leu Lys Tyr Asn Pro Ser Arg Val Glu Ala
            245                 250                 255

Phe His Arg Tyr Gly Thr Thr Val Asn Cys Ile Val Glu Glu Val Asp
            260                 265                 270

Ala Arg Ser Val Tyr Pro Tyr Asp Glu Phe Val Leu Ala Thr Gly Asp
        275                 280                 285

Phe Val Tyr Met Ser Pro Phe Tyr Gly Tyr Arg Glu Gly Ser His Thr
290                 295                 300

Glu His Thr Ser Tyr Ala Ala Asp Arg Phe Lys Gln Val Asp Gly Phe
305                 310                 315                 320

Tyr Ala Arg Asp Leu Thr Thr Lys Ala Arg Ala Thr Ser Pro Thr Thr
                325                 330                 335

Arg Asn Leu Leu Thr Thr Pro Lys Phe Thr Val Ala Trp Asp Trp Val
            340                 345                 350

Pro Lys Arg Pro Ala Val Cys Thr Met Thr Lys Trp Gln Glu Val Asp
        355                 360                 365

Glu Met Leu Arg Ala Glu Tyr Gly Gly Ser Phe Arg Phe Ser Ser Asp
370                 375                 380

Ala Ile Ser Thr Thr Phe Thr Thr Asn Leu Thr Glu Tyr Ser Leu Ser
385                 390                 395                 400

Arg Val Asp Leu Gly Asp Cys Ile Gly Arg Asp Ala Arg Glu Ala Ile
                405                 410                 415

Asp Arg Met Phe Ala Arg Lys Tyr Asn Ala Thr His Ile Lys Val Gly
                420                 425                 430

Gln Pro Gln Tyr Tyr Leu Ala Thr Gly Gly Phe Leu Ile Ala Tyr Gln
            435                 440                 445

Pro Leu Leu Ser Asn Thr Leu Ala Glu Leu Tyr Val Arg Glu Tyr Met
        450                 455                 460

Arg Glu Gln Asp Arg Lys Pro Arg Asn Ala Thr Pro Ala Pro Leu Arg
465                 470                 475                 480

Glu Ala Pro Ser Ala Asn Ala Ser Val Glu Arg Ile Lys Thr Thr Ser
                485                 490                 495

Ser Ile Glu Phe Ala Arg Leu Gln Phe Thr Tyr Asn His Ile Gln Arg
                500                 505                 510

His Val Asn Asp Met Leu Gly Arg Ile Ala Val Ala Trp Cys Glu Leu
            515                 520                 525

Gln Asn His Glu Leu Thr Leu Trp Asn Glu Ala Arg Lys Leu Asn Pro
530                 535                 540

Asn Ala Ile Ala Ser Ala Thr Val Gly Arg Arg Val Ser Ala Arg Met
545                 550                 555                 560

Leu Gly Asp Val Met Ala Val Ser Thr Cys Val Pro Val Ala Pro Asp
                565                 570                 575

Asn Val Ile Val Gln Asn Ser Met Arg Val Ser Ser Arg Pro Gly Thr
            580                 585                 590

Cys Tyr Ser Arg Pro Leu Val Ser Phe Arg Tyr Glu Asp Gln Gly Pro
        595                 600                 605

Leu Ile Glu Gly Gln Leu Gly Glu Asn Asn Glu Leu Arg Leu Thr Arg
610                 615                 620

Asp Ala Leu Glu Pro Cys Thr Val Gly His Arg Arg Tyr Phe Ile Phe

```
                625                 630                 635                 640
Gly Gly Gly Tyr Val Tyr Phe Glu Gly Tyr Ala Tyr Ser His Gln Leu
                    645                 650                 655

Ser Arg Ala Asp Val Thr Thr Val Ser Thr Phe Ile Asp Leu Asn Ile
                    660                 665                 670

Thr Met Leu Glu Asp His Glu Phe Val Pro Leu Glu Val Tyr Thr Arg
                    675                 680                 685

His Glu Ile Lys Asp Ser Gly Leu Leu Asp Tyr Thr Glu Val Gln Arg
                    690                 695                 700

Arg Asn Gln Leu His Asp Leu Arg Phe Ala Asp Ile Asp Thr Val Ile
705                 710                 715                 720

Arg Ala Asp Ala Asn Ala Ala Met Phe Ala Gly Leu Cys Ala Phe Phe
                    725                 730                 735

Glu Gly Met Gly Asp Leu Gly Arg Ala Val Gly Lys Val Val Met Gly
                    740                 745                 750

Val Val Gly Gly Val Val Ser Ala Val Ser Gly Val Ser Ser Phe Met
                    755                 760                 765

Ser Asn Pro Phe Gly Ala Leu Ala Val Gly Leu Leu Val Leu Ala Gly
                    770                 775                 780

Leu Val Ala Ala Phe Phe Ala Phe Arg Tyr Val Leu Gln Leu Gln Arg
785                 790                 795                 800

Asn Pro Met Lys Ala Leu Tyr Pro Leu Thr Thr Lys Glu Leu Lys Thr
                    805                 810                 815

Ser Asp Pro Gly Gly Val Gly Gly Glu Gly Glu Glu Gly Ala Glu Gly
                    820                 825                 830

Gly Gly Phe Asp Glu Ala Lys Leu Ala Glu Ala Arg Glu Met Ile Arg
                    835                 840                 845

Tyr Met Ala Leu Val Ser Ala Met Glu Arg Thr Glu His Lys Ala Arg
                    850                 855                 860

Lys Lys Gly Thr Ser Ala Leu Leu Ser Ser Lys Val Thr Asn Met Val
865                 870                 875                 880

Leu Arg Lys Arg Asn Lys Ala Arg Tyr Ser Pro Leu His Asn Glu Asp
                    885                 890                 895

Glu Ala Gly Asp Glu Asp Glu Leu
                    900
```

<210> SEQ ID NO 48
<211> LENGTH: 393
<212> TYPE: PRT
<213> ORGANISM: Herpes simplex virus-2

<400> SEQUENCE: 48

```
Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
                20                  25                  30

Ser Leu Lys Met Ala Asp Pro Asn Arg Phe Arg Gly Lys Asn Leu Pro
            35                  40                  45

Val Leu Asp Arg Leu Thr Asp Pro Pro Gly Val Lys Arg Val Tyr His
        50                  55                  60

Ile Gln Pro Ser Leu Glu Asp Pro Phe Gln Pro Ser Ile Pro Ile
65                  70                  75                  80

Thr Val Tyr Tyr Ala Val Leu Glu Arg Ala Cys Arg Ser Val Leu Leu
                85                  90                  95
```

-continued

```
His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Glu Leu Ser Asp Thr Thr Asn Ala
        275                 280                 285

Thr Gln Pro Glu Leu Val Pro Glu Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His Ala Pro Ala Ala Pro
                325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Ala Gln
        355                 360                 365

Met Ala Pro Lys Arg Leu Arg Leu Pro His Ile Arg Asp Asp Ala
    370                 375                 380

Pro Pro Ser His Gln Pro Leu Phe Tyr
385                 390

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 49

His His His His His His
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 50

Arg Arg Arg Arg Asp
1               5

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tcgtcgttgt cgttttgtcg tt                                           22

<210> SEQ ID NO 52
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tcataacgtt cc                                                      12

<210> SEQ ID NO 53
<211> LENGTH: 5
<212> TYPE: PRT
<213> ORGANISM: Human cytomegalovirus

<400> SEQUENCE: 53

Arg Thr Lys Arg Ser
1               5

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
aaaaaaaaaa aaaacgttaa aaaaaaaaaa                                   30

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Arg Arg Arg Arg Asp
1               5
```

VACCINE COMPOSITIONS OF HERPESVIRUS ENVELOPE PROTEIN COMBINATIONS TO INDUCE IMMUNE RESPONSE

CROSS-REFERENCE TO RELATED APPLICATIONS

This application is a U.S. National Stage application of PCT/US2018/015459 filed 26 Jan. 2018, which claims the benefit of, and relies on the filing date of, U.S. provisional patent application No. 62/451,396, filed 27 Jan. 2017, the entire disclosure of which is incorporated herein by reference.

GOVERNMENT INTEREST

This invention was made with government support under grant Q574LJ15 awarded by the Uniformed Services University. The government has certain rights in the invention.

SEQUENCE LISTING

The instant application contains a Sequence Listing which has been submitted electronically in ASCII format and is hereby incorporated by reference in its entirety. Said ASCII copy, created on 25 Jan. 2018, is named HMJ-153-PCT_SL.txt and is 207,545 bytes in size.

BACKGROUND

Human herpes viruses are a group of enveloped DNA viruses responsible for significant global morbidity and mortality in humans. (Eisenberg et al., Viruses, 4:800-32, 2012). There are eight types of known human herpes virus (HHV), including: (i) Type 1 human herpes virus (HHV-1), which is herpes simplex virus-1 (HSV-1); (ii) HHV-2 which is herpes simplex virus-2 (HSV-2); (iii) HHV-3 which is varicella-Zoster virus (VZV); (iv) HHV-4 which is Epstein Barr virus (EBV); (v) HHV-5, which is human cytomegalovirus (HCMV); (vi) HHV-6; (vii) HHV-7; and (viii) HHV-8 which is Kaposi's sarcoma-associated herpesvirus (KSHV).

In humans, these viruses are known to cause the following diseases. HSV-1 causes oral herpes, HSV-2 causes genital herpes, and VZV causes chickenpox and shingles. EBV causes infectious mononucleosis and is strongly associated with several B cell lymphomas, nasopharyngeal carcinoma, and gastric adenocarcinoma. HCMV causes severe infection in immunosuppressed patients and is the leading non-genetic cause of hearing loss. HHV-6 and 7 cause roseola *infantum* (Sixth disease), and HVV-8 causes Kaposi's sarcoma in several clinical settings including in patients infected with human immunodeficiency virus (HIV).

EBV primarily infects B cells and nasopharyngeal epithelial cells. EBV infection of B cells is initiated by binding of the EBV envelope protein gp350 to the complement receptor CR2/CD21. (Hutt-Fletcher, *J. Virol.*, 81:7825-32, 2007; and Shannon-Lowe et al., *Curr. Opin. Virol.*, 4:78-84, 2014). Upon binding to B cell CR2, EBV gp42 interacts with cell surface MHC-II receptors, leading to its association with the heterodimeric EBV gH/gL protein. The heterodimer gH/gL then undergoes a conformational change upon binding gp42, leading to activation of the EBV fusion protein gB, that directly mediates viral-host cell membrane fusion. (Neuhierl et al., *Proc. Natl. Acad. Sci. U.S.A.*, 99:15036-41, 2002). Like EBV, the binding, fusion and host cell entry of other HHV family members is mediated primarily by the gB, gH, and gL polypeptides, in conjunction with other accessory proteins, which typically bind to different receptors on the host cell surface.

There is currently no prophylactic EBV vaccine in clinical use. Studies in non-human primates using gp350-based vaccination strategies have shown protection against EBV-induced lymphoma and EBV replication. (Cohen, *Clin. Transl. Immunology*, 4:e32, 2015). A phase II clinical trial conducted in EBV-seronegative young adults using a recombinant monomeric gp350 protein versus placebo suggested a partial protective effect of gp350 vaccination on infectious mononucleosis (IM) development. (Sokal et al., *J. Infect. Dis.*, 196:1749-53, 2007; and Moutschen et al., *Vaccine*, 25:4697-705, 2007). However, the vaccine did not prevent asymptomatic EBV infection. A phase I trial of recombinant monomeric gp350 protein given to children with chronic kidney disease demonstrated only a minority of subjects developing detectable neutralizing serum anti-gp350 titers. (Rees et al., *Transplantation*, 88:1025-9, 2009).

There is also no prophylactic HCMV vaccine commercially available today. Earlier clinical trials using live attenuated Towne or AD169 HCMV viral vaccines, both of which lacked expression of a pentameric complex (gH/gL/UL128/UL130/UL131A), proved to be ineffective in preventing HCMV infection in either healthy volunteers or renal transplant recipients, though some efficacy was demonstrated in overt HCMV disease in high risk Recipient-Donor+renal transplant recipients (Fu et al., *Vaccine*, 32:2525-33, 2014). New HCMV viral strains engineered to express the pentameric complex are currently being evaluated, but safety concerns persist using this approach. A phase II clinical trial using recombinant HCMV gB protein derived from the Towne strain of HCMV (Spaete RR, *Transplant Proc.*, 23:90-6, 1991) demonstrated 50% efficacy in preventing HCMV infection in HCMV seronegative women (Pass RF, *J. Clin. Virol.*, 46 Suppl 4:S73-6, 2009) and 50% efficacy in preventing HCMV viremia in solid organ transplantation patients. The HCMV gB protein used in Phase II clinical trials had been modified to remove the furin cleavage site. Thus, the gB did not assume its native trimeric conformation (Sharma et al., *Virology*, 435:239-49, 2013). Although these two studies have encouraged further evaluation of gB as a prophylactic HCMV vaccine, they indicate a compelling need for a more effective prophylactic vaccine formulation.

WO2014/018858 and WO2015/089340 describe strategies for enhancing immunity that involve multimerizing antigens. For example, WO2014/018858 describes fusion proteins comprising at least two antigens, separated by a linker sequence, and an oligomerization domain, including multimeric HHV antigens, such as gp350, gB, gH, and gL. WO2015/089340 describes a modified herpesvirus gB obtained by inserting a peptide linker at the furin cleavage site in the herpesvirus gB polypeptide extracellular domain. Inserting the peptide linker removes the furin recognition sequence, such that expression of the modified herpesvirus gB results in the production of a homotrimeric gB complex that provides enhanced immunogenicity.

Combining multiple antigens in a vaccine does not necessarily result in enhanced immunity or even additive effects. In fact, when multiple antigens are co-administered as part of a multicomponent vaccine or as part of a sequential immunization schedule, the antibody response to one or more of the antigens may be reduced or diminished due to vaccine or immune interference. (PrabhuDas et al., *Nature Immunology*, 12(3):189-194, 2011). Similarly, when certain haptens are combined with a carrier protein, the antibody response to the hapten is often inhibited if the recipient has been previously immunized with the carrier protein. This phenomenon has been called carrier-induced epitope suppression and has been demonstrated to occur with a number of peptide-carrier protein conjugates. (Peeters et al., *Infection and Immunity*, 59(10):3504-3510, 1991). It can also occur when certain saccharides are combined with a carrier protein, particularly when the recipient is primed with a high dose of the carrier protein (i.e., a dose high enough to induce an antibody response to the carrier protein). (Peeters et al., *Infection and Immunity*, 59(10):3504-3510, 1991). Thus, often times, when two or more antigens are administered to a subject, the antibody response to one or more of the antigens is diminished due to immune interference. Therefore, when administering multiple proteins as part of a vaccination or immunization schedule, it is important to carefully evaluate the interactions between the proteins and how those interactions might affect the immune system's response.

New and improved antigen compositions for enhancing immune responses to HHV are needed.

SUMMARY

Human herpes viruses share a general strategy for infection of host cells. Specifically, the envelope membrane of the virus fuses with the plasma membrane of the host cell, with subsequent entry into the cytoplasm, or the envelope membrane of the virus fuses with the endosomal membrane after the virus is endocytosed and then enters the cytoplasm of the host cell. The core HHV envelope proteins involved in the fusion process are the conserved glycoprotein B (gB), glycoprotein H (gH), and glycoprotein L (gL). The gH and gL proteins typically form a noncovalently associated heterodimeric complex during the fusion process.

As disclosed in this application, immunization with a combination of two or more of these HHV proteins involved in mediating HHV binding, fusion, and entry into host cells, such as gp350, gH, gL, and gB, produces additive or synergistic antibody responses. These robust results are particularly unexpected in view of the art-recognized problem of vaccine or immune interference, commonly observed when administering multiple antigens as part of a multicomponent vaccine or a sequential vaccination schedule. Without intending to be bound by any theory, it appears that the combination of two or more HHV polypeptides elicits high-titer, neutralizing antibody responses that block different steps of the virus-host cell fusion process and, thus, provide improved protection against HHV infection in vivo.

Although strategies for multimerizing HHV proteins to enhance immunogenicity have recently been reported (see e.g., WO2014/018858 and WO2015/089340), we have discovered that unexpected additive and synergistic antibody responses can be obtained by combining monomeric or multimeric forms of the HHV fusion and host cell entry protein. Thus, in certain embodiments, one or more of the HHV fusion and host cell entry proteins is monomeric and/or multimeric. The HHV fusion and host cell entry proteins can be recombinant proteins or native proteins. In certain embodiments, the HHV fusion and host cell entry proteins have been modified and are not naturally occurring proteins. For example, the proteins may be truncated, multimerized, or combined in a fusion protein.

Although typically administered as polypeptides, it is also possible to administer nucleic acids encoding the HHV fusion and host cell entry proteins as a DNA vaccine, an RNA vaccine, or a viral vector vaccine. It is also possible to administer virus-like particles that express the HHV fusion and host cell entry proteins.

The present disclosure also discloses for the first time that high titer anti-HHV antibodies, such as antibodies generated in response to the HHV protein combinations disclosed herein, can passively transfer immunity and protect against HHV infection. This aspect covers methods of identifying biological samples that contain high titer anti-HHV antibodies and collecting antibodies and/or immune cells from individuals that are highly seropositive for HHV antigens, and/or individuals who have been administered the antigenic compositions disclosed herein, and administering those antibodies and/or immune cells to a subject in need thereof, thereby passively transferring immunity to the subject and protecting the subject from HHV infection, particularly in individuals who are immunocompromised or otherwise at risk of developing an HHV infection.

In a first aspect, the present disclosure provides antigenic compositions that include at least two of the following antigenic human herpesvirus polypeptides (or one or more nucleic acids encoding the same): a glycoprotein B (gB) polypeptide comprising an extracellular domain of human herpesvirus gB; a glycoprotein 350 (gp350) polypeptide comprising an extracellular domain of human herpesvirus gp350; a glycoprotein L (gL) polypeptide; and a glycoprotein H (gH) polypeptide comprising an extracellular domain of human herpesvirus gH. Such compositions may optionally include adjuvants and/or excipients common in the field of vaccine development.

The human herpes virus from which the polypeptides are obtained can be human cytomegalovirus (HCMV), Herpes Simplex Virus-1 (HSV-1), Herpes Simplex Virus-2 (HSV-2), Varicella-Zoster Virus (VZV), Epstein-Barr Virus (EBV), Human Herpes Virus 6 (HHV 6), Human Herpes Virus 7 (HHV 7), and/or Kaposi Sarcoma-related Herpes Virus (HSHV). In one embodiment, the polypeptides are EBV polypeptides.

In certain embodiments, the gB polypeptide, the gp350 polypeptide, the gL polypeptide, and/or the gH polypeptide, when present in the antigenic composition, each further comprises a corresponding intracellular domain. The extracellular domain of the selected polypeptides can be fused to the intracellular domain via a polypeptide linker sequence of about 6 to about 70 amino acids in length, or in particular about 15 amino acids in length, for example. In other embodiments, at least two, or optionally three, of the human herpesvirus polypeptides form a fusion protein, wherein the fusion protein optionally comprises a polypeptide linker sequence that covalently links the polypeptides.

In a further embodiment, the antigenic composition includes the gB polypeptide and one or more of the gp350, gL, and gH polypeptides. In various embodiments mentioned herein, the gB polypeptide can be monomeric or multimeric (e.g., dimeric, trimeric, tetrameric, etc.). In certain embodiments, the antigenic composition comprises the gB polypeptide, the gH polypeptide, and the gL polypeptide. The gL and gH polypeptides can optionally be present as a heterodimer. In certain embodiments, the heterodimer is a fusion protein. In other embodiments, the heterodimer is a non-covalently associated protein complex. In one embodiment, the gB polypeptide is monomeric, dimeric, or trimeric and the gL and gH polypeptides form a heterodimer. In another embodiment, the gB polypeptide is monomeric and the gL and gH polypeptides form a monomeric heterodimer.

In HCMV embodiments of the antigenic compositions, at least the following combinations are contemplated: gB polypeptide, the gH polypeptide, and the gL polypeptide. In one embodiment, the gB polypeptide is monomeric, dimeric, or trimeric and the gL and gH polypeptides form a heterodimer, which can be monomeric or multimeric (e.g., monomeric, dimeric, trimeric, or tetrameric). In another embodiment, the gB polypeptide is monomeric or trimeric and the gL and gH polypeptides form a monomeric or trimeric heterodimer. These antigenic compositions can further include a HCMV glycoprotein O (gO) polypeptide or an HCMV unique long 128 (UL128) polypeptide, an HCMV unique long 130 (UL130) polypeptide, and an HCMV unique long 131A (UL131A) polypeptide, and optionally an HCMV glycoprotein M polypeptide, and/or an HCMV glycoprotein N polypeptide.

In EBV embodiments of the antigenic compositions, at least the following combinations are contemplated: (a) the gp350 polypeptide and the gB polypeptide, wherein the gp350 polypeptide is monomeric or tetrameric gp350, and wherein the gB polypeptide is trimeric gB; (b) the gp350 polypeptide, the gH polypeptide, and the gL polypeptide, where (i) the polypeptides are monomeric, or (ii) the gp350 polypeptide is tetrameric, and the gH and gL polypeptides are trimeric; (c) the gB polypeptide, the gH polypeptide, and the gL polypeptide, where the gB polypeptide is trimeric gB, and where the gH polypeptide and gL polypeptide are both monomeric or trimeric; and (d) monomeric gp350 polypeptide, monomeric gH polypeptide and monomeric gL polypeptide, and trimeric gB polypeptide, where the gp350 polypeptide is tetrameric, the gH and gL polypeptides are monomeric or trimeric, and the gB polypeptide is trimeric. EBV antigen compositions can also optionally include a human EBV glycoprotein 42 (gp42) polypeptide, BDLF2 polypeptide, and/or a human EBV BamH1-M rightward reading frame 2 (BMRF-2) polypeptide.

In HSV-1 and/or HSV-2 embodiments of the antigenic compositions, at least the following combinations are contemplated: the gH polypeptide, the gL polypeptide, and the gB polypeptide, wherein each polypeptide is monomeric or multimeric and optionally wherein the gH and gL polypeptides form a gH/gL heterodimer. In certain embodiments, the gH/gL heterodimer is monomeric, dimeric, trimeric, or tetrameric and the gB polypeptide is monomeric, dimeric, or trimeric. In one embodiment, the combination comprises a monomeric or trimeric gH/gL heterodimer and a monomeric or trimeric gB polypeptide. These antigenic compositions can also optionally include an HSV-1 or HSV-2 glycoprotein D (gD) polypeptide, in monomeric, dimeric, trimeric, or tetrameric form.

In VZV embodiments of the antigenic compositions, at least the following combinations are contemplated: the gH polypeptide, the gL polypeptide, and the gB polypeptide, wherein each polypeptide is monomeric or multimeric and optionally wherein the gH and gL polypeptides form a gH/gL heterodimer. In certain embodiments, the gH/gL heterodimer is monomeric, dimeric, trimeric, or tetrameric and the gB polypeptide is monomeric, dimeric, or trimeric. In one embodiment, the combination comprises a monomeric or trimeric gH/gL heterodimer and a monomeric or trimeric gB polypeptide. These antigenic compositions can also optionally include one or more of a human VZV glycoprotein C (gC) polypeptide, human VZV glycoprotein E (gE) polypeptide, and/or human VZV glycoprotein I (gI) polypeptide.

In HHV-6 or HHV-7 embodiments of the antigenic compositions at least the following combinations are contemplated: the gH polypeptide, the gL polypeptide, and the gB polypeptide, wherein each polypeptide is monomeric or multimeric and optionally wherein the gH and gL polypeptides form a gH/gL heterodimer. In certain embodiments wherein the gH/gL heterodimer is monomeric, dimeric, trimeric, or tetrameric and the gB polypeptide is monomeric, dimeric, or trimeric. In one embodiment, the combination comprises a monomeric or trimeric gH/gL heterodimer and a monomeric or trimeric gB polypeptide.

In KSHV embodiments of the antigenic compositions, at least the following combinations are contemplated: the gH polypeptide, the gL polypeptide, and the gB polypeptide, wherein each polypeptide is monomeric or multimeric and optionally wherein the gH and gL polypeptides form a gH/gL heterodimer. In certain embodiments, the gH/gL heterodimer is monomeric, dimeric, trimeric, or tetrameric and the gB polypeptide is monomeric, dimeric, or trimeric. In one embodiment, the combination comprises a monomeric or trimeric gH/gL heterodimer and a monomeric or trimeric gB polypeptide. These antigenic compositions can also optionally include one or more of a human KSHV glycoprotein M (gM) polypeptide, a human KSHV glycoprotein N (gN) polypeptide, a human KSHV Open Reading Frame 68 (ORF68) polypeptide, and/or a human KSHV K8.1 polypeptide.

In antigenic compositions comprising nucleic acids, the nucleic acids can be in a viral vector that permits expression of the human herpesvirus polypeptides.

Also provided are methods for preventing or treating a human herpesvirus infection in a subject by administering a therapeutically effective amount of two or more of the HHV polypeptides that comprise the disclosed antigen compositions. Further, provided are methods for inducing immunity to a human herpesvirus in a subject by administering a therapeutically effective amount of two or more of the HHV fusion and host cell entry proteins that comprise one or more of the disclosed antigenic compositions. The two or more HHV fusion and host cell entry proteins may be administered simultaneously or separately.

The treated subjects can be those who are at risk of developing post-transplantation lymphoproliferative disorder (PTLD) following hematopoietic stem cell or solid organ transplantation and/or those suffering from a primary immunodeficiency syndrome. In the disclosed methods, the antigenic compositions can be administered sequentially or concurrently.

Recombinant nucleic acid constructs for expressing the HHV polypeptides or protein complexes are also disclosed, as well as their corresponding encoded polypeptides.

In one embodiment, the recombinant nucleic acid construct includes a first nucleic acid molecule encoding a HHV gL polypeptide, a second nucleic acid molecule encoding a HHV gH polypeptide, a third nucleic acid molecule encoding a HHV UL128 polypeptide, a fourth nucleic acid molecule encoding a HHV UL130 polypeptide, and a fifth nucleic acid molecule encoding a HHV UL131A polypeptide. In certain embodiments, a pentameric gH/gL/UL128/UL130/UL131A protein complex is formed when the polypeptides are expressed from the nucleic acid construct in a host cell. The polypeptides optionally do not include a transmembrane domain and/or an intracellular domain. In one embodiment, the recombinant nucleic acid construct further includes a first promoter operatively linked to the first nucleic acid and a second promoter operatively linked to the third nucleic acid molecule. The nucleic acid construct optionally also includes a first internal ribosome entry site (IRES) located between the first nucleic acid molecule and the second nucleic acid molecule, a second IRES located between the third nucleic acid molecule and the fourth nucleic acid molecule, and a third IRES located between the fourth nucleic acid molecule and the fifth nucleic acid molecule. Optionally, the nucleic acid construct also includes a first, second, third, fourth, and fifth nucleotide sequence encoding an IgG kappa light chain leader peptide, wherein the first, second, third, fourth, and fifth nucleotide sequence encoding the IgG kappa light chain leader peptide is in frame with the first, second, third, fourth, and fifth nucleic acid molecules, respectively. In certain embodiments, the HHV is HCMV, EBV, HSV-1, HSV-2, VZV, KSHV.

In another embodiment, the recombinant nucleic acid construct includes a first nucleic acid molecule encoding a HHV gL polypeptide, a second nucleic acid molecule encoding a HHV gH polypeptide, and a third nucleic acid molecule encoding a HHV gO polypeptide. In certain embodiments, a trimeric gL/gH/gO protein complex is formed when the polypeptides are expressed from the nucleic acid construct in a host cell. In certain embodiments, the HHV is HCMV, EBV, HSV-1, HSV-2, VZV, or KSHV.

Methods of passively transferring immunity against Epstein-Barr virus (EBV) are also disclosed. These methods are achieved by administering to a subject in need thereof immune cells or high titer anti-EBV immunoglobulins, wherein the immune cells or high titer anti-EBV immunoglobulins have been obtained from one or more blood, plasma, or serum samples, optionally human blood, plasma, or serum samples, that have been selected for the high titer anti-EBV immunoglobulins. In these embodiments, the titer of the high titer anti-EBV immunoglobulins can be up to 25-fold, 4- to 25-fold, or 10- to 20-fold, higher than the average titer of anti-EBV immunoglobulins obtained from unselected blood, plasma, or serum samples. The blood, plasma, or serum samples can be obtained from a donor who was immunized with two or more EBV fusion and host cell entry proteins. The blood, plasma, or serum samples can also be obtained from a donor who was immunized with a single multimeric EBV protein involved in mediating EBV binding, fusion, and entry into host cells, including but not limited to, tetrameric gp350, trimeric gH/gL, or trimeric gB. Subjects in need thereof can be subjects that are at risk of developing post-transplantation lymphoproliferative disorder (PTLD) following hematopoietic stem cell or solid organ transplantation, or that have or are at risk of developing nasopharyngeal carcinoma (NPC), Burkitt lymphoma, Hodgkin's lymphoma, non-Hodgkin's lymphoma, gastric carcinoma, severe infectious mononucleosis, chronic active EBV infection, multiple sclerosis, systemic lupus erythematosus, or rheumatoid arthritis. In certain embodiments, the subject is seronegative for EBV.

In one embodiment, the method of passively transferring immunity against EBV is performed on a subject that is concurrently receiving one or more of anti-CD20 antibody administration, anti-viral therapy, interferon alpha administration, radiotherapy, and chemotherapy.

In another embodiment of the passive transfer method, the method includes one or more of the following steps: (i) identifying a blood, plasma, or serum sample obtained from one or more human subjects that contain high EBV neutralizing activity; and/or (ii) collecting high titer anti-EBV immunoglobulins from the blood, plasma or serum sample containing high EBV neutralizing activity. In this embodiment and related method embodiments, the identifying step optionally includes subjecting the blood, plasma, or serum sample to a Raji B cell neutralization assay and/or a HeLa cell neutralization assay. In this embodiment, the HeLa cell neutralization assay includes the steps of infecting HeLa cells with GFP labeled EBV to yield EBV-infected HeLa cells, incubating the blood, plasma, or serum sample with the EBV-infected HeLa cells, analyzing the neutralization activity of the blood, plasma, or serum sample with flow cytometry or ELISpot assay and optionally calculating the $IC_{50}$ of the blood, plasma, or serum sample. Also in this embodiment, the blood, plasma, or serum sample is identified as containing high EBV neutralizing activity if the blood, plasma, or serum sample has an $IC_{50}$ that is 4- to 25-fold, or 10- to 20-fold, higher than the average $IC_{50}$ of unselected blood, plasma or serum samples.

In another embodiment of the passive transfer method, the method includes administering to one or more human donor subjects at least two of the following EBV polypeptides: an EBV gp350 polypeptide, an EBV gH/gL heterodimer comprising an EBV gH polypeptide and an EBV gL polypeptide, and an EBV gB polypeptide, in an amount sufficient to generate high titer anti-EBV immunoglobulin, and collecting the high titer anti-EBV immunoglobulins from the one or more human donor subjects before the step of administering to the subject the high titer anti-EBV immunoglobulins. In certain embodiments, the EBV gp350 polypeptide is monomeric, dimeric, trimeric, or tetrameric, the EBV gB polypeptide is monomeric, dimeric, or trimeric, and the gH/gL heterodimer is monomeric, dimeric, trimeric, or tetrameric.

In a further embodiment, methods are provided for passively transferring immunity against human cytomegalovirus (HCMV). The methods include the step of administering to a subject in need thereof immune cells or high titer anti-HCMV immunoglobulins, where the immune cells or high titer anti-HCMV immunoglobulins have been obtained from one or more blood, plasma, or serum samples, optionally human blood, plasma, or serum samples, that have been selected for the high titer anti-HCMV immunoglobulins. Optionally, the blood, plasma or serum samples have been obtained from a donor who was immunized with two or more HCMV fusion and host cell entry proteins. The blood, plasma, or serum samples can also be obtained from a donor who was immunized with a single multimeric HCMV protein involved in mediating HCMV binding, fusion, and entry into host cells, including but not limited to, trimeric gH/gL or trimeric gB. In one embodiment of this passive transfer method, the subject is at risk of contracting HCMV infection is a pregnant woman, a transplantation patient, a patient who is immunosuppressed during chemotherapy or radiotherapy, or a patient infected with human immunodeficiency virus (HIV).

In another embodiment of the HCMV passive transfer method, the method also includes one or more of the following steps performed before the step of administering to the subject the high titer anti-HCMV immunoglobulins: (i) administering to one or more human donor subjects at least two of an HCMV gB polypeptide, an HCMV gH/gL heterodimer comprising an HCMV gH polypeptide and an HCMV gL polypeptide, an HCMV glycoprotein O (gO) polypeptide, an HCMV UL128 polypeptide, an HCMV UL130 polypeptide, and an HCMV unique UL131A polypeptide, in an amount sufficient to generate a high titer anti-HCMV immunoglobulin response in the subject; and (ii) collecting the high titer anti-HCMV immunoglobulins from the one or more human donor subjects. In certain embodiments, the HCMV gB polypeptide is monomeric, dimeric, or trimeric, and the gH/gL heterodimer is monomeric, dimeric, trimeric, or tetrameric.

Also disclosed are methods of passively transferring immunity against Herpes Simplex Virus Type 1 (HSV-1) or Herpes Simplex Virus Type 2 (HSV-2). These methods achieve passive transfer by administering to a subject in need thereof immune cells or high titer anti-HSV-1 and/or anti-HSV-2 immunoglobulins, wherein the immune cells or high titer anti-HSV-1 or anti-HSV-2 immunoglobulins have been obtained from one or more blood, plasma, or serum samples, optionally human blood, plasma, or serum samples, that have been selected for the high titer anti-HSV-1 or anti-HSV-2 immunoglobulins. Optionally, the blood, plasma or serum samples have been obtained from a donor who was immunized with two or more HSV-1 or HSV-2 fusion and host cell entry proteins. The blood, plasma, or serum samples can also be obtained from a donor who was immunized with a single multimeric HSV-1 or HSV-2 protein involved in mediating HSV-1 or HSV-2 binding, fusion, and entry into host cells, including but not limited to, trimeric gH/gL or trimeric gB. In another embodiment of this method, the subject is at risk of developing encephalitis caused by HSV-1 or HSV-2 infection, or wherein the subject is a pregnant woman with active HSV-2 or HSV-1 infection and/or HSV encephalitis.

In another embodiment of the HSV-2 or HSV-1 passive transfer method, the method also includes one or more of the following steps performed before the step of administering to the subject the high titer anti-HSV-2 or HSV-1 immunoglobulins: (i) administering to one or more human donor subjects at least two of an HSV-1 or HSV-2 glycoprotein D (gD) polypeptide, an HSV-1 or HSV-2 gH/gL heterodimer comprising an HSV-1 or HSV-2 gH polypeptide and an HSV-1 or HSV-2 gL polypeptide, an HSV-1 or HSV-2 gB polypeptide, in an amount sufficient to generate high titer anti-HSV-1 or HSV-2 immunoglobulins; and/or (ii) collecting the high titer anti-HSV-1 and/or anti-HSV-2 immunoglobulins from the one or more human donor subjects. In certain embodiments, the HSV-1 or HSV-2 gB polypeptide is monomeric, dimeric, or trimeric, and the HSV-1 or HSV-2 gH/gL heterodimer is monomeric, dimeric, trimeric or tetrameric.

Also disclosed are methods of passively transferring immunity against VZV. These methods achieve passive transfer by administering to a subject in need thereof immune cells or high titer anti-VZV immunoglobulins, wherein the immune cells or high titer anti-VZV immunoglobulins have been obtained from one or more blood, plasma, or serum samples, optionally human blood, plasma, or serum samples, that have been selected for the high titer anti-VZV immunoglobulins. Optionally, the blood, plasma or serum samples have been obtained from a donor who was immunized with two or more VZV fusion and host cell entry proteins. The blood, plasma, or serum samples can also be obtained from a donor who was immunized with a single multimeric VZV protein involved in mediating VZV binding, fusion, and entry into host cells, including but not limited to, trimeric gH/gL or trimeric gB. In another embodiment of this method, the subject is at risk of developing Zoster (shingles) or Varicella (chickenpox).

In another embodiment of the VZV passive transfer method, the method also includes one or more of the following steps performed before the step of administering to the subject the high titer anti-VZV immunoglobulins: (i) administering to one or more human donor subjects at least two of a VZV gH/gL heterodimer comprising a VZV gH polypeptide and a VZV gL polypeptide, a VZV gB polypeptide, a VZV glycoprotein C (gC) polypeptide, a VZV glycoprotein E (gE) polypeptide, and a VZV glycoprotein I (gI) polypeptide, in an amount sufficient to generate high titer anti-VZV immunoglobulins; and/or (ii) collecting the high titer anti-VZV immunoglobulins from the one or more human donor subjects. In certain embodiments, the VZV gB polypeptide is monomeric, dimeric, or trimeric, and the VZV gH/gL heterodimer is monomeric, dimeric, trimeric, or tetrameric.

Also disclosed are methods of passively transferring immunity against human herpesvirus 6 (HHV-6) or human herpesvirus 7 (HHV-7). These methods achieve passive transfer by administering to a subject in need thereof immune cells or high titer anti-HHV-6 or anti-HHV-7 immunoglobulins, wherein the immune cells or high titer anti-HHV-6 or anti-HHV-7 immunoglobulins have been obtained from one or more blood, plasma, or serum samples, optionally human blood, plasma, or serum samples, that have been selected for the high titer anti-HHV-6 or anti-HHV-7 immunoglobulins. Optionally, the blood, plasma or serum samples have been obtained from a donor who was immunized with two or more HHV-6 or HHV-7 fusion and host cell entry proteins. The blood, plasma, or serum samples can also be obtained from a donor who was immunized with a single multimeric HHV-6 or HHV-7 protein involved in mediating HHV-6 or HHV-7 binding, fusion, and entry into host cells, including but not limited to, trimeric gH/gL or trimeric gB.

In another embodiment of the HHV-6 or HHV-7 passive transfer method, the method also includes one or more of the following steps performed before the step of administering to the subject the high titer anti-HHV-6 or anti-HHV-7 immunoglobulins: (i) administering to one or more human donor subjects at least a HHV-6 or HHV-7 gH/gL heterodimer and a HHV-6 or HHV-7 gB polypeptide, in an amount sufficient to generate high titer anti-HHV-6 or anti-HHV-7 immunoglobulins; and/or (ii) collecting the high titer anti-HHV-6 or anti-HHV-7 immunoglobulins from the one or more human donor subjects. In certain embodiments, the HHV-6 or HHV-7 gB polypeptide is monomeric, dimeric, or trimeric, and the gH/gL heterodimer is monomeric, dimeric, trimeric, or tetrameric, Also disclosed are methods of passively transferring immunity against Kaposi's sarcoma herpesvirus (KSHV). These methods achieve passive transfer by administering to a subject in need thereof immune cells or high titer anti-KSHV immunoglobulins, wherein the immune cells or high titer anti-KSHV immunoglobulins have been obtained from one or more blood, plasma, or serum samples, optionally human blood, plasma, or serum samples, that have been selected for the high titer anti-KSHV immunoglobulins. Optionally, the blood, plasma or serum samples have been obtained from a donor who was immunized with two or more KSHV fusion and host cell entry proteins. The blood, plasma, or serum samples can also be obtained from a donor who was immunized with a single multimeric KSHV protein involved in mediating KSHV binding, fusion, and entry into host cells, including but not limited to, trimeric gH/gL or trimeric gB. In another embodiment of this method, the subject is at risk of developing KSHV-associated Kaposi's sarcoma, primary effusion lymphoma, multicentric Cattleman's disease, KSHV-associated inflammatory cytokine syndrome, or KSHV immune reconstitution inflammatory syndrome.

In another embodiment of the KSHV passive transfer method, the method also includes one or more of the following steps performed before the step of administering to the subject the high titer anti-KSHV immunoglobulins: (i) administering to one or more human donor subjects at least two of a KSHV gH/gL heterodimer comprising a KSHV gH polypeptide and a KSHV gL polypeptide, a KSHV gB polypeptide, a KSHV gM polypeptide, a KSHV gN polypeptide, a KSHV ORF68 polypeptide, and a KSHV K8.1 polypeptide, in an amount sufficient to generate high titer anti-KSHV immunoglobulins; and/or (ii) collecting the high titer anti-KSHV immunoglobulins from the one or more human donor subjects. In certain embodiments, the KSHV gB polypeptide is monomeric, dimeric, or trimeric, and the gH/gL heterodimer is monomeric, dimeric, trimeric, or tetrameric.

BRIEF DESCRIPTION OF THE DRAWINGS

The accompanying drawings, which are incorporated in and constitute a part of this specification, illustrate certain embodiments, and together with the written description, serve to explain certain principles of the constructs and methods disclosed herein.

FIG. 1 shows a schematic of recombinant constructs for expressing non-limiting embodiments of multimeric EBV gp350, gH/gL, and gB. FIG. 1 discloses "$(Gly_4Ser_1)3$" as SEQ ID NO: 3, "$His_6$" as SEQ ID NO: 49, and "RRRRRD" as SEQ ID NO: 55.

FIGS. 2A-C show images of a Western blot of monomeric and multimeric EBV gH/gL (FIG. 2A), EBV gB (FIG. 2B), and EBV gp350 (FIG. 2C) polypeptides.

FIG. 3 shows EBV in vitro neutralization analysis of the sera from rabbits immunized with gp350 monomer (left panel, open circles), gp350 tetramer (left panel, closed circles), gB trimer (right panel), gH/gL monomer (middle panel, open circles), and gH/gL trimer (middle panel, closed circles).

FIGS. 4A-B show neutralization titers of serum from rabbits immunized with monomeric or tetrameric EBV gp350, monomeric or trimeric EBV gH/gL, or trimeric EBV gB in alum+CpG-ODN adjuvant in either Raji cells (FIG. 4A) or naïve peripheral blood human B cells (FIG. 4B).

FIG. 5 shows EBV neutralization activity of immune sera from rabbits immunized with trimeric EBV gB or monomeric EBV gH/gL or the synergistic combination of trimeric EBV gB and monomeric EBV gH/gL.

FIGS. 6A-B show EBV neutralization activity of pooled immune sera from rabbits (n=5) immunized with tetrameric EBV gp350, trimeric EBV gB, trimeric EBV gH/gL, or combinations thereof (FIG. 6A) demonstrating synergism, or with monomeric EBV gp350, trimeric EBV gB, monomeric EBV gH/gL, or synergistic combinations thereof (FIG. 6B).

FIGS. 7A-C show that passive transfer of immune rabbit sera prior to EBV-infection of humanized mice decreased EBV DNA load and increased survival rate of challenged mice. FIG. 7A shows survival rate of mice exposed to high-dose, live EBV infection after passive transfer of sera from rabbits immunized with tetrameric EBV gp350, trimeric EBV gH/gL, trimeric EBV gB, or adjuvant alone (control). FIG. 7B shows pooled immune sera from rabbits immunized with tetrameric EBV gp350 or trimeric EBV gH/gL decreased the copy number of EBV DNA in multiple organs of three humanized mice (geometric mean). FIG. 7C shows pooled immune sera from rabbits immunized with tetrameric EBV gp350, trimeric EBV gH/gL or trimeric EBV gB markedly decreased the EBV viral load in peripheral blood (geometric mean of 3 mice) compared to the control.

FIG. 8 shows a schematic of a wild type HCMV gB polypeptide and a recombinant construct for expressing a non-limiting embodiment of a trimeric HCMV gB polypeptide. FIG. 8 discloses "GGGGSGGGGSGGGGS" as SEQ ID NO: 3, "$His_6$" as SEQ ID NO: 49, and "RTKRS" as SEQ ID NO: 53.

FIGS. 9A-E show images of a Western blot of monomeric HCMV gB (FIG. 9A), trimeric HCMV gB (FIG. 9B), monomeric HCMV gH/gL (FIG. 9C), trimeric HCMV gH/gL (FIG. 9D), and monomeric HCMV UL128/130/131A (FIG. 9E).

FIG. 10 shows a schematic representing a non-limiting cloning strategy for expressing recombinant trimeric UL128/130/131A. FIG. 10 discloses "$(Gly_4Ser)_3$" as SEQ ID NO: 3 and "$His_6$" as SEQ ID NO: 49.

FIG. 11 shows the serum IgG titers of anti-gH/gL antibodies (left panel) and anti-gB antibodies (right panel) following immunization of rabbits with monomeric HCMV gH/gL, trimeric HCMV gB, trimeric HCMV gB+monomeric HCMV gH/gL, or a complex of trimeric HCMV gB+monomeric HCMV gH/gL.

FIG. 12A shows in vitro HCMV neutralization titers ($IC_{50}$) of non-heat inactivated serum from rabbits immunized with monomeric HCMV gH/gL, HCMV UL128/UL130/UL131A, monomeric HCMV gB (Sino gB), trimeric gB, or certain synergistic combinations thereof using the ARPE19 epithelial cell line.

FIG. 12B shows in vitro HCMV neutralization titers ($IC_{50}$) of heat-inactivated serum from rabbits immunized with monomeric HCMV gB (Sino gB), trimeric HCMV gB, monomeric HCMV gH/gL, or a synergistic combination of trimeric HCMV gB and monomeric HCMV gH/gL using the MRC-5 fibroblast cell line.

FIG. 13 shows a schematic diagram of a non-limiting DNA construct for expression of the pentameric complex gH/gL/UL128/UL130/UL131A.

FIG. 14 shows a schematic diagram of a non-limiting DNA construct for expression of a gH/gL/gO complex.

FIG. 15 shows in vitro HCMV neutralization activity of pooled immune sera from rabbits immunized with monomeric HCMV gB.

FIG. 16 shows in vitro HCMV neutralization activity of pooled immune sera from rabbits immunized with trimeric HCMV gB.

FIG. 17 shows in vitro HCMV neutralization activity of pooled immune sera from rabbits immunized with monomeric HCMV gH/gL.

FIG. 18 shows in vitro HCMV neutralization activity of in vitro combined immune sera from rabbits immunized with monomeric HCMV gB and monomeric HMCV gH/gL.

FIG. 19 shows in vitro HCMV neutralization activity of in vitro combined immune sera from rabbits immunized with trimeric HCMV gB and monomeric HMCV gH/gL.

FIG. 20 compares the in vitro HCMV neutralization activity of pooled immune sera from rabbits immunized with individual HCMV proteins (monomeric gB, trimeric gB, and monomeric gH/gL) or in vitro combinations of sera from rabbits immunized with HCMV proteins (monomeric gB and monomeric gH/gL or trimeric gB and monomeric gH/gL) and shows that the combination of HCMV proteins exhibit synergy.

FIG. 21A shows mouse serum titers of gB-specific IgG from mice immunized with different amounts of HCMV trimeric gB or HCMV monomeric gB.

FIGS. 21B-C show neutralization titers ($IC_{50}$) of heat-inactivated serum (FIG. 21B) or non-heat inactivated-serum (FIG. 21C) from mice immunized with monomeric HCMV gB or trimeric HCMV gB at various amounts (1 μg, 5 μg, and 25 μg) or CytoGam® IVIg at 10 mg/mL as a control (CSL Behring, King of Prussia, Pa., USA).

DETAILED DESCRIPTION

It is to be understood that the following detailed description is provided to give the reader a fuller understanding of certain embodiments, features, and details of aspects of the invention, and should not be interpreted as a limitation of the scope of the invention.

Definitions

In order that the present invention may be more readily understood, certain terms are first defined. Additional definitions are set forth throughout the detailed description.

The term "antibody" as used in this disclosure refers to an immunoglobulin or an antigen-binding fragment thereof. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: $IgG_1$, $IgG_2$, $IgG_3$, $IgG_4$, IgM, $IgA_1$, $IgA_2$, IgD, and IgE. By way of example, the light chain constant region can be kappa or lambda.

The terms "antigen-binding domain" and "antigen-binding fragment" refer to a part of an antibody molecule that comprises amino acids responsible for the specific binding between the antibody and antigen. For certain antigens, the antigen-binding domain or antigen-binding fragment may only bind to a part of the antigen. The part of the antigen that is specifically recognized and bound by the antibody is referred to as the "epitope" or "antigenic determinant" Antigen-binding domains and antigen-binding fragments include Fab (Fragment antigen-binding); a $F(ab')_2$ fragment, a bivalent fragment having two Fab fragments linked by a disulfide bridge at the hinge region; Fv fragment; a single chain Fv fragment (scFv) see e.g., Bird et al. (1988) *Science* 242:423-426; and Huston et al. (1988) *Proc. Natl. Acad. Sci. USA* 85:5879-5883); a Fd fragment having the two VH and $C_H1$ domains; dAb (Ward et al., (1989) *Nature* 341:544-546), and other antibody fragments that retain antigen-binding function. The Fab fragment has $V_H$-$C_H1$ and $V_L$-$C_L$ domains covalently linked by a disulfide bond between the constant regions. The $F_v$ fragment is smaller and has $V_H$ and $V_L$ domains non-covalently linked. To overcome the tendency of non-covalently linked domains to dissociate, a $scF_v$ can be constructed. The $scF_v$ contains a flexible polypeptide that links (1) the C-terminus of $V_H$ to the N-terminus of $V_L$, or (2) the C-terminus of $V_L$ to the N-terminus of $V_H$. A 15-mer $(Gly_4Ser)_3$ peptide (SEQ ID NO:3) may be used as a linker, but other linkers are known in the art. These antibody fragments are obtained using conventional techniques known to those with skill in the art, and the fragments are evaluated for function in the same manner as are intact antibodies.

As used in this application, "antigen" means a protein or fragment thereof or a polysaccharide linked to a protein carrier that, when expressed in an animal or human cell or tissue, is capable of triggering an immune response. The protein or fragment thereof may be glycosylated or non-glycosylated.

The term "extracellular domain" means refers to the portion of a full length polypeptide that extends beyond the cellular membrane and into the media in which the cell harboring the polypeptide resides. Polypeptides are known to generally contain an intracellular domain, transmembrane domain, and the remaining is the extracellular domain ("ECD"). When the term "extracellular domain" or "ECD" is used herein, it refers to the amino acids of a polypeptide that in wild type form extend beyond the cellular membrane, or any portion thereof recognizable by an antibody. Thus, the extracellular domain includes the entire domain, or any number of residues amenable to recombinant expression and inclusion in an antigenic composition, including polypeptides representing 75%, 80%, 85%, 90%, 95%, 96%, 97%, 98%, 99%, or 100% of the entire wild type extracellular domain of a polypeptide. That is, the extracellular domain may be shortened, or truncated, by known methods in the art, to remove extraneous domains, on either the carboxy-terminus or amino-terminus end, or both, of the polypeptide as needed to obtain more efficient and robust expression of the extracellular domain of the polypeptide.

The term "full length" with respect to a given polypeptide means the form of the polypeptide naturally translated from the coding DNA sequence, beginning with the ATG start codon, which encodes the first methionine in the amino acid sequence, and ending at the TGA, TAG, or TTA stop codon, or whichever stop codon employed by the organism.

The term "fusion protein" refers to a protein translated from a nucleic acid transcript generated by combining a first nucleic acid sequence that encodes a first protein and at least a second nucleic acid that encodes a second protein, where the fusion protein is not a naturally occurring protein. The nucleic acid construct may encode two or more proteins that are joined in the fusion protein to create a single polypeptide chain. The two or more nucleic acid sequences are optionally operatively linked to a single promoter, or operatively linked to two or more separate promoters.

The term "glycoprotein" means a polypeptide that has covalently attached to it one or more carbohydrate moieties, or oligosaccharide chains. The carbohydrate moieties are normally attached to glycoproteins co-translationally or as post-translational modifications.

The term "isolated," when used in the context of a polypeptide or nucleic acid refers to a polypeptide or nucleic acid that is substantially free of its natural environment and is thus distinguishable from a polypeptide or nucleic acid that might happen to occur naturally. For instance, an isolated polypeptide or nucleic acid is substantially free of cellular material or other polypeptides or nucleic acids from the cell or tissue source from which it was derived. The term also refers to preparations where the isolated polypeptide or nucleic acid is sufficiently pure for pharmaceutical compositions; or at least 70-80% (w/w) pure; or at least 80-90% (w/w) pure; or at least 90-95% pure; or at least 95%, 96%, 97%, 98%, 99%, or 100% (w/w) pure.

The term "leader sequence" refers to a short peptide sequence at the N-terminus of a recombinant protein that directs the recombinant protein to be secreted from a host cell.

The term "HHV fusion and host cell entry protein" refers to a human herpesvirus gB polypeptide, gH polypeptide, gL polypepide, gH/gL heterodimer, or gp350 polypeptide.

The term "HHV accessory protein" refers to a human herpes virus polypeptide other than gB, gH, gL, gH/gL, or gp350 that are involved in mediating viral binding, fusion, and host cell entry including, but not limited to, gp42, gM, gN, gI, gC, gD, ORF68, BMRF-2, BDLF2, UL128, UL130, UL131A, and gpK8.1.

The term "immune cell" means any cell of hematopoietic lineage involved in regulating an immune response against an antigen (e.g., an autoantigen). In typical embodiments, an immune cell is a leukocyte, such as a white blood cell Immune cells include neutrophils, eosinophils, basophils, lymphocytes, and/or monocytes. Lymphocytes include T lymphocytes and B lymphocytes. Immune cells can also be dendritic cells, natural killer (NK) cells, and/or a mast cell.

The term "intracellular domain" means the portion of a polypeptide that resides in the cytoplasm of a host cell. The intracellular domain includes that portion of the polypeptide that is not the transmembrane domain and is not the extracellular domain.

The term "gH/gL heterodimer" refers to a polypeptide or polypeptide complex comprising a HHV gH polypeptide and a HHV gL polypeptide. For example, the heterodimer can be a non-covalently associated complex between a HHV gH polypeptide and a HHV gL polypeptide. Alternatively, the heterodimer can be a recombinant fusion protein comprising a HHV gH protein joined to a HHV gL protein. The HHV gH protein can be joined to the HHV gL protein with a peptide linker.

As used herein, the term "modified gB polypeptide," refers to a HHV gB polypeptide in which the furin cleavage site in the extracellular domain of the gB polypeptide is replaced by a linker sequence, as described in WO 2015/089340.

The term "operatively linked" means that a promoter, or similar regulatory element, is positioned next to an expressible nucleotide sequence or coding region such that the transcription of that coding region is controlled and regulated by that promoter.

The terms "polypeptide," "peptide," and "protein" are used interchangeably herein to refer to polymers of amino acids.

The term "peptide linker" refers to a short, non-native peptide sequence that links two proteins or fragments of a protein.

The term "recombinant" when used in the context of a nucleic acid means a nucleic acid having nucleotide sequences that are not naturally joined together and can be made by artificially combining two otherwise separated segments of sequence. This artificial combination is often accomplished by chemical synthesis or, more commonly, by the artificial manipulation of isolated segments of nucleic acids, for example, by genetic engineering techniques. Recombinant nucleic acids include nucleic acid vectors comprising an amplified or assembled nucleic acid, which can be used to transform or transfect a suitable host cell. A host cell that comprises the recombinant nucleic acid is referred to as a "recombinant host cell." The gene is then expressed in the recombinant host cell to produce a "recombinant polypeptide." A recombinant nucleic acid can also serve a non-coding function (for example, promoter, origin of replication, ribosome-binding site and the like).

The term "transmembrane domain" (or "TM") means the portion of a polypeptide that naturally and completely traverses the cell membrane, which is a hydrophobic phospholipid bilayer that separates the cytoplasm from the external media in which the host cell resides. Transmembrane domains are typically between about 20 to about 25 amino acids in length, depending on the polypeptide. The transmembrane is typically lipophilic and therefore typically not included in antigenic compositions disclosed herein because it is difficult to express, purify and solubilize.

The term "pharmaceutically acceptable carrier" or "pharmaceutically acceptable excipient" means solvents, dispersion media, coatings, antibacterial agents and antifungal agents, isotonic agents, and absorption delaying agents, and the like, that are compatible with pharmaceutical administration. The use of such media and agents for pharmaceutically active substances is well known in the art. In certain embodiments, the pharmaceutically acceptable carrier or excipient is not naturally occurring.

The term "preventing" when used in the context of a disease or disease condition means prophylactic administration of a composition that stops or otherwise delays the onset of a pathological hallmark or symptom of a disease or disorder.

The term "treating" when used in the context of a disease or disease condition means ameliorating, improving or remedying a disease, disorder, or symptom of a disease or condition associated with the disease, or can mean completely or partially stopping, on a molecular level, the biochemical basis of the disease, such as halting replication of a virus, etc.

The term "therapeutically effective amount" when used in the context of an amount of an active agent means an amount that results in an improvement or remediation of the disease, disorder, or symptoms of the disease or condition.

The term "passive transfer" or "passive immunotherapy" or "passive immunity" means obtaining antibodies and/or immune cells from a subject exposed to an antigen and administering those antibodies and/or immune cells to a second subject, thereby providing the second subject with immune protection against challenge with the antigen. Antibodies or immune cells can be transferred in the form of blood, plasma, purified antibodies or immune cells, serum, etc. The second subject may be immunocompromised and/or naïve (never exposed to the antigen). (See, Keller et al., *Clin. Microbiol. Rev.*, 13 (4): 602-614, 2000).

Human Herpes Viruses. Herpesviridae are subdivided into three subfamilies: alphaherpesvirus, betaherpesvirus, and gammaherpes, based on biological properties and DNA genome similarities (Davison et al., *Antiviral Res.*, 56:1-11, 2002; MacDonald et al., *Am. J. Cardiol.*, 64:359-362, 1989). (See Table 1; Willis et al., *Br. Med. Bull.*, 62(1):125-138, 2002). The alphaherpesviruses include HHV-1, HHV-2, VZV, and pseudorabies virus (PRV), and are neurotropic, i.e., they tend to infect or attack mainly the nervous system of hosts. The alphaherpesvirus family has the broadest host range and spread rapidly in a cell culture. Latent alphaherpesvirus infections are usually established in sensory neurons and lytic infection occurs in epidermal cells (Roizman B, Sears AE. Herpes simplex viruses and their replication. In: Fields B N, Knipe D M, Howley P M, eds. Fields virology. Philadelphia: Lippincott-Raven, 1996:2231-95).

TABLE 1

| Common name | Designation | Subfamily | Genome size (kb pairs) | Site of latency and persistence |
| --- | --- | --- | --- | --- |
| Herpes simplex virus 1 | Human herpes virus 1 | α | 152 | Neurones (sensory ganglia) |
| Herpes simplex virus 2 | Human herpes virus 2 | α | 152 | Neurones (sensory ganglia) |
| Varicella zoster virus | Human herpes virus 3 | α | 125 | Neurones (sensory ganglia) |
| Epstein-Barr virus | Human herpes virus 4 | γ | 172 | B lymphocytes (oropharyngeal epithelium) |
| Human cytomegalovirus | Human herpes virus 5 | β | 235 | Blood monocytes (probably epithelial cells) |
| | Human herpes virus 6 | β | 170 | Monocytes, T lymphocytes |
| | Human herpes virus 7 | β | 145 | Monocytes, T lymphocytes |

TABLE 1-continued

| Common name | Designation | Sub-family | Genome size (kb pairs) | Site of latency and persistence |
|---|---|---|---|---|
| Kaposi's sarcoma associated herpes virus | Human herpes virus 8 | γ | 230 | Uncertain |

The betaherpesvirus subfamily consists of all cytomegaloviruses including human cytomegalovirus (HCMV, HHV-8), HHV-6, and HHV-7 and are commonly referred to as the roseoloviruses. The betaherpesvirus family has a restricted host range and a long infection cycle. Virus latency of betaherpesvirus is maintained in secretory glands, kidneys and other tissues (Hendrix et al., Expert Rev. Anti Infect. Ther., 5:427-439, 2007).

The gammaherpesvirus subfamily is divided into the Lymphocryptoviruses, which includes EBV, Rhadinovirus, and HHV-8 (KSHV). Gammaherpesviruses have a very narrow host range, and virus replication typically occurs in lymphoblastoid cells but can also lytically infect epithelial cells and fibroblasts. The latent form of gammaherpes virus infection is primarily observed in B and T lymphocytes (Ackerman, Vet. Microbiol., 113:211-222, 2006).
Gammaherpesviruses: Epstein Barr Virus (EBV, HHV-4), and Kaposi's Sarcoma Virus-Associated Herpes (KSHV, HHV-8)

Epstein Barr Virus (EBV, HHV-4). Epstein-Barr virus (EBV) is the first human cancer virus discovered, and it is strongly implicated in the etiology of post-transplant lymphoproliferative disorder (PTLD) and undifferentiated nasopharyngeal carcinoma (NPC). In both instances, the onset and severity of disease is positively correlated with the level of EBV viremia, strongly suggesting a role for lytic EBV re-activation in perpetuating disease. Epstein Barr virus (EBV), also known as human herpesvirus 4 (HHV-4), is a major, global source of morbidity and mortality, responsible for such pathologic entities as Burkitt lymphoma, nasopharyngeal carcinoma, infectious mononucleosis, a subset of Hodgkin's disease, and the lymphoproliferative syndrome in immunosuppressed patients. (Cohen JI, Curr. Opin. Immunol., 1999 August; 11(4):365-70; Thorley-Lawson DA, J., Allergy Clin. Immunol., 2005 August; 116(2):251-61; quiz 62; and Vetsika E K, Callan M., Expert Rev. Mol. Med., 2004 Nov. 5; 6(23):1-16). EBV has a double stranded, linear DNA genome. The nucleotide sequence of the EBV genome and the amino acid sequences of the viral proteins encoded thereby are known and set forth under the NCBI Reference Number NC_009334, Version NC_009334.1, GI:139424470, which sequences are hereby incorporated by reference.

EBV is a member of the gammaherpesvirus subfamily, which is further divided into lymphocryptoviruses, of which KSHV (HHV-8) is also a member. Replication for these family members typically occurs in lymphoblastoid cells, however they can also infect epithelial cells (e.g., nasopharyngeal epithelial cells) and fibroblasts. Latent infection is primarily observed in B and T lymphocytes. (Ackerman, Vet. Microbiol., 113:211-222, 2006).

Post-Transplant Lymphoproliferative Disease (PLTD).

Patients undergoing solid organ or stem cell transplantation are at risk of developing post-transplant lymphoproliferative disorder (PTLD), characterized by uncontrolled EBV-driven B cell proliferation that can evolve into non-Hodgkin lymphoma. (LaCasce, Oncologist, 11:674-80, 2006). PTLD may arise from EBV reactivation in seropositive recipients, or from primary EBV infection from the donor allograft, which poses even greater risk. (Dharnidharka et al., Am. J. Transplant, 12:976-83, 2012). A similar phenomenon also occurs in patients with AIDS.

Most cases of PTLD involve excessive EBV-driven proliferation of B cells, with a minority (10-15%) of cases being of the NK cell/T cell type (Petrara et al., Cancer Lett., 369(1):37-44, 2015; and Starzl et al., Lancet, 1:583-7, 1984). The frequency of PTLD ranges from 1-20% depending on the type of transplant, age of recipient, duration and type of immunosuppressive treatment (Ibrahim et al., Adv Hematol., 2012:230173, 2012; and Smets et al., Recent Results Cancer Res., 193:173-90, 2014). Younger patients, who are EBV seronegative, are at highest risk of developing PTLD following hematopoietic stem cell or solid organ transplantation, due to a lack of prior immunity. Patients with primary immunodeficiency syndromes are also at high risk for developing EBV-driven B cell lymphoproliferation and lymphoma (Rickinson et al., Trends Immunol., 35:159-69, 2014). The WHO defines three major histological types of PTLD of increasing severity: early lesions, polymorphic (P-PTLD), and monomorphic (M-PTLD) (Harris et al., Semin. Diagn. Pathol., 14:8-14, 1997), with the latter typically manifesting as non-Hodgkin lymphoma.

The initial management of PTLD is a reduction in immunosuppression. Additional therapeutic options include B cell-depleting anti-CD20 mAb treatment, anti-viral therapy, intravenous immunoglobulin (IVIg) and interferon (IFN)-γ (LaCasce A S, Oncologist, 11:674-80, 2006). Although IVIg in particular has been used empirically in combination with other therapies to treat PTLD, there have been no studies assessing its potential clinical benefit.

Nasopharyngeal Carcinoma and EBV.

The non-keratinizing variant of squamous cell carcinoma of the nasopharynx (NPC) is endemic in east and southeast Asia and in parts of north and east Africa, and in 2012 accounted for 86,500 cases of cancer worldwide. (Chua et al., Lancet, 387(10022):1012-1024, 2016). NPC manifests clinically as epistaxis, unilateral nasal obstruction, auditory complaints, and cranial nerve palsies, with frequent metastasis to cervical lymph nodes. Radiotherapy is the primary treatment for NPC, with additional chemotherapy utilized for more advanced cases. (Id.). 5-year survival is 70-98% depending upon the stage, but NPC has a tendency to recur.

Undifferentiated NPC is invariably associated with EBV, which is believed to play a pathogenic role in tumor development and progression. (Tsang et al., Virol. Sin., 30:107-21, 2015). Establishment of latent EBV infection in pre-malignant nasopharyngeal epithelial cells appears to drive further malignant transformation. Rising levels of serum IgA specific for EBV lytic antigens such as viral capsid antigen and early antigen correlate with progression to NPC. (Ji et al., Br. J. Cancer, 96:623-30, 2007). The level of plasma EBV DNA is directly correlated with NPC tumor burden. (To et al., Clin. Cancer Res., 9:3254-9, 2003). Thus, latent EBV reactivation is a key feature of NPC formation and progression, suggesting a possible role for antibody-based immunotherapy. Although multiple strains of EBV can be isolated from the blood and saliva of healthy seropositive individuals, only a single strain of EBV is typically isolated from NPC cells, consistent with its pathogenic role. (Tsang et al., Virol. Sin., 30:107-21, 2015). Although strain variations in the sequences of EBNA2, 3A, 3B, and 3C have been described, the envelope proteins gp350, gH/gL, and gB are highly conserved, making these latter proteins ideal vaccine candidates for cross-strain protection. (Sample et al., *J. Virol.*, 64:4084-92, 1990; and Rowe et al., *J. Virol.*, 63:1031-9, 1989).

Circulating EBV DNA copy number is positively correlated with imminent onset of EBV-associated malignancies and clinical severity. EBV qPCR assays are commonly used post-transplantation. (Meerbach et al., *J. Med. Virol.*, 80:441-54, 2008; Tsai et al., *Am. J. Transplant*, 8:1016-24, 2008; Wagner et al., *Transplantation*, 74:656-64, 2002; and van Esser et al., *Blood* 98:972-8, 2001). Elevated EBV DNA in the blood is associated with an increased risk for PTLD, whereas decreases correlate with treatment success. (Baldanti et al., *J. Clin. Microbiol.*, 38:613-9, 2000; Hakim et al., *J. Clin. Microbiol.*, 45:2151-5, 2007; Wagner et al., *Transplantation*, 72:1012-9, 2001; and Clave et al., *Transplantation*, 77:76-84, 2004). Circulating EBV DNA is also positively correlated with adverse survival outcomes in NPC (Jin et al., *Eur. J. Cancer*, 48:882-8, 2012; Hsu et al., *Head Neck*, 34:1064-70, 2012; and Hsu et al., *Oral Oncol.*, 49:620-5, 2013), as well as Hodgkin (Kanakry et al., *Blood*, 121:3547-53, 2013) and extranodal NK/T cell lymphomas, which also linked pathogenically with EBV (Wang et al., *Oncotarget.*, 6(30):30317-30326, 2015).

In the developing world, EBV seroconversion typically occurs in infancy, whereas in developed countries it is more likely contracted in adolescence. Infectious mononucleosis typically occurs only in this latter group (Vetsika et al., *Expert Rev. Mol. Med.*, 2004 Nov. 5; 6(23):1-16). The major human reservoir for latent EBV and EBV transmission is the resting memory B lymphocyte (Babcock et al., *Immunity*, 1998 September; 9(3):395-404). EBV is dependent upon the gp350-CD21 binding event for viral entry into the B cell (Tanner et al., *Cell*, 1987 Jul. 17; 50(2):203-13; and Tanner et al., *J. Virology*, 1988; 62(12):4452-64), an event that is critical for infectivity and B cell neoplastic transformation (Thorley-Lawson DA, *J. Allergy Clin. Immunol.*, 2005 August; 116(2):251-61; quiz 62). Gp350 is the major EBV outer membrane glycoprotein, while CD21, also known as complement receptor type 2 (CR2), is a receptor on the surface of B cells that binds to iC3b complement protein. Sera from patients with active EBV infection contain antibody that prevent EBV entry into B cells ("neutralizing" antibody). Adsorption of these sera with gp350, eliminates most of this neutralizing activity (Thorley-Lawson et al., *J. Virology*, 1982 August; 43(2):730-6), indicating that gp350 serves as the major EBV antigen to which a protective humoral immune response is directed.

A number of studies have demonstrated that immunization of non-human primates with a subunit gp350 vaccine in adjuvant protects against experimental EBV-induced lymphoma or EBV replication. Thus, purified native gp350, injected into cottontop marmosets (CTM), in association with liposomes, ISCOM's, or muramyl dipeptide, protected against EBV-induced lymphoma. (Morgan et al., *J. Med. Virol.*, 1984; 13(3):281-92; and Morgan et al., *J. Med. Virol.*, 1989 September; 29(1):74-8). Recombinant gp350 in alum or muramyl dipeptide was similarly protective. (Finerty et al., *J. Gen. Virol.*, 1992 February; 73 (Pt 2):449-53; and Finerty et al., *Vaccine*, 1994 October; 12(13):1180-4). Common marmosets also showed decreased viral replication after EBV challenge following immunization with recombinant gp350 in alum. (Cox et al., *J. Med. Virol.*, 1998 August; 55(4):255-61). Non-human primate studies using gp350 expressed by adenoviral or vaccinia viral vectors have similarly shown protection against experimental EBV-induced lymphoma or EBV replication in CTM or common marmosets. (Mackett et al., *J. Med. Virol.*, 1996 November; 50(3):263-71; Ragot et al., *J. Gen. Virol.*, 1993 March; 74 (Pt 3):501-7; and Morgan et al., *J. Med. Virol.*, 1988 June; 25 (2): 189-95).

A pilot study in humans has also suggested a potential role for gp350 vaccination in host protection against EBV. In a study by Gu et al. (*Dev. Biol. Stand.*, 1995; 84:171-7) a single dose of gp350/220 expressed by vaccinia virus (VV) was given by scarification to 1- to 3-year-olds who were EBV-seronegative, and VV-seronegative. These children developed neutralizing antibodies to EBV (1:40-1:160). Whereas 10/10 unvaccinated controls became infected at 16 months of follow-up, only 3/9 vaccinated children became infected at this time. More recently, Phase I/II studies were conducted in which healthy EBV-seronegative adults were immunized with a recombinant monomeric gp350 protein in alum +/−monophosphoryl lipid A. (Sokal et al., *J. Infect. Dis.*, 2007 Dec. 15; 196(12):1749-53; and Moutschen et al., *Vaccine*, 2007 Jun. 11; 25(24):4697-705). Following 3 doses, up to 82% of subjects had detectable neutralizing serum anti-gp350 antibody titers. The vaccine demonstrated an efficacy of 78.0% in preventing the development of infectious mononucleosis but not in preventing asymptomatic EBV infection. Finally, an additional phase I trial of recombinant monomeric gp350 protein in alum given to children with chronic kidney disease demonstrated only a minority of subjects developing detectable neutralizing serum anti-gp350 titers. (Rees et al., *Transplantation*, 2009 Oct. 27; 88(8):1025-9).

There is currently no effective immunotherapy for EBV-associated diseases, or a clinically licensed prophylactic EBV vaccine. EBV gp350, gH/gL complex, and gB are three envelope proteins that represent potential vaccine target antigens for EBV. EBV gp350 mediates EBV attachment to B cells through its binding to CD21. EBV gH/gL and gB are involved in mediating EBV fusion and entry into both B cells and epithelial cells.

EBV gp350/gp220.

The EBV glycoprotein gp350 and the related splice variant gp220 are responsible for attachment of EBV with high affinity to CR2 on B cells. Antibodies to gp350 or gp220 that block EBV binding neutralize B-cell infection. Each of gp350 and gp220 is a highly glycosylated single-pass membrane protein. As a result of alternative splicing, the viral glycoprotein appears in two forms, with approximate masses of 350 and 220 kDa. The 200 kDa splice form lacks residues 500-757 of the full length gp350. Both gp350 and gp220 retain the CR2 binding domain at the amino terminus. A truncated version of gp350 or gp220 having amino acids 1-470 of gp350 retains the ability to bind CR2 and can inhibit the binding of EBV to CR2 and can be substituted for full length gp350 or gp200 in the compositions described herein or for extracellular domain forms of gp350. (Sarrias et al., *J. Immunol.*, 2001 Aug. 1; 167(3):1490-9). In addition, portions of the gp350 and gp220 protein between amino acids 21-26 or between amino acids 372-378 of the gp350 sequence have been linked to CR2 binding. (Tanner et al., *Cell*, 203-213 (1987), and Nemerow et al., *Cell*, 61:1416-20, 1987). Thus, the term gp350 protein or gp350 antigen (or gp220 protein or antigen) refers to the full length gp350 or gp220 proteins as well as fragments or modified versions thereof that retain the ability to bind the CR2.

The amino acid and nucleic acid sequence of gp350, set forth in GenBank under Accession Number M10593, Version M10593.1, GI 330360, is hereby incorporated by reference. The amino acid sequence of gp350 is (SEQ ID NO: 1):

```
MEAALLVCQY TIQSLIHLTG EDPGFFNVEI PEFPFYPTCN VCTADVNVTI    50
NFDVGGKKHQ LDLDFGQLTP HTKAVYQPRG AFGGSENATN LFLLELLGAG   100
ELALTMRSKK LPINVTTGEE QQVSLESVDV YFQDVFGTMW CHHAEMQNPV   150
YLIPETVPYI KWDNCNSTNI TAVVRAQGLD VTLPLSLPTS AQDSNFSVKT   200
EMLGNEIDIE CIMEDGEISQ VLPGDNKFNI TCSGYESHVP SGGILTSTSP   250
VATPIPGTGY AYSLRLTPRP VSRFLGNNSI LYVFYSGNGP KASGGDYCIQ   300
SNIVFSDEIP ASQDMPTNTT DITYVGDNAT YSVPMVTSED ANSPNVTVTA   350
FWAWPNNTET DFKCKWTLTS GTPSGCENIS GAFASNRTFD ITVSGLGTAP   400
KTLIITRTAT NATTTHKVI  FSKAPESTTT SPTLNTTGFA DPNTTTGLPS   450
STHVPTNLTA PASTGPTVST ADVTSPTPAG TTSGASPVTP SPSPWDNGTE   500
SKAPDMTSST SPVTTPTPNA TSPTPAVTTP TPNATSPTPA VTTPTPNATS   550
PTLGKTSPTS AVTTPTPNAT SPTLGKTSPT SAVTTPTPNA TSPTLGKTSP   600
TSAVTTPTPN ATGPTVGETS PQANATNHTL GGTSPTPVVT SQPKNATSAV   650
TTGQHNITSS STSSMSLRPS SNPETLSPST SDNSTSHMPL LTSAHPTGGE   700
NITQVTPASI STHHVSTSSP EPRPGTTSQA SGPGNSSTST KPGEVNVTKG   750
TPPQNATSPQ APSGQKTAVP TVTSTGGKAN STTGGKHTTG HGARTSTEPT   800
TDYGGDSTTP RPRYNATTYL PPSTSSKLRP RWTFTSPPVT TAQATVPVPP   850
TSQPRFSNLS MLVLQWASLA VLTLLLLLVM ADCAFRRNLS TSHTYTTPPY   900
DDAETYV                                                  907
```

The amino acid sequence of gp220, set forth in GenBank under Accession Number M10593, Version M10593.1, GI 330360, and hereby incorporated by reference, is (SEQ ID NO: 2):

```
MEAALLVCQY TIQSLIHLTG EDPGFFNVEI PEFPFYPTCN VCTADVNVTI    50
NFDVGGKKHQ LDLDFGQLTP HTKAVYQPRG AFGGSENATN LFLLELLGAG   100
ELALTMRSKK LPINVTTGEE QQVSLESVDV YFQDVFGTMW CHHAEMQNPV   150
YLIPETVPYI KWDNCNSTNI TAVVRAQGLD VTLPLSLPTS AQDSNFSVKT   200
EMLGNEIDIE CIMEDGEISQ VLPGDNKFNI TCSGYESHVP SGGILTSTSP   250
VATPIPGTGY AYSLRLTPRP VSRFLGNNSI LYVFYSGNGP KASGGDYCIQ   300
SNIVFSDEIP ASQDMPTNTT DITYVGDNAT YSVPMVTSED ANSPNVTVTA   350
FWAWPNNTET DFKCKWTLTS GTPSGCENIS GAFASNRTFD ITVSGLGTAP   400
KTLIITRTAT NATTTHKVI  FSKAPESTTT SPTLNTTGFA DPNTTTGLPS   450
STHVPTNLTA PASTGPTVST ADVTSPTPAG TTSGASPVTP SPSPWDNGTE   500
STPPQNATSP QAPSGQKTAV PTVTSTGGKA NSTTGKHTT  GHGARTSTEP   550
TTDYGGDSTT PRPRYNATTY LPPSTSSKLR PRWTFTSPPV TTAQATVPVP   600
PTSQPRFSNL SMLVLQWASL AVLTLLLLLV MADCAFRRNL STSHTYTTPP   650
YDDAETYV                                                 658
```

EBV gH, gL, gB, and gp42.

The minimal requirement for viral fusion with B cells includes EBV glycoproteins gH, gL, gB, and gp42. For infection of B cells, gp42 binds to the host cell MHC class II molecules to trigger viral cell membrane fusion. On the other hand, for infection of epithelial cells, gp42 is not required. Rather, the EBV gH, gL, and gB proteins are sufficient for viral fusion with epithelial cells. EBV gH/gL exists in certain environments as a noncovalently associated complex.

The amino acid sequence of EBV gH is (SEQ ID NO: 4):

```
MQLLCVFCLV LLWEVGAASL SEVKLHLDIE GHASHYTIPW TELMAKVPGL    50
SPEALWREAN VTEDLASMLN RYKLIYKTSG TLGIALAEPV DIPAVSEGSM   100
QVDASKVHPG VISGLNSPAC MLSAPLEKQL FYYIGTMLPN TRPHSYVFYQ   150
LRCHLSYVAL SINGDKFQYT GAMTSKFLMG TYKRVTEKGD EHVLSLIFGK   200
TKDLPDLRGP FSYPSLTSAQ SGDYSLVIVT TFVHYANFHN YFVPNLKDMF   250
SRAVTMTAAS YARYVLQKLV LLEMKGGCRE PELDTETLTT MFEVSVAFFK   300
VGHAVGETGN GCVDLRWLAK SFFELTVLKD IIGICYGATV KGMQSYGLER   350
LAAVLMATVK MEELGHLTTE KQEYALRLAT VGYPKAGVYS GLIGGATSVL   400
LSAYNRHPLF QPLHTVMRET LFIGSHVVLR ELRLNVTTQG PNLALYQLLS   450
TALCSALEIG EVLRGLALGT ESGLFSPCYL SLRFDLTRDK LLSMAPQEAM   500
LDQAAVSNAV DGFLGRLSLE REDRDAWHLP AYKCVDRLDK VLMIIPLINV   550
TFIISSDREV RGSALYEAST TYLSSSLFLS PVIMNKCSQG AVAGEPRQIP   600
KIQNFTRTQK SCIFCGFALL SYDEKEGLET TTYITSQEVQ NSILSSNYFD   650
FDNLHVHYLL LTTNGTVMEI AGLYEERAHV VLAIILYFIA FALGIFLVHK   700
IVMFFL                                                   706
```

The amino acid sequence of EBV gL is (SEQ ID NO: 5):

```
MRTVGVFLAT CLVTIFVLPT WGNWAYPCCH VTQLRAQHLL ALENISDIYL    50
VSNQTCDGFS LASLNSPKNG SNQLVISRCA NGLNVVSFFI SILKRSSSAL   100
TGHLRELLTT LETLYGSFSV EDLFGANLNR YAWHRGG                 137
                                                          40
```

The amino acid sequence of EBV gB is (SEQ ID NO: 6):

```
MTRRRVLSVV VLLAALACRL GAQTPEQPAP PATTVQPTAT RQQTSFPFRV    50
CELSSHGDLF RFSSDIQCPS FGTRENHTEG LLMVFKDNII PYSFKVRSYT   100
KIVTNILIYN GWYADSVTNR HEEKFSVDSY ETDQMDTIYQ CYNAVKMTKD   150
GLTRVYVDRD GVNITVNLKP TGGLANGVRR YASQTELYDA PGWLIWTYRT   200
RTTVNCLITD MMAKSNSPFD FFVTTTGQTV EMSPFYDGKN KETFHERADS   250
FHVRTNYKIV DYDNRGTNPQ GERRAFLDKG TYTLSWKLEN RTAYCPLQHW   300
QTFDSTIATE TGKSIHFVTD EGTSSFVTNT TVGIELPDAF KCIEEQVNKT   350
MHEKYEAVQD RYTKGQEAIT YFITSGGLLL AWLPLTPRSL ATVKNLTELT   400
TPTSSPPSSP SPPAPPAARG STSAAVLRRR RRDAGNATTP VPPAAPGKSL   450
GTLNNPATVQ IQFAYDSLRR QINRMLGDLA RAWCLEQKRQ NMVLRELTKI   500
NPTTVMSSIY GKAVAAKRLG DVISVSQCVP VNQATVTLRK SMRVPGSETM   550
CYSRPLVSFS FINDTKTYEG QLGTDNEIFL TKKMTEVCQA TSQYYFQSGN   600
EIHVYNDYHH FKTIELDGIA TLQTFISLNT SLIENIDFAS LELYSRDEQR   650
ASNVFDLEGI FREYNFQAQN IAGLRKDLDN AVSNGRNQFV DGLGELMDSL   700
```

```
GSVGQSITNL VSTVGGLFSS LVSGFISFFK NPFGGMLILV LVAGVVILVI    750

SLTRRTRQMS QQPVQMLYPG IDELAQQHAS GEGPGINPIS KTELQAIMLA    800

LHEQNQEQKR AAQRAAGPSV ASRALQAARD RFPGLRRRRY HDPETAAALL    850

GEAETEF                                                   857
```

The amino acid sequence of EBV gp42 is (SEQ ID NO: 7):

```
MVSFKQVRVP LFTAIALVIV LLLAYFLPPR VRGGGRVSAA AITWVPKPNV     50

EVWPVDPPPP VNFNKTAEQE YGDKEIKLPH WTPTLHTFQV PKNYTKANCT    100

YCNTREYTFS YKERCFYFTK KKHTWNGCFQ ACAELYPCTY FYGPTPDILP    150

VVTRNLNAIE SLWVGVYRVG EGNWTSLDGG TFKVYQIFGS HCTYVSKFST    200

VPVSHHECSF LKPCLCVSQR SNS                                 223
```

The amino acid sequence of EBV BMRF-2 is (SEQ ID NO: 8):

```
MFSCKQHLSL GACVFCLGLL ASTPFIWCFV FANLLSLEIF SPWQTHVYRL     50

GFPTACLMAV LWTLVPAKHA VRAVTPAIML NIASALIFFS LRVYSTSTWV    100

SAPCLFLANL PLLCLWPRLA IEIVYICPAI HQRFFELGLL LACTIFALSV    150

VSRALEVSAV FMSPFFIFLA LGSGSLAGAR RNQIYTSGLE RRRSIFCARG    200

DHSVASLKET LHKCPWDLLA ISALTVLVVC VMIVLHVHAE VFFGLSRYLP    250

LFLCGAMASG GLYLGHSSII ACVMATLCTL TSVVVYFLHE TLGPLGKTVL    300

FISIFVYYFS GVAALSAAMR YKLKKFVNGP LVHLRVVYMC CFVFTFCEYL    350

LVTFIKS
```

The amino acid sequence of EBV BDLF2 is (SEQ ID NO: 9):

```
MVDEQVAVEH GTVSHTISRE EDGVVHERRV LASGERVEVF YKAPAPRPRE     50

GRASTFHDFT VPAAAAVPGP EPEPEPHPPM PIHANGGGET KTNTQDQNQN    100

QTTRTRTNAK AEERTAEMDD TMASSGGQRG APISADLLSL SSLTGRMAAM    150

APSWMKSEVC GERMRFKEDV YDGEAETLAE PPRCFMLSFV FIYYCCYLAF    200

LALLAFGFNP LFLPSFMPVG AKVLRGKGRD FGVPLSYGCP TNPFCKVYTL    250

IPAVVINNVT YYPNNTDSHG GHGGFEAAAL HVAALFESGC PNLQAVTNRN    300

RTFNVTRASG RVERRLVQDM QRVLASAVVV MHHHCHYETY YVFDGVGPEF    350

GTIPTPCFKD VLAFRPSLVT NCTAPLKTSV KGPNWSGAAG GMKRKQCRVD    400

RLTDRSFPAY LEEVMYVMVQ
```

The antigenic compositions and methods of this application typically involve two or more HHV proteins involved in mediating HHV binding, fusion, and entry into host cells. In certain embodiments, two or more EBV proteins disclosed herein are combined in an antigenic composition. The two or more EBV proteins can be administered simultaneously or separately to induce an immune response or to treat or prevent an EBV infection in a subject. In certain embodiments, the antigenic composition (or method of administration) comprises two or more of the following EBV polypeptides (or nucleic acids encoding the same): gB, gH, gL, and gp350. In some embodiments, the gB polypeptide is monomeric, dimeric, or trimeric. In some embodiments, the gH and gL polypeptides are monomeric, dimeric, trimeric, or tetrameric. Typically, gH and gL form a gH/gL heterodimer. In some embodiments, the gp350 polypeptides are monomeric, dimeric, trimeric, or tetrameric.

In certain embodiments, the two or more EBV proteins (or nucleic acids encoding the same) comprise a monomeric or multimeric gp350 and monomeric or multimeric gB. In certain embodiments, the gp350 is monomeric or tetrameric and the gB is monomeric or trimeric. In certain embodiments, the gp350 is monomeric and the gB is trimeric. In certain embodiments, the gp350 is tetrameric and the gB is trimeric.

In certain embodiments, the two or more EBV proteins (or nucleic acids encoding the same) comprise a monomeric or multimeric gp350 and a monomeric or multimeric gH/gL heterodimer. In certain embodiments, the gp350 is monomeric or tetrameric and the gH/gL heterodimer is monomeric or trimeric. In certain embodiments, the gp350 is monomeric and the gH/gL heterodimer is monomeric. In certain embodiments, the gp350 is tetrameric and the gH/gL heterodimer is trimeric.

In certain embodiments, the two or more EBV proteins (or nucleic acids encoding the same) comprise a monomeric or multimeric gB and a monomeric or multimeric gH/gL heterodimer. In certain embodiments, the gB is monomeric, dimeric or trimeric and the gH/gL heterodimer is monomeric or trimeric. In certain embodiments, the gB is monomeric and the gH/gL heterodimer is monomeric or trimeric. In certain embodiments, the gB is trimeric and the gH/gL heterodimer is monomeric. In certain embodiments, the gB is trimeric and the gH/gL heterodimer is trimeric. In certain embodiments, the EBV gB, gH, and gL polypeptides form a protein complex when mixed together. In certain embodiments, the EBV gB, gH, and gL polypeptides are not administered as a protein complex comprising the gB, gH, and gL polypeptides. For example, the gB can be administered separately from the gH and/or gL or administered with the gH and gL but not as a protein complex.

In certain embodiments, the two or more EBV proteins (or nucleic acids encoding the same) comprise a monomeric or multimeric gp350, a monomeric or multimeric gB and a monomeric or multimeric gH/gL heterodimer. In certain embodiments, the gp350 is monomeric or tetrameric, the gB is monomeric or trimeric and the gH/gL heterodimer is monomeric or trimeric. In certain embodiments, the gp350 is monomeric, the gB is trimeric and the gH/gL heterodimer is monomeric. In certain embodiments, the gp350 is tetrameric, the gB is trimeric and the gH/gL heterodimer is trimeric.

In some embodiments, the two or more EBV proteins further comprises one or more of a BMRF-2 polypeptide, a BDLF2 polypeptide, and/or a gp42 polypeptide, which can be monomeric or multimeric (e.g., dimeric, trimeric, or tetrameric).

Kaposi's Sarcoma Virus-Associated Herpes (KSHV, HHV-8).

The two human gammaherpesviruses, Epstein-Barr virus (EBV), a gamma 1 lymphocryptovirus, and Kaposi's sarcoma associated virus (KSHV), a gamma 2 rhadinovirus, have many features in common. They share an architecture that is typical of all members of the herpesvirus family, they share an ability to establish latency in lymphocytes, and they are both initiators or potentiators of human tumors. (Chandran et al., Human Herpesviruses: Biology, Therapy, and Imunoprophylaxis, Eds. Arvin, A., Campadelli-Fiume, G., and Mocarski E., et al., Cambridge University Press, 2007, Ch. 23). KSHV broadly infects many types of host cells, including B-cells from the peripheral blood, B-cells in primary effusion lymphomas (PEL) or body-cavity based B-cell lymphomas (BCBL) and multicentric Cattleman's disease (MCD), flat endothelial cells lining the vascular spaces of Kaposi's sarcoma (KS) lesions, typical KS spindle cells, CD 45+/CD68+ monocytes in KS lesions, keratinocytes, and epithelial cells. (Id.). Further, KSHV infection has been associated with multiple myeloma. (Rettig et al., *Science*, 276:1851-4, 1997). Like EBV, KSHV also expresses gB, gH, and gL that mediate cell fusion and entry. KSHV also expresses the conserved glycoproteins, gM and gN, which mediate similar, if not identical, roles as compared to their EBV counterparts. (Id.).

However, the gp350 glycoprotein of EBV is replaced in KSHV with a polypeptide termed K8.1. The K8.1 gene encodes a 197-amino acid with a predicted molecular weight of about 22 kDa and possessing no sequence corresponding to a TM domain. Similar to the EBV gp350/220, the KSHV K8.1 gene encodes two ORF s, designated gpK8.1A and gpK8.1B, from spliced messages. The larger cDNA is 752 bp long (76,214-76,941 bp) and utilizes the polyadenylation signal sequence (AATAAA) at position 77 013 bp. The 228-aa long encoded protein is designated gpK8.1A, which contains a signal sequence, transmembrane domain, and four N-glycosylation sites. Otherwise, the KSHV gpK18.1 polypeptide performs similar functions as reported for EBV gp350, forming a complex with gB and binding to a cell surface heparin sulfate molecule on the host cell.

KSHV ORF68 is a late lytic, delayed early structural and assembly gene encoding a transmembrane glycoprotein that is a component of the KSHV envelope. (Nakamura et al., *J. Virol.*, 77(7):4205-20, 2003; and Jha et al., *mBio*, 5(6): e02261-14, 2014; and Stürzl et al., *Thromb. Haemost.*, 102:1117-34, 2009). ORF68 is known to interact with and inhibit the host cell's ubiquitin proteasome pathway, thereby inhibiting protein degradation. (Gardner, M., $8^{th}$ Annual CEND Symposium, 22 Mar. 2016). ORF68 is essential for viral genome replication in KSHV. It is postulated that KSHV ORF68 encodes a protein that suppresses the proteasome-mediated degradation of a protein in the cytoplasm of the host cell that is essential for KSHV DNA replication. (Id.).

The antigenic compositions and methods of this application typically involve two or more HHV proteins involved in mediating HHV binding, fusion, and entry into host cells. In certain embodiments, two or more KSHV proteins disclosed herein are combined in an antigenic composition. The two or more KSHV proteins can be administered simultaneously or separately to induce an immune response or to treat or prevent a KSHV infection in a subject. In certain embodiments, the antigenic composition (or method of administration) comprises two or more of the following KSHV polypeptides (or nucleic acids encoding the same): gB, gH, and gL. In some embodiments, the gB polypeptide is monomeric, dimeric, or trimeric. In some embodiments, the gH and gL polypeptides are monomeric, dimeric, trimeric, or tetrameric. Typically, gH and gL form a gH/gL heterodimer.

In certain embodiments, the two or more KSHV proteins (or nucleic acids encoding the same) comprise a monomeric or multimeric gB and a monomeric or multimeric gH/gL heterodimer. In certain embodiments, the gB is monomeric, dimeric or trimeric and the gH/gL heterodimer is monomeric or trimeric. In certain embodiments, the gB is monomeric and the gH/gL heterodimer is monomeric or trimeric. In certain embodiments, the gB is trimeric and the gH/gL heterodimer is monomeric. In certain embodiments, the gB is trimeric and the gH/gL heterodimer is trimeric. In certain embodiments, the KSHV gB, gH, and gL polypeptides form a protein complex when mixed together. In certain embodiments, the KSHV gB, gH, and gL polypeptides are not administered as a protein complex comprising the gB, gH, and gL polypeptides. For example, the gB can be administered separately from the gH and/or gL or administered with the gH and gL but not as a protein complex.

In certain embodiments, the two or more KSHV proteins further comprises one or more of the gN polypeptide, the gM polypeptide, the ORF68 polypeptide and/or the gpK8.1 polypeptide, which can be monomeric or multimeric (e.g., dimeric, trimeric, or tetrameric).

The amino acid and nucleic acid sequence of KSHV gpK8.1A, set forth in GenBank under Accession Number AAC63270.1, GI 3414867, is hereby incorporated by reference. The amino acid sequence of gpK8.1 is (SEQ ID NO: 10):

```
  1 MSSTQIRTEI PVALLILCLC LVACHANCPT YRSHLGFWQE GWSGQVYQDW LGRMNCSYEN

61 MTALEAVSLN GTRLAAGSPS SEYPNVSVSV EDTSASGSGE DAIDESGSGE EERPVTSHVT

121 FMTQSVQATT ELTDALISAF SGSYSSGEPS RTTRIRVSPV AENGRNSGAS NRVPFSATTT

181 TTRGRDAHYN AEIRTHLYIL WAVGLLLGLV LILYLCVPRC RRKKPYIV
```

The amino acid and nucleic acid sequence of KSHV gpK8.1B, set forth in GenBank under Accession Number AJE29698.1, GI 748016404, and hereby incorporated by reference. The amino acid sequence of gpK8.1B is (SEQ ID NO: 11):

```
  1 MSSTQIRTEI PVALLILCLC LVACHANCPT YRSHLGFWQE GWSGQVYQDW LGRMNCSYEN

61 MTALEAVSLN GTRLAAGSPS RSYSSGEPSR TTRIRVSPVA ENGRNSGASN RVPFSATTTT

121 TRGRDAHYNA EIRTHLYILW AVGLLLGLVL ILYLCVPRCR RKKPYIV
```

The amino acid sequence of KSHV gH is (SEQ ID NO: 12):

```
MQGLAFLAAL ACWRCISLTC GATGALPTTA TTITRSATQL INGRTNLSIE      50

LEFNGTSFFL NWQNLLNVIT EPALTELWTS AEVAEDLRVT LKKRQSLFFP     100

NKTVVISGDG HRYTCEVPTS SQTYNITKGF NYSALPGHLG GFGINARLVL     150

GDIFASKWSL FARDTPEYRV FYPMNVMAVK FSISIGNNES GVALYGVVSE     200

DFVVVTLHNR SKEANETASH LLFGLPDSLP SLKGHATYDE LTFARNAKYA     250

LVAILPKDSY QTLLTENYTR IFLNMTESTP LEFTRTIQTR IVSIEARRAC     300

AAQEAAPDIF LVLFQMLVAH FLVARGIAEH RFVEVDCVCR QYAELYFLRR     350

ISRLCMPTFT TVGYNHTTLG AVAATQIARV SATKLASLPR SSQETVLAMV     400

QLGARDGAVP SSILEGIAMV VEHMYTAYTY VYTLGDTERK LMLDIHTVLT     450

DSCPPKDSGV SEKLLRTYLM FTSMCTNIEL GEMIARFSKP DSLNIYRAFS     500

PCFLGLRYDL HPAKLRAEAP QSSALTRTAV ARGTSGFAEL LHALHLDSLN     550

LIPAINCSKI TADKIIATVP LPHVTYIISS EALSNAVVYE VSEIFLKSAM     600

FISAIKPDCS GFNFSQIDRH IPIVYNISTP RRGCPLCDSV IMSYDESDGL     650

QSLMYVTNER VQTNLFLDKS PFFDNNNLHI HYLWLRDNGT VVEIRGMYRR     700

RAASALFLIL SFIGFSGVIY FLYRLFSILY
```

The amino acid sequence of KSHV gL is (SEQ ID NO: 13):

```
MGIFALFAVL WTTLLVTSHA YVALPCCAIO ASAASTLPLF FAVHSIHFAD    50
PNHCNGVCIA KLRSKTGDIT VETCVNGFNL RSFLVAVVRR LGSWASQENL   100
RLLWYLQRSL TAYTVGFNAT TADSSIHNVN IIIISVGKAM NRTGSVSGSQ   150
TRAKSSSRRA HAGOKGK
```

The amino acid sequence of KSHV gB is (SEQ ID NO: 12):

```
MQGLAFLAAL ACWRCISLTC GATGALPTTA TTITRSATQL INGRTNLSIE   50
LEFNGTSFFL NWQNLLNVIT EPALTELWTS AEVAEDLRVT LKKRQSLFFP  100
NKTVVISGDG HRYTCEVPTS SQTYNITKGF NYSALPGHLG GEGINARLVL  150
GDIFASKWSL FARDTPEYRV FYPMNVMAVK FSISIGNNES GVALYGVVSE  200
DFVVVTLHNR SKEANETASH LLFGLPDSLP SLKGHATYDE LTFARNAKYA  250
LVAILPKDSY QTLLTENYTR IFLNMTESTP LEFTRTIQTR IVSIEARRAC  300
AAQEAAPDIF LVLFQMLVAH FLVARGIAEH RFVEVDCVCR QYAELYFLRR  350
ISRLCMPTFT TVGYNHTTLG AVAATQIARV SATKLASLPR SSQETVLAMV  400
QLGARDGAVP SSILEGIAMV VEHMYTAYTY VYTLGDTERK LMLDIHTVLT  450
DSCPPKDSGV SEKLLRTYLM FTSMCTNIEL GEMIARFSKP DSLNIYRAFS  500
PCFLGLRYDL HPAKLRAEAP QSSALTRTAV ARGTSGFAEL LHALHLDSLN  550
LIPAINCSKI TADKIIATVP LPHVTYIISS EALSNAVVYE VSEIFLKSAM  600
FISAIKPDCS GFNFSQIDRH IPIVYNISTP RRGCPLCDSV IMSYDESDGL  650
QSLMYVTNER VQTNLFLDKS PFFDNNNLHI HYLWLRDNGT VVEIRGMYRR  700
PAASALFLIL SFIGFSGVIY FLYRLFSILY
```

The amino acid sequence of KSHV gN is (SEQ ID NO: 14):

```
MTASTVALAL FVASILGHCW VTANSTGVAS STERSSPSTA GLSARPSPGP   50
TSVTTPGFYD VACSADSFSP SLSSFSSVWA LINALLVVVA TFFYLVYLCF  100
FKFVDEVVHA
```

The amino acid sequence of KSHV gM is (SEQ ID NO: 15):

```
MRASKSDRFL MSSWVKLLFV AVIMYICSAV VPMAATYEGL GFPCYFNNLV   50
NYSALNLTVR NSAKHLTPTL FLEKPEMLVY IFWTFIVDGI AIVYYCLAAV  100
AVYRAKHVHA TTMMSMQSWI ALLGSHSVLY VAILRMWSMQ LFIHVLSYKH  150
VLMAAFVYCI HFCISFAHIQ SLITCNSAQW EIPLLEQHVP DNTMMESLLT  200
RWKPVCVNLY LSTTALEMLL FSLSTMMAVG NSFYVLVSDA IFGAVNMFLA  250
LTVVWYINTE FFLVKFMRRQ VGFYVGVFVG YLILLLPVIR YENAFVQANL  300
HYIVAINISC IPILCILAIV IRVIRSDWGL CTPSAAYMPL ATSAPTVDRT  350
PTVHQKPPPL PAKTRARAKV KDISTPAPRT QYQSDHESDS EIDETQMIFI  400
```

The amino acid sequence of KSHV ORF68 is (SEQ ID NO: 16):

```
MFVPWQLGTI TRHRDELQKL LAASLLPEHP EESLGNPIMT QIHQSLQPSS   50
PCRVCQLLFS LVRDSSTPMG FFEDYACLCF FCLYAPHCWT STMAAAADLC  100
EIMHLHFPEE EATYGLFGPG RLMGIDLQLH FFVQKCFKTT AAEKILGISN  150
LQFLKSEFIR GMLTGTITCN FCFKTSWPRT DKEEATGPTP CCQITDTTTA  200
PASGIPELAR ATFCGASRPT KPSLLPALID IWSTSSELLD EPRPRLIASD  250
```

```
                   -continued
MSELKSVVAS HDPFFSPPLQ ADTSQGPCLM HPTLGLRYKN GTASVCLLCE   300

CLAAHPEAPK ALQTLQCEVM GHIENNVKLV DRIAFVLDNP FAMPYVSDPL   350

LRELIRGCTP QEIHKHLFCD PLCALNAKVV SEDVLFRLPR EQEYKKLRAS   400

AAAGQLLDAN TLFDCEVVQT LVFLFKGLQN ARVGKTTSLD IIRELTAQLK   450

RHRLDLAHPS QTSHLYA
```

Betaherpesviruses: Human Cytomegalovirus (HCMV, HHV-5); Human Herpes Virus 6 (HHV-6); & Human Herpes Virus 7 (HHV-7)

Human Cytomegalovirus (HCMV, HHV-5). Human cytomegalovirus (HCMV) is an enveloped, double-stranded DNA β-herpesvirus of the Herpesviridae family HCMV further belongs to the betaherpesvirus subfamily, of which HHV-6 and HHV-7 are also members. Cells infected with this family of viruses often become enlarged (cytomegaly). HCMV is the leading non-genetic cause of hearing loss in childhood and a significant cause of neurodevelopmental delay, including mental retardation. (Demmler-Harrison G J, J. Clin. Virol., 46 Suppl 4, 2009: S1-5; Jeon et al., Infect. Dis. Obstet. Gynecol., 2006:80383, 2006; and Morton et al., N Engl. J. Med., 354:2151-64, 2006). In the U.S., between 20,000 and 40,000 infants per year are born with HCMV infection, accounting for an annual 8,000 permanent disabilities and a healthcare cost of S1.86 billion. HCMV also causes significant clinical diseases in immunosuppressed individuals, including transplant recipients and patients with AIDS. (Bonaros et al., Clin. Transplant., 22:89-97, 2008; and Steininger et al., J. Clin. Virol., 37:1-9, 2006). Although HCMV infection in immunocompetent individuals is generally asymptomatic, it may produce a mononucleosis syndrome in 10% of primary infections of older children and adults. (Horwitz et al., Medicine (Baltimore), 65:124-34, 1986). In 2001, the Institute of Medicine of the U.S. National Academy of Sciences stated that a vaccine to prevent congenital HCMV infection is among the highest U.S. priorities. (Stratton et al., "Vaccines for the 21st Century: A tool for decisionmaking," Washington, D.C., National Academy Press, 2001).

HCMV is spread mainly through saliva and urine, and via transplacental transmission to the fetus (Krause et al., Vaccine, 32:4-10, 2014). HCMV can also be transmitted to infants through breast milk (Maschmann et al., Clin. Infect. Dis., 33:1998-2003, 2001), through sexual activity, through solid organ or hematopoietic stem cell transplantation, and rarely by transfusion of blood products. HCMV primarily infects fibroblasts, epithelial cells, endothelial cells, monocyte-macrophages, hepatocytes, and neurons. The mechanism of HCMV fusion and entry into mammalian cells is analogous to that employed by other members of the herpesvirus family (Heldwein et al., Cell. Mol. Life Sci., 65:1653-68, 2008; and White et al., Crit. Rev. Biochem. Mol. Biol., 43:189-219, 2008). HCMV enters cells by fusing its envelope with either the plasma membrane (fibroblasts) (Compton et al., Virology, 191:387-95, 1992) or endosomal membrane (epithelial and endothelial cells) (Ryckman et al., J. Virol., 80:710-22, 2006).

HCMV gB, gH, gL, gO (UL74), gM, gN (gpUL73), and UL128/130/131A.

The nine glycoproteins gB, gH, gL, gO (UL74), gM, gN (gpUL73), and UL128/130/131A, have collectively been identified as the envelope glycoproteins that play important roles in HCMV fusion and entry into host cells (Hahn et al., J. Virol., 78:10023-33, 2004; Ryckman et al., J. Virol., 82:60-70, 2008; Wang et al., Proc. Natl. Acad. Sci. USA, 102:18153-8, 2005; and Wille et al., J. Virol., 84:2585-96, 2010). Similar to gammaherpesvirus family members, HCMV gH/gL and gB proteins play an important role in HCMV fusion and entry into host cells. The gB protein is the direct mediator of HCMV fusion with all host cell membranes. Activation of HCMV gB and its fusogenic activity requires association with gH/gL and gO, which together form a gH/gL/gO heterotrimer protein complex. However, the gH/gL/UL128/130/131A (pentameric complex) protein is also important for efficient targeting of HCMV to epithelial and endothelial cells, since UL128/130/131A mutants failed to infect these cells (Ryckman et al., J. Virol., 80:710-22, 2006; Hahn et al., J. Virol., 78:10023-33, 2004; Adler et al., J. Gen. Virol., 87: 2451-60, 2006; and Wang et al., J. Virol., 79:10330-8, 2005). In contrast, gO seems to be involved in HCMV fusion with all HCMV host cells, since gO null HCMV failed to infect all cell types tested including fibroblasts, epithelial and endothelial cells, and infection of both fibroblasts and epithelial cells was generally correlated with the abundance of gH/gL/gO complex, but not with pentameric complex gH/gL/UL128/UL130/UL131A (Wille et al., J. Virol., 84:2585-96, 2010; Jiang et al., J. Virol., 82:2802-12, 2008; and Zhou et al., J. Virol., 89(17):8999-9009, 2015). All three of the UL128-131 genes share a common architecture including an amino-terminal signal peptide, a central chemokine-like domain, and a carboxy-terminal domain with no homology to any known class of proteins. (Patrone et al., J. Virol., 79(13):8361-8373, 2005). HCMV gB or gH/gL proteins have been shown to elicit serum HCMV neutralizing antibodies for both fibroblasts and epithelial cells. However, the pentameric complex induces the highest serum neutralizing titers for epithelial and endothelial cells, though with no further improvement for fibroblasts (Wen et al., Vaccine, 32:3796-804, 2014; Freed et al., Proc. Natl. Acad. Sci. USA, 110:E4997-5005, 2013; and Schuessler et al., J. Virol., 86:504-12, 2012). Although an HCMV gH/gL/gO complex was produced in mammalian cells (HEK-239) (Kinzler et al., J. Clin. Virol., 25 Suppl 2:S87-95, 2002), there have been no reports on its ability to induce HCMV neutralizing antibodies.

The glycoprotein M and N polypeptides are glycoprotein complex II (GCII) antigens. Glycoprotein N is an envelope component of the mature viral particle with a portion exposed at the virus surface and a portion extending to the internal side of the envelope. It is present in the matrix of defense bodies and "block holes." (Pignatelli, et al., Arch. Virol., 147:1247, 2002). HCMV gM polypeptide is 372 amino acids in length and has an approximate molecular weight of 42 kDa, possessing seven TM domains. HCMV gN is 129 amino acids in length and has a predicted molecular weight of about 15 kDa, but due to heavy glycosylation tends to appear as a 40 to 50 kDa protein. The glycoprotein M (gM, UL100) and glycoprotein N (gN, UL73) form a gM/gN protein complex which is the most abundant protein component of the HCMV envelope. Recent studies have indicated that deletion of the viral gene encoding either gM or gN is lethal for HCMV, but not for other HHV. (Baines et al., *J. Virol.*, 67:1441-1452, 1993; Fuchs et al., *Virus Res.*, 112:108-114, 2005; Hobom et al., *J. Virol.*, 74:7720-7729, 2000; Mach et al., *J. Virol.*, 81:5212-5224, 2007; and MacLean et al., *J. Gen. Virol.*, 74(pt. 6):975-983, 1993).

The antigenic compositions and methods of this application typically involve two or more HHV proteins involved in mediating HHV binding, fusion, and entry into host cells. In certain embodiments, two or more HCMV proteins disclosed herein are combined in an antigenic composition. The two or more HCMV proteins can be administered simultaneously or separately to induce an immune response or to treat or prevent an HCMV infection in a subject. In certain embodiments, the antigenic composition (or method of administration) comprises two or more of the following HCMV polypeptides (or nucleic acids encoding the same): gB, gH, and gL. In some embodiments, the gB polypeptide is monomeric, dimeric, or trimeric. In some embodiments, the gH and gL polypeptides are monomeric, dimeric, trimeric, or tetrameric. Typically, gH and gL form a gH/gL heterodimer.

In certain embodiments, the two or more HCMV proteins (or nucleic acids encoding the same) comprise a monomeric or multimeric gB and a monomeric or multimeric gH/gL heterodimer. In certain embodiments, the gB is monomeric, dimeric or trimeric and the gH/gL heterodimer is monomeric or trimeric. In certain embodiments, the gB is monomeric and the gH/gL heterodimer is monomeric or trimeric. In certain embodiments, the gB is trimeric and the gH/gL heterodimer is monomeric. In certain embodiments, the gB is trimeric and the gH/gL heterodimer is trimeric. In certain embodiments, the HCMV gB, gH, and gL polypeptides form a protein complex when mixed together. In certain embodiments, the HCMV gB, gH, and gL polypeptides are not administered as a protein complex comprising the gB, gH, and gL polypeptides. For example, the gB can be administered separately from the gH and/or gL or administered with the gH and gL but not as a protein complex.

In some embodiments, the two or more HCMV proteins (or nucleic acids encoding the same) further comprises the gO polypeptide, which is optionally multimeric (e.g., dimeric, trimeric, or tetrameric). In other embodiments, the two or more HCMV proteins (or nucleic acids encoding the same) further comprises a gN and/or a gM polypeptide, which can be monomeric or multimeric (e.g., dimeric, trimeric, or tetrameric). In still other embodiments, the two or more HCMV proteins (or nucleic acids encoding the same) comprise the gB polypeptide, the gH polypeptide, the gL polypeptide, and the UL128, UL130, and UL131A polypeptides. In certain embodiments, the two or more HCMV proteins (or nucleic acids encoding the same) comprise trimeric gB, monomeric gH/gL and UL128, UL130, and UL131A, wherein UL128, UL130, and UL131A are preferably combined as a fusion protein. In certain embodiments, these five HCMV polypeptides are present in the composition as a pentameric protein complex. In certain embodiments, they are present in the composition as a fusion protein.

Figure 13:
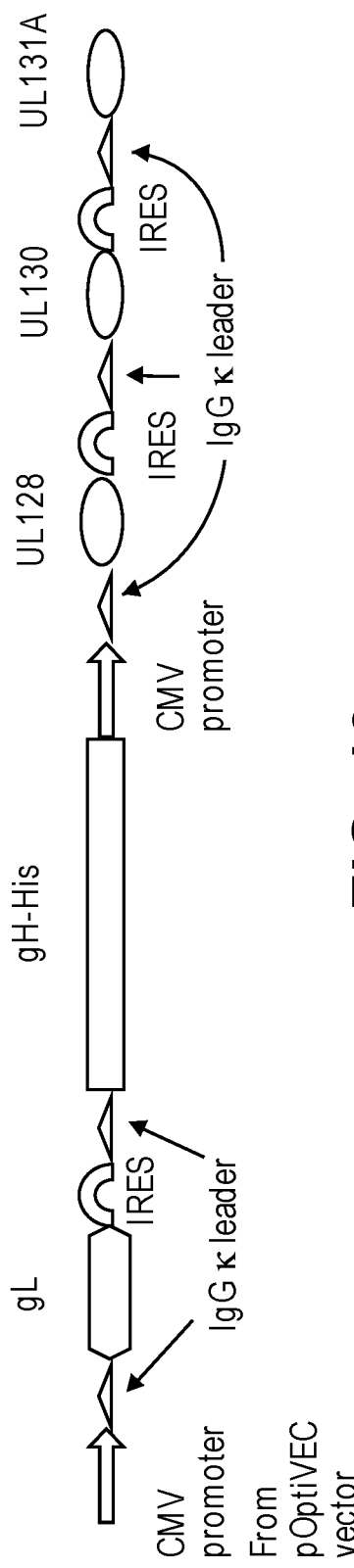

Also disclosed is a recombinant nucleic acid encoding a protein complex or a fusion protein comprising HHV polypeptides gH, gL, UL128, UL130, and UL131A. The sequences of these HHV polypeptides making up the pentameric complex can be from any betaherpesvirus subfamily member, including, for example, HCMV. An embodiment of a nucleic acid construct encoding all five HCMV polypeptides of the pentameric complex is depicted in FIG. 13, including exemplary operably linked promoter sequences and the like. Additional nucleic acid sequences can be included in such a nucleic acid sequence to aide in purification, such as his-tag sequences or immunoglobulin kappa sequences, etc. known in the art as protein purification tags, etc. In another embodiment, the nucleic acid construct can comprise sequences encoding the HHV polypeptides gH, gL, and gB. These highly conserved polypeptides are found in all HHV genomes and therefore can correspond to any known HHV gB, gH, and/or gL sequence.

The amino acid sequence of HCMV gH is (SEQ ID NO: 17):

```
MRPGLPPYLT VFTVYLLSHL PSQRYGADAA SEALDPHAFH LLLNTYGRPI    50

RFLRENTTQC TYNSSLRNST VVRENAISFN FFQSYNQYYV FHMPRCLFAG   100

PLAEQFLNQV DLTETLERYQ QRLNTYALVS KDLASYRSFS QQLKAQDSLG   150

QQPTTVPPPI DLSIPHVWMP PQTTPHDWKG SHTTSGLHRP HFNQTCILFD   200

GHDLLFSTVT PCLHQGFYLM DELRYVKITL TEDFFVVTVS IDDDTPMLLI   250

FGHLPRVLFK APYQRDNFIL RQTEKHELLV LVKKAQLNRH SYLKDSDFLD   300

AALDFNYLDL SALLRNSFHR YAVDVLKSGR CQMLDRRTVE MAFAYALALF   350

AAARQEEAGT EISIPRALDR QAALLQIQEF MITCLSQTPP RTTLLLYPTA   400

VDLAKRALWT PDQITDITSL VRLVYILSKQ NQQHLIPQWA LRQIADFALQ   450

LHKTHLASFL SAFARQELYL MGSLVHSMLV HTTERREIFI VETGLCSLAE   500

LSHFTQLLAH PHHEYLSDLY TPCSSSGRRD HSLERLTRLF PDATVPATVP   550

AALSILSTMQ PSTLETFPDL FCLPLGESFS ALTVSEHVSY VVTNQYLIKG   600

ISYPVSTTVV GQSLIITQTD SQTKCELTRN MHTTHSITAA LNISLENCAF   650

CQSALLEYDD TQGVINIMYM HDSDDVLFAL DPYNEVVVSS PRTHYLMLLK   700

NGTVLEVTDV VVDATDSRLL MMSVYALSAI IGIYLLYRML KTC
```

The amino acid sequence of HCMV gL is (SEQ ID NO: 18):

MCRRPDCGFS FSPGPVILLW CCLLLPIVSS AAVSVAPTAA EKVPAECPEL  50
TRRCLLGEVF EGDKYESWLR PLVNVTGRDG PLSQLIRYRP VTPEAANSVL 100
LDEAFLDTLA LLYNNPDQLR ALLTLLSSDT APRWMTVMRG YSECGDGSPA 150
VYTCVDDLCR GYDLTRLSYG RSIFTEHVLG FELVPPSLFN VVVAIRNEAT 200
RTNRAVRLPV STAAAPEGIT LFYGLYNAVK EFCLRHQLDP PLLRHLDKYY 250
AGLPPELKQT RVNLPAHSRY GPQAVDAR

The amino acid sequence of HCMV gB is (SEQ ID NO: 19):

MESRIWCLVV CVNLCIVCLG AAVSSSSTSH ATSSTHNGSH TSRTTSAQTR  50
SVYSQHVTSS EAVSHRANET IYNTTLKYGD VVGVNTTKYP YRVCSMAQGT 100
DLIRFERNII CTSMKPINED LDEGIMVVYK RNIVAHTFKV RVYQKVLTFR 150
RSYAYIYTTY LLGSNTEYVA PPMWEIHHIN KFAQCYSSYS RVIGGTVFVA 200
YHRDSYENKT MQLIPDDYSN THSTRYVTVK DQWHSRGSTW LYRETCNLNC 250
MLTITTARSK YPYHFFATST GDVVYISPFY NGTNRNASYF GENADKFFIF 300
PNYTIVSDFG RPNAAPETHR LVAFLERADS VISWDIQDEK NVTCQLTFWE 350
ASERTIRSEA EDSYHFSSAK MTATELSKKQ EVNMSDSALD CVRDEAINKL 400
QQIFNTSYNQ TYEKYGNVSV FETSGGLVVF WQGIKQKSLV ELERLANRSS 450
LNITHRTRRS TSDNNTTHLS SMESVHNLVY AQLQFTYDTL RGYINRALAQ 500
IAEAWCVDQR RTLEVFKELS KINPSAILSA IYNKPIAARF MGDVLGIASC 550
VTINQTSVKV LRDMNVKESP GRCYSRPVVI FNFANSSYVQ YGQLGEDNEI 600
LLGNHRTEEC QLPSLKIFIA GNSAYEYVDY LFKRMIDLSS ISTVDSMIAL 650
DIDPLENTDF RVLELYSQKE LRSSNVFDLE EIMREFNSYK QRVKYVEDKV 700
VDPLPPYLKG LDDLMSGLGA AGKAVGVAIG AVGGAVASVV EGVATFLKNP 750
FGAFTIILVA IAVVIITYLI YTRQRRLCTQ PLQNLFPYLV SADGTTVTSG 800
STKDTSLQAP PSYEESVYNS GRKGPGPPSS DASTAAPPYT NEQAYQMLLA 850
LARLDAEQRA QQNGTDSLDG QTGTQDKGQK PNLLDRLRHR KNGYRHLKDS 900
DEEENV

The amino acid sequence of HCMV gN is (SEQ ID NO: 20):

MEWNTLVLGL LVLSVVAESS GNNSSTSTSA TTSKSSASVS TTKLTTVATT  50
SATTTTTTTL STTSTKLSST THDPNVMRRH ANDDFYKAHC TSHMYELSLS 100
SFAAWWTMLN ALILMGAFCI VLRHCCFQNF TATTTKGY

The amino acid sequence of HCMV gM is (SEQ ID NO: 21):

MAPSHVDKVN TRTWSASIVF MVLTFVNVSV HLVLSNFPHL GYPCVYYHVV  50
DFERLNMSAY NVMHLHTPML FLDSVQLVCY AVFMQLVFLA VTIYYLVCWI 100
KISMRKDKGM SLNQSTRDIS YMGDSLTAFL FILSMDTFQL FTLTMSFRLP 150

-continued

```
SMIAFMAAVH FFCLTIFNVS MVTQYRSYKR SLFFFSRLHP KLKGTVQFRT 200

LIVNLVEVAL GFNTTVVAMA LCYGFGNNFF VRTGHMVLAV FVVYAIISII 250

YFLLIEAVFF QYVKVQFGYH LGAFFGLCGL IYPIVQYDTF LSNEYRTGIS 300

WSFGMLFFIW AMFTTCRAVR YFRGRGSGSV KYQALATASG EEVAVLSHHD 350

SLESRRLREE EDDDDDEDFE DA
```

The amino acid sequence of HCMV gO is (SEQ ID NO: 22):

```
MGRKEMMVRD VPKMVFLISI SFLLVSFINC KVMSKALYNR PWRGLVLSKI  50

GKYKLDQLKL EILRQLETTI STKYNVSKQP VKNLTMNMTE FPQYYILAGP 100

IQNYSITYLW FDFYSTQLRK PAKYVYSQYN HTAKTITFRP PPCGTVPSMT 150

CLSEMLNVSK RNDTGEQGCG NFTTFNPMFF NVPRWNTKLY VGPTKVNVDS 200

QTIYFLGLTA LLLRYAQRNC THSFYLVNAM SRNLFRVPKY INGTKLKNTM 250

RKLKRKQAPV KEQFEKKAKK TQSTTTPYFS YTTSAALNVT TNVTYSITTA 300

ARRVSTSTIA YRPDSSFMKS IMATQLRDLA TWVYTTLRYR QNPFCEPSRN 350

RTAVSEFMKN THVLIRNETP YTIYGTLDMS SLYYNETMFV ENKTASDSNK 400

TTPTSPSMGF QRTFIDPLWD YLDSLLFLDE IRNFSLRSPT YVNLTPPEHR 450

RAVNLSTLNS LWWWLQ
```

The amino acid sequence of HCMV UL128 is (SEQ ID NO: 23):

```
MSPKNLTPFL TALWLLLGHS RVPRVRAEEC CEFINVNHPP ERCYDFKMCN  50

RFTVALRCPD GEVCYSPEKT AEIRGIVTTM THSLTRQVVH NKLTSCNYNP 100

LYLEADGRIR CGKVNDKAQY LLGAAGSVPY RWINLEYDKI TRIVGLDQYL 150

ESVKKHKRLD VCRAKMGYML Q
```

The amino acid sequence of HCMV UL130 is (SEQ ID NO: 24):

```
MLRLLLRHYF HCLLLCAVWA TPCLASSWST LTANQNPSPP WSKLTYSKPH  50

DAATFYCPFL YPSPPRSPSQ FSGFQRVSTG PECRNETLYL LYNREGQTLV 100

ERSSTWVKKV IWYLSGRNQT ILQRMPRTAS KPSDGNVQIS VEDAKIFGAH 150

MVPKQTKLLR FVVNDGTRYQ MCVMKLESWA HVFRDYSVSF QVRLTFTEAN 200

NQTYTFCTHP NLIV
```

The amino acid sequence of HCMV UL131A is (SEQ ID NO: 25):

```
MRLCRVWLSV CLCAVVLGQC QRETAEKNDY YRVPHYWDAC SRALPDQTRY  50

KYVEQLVDLT LNYHYDASHG LDNFDVLKRI NVTEVSLLIS DFRRQNRRGG 100

TNKRTTFNAA GSLAPHARSL EFSVRLFAN
```

Human Herpes Virus 6 (HHV-6) and Human Herpes Virus 7 (HHV-7).

Although HHV-6 and HHV-7 are distinct from HCMV in terms of genomic sequence, they retained a core of 80 herpesvirus-common ORFs that are also conserved in rodent CMVs. (Mocarski E., *Cell. Microb.*, 6(8):707-717, 2004). HHV-6 was first isolated in 1986 from peripheral blood leukocytes in patients presenting with lymphoproliferative disorders and AIDS. (Flamand et al., *J. Virol.*, 67(11):6768-6777, 1993). It is estimated that about 90% of individuals are infected by HHV-6 by the age of two, and approaches 100% in non-industrialized countries. (Salahuddin et al., *Science*, 234:596, 1986; Willis et al., *Br. Med. Bull.*, 62(1):125-138, 2002). HHV-6 infections cause roseola *infantum* (sixth disease), exanthem subitum rash (roseola) and is associated with heterophile-negative infectious mononucleosis, as well as meningoencephalitis, hepatitis, fatal hemophagocytic syndrome, and interstitial pneumonitis. (Id.). Further, there is some evidence suggesting a role in HHV-6 in certain cancers due to the detection of its genomic sequences in some B-cell lymphomas and the potential of HHV-6 to transform rodent cells. (Ablashi et al., *J. Virol. Methods,* 21:29-48, 1988; Josephs et al., *Science,* 234:601-603, 1986; Razzaque, A., *Oncogene,* 5:1356-1370, 1990; and Torelli et al., *Blood,* 77:2251-2258, 1991). There are two variants of HHV-6 confirmed by genetic sequencing: HHV-6A and HHV-6B. (Ablashi et al., *Arch. Virol.,* 159(5):863-870, 2014). The genomes of the two variants are co-linear and share an overall sequence identity of 90%. (Id.). Even the highly conserved glycoproteins gH, gB, gN, and gO are distinguishably different in sequence, and consistently different (conserved across isolates). The two variants also appear to exhibit slightly different epidemiology and disease associations. (Id.). Nonetheless, the same glycoproteins present in other HHV family members are encoded by the HHV-6 and HHV-7 genomes.

HHV-6 encodes many of the same surface glycoproteins as previously mentioned for other HHV family members, including gB, gH, gL, and gM, for which relatively conserved homologs have been identified in all known mammalian herpesviruses. (Santoro et al., *J. Biol. Chem.,* 278: 25964-25969, 2003; and Dockrell, D. H., *J. Med. Microbiol.,* 52:5-18, 2003). As with other family members, glycoproteins gH and gL play prominent roles in HHV-6 membrane fusion based on inhibitory activities of specific antibodies. (Foa-Tomasi et al., *J. Virol.,* 65:4124-4129, 1991; Gompels et al., *J. Virol.,* 65:2393-2401, 1991; Liu et al., *Virology,* 197:12-22, 1993; and Qian et al., *Virology,* 194:380-386, 1993). As in other herpesviruses, these glycoproteins form a heterodimeric complex, with gL being required for correct folding, intracellular maturation, and surface expression of gH. (Anderson et al., *J. Gen. Virol.,* 80:1485-1494, 1999; Hutchinson et al., *J. Virol.,* 66:2240-2250, 1992; Liu et al., *J. Gen. Virol.,* 74:1847-1857, 1993; and Roop et al., *J. Virol.,* 67:2285-2297, 1993). HHV-6 glycoprotein gB, known to be the most highly conserved glycoprotein among herpesviruses, and glycoprotein gp82-gp105 (only found in HHV-6 and the related β-herpesvirus, HHV-7) are important for the fusion/entry process. (Takeda et al., *Virology,* 222:176-183, 1996; Pfeiffer et al., *J. Virol.,* 69:3490-3500, 1995; and Pfeiffer et al., *J. Virol.,* 67:4611-4620, 1993).

The antigenic compositions and methods of this application typically involve two or more HHV proteins involved in mediating HHV binding, fusion, and entry into host cells. In certain embodiments, two or more HHV-6 and HHV-7 proteins disclosed herein are combined in an antigenic composition. The two or more HHV-6 and HHV-7 proteins can be administered simultaneously or separately to induce an immune response or to treat or prevent an HHV-6 or HHV-7 infection in a subject. In certain embodiments, the antigenic composition (or method of administration) comprises two or more of the following HHV-6 and HHV-7 polypeptides (or nucleic acids encoding the same): gB, gH, and gL. In some embodiments, the gB polypeptide is monomeric, dimeric, or trimeric. In some embodiments, the gH and gL polypeptides are monomeric, dimeric, trimeric, or tetrameric. Typically, gH and gL form a gH/gL heterodimer.

In certain embodiments, the two or more HHV-6 or HHV-7 proteins (or nucleic acids encoding the same) comprise a monomeric or multimeric gB and a monomeric or multimeric gH/gL heterodimer. In certain embodiments, the gB is monomeric, dimeric or trimeric and the gH/gL heterodimer is monomeric or trimeric. In certain embodiments, the gB is trimeric and the gH/gL heterodimer is monomeric. In certain embodiments, the gB is trimeric and the gH/gL heterodimer is trimeric. In certain embodiments, the gB is monomeric and the gH/gL heterodimer is monomeric or trimeric. In certain embodiments, the HHV-6 or HHV-7 gB, gH, and gL polypeptides form a protein complex when mixed together. In certain embodiments, the HHV-6 or HHV-7 gB, gH, and gL polypeptides are not administered as a protein complex comprising the gB, gH, and gL polypeptides. For example, the gB can be administered separately from the gH and/or gL or administered with the gH and gL but not as a protein complex.

The amino acid sequence of HHV-6A gH is (SEQ ID NO: 26):

```
MLLRLWVFVL LTPCYGWRPL NISNSSHCRN GNFENPIVRP GFITFNFYTK  50
NDTRIYQVPK CLLGSDITYH LFDAINTTES LTNYEKRVIR FYEPPMNDIL 100
RLSPVPSVKQ FNLDRSIQPQ VVYSLNMYPS QGIYYVRVVE VRQMQYDNVS 150
CKLPNSLKEL IFPVQVRCAK ITRYVGEDIY THFFTPDFMI LYIQNPAGDL 200
TMMYGNTTSI NFKAPYKKSS FIFKQTLTDD LLLIVEKDVI DVQYRFISDA 250
TFVDETLNDV DEVEALLLKF NNLGIQTLLR GDCKKPNYAG IPQMMFLYGI 300
VHFSYSTKNT GPMPVLRVLK THENLLSIDS FVNRCVNVSE GTLQYPKMKE 350
FLKYEPSDYS YITKNKSISV STLLTYLATA YESNVTISKY KWTDIANTLQ 400
NIYEKHMFFT NLTFSDRETL FMLAEIANII PTDERMQRHM QLLIGNLCNP 450
VEIVSWARML TADRAPNLEN IYSPCASPVR RDVINSFLKT VLTYASLDRY 500
RSDMMEMLSV YRPPNMERVA AIQCLSPSEP AASLTLPNVT FVISPSYVIK 550
GVSLTITTTI VATSIIITAI PLNSTCVSTN YKYAGQDLLV LRNISSQTCE 600
FCQSVVMEYD DIDGPLQYIY IKNIDELKTL TDPNNNLLVP NTRTHYLLLA 650
KNGSVFEMSE VGIDIDQVSI ILVIIYILIA IIALFGLYRL IRLC
```

The amino acid sequence of HHV-6B gH is (SEQ ID NO: 27):

```
MLFRLWVFVL LTPCYSWRPW TISDESHCKN GNSENPIVRP GFITFNFYTK  50
NDTRIYQVPK CLLGSDITYH LFDAINTTES LTNYEKRVTR FYEPPMNDIL 100
RLSTVPAVKQ FNLDHSIQPQ IVYSLNLYPS HGIYYIRVVE VRQMQYDNVS 150
CKLPNSLNEL IFPVQVRCAK ITRYAGENIY THFFTPDFMI LYIQNPAGDL 200
IMMYGNTTDI NFKAPYRKSS FIFKQTLTDD LLLIVEKDVV DEEYRFISDA 250
TFVDETLDDV DEVEALLLKF NNLGIQTLLR GDCKKPDYAG IPQMMFLYGI 300
VHFSYSTKNT GPMPVLRVLK THENLLSIDS FVNRCVNVSE GTIQYPKMKE 350
FLKYEPSDYS YITKNKSIPV STLLTYLATA YETNVTISRY KWSDIANTLQ 400
KIYEKHMFFT NLTFSDRETL FMLAEIANFI PADERMQRHM QLLIGNLCNP 450
VEIVSWAHML TADKAPNLEN IYSPCASPVR RDVINSFVKT VLTYASLDRY 500
RSDMMEMLSV YRPPDMARVA AIQCLSPSEP AASLPLPNVT FVISPSYVIK 550
GVSLTITTTI VATSIIITAI PLNSTCVSTN YKYAGQDLLV LRNISSQTCE 600
FCQSVVMEYD DIDGPLQYIY IKNIDELKTL TDPNNNLLVP NTRTHYLLLA 650
KNGSVFEMSE VGIDIDQVSI ILVIIYVLIA IIALFGLYRL IRLC
```

The amino acid sequence of HHV-6A gL is (SEQ ID NO: 28):

```
MELLLFVMSL ILLTFSKAIP LFNHNSFYFF YLDDCIAAVI NCTKSEVPLL  50
LEPIYQPPAY NEDVMSILLQ PPTKKKPFSR IMVTDEFLSD FLLLQDNPEQ 100
LRTLFALIRD PESRDNWLNF FNGFQTCSPS VGITTCIRDN CRKYSPEKIT 150
YVNNFFVDNI AGLEFNISEN TDSFYSNIGF LLYLENPAKG VTKIIRFPFN 200
SLTLFDTILN CLKYFHLKTG VELDLLKHME TYNSKLPFRS SRPTILIRNT 250
```

The amino acid sequence of HHV-6B gL is (SEQ ID NO: 29):

```
MELLLFVMSL ILLTFSKAMP LFDHNSFYFE KLDDCIAAVI NCTRSEVPLL  50
LEPIYQPPVY NEDVMSILLK PPTKKKPFSR IMVTNEFLSD FLLLQDNPEQ 100
LRTLFALIGD PESRDNWLNF FNGFQTCSPS VGITTCISDN CRKYLPERIT 150
YVNNFFVDNI AGLEFNISEN TDSFYSNIGF LLYLENPATG ITKIIRFPFN 200
SLTLFDTILN CLKYFHLKTG VEFDLLKQME AYNSKLPFRS SRPTILIRNT 250
```

The amino acid sequence of HHV-6A gB is (SEQ ID NO: 30):

```
MSKMAVLFLA VFLMNSVLMI YCDPDHYIRA GYNHKYPFRI CSIAKGTDLM  50
RFDRDISCSP YKSNAKMSEG FFIIYKTNIE TYTFPVRTYK KELTFQSSYR 100
DVGVVYFLDR TVMGLAMPVY EANLVNSHAQ CYSAVAMKRP DGTVFSAFHE 150
DNNKNNTLNL FPLNFKSITN KRFITTKEPY FARGPLWLYS TSTSLNCIVT 200
EATAKAKYPF SYFALTTGEI VEGSPFFNGS NGKHFAEPLE KLTILENYTM 250
IEDLMNGMNG ATTLVRKIAF LEKADTLFSW EIKEENESVC MLKHWTTVTH 300
GLRAETNETY HFISKELTAA FVAPKESLNL TDPKQTCIKN EFEKIINEVY 350
```

-continued

```
MSDYNDTYSM NGSYQIFKTT GDLILIWQPL VQKSLMFLEQ GSEKIRRRRD 400
VGDVKSRHDI LYVQLQYLYD TLKDYINDAL GNLAESWCLD QKRTITMLHE 450
LSKISPSSIV SEVYGRPISA QLHGDVLAIS KCIEVNQSSV QLHKSMRVVD 500
AKGVRSETMC YNRPLVTFSF VNSTPEVVPG QLGLDNEILL GDHRTEECEI 550
PSTKIFLSGN HAHVYTDYTH TNSTPIEDIE VLDAFIRLKI DPLENADFKV 600
LDLYSPDELS RANVFDLENI LREYNSYKSA LYTIEAKIAT NTPSYVNGIN 650
SFLQGLGAIG TGLGSVISVT AGALGDIVGG VVSFLKNPFG GGLMLILAIV 700
VVVIIIVVFV RQRHVLSKPI DMMFPYATNP VTTVSSVTGT TVVKTPSVKD 750
VDGGTSVAVS EKEEGMADVS GQVSDDEYSQ EDALKMLKAI KSLDESYRRK 800
PSSSESHASK PSLIDRIRYR GYKSVNVEEA
```

The amino acid sequence of HHV-6B gB is (SEQ ID NO: 31):

```
MSKMRVLFLA VFLMNSVLMI YCDSDDYIRA GYNHKYPFRI CSIAKGTDLM  50
RFDRDISCSP YKSNAKMSEG FFIIYKTNIE TYTFPVRTYK NELTFPTSYR 100
DVGVVYFLDR TVMGLAMPVY EANLVNSRAQ CYSAVAIKRP DGTVFSAYHE 150
DNNKNETLEL FPLNFKSVTN KRFITTKEPY FARGPLWLYS TSTSLNCIVT 200
EATAKAKYPF SYFALTTGEI VEGSPFFDGS NGKHFAEPLE KLTILENYTM 250
IEDLMNGMNG ATTLVRKIAF LEKGDTLFSW EIKEENESVC MLKHWTTVTH 300
GLRAETDETY HFISKELTAA FVASKESLNL TDPKQTCIKN EFEKIITDVY 350
MSDYNDAYSM NGSYQIFKTT GDLILIWQPL VQKSLMVLEQ GSVNLRRRRD 400
LVDVKSRHDI LYVQLQYLYD TLKDYINDAL GNLAESWCLD QKRTITMLHE 450
LSKISPSSIV SEVYGRPISA QLHGDVLAIS KCIEVNQSSV QLYKSMRVVD 500
AKGVRSETMC YNRPLVTFSF VNSTPEVVLG QLGLDNEILL GDHRTEECEI 550
PSTKIFLSGN HAHVYTDYTH TNSTPIEDIE VLDAFIRLKI DPLENADFKL 600
LDLYSPDELS RANVFDLENI LREYNSYKSA LYTIEAKIAT NTPSYVNGIN 650
SFLQGLGAIG TGLGSVISVT AGALGDIVGG VVSFLKNPFG GGLMLILAIV 700
VVVIIIVVFV RQKHVLSKPI DMMFPYATNP VTTVSSVTGT TVVKTPSVKD 750
ADGGTSVAVS EKEEGMADVS GQISGDEYSQ EDALKMLKAI KSLDESYRRK 800
PSSSESHASK PSLIDRIRYR GYKSVNVEEA
```

The amino acid sequence of HHV-7 gH is (SEQ ID NO: 32):

```
MYFYINSLLL IVSINGWKHW NILNSSICVN EKTNQIIIQP GLITFNFHDY  50
NETRVYQIPK CLFGYTFVSN LFDSVNFDES FDQYKHRITR FFNPSTEKAV 100
KIYAQKFQTN IKPVSHTKTI TVSFLPLFYE KDVYFANVSE IRKLYYNQYI 150
CTLSNGLTDY LFPITERCVM RHYNYLNTVF MLALTPSFFI ISVETGMDDV 200
VFIFGNVSRI FFKAPFRKSS FIYRQTVSDD LLLITKKITI ERFYPFLKID 250
FLDDIWKQNY DISFLIAKFN KLATVYIMEG FCGKPVNKDT FHLMFLFGLT 300
HFLYSTRGDG LLPLLEILNT HQSIITMGRF LEKCFKMTKS HLLYPEMEKL 350
QNFQLVDYSY ITSDLTIPIS AKLAFLSLAD GRIVTVPQNK WKEIENNIET 400
```

```
LYEKHKLFTN LTQPERANLF LLSEIGNSLV FQEKIKRKIH VLLASLCNPL 450

EMYFWTHMLD NVMDIETMFS PCATATRKDL TQRVVNNILS YKNLDAYTNK 500

VMNTLSVYRK KRLDMFKSIS CVSNEQAAFL TLPNITYTIS SKYILAGTSF 550

SVTSTVISTT IIITVVPLNS TCTPTNYKYS VKNIKPIYNI SSHDCVFCES 600

LVVEYDDIDG IIQFVYIMDD KQLLKLIDPD INFIDVNPRT HYLLFLRNGS 650

VFEITALDLK SSQVSIMLVL LYLIIIIIVL FGIYHVFRLF
```

The amino acid sequence of HHV-7 gL is (SEQ ID NO: 33):

```
MKTNIFFIFL ISILNQIYAL FNNSYYSNLE QECIKNILNC TQSKTLSLLE 50

PIDQAPIPKS DIISRLLYHT PYISRRDQVL IDEDFLETFY LLYNNPNQLH 100

TLLSLIKDSE SGHNWLGFLN NFERCLSDNT LLTCRDNVCK SYSYEKLKFT 150

GNIFVENIIG FEFNIPSNMI NFNMSILIYL ENEETRTQRI VRIDHHGINV 200

FDALLNCLRY FSRYYNFSFP LIQEMEKYNE VLPFRSEFSN LLIRTY
```

The amino acid sequence of HHV-7 gB is (SEQ ID NO: 34):

```
MKILFLSVFI  TFSLQLSLQT  EADFVMTGHN  QHLPFRICSI  ATGTDLVRFD   50

REVSCASYGS  NIKTTEGILI  IYKTKIEAHT  FSVRTFKKEL  TFQTTYRDVG  100

TVYFLDRTVT  TLPMPIEEVH  MVNTEARCLS  SISVKRSEEE  EYVAYHKDEY  150

VNKTLDLIPL  NFKSDTVRRY  ITTKEPFLRN  GPLWFYSTST  SINCIVTDCI  200

AKTKYPFDFF  ALSTGETVEG  SPFYNGINSK  TFNEPTEKIL  FRNNYTMLKT  250

FDDGSKGNFV  TLTKMAFLEK  GNTIFSWEVQ  NEESSICLLK  HWMTIPHALR  300

AENANSFHFI  AQELTASFVT  GKSNYTLSDS  KYNCINSNYT  SILDEIYQTQ  350

YNNSHDKNGS  YEIFKTEGDL  ILIWQPLIQR  KLTVLENFSN  ASRKRRKREL  400

ETNKDIVYVQ  LQYLYDTLKD  YINTALGKLA  EAWCLNQKRT  ITVLHELSKI  450

SPSGIISAVY  GKPMSAKLIG  DVLAVSKCIE  VNQTSVQLHK  SMRLTKDSSY  500

DALRCYSRPL  LTYSFANSSK  ETYLGQLGLD  NEILLGNHRT  EECEQSNTKI  550

FLSGKFAHIF  KDYTYVNSSL  ITEIEALDAF  VDLNIDPLEN  ADFTLLELYT  600

KDELSKANVF  DLETILREYN  SYKSALHHIE  TKIATVTPTY  IGGIDTFFKG  650

LGALGLGLGA  VLGVTAGALG  DVVNGVFSFL  KNPFGGALTI  LLTLGVIGLV  700

IFLFLRHKRL  AQTPIDILFP  YTSKSTNSVL  QATQSVQAQV  KEPLDSSPPY  750

LKTNKDTEPQ  GDDITHTNEY  SQVEALKMLK  AIKLLDESYK  KAEIAEAKKS  800

QRPSLLERIQ  YRGYQKLSTE  EL
```

Alphaherpesviruses: Type 1 Human Herpes Virus (HHV-1), Type 2 Human Herpes Virus (HHV-2), & Varicella-Zoster Virus (VZV, HHV-3)

HHV-1, or herpes simplex virus-1 (HSV-1), causes oral herpes, HHV-2, or herpes simplex virus-1 (HSV-2) causes genital herpes, and HHV-3, or VZV, causes chickenpox and shingles. Each of these viruses belong to the alphaherpesvirus sub-family of the herpesvirus family and are neurotropic viruses. VZV infects nearly all humans and primary infection causes chickenpox (varicella). Latent VZV resides most commonly in the cranial nerve ganglia, dorsal root ganglia, and autonomic ganglia along the neuroaxis. The viruses of this sub-family and reactivate spontaneously, resulting in shingles (zoster). Zoster skin lesions usually last more than a week, but in some individuals infection can lead to chronic pain or postherpetic neuralgia (PHN, pain that lasts more than three months) as well as vasculopathy can occur in about 40% of patients older than 60 years of age. Zoster paresis (zoster with lower motor neuron type weakness) may also occur in the arms, legs, diaphragm, and/or abdominal muscles. Pathological features of zoster include inflammation and haemorrhagic necrosis with associated neuritis, localized leptomeningitis, unilateral segmental poliomyelitis, and degeneration of related motor and sensory roots. Demyelination is seen in areas with mononuclear cell (MNC) infiltration and microglial proliferation. Intranuclear inclusions, viral antigen, and herpesvirus particles have been found in acutely infected ganglia. Vasculopathy (or stroke)

can be caused by productive virus infection of cerebral arteries and is referred to as granulomatous angiitis, VZV vasculitis/encephalitis, post-varicella arteriopathy, and herpes zoster ophthalmicus with delayed contralateral hemiparesis. Symptoms can include fever, altered mental status, headaches, and focal neurological deficits. (Gilden et al., *Neuropathol. Appl. Neurobiol.,* 37(5):441-463, 2012). Other serious complications of VZV infection include Mollaret's meningitis, zoster multiplex, muelitis, herpes ophthalmicus (zoster sine herpete), and Ramsay Hunt Syndrome. Studies have indicated an increased risk of stroke after zoster. (Kang et al., *Stroke,* 40(11):3443-3448, 2009; and Lin et al., *Neurology,* 74(10):792-797, 2010). Acute infections of VZV can lead to mengitis, meningoencephalitis, meningoradiculitis, and cerebellitis. (Habib et al., *J. Neurovirol.,* 15(2): 206-208, 2009; Klein et al., *Scan. J. Infect. Dis.,* 42(8):631-633, 2010; Gunson et al., *J. Clin. Virol.,* 50(3):191-193, 2011; and Moses et al., *Lancet Neurol.,* 5(11):984-988, 2006).

The VZV genome was the first herpesvirus genome to be completely sequenced, in 1986. The VZV genome is exceedingly stable, yielding only three point mutations in over 1200 passages. (Liu et al., *Arch. Virol.,* 153(10):1943-7, 2008). Infection proceeds from Langerhans cells to resident T cells near draining lymph nodes. T cells are induced to express skin-homing factors that transport the virus-loaded T cell to the dermis where fibroblasts and keratinocytes are exposed to infection and produce proinflammatory cytokines yielding varicella. (Taylor et al., *J. Virol.,* 79(17):11501-6, 2005; and Huch et al., *J. Virol.,* 84(8):4060-72, 2010). VZV triggers apoptosis in several cell types, including kidney cells, melanoma cells, fibroblasts, and others. (Pugazhenthi et al., *J. Virol.,* 83(18):9273-82, 2009).

Various pharmaceutical treatments are available for VZV infections, including acyclovir for the chicken pox, famciclovir, valaciclovir for the shingles, zoster-immune globulin (ZIG), and vidarabine. VZV immune globulin is also a treatment. (Centers for Disease Control and Prevention (CDC), March 2012, "FDA approval of an extended period for administering VariZIG for postexposure prophylaxis of varicella," *Morb. Mortal. Wkly. Rep.,* 61(12):212, PMID 2245612).

VZV and HSV-1/HSV-2 produce the known envelope glycoproteins gB, gH and gL, gM, gN, corresponding to the same or similar glycoproteins and associated protein functions found in other HHV species. Although there is no equivalent of the HHV-1/HHV-2 glycoprotein gD in VZV, glycoprotein gE of VZV performs a similar function. (Cohen, J. I., *Curr. Top. Microbiol. Immunol.,* 342:1-14, 2010). Expression of gB, gH, and gL is necessary and sufficient to induce membrane fusion, prior to virion entry into a host cell, allowing the nucleocapsid to gain access to the cytoplasm. Other accessory glycoproteins similar to gp42, gD, gO, or UL128-130, are not needed for fusion. (Eisenberg et al., *Viruses,* 4:800-832, 2012; Vleck et al., *Proc. Natl. Acad. Sci. USA,* 108:18412-7, 2011; and Oliver et al., *Proc. Natl. Acad. Sci. USA,* 110:1911-6, 2013).

At least two cell proteins, insulin-degrading enzyme (IDE), and myelin-associated glycoprotein (MAG), are thought to function as receptors for VZV entry into host cells; however, other studies implicate the αV subunit of integrins as playing a role in membrane fusion for VZV. (Yang et al., *J. Virol.,* 90(16):7567-78, 2016).

The antigenic compositions and methods of this application typically involve two or more HHV proteins involved in mediating HHV binding, fusion, and entry into host cells. In certain embodiments, two or more VZV proteins disclosed herein are combined in an antigenic composition. The two or more VZV proteins can be administered simultaneously or separately to induce an immune response or to treat or prevent a VZV infection in a subject. In certain embodiments, the antigenic composition (or method of administration) comprises two or more of the following VZV polypeptides (or nucleic acids encoding the same): gB, gH, and gL. In some embodiments, the gB polypeptide is monomeric, dimeric, or trimeric. In some embodiments, the gH and gL polypeptides are monomeric, dimeric, trimeric, or tetrameric. Typically, gH and gL form a gH/gL heterodimer.

In certain embodiments, the two or more VZV proteins (or nucleic acids encoding the same) comprise a monomeric or multimeric gB and a monomeric or multimeric gH/gL heterodimer. In certain embodiments, the gB is monomeric, dimeric or trimeric and the gH/gL heterodimer is monomeric or trimeric. In certain embodiments, the gB is monomeric and the gH/gL heterodimer is monomeric. In certain embodiments, the gB is trimeric and the gH/gL heterodimer is trimeric. In certain embodiments, the gB is trimeric and the gH/gL heterodimer is monomeric or trimeric. In certain embodiments, the VZV gB, gH, and gL polypeptides form a protein complex when mixed together. In certain embodiments, the VZV gB, gH, and gL polypeptides are not administered as a protein complex comprising the gB, gH, and gL polypeptides. For example, the gB can be administered separately from the gH and/or gL or administered with the gH and gL but not as a protein complex. In certain embodiments, the two or more VZV proteins further comprise one or more of the following glycoproteins: gI, gC, and/or gE, which can be monomeric or multimeric (e.g., dimeric, trimeric, or tetrameric).

The amino acid sequence of VZV gH is (SEQ ID NO: 35):

```
MFALVLAVVI LPLWTTANKS YVTPTPATRS IGHMSALLRE YSDRNMSLKL  50

EAFYPTGFDE ELIKSLHWGN DRKHVFLVIV KVNPTTHEGD VGLVIFPKYL 100

LSPYHFKAEH RAPFPAGRFG FLSHPVTPDV SFFDSSFAPY LTTQHLVAFT 150

TFPPNPLVWH LERAETAATA ERPFGVSLLP ARPTVPKNTI LEHKAHFATW 200

DALARHTFFS AEAIITNSTL RIHVPLFGSV WPIRYWATGS VLLTSDSGRV 250

EVNIGVGFMS SLISLSSGPP IELIVVPHTV KLNAVTSDTT WFQLNPPGPD 300

PGPSYRVYLL GRGLDMNFSK HATVDICAYP EESLDYRYHL SMAHTEALRM 350

TTKADQHDIN EESYYHIAAR IATSIFALSE MGRTTEYFLL DEIVDVQYQL 400

KFLNYILMRI GAGAHPNTIS GTSDLIFADP SQLHDELSLL FGQVKPANVD 450
```

-continued

```
YFISYDEARD   QLKTAYALSR  GQDHVNALSL  ARRVIMSIYK  GLLVKQNLNA  500
TERQALFFAS   MILLNFREGL  ENSSRVLDGR  TTLLLMTSMC  TAAHATQAAL  550
NIQEGLAYLN   PSKHMFTIPN  VYSPCMGSLR  TDLTEEIHVM  NLLSAIPTRP  600
GLNEVLHTQL   DESEIFDAAF  KTMMIFTTWT  AKDLHILHTH  VPEVFTCQDA  650
AARNGEYVLI   LPAVQGHSYV  ITRNKPQRGL  VYSLADVDVY  NPISVVYLSR  700
DTCVSEHGVI   ETVALPHPDN  LKECLYCGSV  FLRYLTTGAI  MDIIIIDSKD  750
TERQLAAMGN   STIPPFNPDM  HGDDSKAVLL  FPNGTVVTLL  GFERRQAIRM  800
SGQYLGASLG   GAFLAVVGFG  IIGWMLCGNS  RLREYNKIPL  T
```

The amino acid sequence of VZV gL is (SEQ ID NO: 36):

```
MASHKWLLQI   VFLKTITIAY  CLHLQDDTPL  FFGAKPLSDV  SLIITEPCVS   50
SVYEAWDYAA   PPVSNLSEAL  SGIVVKTKCP  VPEVILWFKD  KQMAYWTNPY  100
VTLKGLAQSV   GEEHKSGDIR  DALLDALSGV  WVDSTPSSTN  IPENGCVWGA  150
DRLFQRVCQ
```

The amino acid sequence of VZV gB is (SEQ ID NO: 37):

```
MSPCGYYSKW   RNRDRPEYRR  NLRFRRFFSS  IHPNAAAGSG  FNGPGVFITS   50
VTGVWLCFLC   IFSMFVTAVV  SVSPSSFYES  LQVEPTQSED  ITRSAHLGDG  100
DEIREAIHKS   QDAETKPTFY  VCPPPTGSTI  VRLEPTRTCP  DYHLGKNFTE  150
GIAVVYKENI   AAYKFKATVY  YKDVIVSTAW  AGSSYTQITN  RYADRVPIPV  200
SEITDTIDKF   GKCSSKATYV  RNNHKVEAFN  EDKNPQDMPL  IASKYNSVGS  250
KAWHTTNDTY   MVAGTPGTYR  TGTSVNCIIE  EVEARSIFPY  DSFGLSTGDI  300
IYMSPFFGLR   DGAYREHSNY  AMDRFHQFEG  YRQRDLDTRA  LLEPAARNFL  350
VTPHLTVGWN   WKPKRTEVCS  LVKWREVEDV  VRDEYAHNFR  FTMKTLSTTF  400
ISETNEFNLN   QIHLSQCVKE  EARAIINRIY  TTRYNSSHVR  TGDIQTYLAR  450
GGFVVVFQPL   LSNSLARLYL  QELVRENTNH  SPQKHPTRNT  RSRRSVPVEL  500
RANRTITTTS   SVEFAMLQFT  YDHIQEHVNE  MLARISSSWC  QLQNRERALW  550
SGLFPINPSA   LASTILDQRV  KARILGDVIS  VSNCPELGSD  TRIILQNSMR  600
VSGSTTRCYS   RPLISIVSLN  GSGTVEGQLG  TDNELIMSRD  LLEPCVANHK  650
RYFLFGHHYV   YYEDYRYVRE  IAVHDVGMIS  TYVDLNLTLL  KDREFMPLQV  700
YTRDELRDTG   LLDYSEIQRR  NQMHSLRFYD  IDKVVQYDSG  TAIMQGMAQF  750
FQGLGTAGQA   VGHVVLGATG  ALLSTVHGFT  TFLSNPFGAL  AVGLLVLAGL  800
VAAFFAYRYV   LKLKTSPMKA  LYPLTTKGLK  QLPEGMDPFA  EKPNATDTPI  850
EEIGDSQNTE   PSVNSGFDPD  KFREAQEMIK  YMTLVSAAER  QESKARKKNK  900
TSALLTSRLT   GLALRNRRGY  SRVRTENVTG  V
```

The amino acid sequence of VZV gI is (SEQ ID NO: 38):

```
MFLIQCLISA   VIFYIQVTNA  LIFKGDHVSL  QVNSSLTSIL  IPMQNDNYTE   50
IKGQLVFIGE   QLPTGTNYSG  TLELLYADTV  AFCFRSVQVI  RYDGCPRIRT  100
SAFISCRYKH   SWHYGNSTDR  ISTEPDAGVM  LKITKPGIND  AGVYVLLVRL  150
```

-continued

```
DHSRSTDGFI   LGVNVYTAGS   HHNIHGVIYT   SPSLQNGYST   RALFQQARLC   200

DLPATPKGSG   TSLFQHMLDL   RAGKSLEDNP   WLHEDVVTTE   TKSVVKEGIE   250

NHVYPTDMST   LPEKSLNDPP   ENLLIIIPIV   ASVMILTAMV   IVIVISVKRR   300

RIKKHPIYRP   NTKIRRGIQN   ATPESDVMLE   AAIAQLATIR   EESPPHSVVN   350

PFVK
```

The amino acid sequence of VZV gC is (SEQ ID NO: 39):

```
MKRIQINLIL   TIACIQLSTE   SQPTPVSITE   LYTSAATRKP   DPAVAPTSAA    50

SRKPDPAVAP   TSAASRKPDP   AVAPTSAASR   KPDPAVAPTS   AATRKPDPAV   100

APTSAASRKP   DPAVAPTSAA   TRKPDPAVAP   TSAASRKPDP   AANTQHSQPP   150

FLYENIQCVH   GGIQSIPYFH   TFIMPCYMRL   TTGQQAAFKQ   QQKTYEQYSL   200

DPEGSNITRW   KSLIRPDLHI   EVWFTRHLID   PHRQLGNALI   RMPDLPVMLY   250

SNSADLNLIN   NPEIFTHAKE   NYVIPDVKTT   SDFSVTILSM   DATTEGTYIW   300

RVVNTKTKNV   ISEHSITVTT   YYRPNITVVG   DPVLTGQTYA   AYCNVSKYYP   350

PHSVRVRWTS   RFGNIGKNFI   TDAIQEYANG   LFSYVSAVRI   PQQKQMDYPP   400

PAIQCNVLWI   RDGVSNMKYS   AVVTPDVYPF   PNVSIGIIDG   HIVCTAKCVP   450

RGVVHFVWWV   NDSPINHENS   EITGVCDQNK   RFVNMQSSCP   TSELDGPITY   500

SCHLDGYPKK   FPPFSAVYTY   DASTYATTFS   VVAVIIGVIS   ILGTLGLIAV   550

IATLCIRCCS
```

The amino acid sequence of VZV gE is (SEQ ID NO: 40):

```
MGTVNKPVVG   VLMGFGIITG   TLRITNPVRA   SVLRYDDFHT   DEDKLDTNSV    50

YEPYYHSDHA   ESSWVNRGES   SRKAYDHNSP   YIWPRNDYDG   FLENAHEHHG   100

VYNQGRGIDS   GERLMQPTQM   SAQEDLGDDT   GIHVIPTLNG   DDRHKIVNVD   150

QRQYGDVFKG   DLNPKPQGQR   LIEVSVEENH   PFTLRAPIQR   IYGVRYTETW   200

SFLPSLTCTG   DAAPAIQHIC   LKHTTCFQDV   VVDVDCAENT   KEDQLAEISY   250

RFQGKKEADQ   PWIVVNTSTL   FDELELDPPE   IEPGVLKVLR   TEKQYLGVYI   300

WNMRGSDGTS   TYATFLVTWK   GDEKTRNPTP   AVTPQPRGAE   FHMWNYHSHV   350

FSVGDTFSLA   MHLQYKIHEA   PFDLLLEWLY   VPIDPTCQPM   RLYSTCLYHP   400

NAPQCLSHMN   SGCTFTSPHL   AQRVASTVYQ   NCEHADNYTA   YCLGISHMEP   450

SFGLILHDGG   TTLKFVDTPE   SLSGLYVFVV   YFNGHVEAVA   YTVVSTVDHF   500

VNAIEERGFP   PTAGQPPATT   KPKEITPVNP   GTSPLLRYAA   WTGGLAAVVL   550

LCLVIFLICT   AKRMRVKAYR   VDKSPYNQSM   YYAGLPVDDF   EDSESTDTEE   600

EFGNAIGGSH   GGSSYTVYID   KTR
```

The antigenic compositions and methods of this application typically involve two or more HHV proteins involved in mediating HHV binding, fusion, and entry into host cells. In certain embodiments, two or more HSV-1 or HSV-2 proteins disclosed herein are combined in an antigenic composition. The two or more HSV-1 or HSV-2 proteins can be administered simultaneously or separately to induce an immune response or to treat or prevent an HSV-1 or HSV-2 infection in a subject. In certain embodiments, the antigenic composition (or method of administration) comprises two or more of the following HSV-1 or HSV-2 polypeptides (or nucleic acids encoding the same): gB, gH, and gL. In some embodiments, the gB polypeptide is monomeric, dimeric, or trimeric. In some embodiments, the gH and gL polypeptides are monomeric, dimeric, trimeric, or tetrameric. Typically, gH and gL form a gH/gL heterodimer.

In certain embodiments, the two or more HSV-1 or HSV-2 proteins (or nucleic acids encoding the same) comprise a monomeric or multimeric gB and a monomeric or multimeric gH/gL heterodimer. In certain embodiments, the gB is monomeric, dimeric or trimeric and the gH/gL heterodimer is monomeric or trimeric. In certain embodiments, the gB is monomeric and the gH/gL heterodimer is monomeric or trimeric. In certain embodiments, the gB is trimeric and the gH/gL heterodimer is monomeric. In certain embodiments, the gB is trimeric and the gH/gL heterodimer is trimeric. In certain embodiments, the HSV-1 or HSV-2 gB, gH, and gL polypeptides form a protein complex when mixed together. In certain embodiments, the HSV-1 or HSV-2 gB, gH, and gL polypeptides are not administered as a protein complex comprising the gB, gH, and gL polypeptides. For example, the gB can be administered separately from the gH and/or gL or administered with the gH and gL but not as a protein complex.

In certain embodiments, the two or more HSV-1 or HSV-2 proteins further comprises a gD polypeptide, which can be monomeric or multimeric (e.g., dimeric, trimeric, or tetrameric).

The amino acid sequence of HSV-1 gH is (SEQ ID NO: 41):

```
MGNGLWFVGV  IILGAAWGQV  HDWTEQTDPW  FLDGLGMDRM  YWRDTNTGRL   50
WLPNTPDPQK  PPRGFLAPPD  ELNLTTASLP  LLRWYEERFC  FVLVTTAEFP  100
RDPGQLLYIP  KTYLLGRPPN  ASLPAPTTVE  PTAQPPPAVA  PLKGLLHNPT  150
ASVLLRSRAW  VTFSAVPDPE  ALTFPRGDNV  ATASHPSGPR  DTPPPRPPVG  200
ARRHPTTELD  ITHLHNASTT  WLATRGLLRS  PGRYVYFSPS  ASTWPVGIWT  250
TGELVLGCDA  ALVRARYGRE  FMGLVISMHD  SPPAEVMVVP  AGQTLDRVGD  300
PADENPPGAL  PGPPGGPRYR  VFVLGSLTRA  DNGSALDALR  RVGGYPEEGT  350
NYAQFLSRAY  AEFFSGDAGA  EQGPRPPLFW  RLTGLLATSG  FAFVNAAHAN  400
GAVCLSDLLG  FLAHSRALAG  LAARGAAGCA  ADSVFFNVSV  LDPTARLQLE  450
ARLQHLVAEI  LEREQSLALH  ALGYQLAFVL  DSPSAYDAVA  PSAAHLIDAL  500
YAEFLGGRVV  TTPVVHRALF  YASAVLRQPF  LAGVPSAVQR  ERARRSLLIA  550
SALCTSDVAA  ATNADLRTAL  ARADHQKTLF  WLPDHFSPCA  ASLRFDLDES  600
VFILDALAQA  TRSETPVEVL  AQQTHGLAST  LTRWAHYNAL  IRAFVPEASH  650
RCGGQSANVE  PRILVPITHN  ASYVVTHSPL  PRGIGYKLTG  VDVRRPLFLT  700
YLTATCEGST  RDIESKRLVR  TQNQRDLGLV  GAVFMRYTPA  GEVMSVLLVD  750
TDNTQQQIAA  GPTEGAPSVF  SSDVPSTALL  LFPNGTVIHL  LAFDTQPVAA  800
IAPGFLAASA  LGVVMITAAL  AGILKVLRTS  VPFFWRRE
```

The amino acid sequence of HSV-1 gL is (SEQ ID NO: 42):

```
MGILGWVGLI  AVGVLCVRGG  LPSTEYVIRS  RVAREVGDIL  KVPCVPLPSD   50
DLDWRYETPS  AINYALIDGI  FLRYHCPGLD  TVLWDRHAQK  AYWVNPFLFV  100
AGFLEDLSYP  AFPANTQETE  TRLALYKEIR  QALDSRKQAA  SHTPVKAGCV  150
NFDYSRTRRC  VGRQDLGPTN  GTSGRTPVLP  PDDEAGLQPK  PLTTPPPIIA  200
TSDPTPRRDA  ATKSRRRPH   SRRL
```

The amino acid sequence of HSV-1 gB is (SEQ ID NO: 43):

```
MHQGAPSWGR  RWFVVWALLG  LTLGVLVASA  APTSPGTPGV  AAATQAANGG   50
PATPAPPPLG  AAPTGDPKPK  KNKKPKNPTP  PRPAGDNATV  AAGHATLREH  100
LRDIKAENTD  ANFYVCPPPT  GATVVQFEQP  RRCPTRPEGQ  NYTEGIAVVF  150
KENIAPYKFK  ATMYYKDVTV  SQVWFGHRYS  QFMGIFEDRA  PVPFEEVIDK  200
INAKGVCRST  AKYVRNNLET  TAFHRDDHET  DMELKPANAA  TRTSRGWHTT  250
DLKYNPSRVE  AFHRYGTTVN  CIVEEVDARS  VYPYDEFVLA  TGDFVYMSPF  300
YGYREGSHTE  HTTYAADRFK  QVDGFYARDL  TTKARATAPT  TRNLLTTPKF  350
```

```
TVAWDWVPKR  PSVCTMTKWQ  EVDEMLRSEY  GGSFRFSSDA  ISTTFTTNLT  400
EYPLSRVDLG  DCIGKDARDA  MDRIFARRYN  ATHIKVGQPQ  YYQANGGFLI  450
AYQPLLSNTL  AELYVREHLR  EQSRKPPNPT  PPPPGASANA  SVERIKTTSS  500
IEFARLQFTY  NHIQRHVNDM  LGRVAIAWCE  LQNHELTLWN  EARKLNPNAI  550
ASVTVGRRVS  ARMLGDVMAV  STCVPVAADN  VIVQNSMRIS  SRPGACYSRP  600
LVSFRYEDQG  PLVEGQLGEN  NELRLTRDAI  EPCTVGHRRY  FTFGGGYVYF  650
EEYAYSHQLS  RADITTVSTF  IDLNITMLED  HEFVPLEVYT  RHEIKDSGLL  700
DYTEVQRRNQ  LHDLRFADID  TVIHADANAA  MFAGLGAFFE  GMGDLGRAVG  750
KVVMGIVGGV  VSAVSGVSSF  MSNPFGALAV  GLLVLAGLAA  AFFAFRYVMR  800
LQSNPMKALY  PLTTKELKNP  TNPDASGEGE  EGGDFDEAKL  AEAREMIRYM  850
ALVSAMERTE  HKAKKKGTSA  LLSAKVTDMV  MRKRRNTNYT  QVPNKDGDAD  900
EDDL
```

The amino acid sequence of HSV-1 gD is (SEQ ID NO: 44):

```
MGGAAARLGA  VILFVVIVGL  HGVRGKYALA  DASLKMADPN  RFRGKDLPVP  50
DRLTDPPGVR  RVYHIQAGLP  DPFQPPSLPI  TVYYAVLERA  CRSVLLNAPS  100
EAPQIVRGGS  EDVRKQPYNL  TIAWFRMGGN  CAIPITVMEY  TECSYNKSLG  150
ACPIRTQPRW  NYYDSFSAVS  EDNLGFLMHA  PAFETAGTYL  RLVKINDWTE  200
ITQFILEHRA  KGSCKYALPL  RIPPSACLSP  QAYQQGVTVD  SIGMLPRFIP  250
ENQRIVAVYS  LKIAGWHGPK  APYTSTLLPP  ELSETPNATQ  PELAPEDPED  300
SALLEDPVGT  VAPQIPPNWH  IPSIQDAATP  YHPPATPNNM  GLIAGAVGGS  350
LLAALVICGI  VYWMRRRTQK  GPKRIRLPHI  REDDQPSSHQ  PLFY
```

The amino acid sequence of HSV-2 gH is (SEQ ID NO: 45):

```
MGPGLWVVMG  VLVGVAGGHD  TYWTEQIDPW  FLHGLGLART  YWRDTNTGRL  50
WLPNTPDASD  PQRGRLAPPG  ELNLTTASVP  MLRWYAERFC  FVLVTTAEFP  100
RDPGQLLYIP  KTYLLGRPRN  ASLPELPEAG  PTSRPPAEVT  QLKGLSHNPG  150
ASALLRSRAW  VTFAAAPDRE  GLTFPRGDDG  ATERHPDGRR  NAPPPGPPAG  200
APRHPTTNLS  IAHLHNASVT  WLAARGLLRT  PGRYVYLSPS  ASTWPVGVWT  250
TGGLAFGCDA  ALVRARYGKG  FMGLVISMRD  SPPAEIIVVP  ADKTLARVGN  300
PTDENAPAVL  PGPPAGPRYR  VFVLGAPTPA  DNGSALDALR  RVAGYPEEST  350
NYAQYMSRAY  AEFLGEDPGS  GTDARPSLFW  RLAGLLASSG  FAFINAAHAH  400
DAIRLSDLLG  FLAHSRVLAG  LAARGAAGCA  ADSVFLNVSV  LDPAARLRLE  450
ARLGHLVAAI  LEREQSLAAH  ALGYQLAFVL  DSPAAYGAVA  PSAARLIDAL  500
YAEFLGGRAL  TAPMVRRALF  YATAVLRAPF  LAGAPSAEQR  ERARRGLLIT  550
TALCTSDVAA  ATHADLRAAL  ARTDHQKNLF  WLPDHFSPCA  ASLRFDLAEG  600
GFILDALAMA  TRSDIPADVM  AQQTRGVASA  LTRWAHYNAL  IRAFVPEATH  650
QCSGPSHNAE  PRILVPITHN  ASYVVTHTPL  PRGIGYKLTG  VDVRRPLFIT  700
YLTATCEGHA  REIEPKRLVR  TENRRDLGLV  GAVFLRYTPA  GEVMSVLLVD  750
```

-continued

```
TDATQQQLAQ    GPVAGTPNVF    SSDVPSVALL    LFPNGTVIHL    LAFDTLPIAT    800

IAPGFLAASA    LGVVMITAAL    AGILRVVRTC    VPFLWRRE
```

The amino acid sequence of HSV-2 gL is (SEQ ID NO: 46):

```
MGFVCLFGLV    VMGAWGAWGG    SQATEYVLRS    VIAKEVGDIL    RVPCMRTPAD    50

DVSWRYEAPS    VIDYARIDGI    FLRYHCPGLD    TFLWDRHAQR    AYLVNPFLFA    100

AGFLEDLSHS    VFPADTQETT    TRRALYKEIR    DALGSRKQAV    SHAPVRAGCV    150

NFDYSRTRRC    VGRRDLRPAN    TTSTWEPPVS    SDDEASSQSK    PLATQPPVLA    200

LSNAPHGGSP    RREVGAGILA    SDATSHVCIA    SHPGSGAGQP    TRLAAGSAVQ    250

RRRPRGCPPG    VMFSASTTPE    QPLGLSGDAT    PPLPTSVPLD    WAAFRRAFLI    300

DDAWRPLLEP    ELANPLTARL    LAEYDRRCQT    EEVLPPREDV    FSWTRYCTPD    350

DVRVVIIGQD    PYHHPGQAHG    LAFSVRADVP    VPPSLRNVLA    AVKNCYPDAR    400

MSGRGCLEKW    ARDGVLLLNT    TLTVKRGAAA    SHSKLGWDRF    VGGVVRRLAA    450

RRPGLVFMLW    GAHAQNAIRP    DPRQHYVLKF    SHPSPLSKVP    FGTCQHFLAA    500

NRYLETRDIM    PIDWSV
```

The amino acid sequence of HSV-2 gB is (SEQ ID NO: 47):

```
MRGGGLICAL    VVGALVAAVA    SAAPAAPAAP    RASGGVAATV    AANGGPASRP    50

PPVPSPATTK    ARKRKTKKPP    KRPEATPPPD    ANATVAAGHA    TLRAHLREIK    100

VENADAQFYV    CPPPTGATVV    QFEQPRRCPT    RPEGQNYTEG    IAVVFKENIA    150

PYKFKATMYY    KDVTVSQVWF    GHRYSQFMGI    FEDRAPVPFE    EVIDKINTKG    200

VCRSTAKYVR    NNMETTAFHR    DDHETDMELK    PAKVATRTSR    GWHTTDLKYN    250

PSRVEAFHRY    GTTVNCIVEE    VDARSVYPYD    EFVLATGDFV    YMSPFYGYRE    300

GSHTEHTSYA    ADRFKQVDGF    YARDLTTKAR    ATSPTTRNLL    TTPKFTVAWD    350

WVPKRPAVCT    MTKWQEVDEM    LRAEYGGSFR    FSSDAISTTF    TTNLTEYSLS    400

RVDLGDCIGR    DAREAIDRMF    ARKYNATHIK    VGQPQYYLAT    GGFLIAYQPL    450

LSNTLAELYV    REYMREQDRK    PRNATPAPLR    EAPSANASVE    RIKTTSSIEF    500

ARLQFTYNHI    QRHVNDMLGR    IAVAWCELQN    HELTLWNEAR    KLNPNAIASA    550

TVGRRVSARM    LGDVMAVSTC    VPVAPDNVIV    QNSMRVSSRP    GTCYSRPLVS    600

FRYEDQGPLI    EGQLGENNEL    RLTRDALEPC    TVGHRRYFIF    GGGYVYFEEY    650

AYSHQLSRAD    VTTVSTFIDL    NITMLEDHEF    VPLEVYTRHE    IKDSGLLDYT    700

EVQRRNQLHD    LRFADIDTVI    RADANAAMFA    GLCAFFEGMG    DLGRAVGKVV    750

MGVVGGVVSA    VSGVSSFMSN    PFGALAVGLL    VLAGLVAAFF    AFRYVLQLQR    800

NPMKALYPLT    TKELKTSDPG    GVGGEGEEGA    EGGGFDEAKL    AEAREMIRYM    850

ALVSAMERTE    HKARKKGTSA    LLSSKVTNMV    LRKRNKARYS    PLHNEDEAGD    900

EDEL
```

The amino acid sequence of HSV-2 gD is (SEQ ID NO: 48):

```
MGRLTSGVGT  AALLVVAVGL  RVVCAKYALA  DPSLKMADPN  RFRGKNLPVL   50
DRLTDPPGVK  RVYHIQPSLE  DPFQPPSIPI  TVYYAVLERA  CRSVLLHAPS  100
EAPQIVRGAS  DEARKHTYNL  TIAWYRMGDN  CAIPITVMEY  TECPYNKSLG  150
VCPIRTQPRW  SYYDSFSAVS  EDNLGFLMHA  PAFETAGTYL  RLVKINDWTE  200
ITQFILEHRA  RASCKYALPL  RIPPAACLTS  KAYQQGVTVD  SIGMLPRFIP  250
ENQRTVALYS  LKIAGWHGPK  PPYTSTLLPP  ELSDTTNATQ  PELVPEDPED  300
SALLEDPAGT  VSSQIPPNWH  IPSIQDVAPH  HAPAAPSNPG  LIIGALAGST  350
LAVLVIGGIA  FWVRRRAQMA  PKRLRLPHIR  DDDAPPSHQP  LFY
```

HHV Proteins.

This application demonstrates that various combinations of HHV proteins involved in mediating viral binding, fusion, and host cell entry unexpectedly induce synergistic or additive neutralizing antibody responses, notwithstanding concerns in the art about vaccine or immune interference. The HHV proteins that are combined in the antigenic compositions disclosed herein (e.g., gB, gH, gL, gp350) or administered (simultaneously or separately) to prevent or treat a HHV infection or induce immunity in a subject can be made using any conventional technique.

For example, in certain embodiments, one or more of the HHV proteins are naturally occurring. In other embodiments, one or more of the HHV proteins are recombinant (i.e., prepared using recombinant DNA techniques). In certain embodiments, the recombinant HHV proteins have one or more differences in the glycosylation pattern of the naturally occurring HHV proteins. In certain embodiments one or more of the HHV proteins have been modified and are not naturally occurring proteins. In certain embodiments all of the HHV proteins have been modified and are not naturally occurring proteins. For example, the HHV proteins may be a mutated version of the wild type protein, a truncated version of the wild type protein, a multimerized protein, or a fusion protein.

In certain embodiments, the modified HHV protein is a protein that binds to a specific target molecule and the modified HHV protein retains its ability to bind to the target molecule. In certain embodiments, the truncated HHV protein consists of the extracellular domain of the HHV protein or a portion thereof that retains the ability to bind to its target molecule, including, for example, the extracellular domain of one or more of gB, gp350, gL, or gH. By way of example, gp350 binds to CD21 (aka CR2) on the surface of B cells; gp42 binds to HLA class II molecules; gD binds to nectin-1 (HveC, CD111) and Herpesvirus Entry Mediator (HVEM); and gpK8.1A and gpK8.1B bind to a cell surface heparin sulfate molecule.

In certain embodiments, the HHV polypeptide is a variant HHV polypeptide comprising one or more deletions, insertions, or substitutions. For example, gp350 and gp220 polypeptides that bind to CR2 include naturally-occurring or synthetically programmed variant polypeptides substantially identical to either the gp350 or gp220 polypeptides, but which have an amino acid sequence different from that of gp350 or gp220 because of one or more deletions, insertions or substitutions. Some gp350/220 variant sequences have already been identified by sequencing the DNA of different strains of EBV, and are readily available to one of ordinary skill in the art (Beisel et al., *J. Viriol.*, 1985, 54(3):665-74).

Similarly, variant gH, gL, gB, gp42, gM, gN, gI, gC, gE, gD, ORF68, BMRF-2, UL128, UL130, UL131A, and gpK8.1 polypeptides can include naturally-occurring or synthetically programmed variant polypeptides substantially identical to either the gH, gL, gB, gp42, gM, gN, gI, gC, gE, gD, ORF68, BMRF-2, UL128, UL130, UL131A, and gpK8.1 polypeptides, but which have an amino acid sequence different from that of gH, gL, gB, gp42, gM, gN, gI, gC, gE, gD, ORF68, BMRF-2, UL128, UL130, UL131A, and gpK8.1 because of one or more deletions, insertions or substitutions.

The variant amino acid sequence preferably is at least 60%, 65%, 70%, or 80%, identical to a gp350, a gp220 polypeptide or a gH, gL, gB, gp42, gM, gN, gI, gC, gE, gD, ORF68, BMRF-2, UL128, UL130, UL131A, and gpK8.1, more preferably at least 85% identical, still more preferably at least 90% identical, and most preferably at least 95% identical. The percent identity can be determined, for example, by comparing sequence information using the GAP computer program, version 6.0 described by Devereux et al. (*Nucl. Acids Res.*, 12:387, 1984) and available from the University of Wisconsin Genetics Computer Group (UWGCG). The GAP program utilizes the alignment method of Needleman and Wunsch (*J. Mol. Biol.*, 48:443, 1970), as revised by Smith and Waterman (*Adv. Appl. Math*, 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.*, 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps.

Variant polypeptides can be obtained by mutation of nucleotide sequences encoding the gp350, gp220, gH, gL, gB, gp42, gM, gN, gI, gC, gE, gD, ORF68, BMRF-2, UL128, UL130, UL131A, and/or gpK8.1 polypeptides. Alterations of the amino acid sequence can occur naturally, or be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene,* 42:133, 1986); Bauer et al. (Gene 37:73, 1985); Craik, (*BioTechniques, Jan.* 12-19, 1985); Smith et al. (*Genetic Engineering: Principles and Methods*, Plenum Press, 1981); Kunkel (*Proc. Natl. Acad. Sci. USA,* 82:488, 1985); Kunkel et al. (*Methods in Enzymol.,* 154:367, 1987); and U.S. Pat. Nos. 4,518,584 and 4,737,462, all of which are incorporated by reference.

Even though multimerizing HHV proteins has been shown to enhance their immunogenicity (see US2015-0174237 A1 and US2016-0303225 A1, which are incorporated by reference in their entirety), unexpected additive and synergistic antibody responses were observed when both multimeric and/or monomeric HHV proteins were combined. Thus, in certain embodiments, one or more of the HHV proteins is a monomeric form of the protein. In certain embodiments, one or more of the HHV proteins is a multimeric form of the protein. In certain embodiments, one or more of the HHV proteins is monomeric and one or more of the HHV proteins is multimeric. In certain embodiments, the antigenic composition comprises a HHV gB polypeptide that is monomeric or multimeric. In certain embodiments, the multimeric gB polypeptide is dimeric or trimeric and preferably trimeric. In certain embodiments, the gp350 polypeptide is monomeric or multimeric. In certain embodiments, the multimeric gp350 is dimeric, trimeric, or tetrameric and preferably tetrameric. Methods for multimerizing HHV proteins are known in the art and are discussed elsewhere in this application.

The HHV gH and gL polypeptides can be combined as individual polypeptides in the antigenic compositions and methods described herein. In other embodiments, gH and gL form a gH/gL heterodimer. In certain embodiments, the gH/gL heterodimer is a non-covalently associated protein complex, such as the gH/gL protein complex that occurs naturally and can form spontaneously under certain in vitro conditions. In other embodiments, the gH/gL heterodimer is a fusion protein. If the HHV antigenic composition comprises the gH polypeptide and gL polypeptide in the form of a gH/gL heterodimer, the antigenic composition further comprises the gB polypeptide or, for EBV, the antigenic composition further comprises gB and/or the gp350 polypeptide. In certain embodiments, the gH or gL polypeptides are monomeric or multimeric. In certain embodiments, the gH or gL polypeptide is dimeric, trimeric, or tetrameric and preferably trimeric. In certain embodiments, the gH/gL heterodimer is monomeric or multimeric. In certain embodiments, the multimeric gH/gL heterodimer is dimeric, trimeric, or tetrameric and preferably trimeric.

Multimerizing HHV Proteins.

As discussed above, the two or more HHV polypeptides in the disclosed antigenic compositions may be multimerized or they may be monomeric. For instance, it is known that at least the gH and gL polypeptides under some conditions form heterodimers. Further, it is known that under some conditions the gB polypeptide exists as a multimer, for instance at least as a homotrimer. (Ma, A., *Virology,* 178(2): 588-592, 1990). Further, it is known that polypeptide gB associates with the heterodimer gH/gL to form a heterotrimer complex of gB/gH/gL under certain circumstances. Thus, upon introducing such HHV polypeptides into a composition, multimerization can spontaneously occur under some circumstances.

While multimerization of the HHV polypeptides can occur spontaneously for some polypeptides under appropriate conditions, others do not form multimers under natural conditions. In some embodiments it is advantageous to modify the two or more HHV polypeptides to form multimers to enhance their immunogenicity. In certain embodiments, a trimeric HHV gB polypeptide is formed by expressing a modified HHV gB polypeptide in a host cell. In the modified gB polypeptide, the furin cleavage site in the extracellular domain of the gB polypeptide is replaced by a linker sequence, as described in WO2015/089340 (also published as US2016-0303225 A1, which is incorporated by reference in its entirety). FIG. 1, right panel, and FIG. 7 depict an exemplary modified EBV and HCMV gB constructs, which form a homotrimeric gB complex when expressed in a host cell. In these embodiments, a linker sequence (e.g., $(Gly_4Ser)_3$ (SEQ ID NO: 3)) replaces the furin cleavage site in the extracellular domain of the EBV or HCMV gB polypeptide. An optional leader sequence can be added to the construct to direct secretion of the recombinant polypeptide. Although these embodiments are shown with the EBV and HCMV gB polypeptides, any HHV gB sequence can be substituted in the construct to produce the desired, modified gB polypeptide.

In certain embodiments, multimeric HHV proteins can be synthesized using recombinant cloning techniques to combine oligomerization domains with a HHV polypeptide, which is optionally expressed as a fusion protein, as described, for example, in WO2014/018858 (also published as US2015-0174237 A1, which is incorporated by reference in its entirety).

Fusion Proteins.

The fusion proteins used to make multimeric HHV proteins can be synthesized using standard, recombinant cloning techniques. For instance, one strategy for making a fusion protein involves creating nucleic acid constructs comprising oligomerization motif sequences and a linker sequence separating two or more antigens such that the encoded fusion protein can form a dimeric, trimeric, tetrameric, hexameric, heptameric, or octameric complex from a single nucleic acid construct. (See, WO 2014/018858, incorporated herein by reference for all purposes). This platform can be used to create multimeric fusion proteins comprising multiple copies of a single antigen of interest, including, for example, a gp350, gp220 polypeptide, or gB. For example, a homodimer, homotrimer, or homotetramer can be created using two, three, or four copies of the same polypeptide with a dimerization, trimerization, or tetramerization domain, respectively. When the oligomerization domains associate together, the construct will form a tetramer (if a dimerization domain is used) comprising four copies of the same polypeptide, a hexamer (if a trimerization domain is used) comprising six copies of the same polypeptide, or an octamer comprising eight copies of the same polypeptide (if a tetramerization domain is used).

Alternatively, this platform can be used to create multimeric fusion proteins comprising two or more different antigens of interest. For example, a heterodimer can be created with a first HHV polypeptide linked to a second different, HHV polypeptide (or a heterotrimer comprising two or three different antigens), such as a heterodimer formed between HHV gH and gL. When the oligomerization domains associate together, the construct will form a tetramer (if a dimerization domain is used) that is dimeric for both the first and second HHV polypeptide, a hexamer (if a trimerization domain is used in the construct) that is dimeric for at least the first and second HHV polypeptide, or trimeric for the first, second, and third HHV polypeptide, or an octamer (if a tetramerization domain is used).

In one embodiment, a trimeric protein can be formed if the original polypeptide is presented in monomeric form in association with the trimerization domain. The fusion protein may optionally further comprise a third polypeptide and a second linker sequence, where the second linker sequence joins the second polypeptide to the third polypeptide, the first polypeptide, or the oligomerization domain. In other embodiments, the fusion protein comprises four or more polypeptides and additional linkers. In one embodiment, the fusion protein forms a multimeric polypeptide when expressed in a host cell. In another embodiment, the first and second polypeptides do not occur naturally as a multimeric protein.

In some embodiments, only a portion of the extracellular domain of each the HHV polypeptide is engineered into the nucleic acid construct encoding the fusion protein. Shorter polypeptides are easier to express in larger quantities and in some embodiments only a portion of the HHV polypeptide is needed or desired to achieve the desired immunological effect, i.e., those portions of the HHV polypeptides that elicit an immune response.

The nucleic acid constructs optionally include a signal peptide-encoding nucleic acid so that the expressed fusion protein is excreted from the mammalian host cell, e.g. a tissue culture comprising one or more host cells, such as, for instance, a HeLa cells, yeast cells, insect cells, Chinese Hamster Ovary (CHO) cells, Human Embryonic Kidney (HEK) cells, COS cells, Vero cells, NSO mouse myeloma cells, and others disclosed in the art, such as Khan, K., *Adv. Pharm. Bull.*, 3(2):257-263, 2013. Secretion of the fusion protein provides an easy means for protein harvesting and purification by known methodologies.

In one embodiment, the fusion protein is formed from expression of a nucleic acid construct comprising nucleic acid sequences encoding one or more gp350 polypeptides, for example two such sequences, such that when expressed with a dimerization domain, such as a leucine zipper oligomerization domain, a gp350 tetramer, is formed. (See, FIG. 1, left panel). The gp350 nucleic acid sequence can be from any HHV genome comprising such a sequence. Alternatively, the gp350 sequences can be substituted with one or more other HHV polypeptide disclosed herein.

As depicted in the middle panel of FIG. 1, in another embodiment the fusion protein can be encoded by a first nucleic acid construct encoding gH and a second nucleic acid encoding gL, and a trimerization domain, such as the T4 foldon oligomerization domain, thereby yielding upon expression, for example, a trimeric gH/gL heterodimer. The gH and gL polypeptides can be any gH/gL polypeptide sequence found in any of the known HHV genomes. Alternatively, in another embodiment, the gH and/or gL polypeptides can be substituted with one or more other HHV polypeptides to form the desired HHV protein complex as described herein.

In such embodiments, it is not necessary that the nucleic acid constructs comprise full length HHV polypeptide sequences. The sequences can be modified. For instance, the modified sequence can be a partial, truncated, or otherwise altered or mutated sequence. Such modified sequences can improve protein expression, for instance by removing the transmembrane and intracellular domain sequences, or can elicit a more robust immune response, for instance by strategically arranging highly immunogenic epitopes of the HHV polypeptides discussed herein.

Linker Sequences.

Linker sequences are used in the modified gB polypeptide to replace the furin cleavage site in the extracellular domain of the gB polypeptide. Linker sequences are also used in the fusion proteins to separate different components of the fusion protein. Thus, in certain embodiments, the amino terminal end of the linker sequence is joined by a peptide bond to a first polypeptide and the carboxy terminal end of the linker sequence is joined by a peptide bind to a second polypeptide. The first and second polypeptides are each one of the HHV fusion and host cell entry proteins or one of the HHV accessory proteins. In certain embodiments, the first and second polypeptides are the same (e.g., gp350). In other embodiments, the first and second polypeptides are different (e.g., gH and gL). Such a linker sequence joins the first polypeptide and the second polypeptide, in contrast to a first polypeptide and a second polypeptide that are joined together without an intervening polypeptide sequence. It is understood that the linker sequence is not a sequence that naturally separates a first and second polypeptide, if the first and second polypeptide happen to naturally exist in combination together.

In one embodiment, the linker sequence is a polypeptide having 5-25 amino acids, particularly a length of 6, 7, 8, 9, 10, 11, 12, 13, 14, 15, 16, 17, 18, 19 or 20 amino acids. In another embodiment, the linker sequence is a polypeptide having 10-25 amino acids. The linker sequence preferably comprises glycine and serine amino acids. In one embodiment, the linker sequence is 15 amino acids in length and has the amino acid sequence $(Gly_4Ser)_3$ (SEQ ID NO: 3).

Other suitable peptide linkers are those described in U.S. Pat. Nos. 4,751,180, 4,935,233, and 5,073,627, each of which is hereby incorporated by reference in its entirety. A DNA sequence encoding a desired linker sequence may be inserted between, and in the same reading frame as, for example, DNA sequences encoding the first and second polypeptide using conventional techniques known in the art. For example, a chemically synthesized oligonucleotide encoding the linker may be ligated between sequences encoding the first and second polypeptide.

Oligomerization Domains.

Oligomerization domains are used in certain embodiments to make multimeric HHV polypeptides. Oligomerization domains are stretches of amino acid residues that cause polypeptides comprising them to oligomerize, i.e., to form covalent and/or non-covalent associations with another polypeptide comprising a corresponding or cognate oligomerization domain. Thus, two or more polypeptides are "oligomerized" if they are bound to each other via their oligomerization domains. Any oligomerization domain known in the art can be used. Examples include leucine zipper domains, complement C1q domains, α-helical coiled coil domains, thrombospondin domains, and fibritin domains. (See, Engel et al., *Matrix Biol.,* 19(4):283-288, 2000). The polypeptides in an oligomer can have identical polypeptide sequences, similar polypeptide sequences, or different polypeptide sequences.

Homodimerization and homo-oligomerization refer to the association of the same polypeptide components to form dimers or oligomers. Heterodimerization and hetero-oligomerization refer to the association of different polypeptides to form dimers or oligomers. Homo-oligomers thus comprise an association of multiple copies of a particular polypeptide, while hetero-oligomers comprise an association of copies of different polypeptides. "Oligomerization," "oligomerize," and "oligomer," with or without prefixes, are intended to encompass "dimerization," "dimerize," and "dimer." Thus, in one embodiment, the oligomerization domain is a dimerization domain that mediates the self-association of two HHV polypeptides and/or two HHV fusion proteins. In another embodiment, the oligomerization domain is a trimerization domain that mediates the self-association of three HHV polypeptides and/or three HHV fusion proteins. In another embodiment, the oligomerization domain is a tetramerization domain that mediates the self-association of four HHV polypeptides and/or four HHV fusion proteins. In one embodiment, the trimerization domain is fibritin motif or a eukaryotic GCN4 transcription factor motif or derivative thereof.

In one embodiment, the oligomerization domain comprises a leucine zipper domain. Leucine zipper domains are peptides that promote oligomerization of the proteins in which they are found. Leucine zippers were originally identified in several DNA-binding proteins (Landschulz et al., Science, 240:1759, 1988), and have since been found in a variety of different proteins. Among the known leucine zippers are naturally occurring peptides and derivatives thereof that dimerize or trimerize. For example, the yeast GCN4 leucine zipper can be used to dimerize polypeptides of interest. (Czerwinski et al., Transfusion, 35(2):137-44, 1995; and O'Shea et al., Science, 243(4890):538-42, 1989). Other examples of leucine zipper domains suitable for producing soluble multimeric proteins are described in PCT application WO 94/10308, and the leucine zipper derived from lung surfactant protein D (SPD) described in Hoppe et al. FEBS Lett. 344:191, 1994. The use of a modified leucine zipper that allows for stable trimerization of a heterologous protein fused thereto is described in Fanslow et al., Semin. Immunol., 6:267, 1994.

In yet another embodiment, the oligomerization domain is a fibritin trimerization motif, particularly a bacteriophage fibritin trimerization motif, more particularly a fibritin trimerization domain from bacteriophage T4 (also called T4 foldon or foldon domain) or phage RB69 or phage AR1 or a derivative thereof. The T4 fibritin trimerization domain and variants thereof are described in U.S. Pat. Nos. 6,911,205; 8,147,843, and WO 01/19958, which are hereby incorporated by reference in their entirety.

Protein Complexes.

In certain embodiments, the HHV polypeptides disclosed herein are present in the antigenic composition as a protein complex. For example, in certain embodiments, the HHV gB, gL, and gH are present in the antigenic composition as a protein complex. In other embodiments, the HHV gH, gL, UL128, UL130, and UL131A polypeptides are present in the antigenic composition as a protein complex. In yet another embodiment, the HHV gH, gL, and gO polypeptides are present in the antigenic composition as a protein complex.

Proteins in the protein complex are typically linked by non-covalent protein-protein interactions, including but not limited to hydrogen bonding and salt bridges. The protein complex has a quaternary structure, corresponding to the arrangement or shape resulting from the assembly and interaction of the individual proteins, and, therefore, is useful for inducing neutralizing antibodies against conformation epitopes on the HHV protein complex. In some embodiments, the protein complex, as used herein, does not refer to the native protein complex as it exists on the surface of a herpesvirus. Rather, the protein complex is formed by incubating the individual proteins in vitro, to create a reconstructed protein complex.

Nucleic Acids, Cloning, and Expression Systems.

The present disclosure further provides isolated nucleic acids encoding the disclosed monomeric or multimeric HHV polypeptides. The nucleic acids may comprise DNA or RNA and may be wholly or partially synthetic or recombinant Reference to a nucleotide sequence as set out herein encompasses a DNA molecule with the specified sequence and encompasses an RNA molecule with the specified sequence in which U is substituted for T, unless context requires otherwise.

The present disclosure also provides constructs in the form of plasmids, vectors, phagemids, transcription or expression cassettes which comprise at least one nucleic acid encoding a monomeric or multimeric HHV fusion or host cell entry protein or a portion thereof. The disclosure further provides a host cell which comprises one or more constructs as above.

Also provided are methods of making the monomeric or multimeric HHV polypeptides encoded by these nucleic acids. The monomeric or multimeric HHV polypeptides may be produced using recombinant techniques. The production and expression of recombinant proteins is well known in the art and can be carried out using conventional procedures, such as those disclosed in Sambrook et al., Molecular Cloning: A Laboratory Manual (4th Ed. 2012), Cold Spring Harbor Press. For example, expression of the fusion protein may be achieved by culturing under appropriate conditions recombinant host cells containing the nucleic acid encoding the monomeric or multimeric HHV polypeptides. Following production by expression a monomeric or multimeric HHV polypeptides may be isolated and/or purified using any suitable technique, then used as appropriate. As discussed herein, under certain conditions, two or more the HHV fusion and host cell entry proteins and optionally one or more HHV accessory proteins form a protein complex when incubated in vitro.

Systems for cloning and expression of a polypeptide in a variety of different host cells are well known in the art. Any protein expression system compatible with the constructs disclosed in this application may be used to produce the disclosed monomeric or multimeric HHV polypeptides.

Suitable vectors can be chosen or constructed, so that they contain appropriate regulatory sequences, including promoter sequences, terminator sequences, polyadenylation sequences, enhancer sequences, marker genes and other sequences as appropriate.

A further aspect of the disclosure provides a host cell comprising a nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. These techniques are well known in the art. (See, e.g., "Current Protocols in Molecular Biology," Ausubel et al. eds., John Wiley & Sons, 2010). DNA introduction may be followed by a selection method (e.g., antibiotic resistance) to select cells that contain the vector.

gH/gL/UL128/UL130/UL131A.

Recombinant nucleic acid constructs were designed to produce a HHV protein complex comprising gH, gL, UL128, UL130, and UL131A. In one embodiment, the recombinant nucleic acid construct comprises a first nucleic acid encoding a HHV gH polypeptide, a second nucleic acid encoding a HHV gL polypeptide, a third nucleic acid encoding a HHV UL128 polypeptide, a fourth nucleic acid encoding a HHV UL130 polypeptide, and a fifth nucleic acid encoding a HHV UL131A polypeptide. In certain embodiments, a pentameric complex is formed when the recombinant nucleic acid is expressed in a host cell. In certain embodiments, none of the encoded polypeptides comprise a transmembrane domain or an intracellular domain. In certain embodiments, the recombinant nucleic acid comprises one or more internal ribosome entry cites (IRES) to facilitate expression of multiple proteins from a single transcript. In certain embodiments, the recombinant nucleic acid comprises a first IRES between the first and second nucleic acids, a second IRES between the second and third nucleic acids, and/or a third IRES between the fourth and fifth nucleic acids. In certain embodiments, the recombinant nucleic acid comprises one or more promoter sequences to facilitate expression of the HHV polypeptides. In certain embodiments the recombinant nucleic acid comprises a first promoter operatively linked to the first nucleic acid and a second promoter operatively linked to the third nucleic acid. In one embodiment, the promoter is a CMV promoter. In certain embodiments, the HHV is a betaherpesvirus subfamily member, including, for example, HCMV. A non-limiting, exemplary embodiment of such a recombinant nucleic acid is depicted in FIG. 13. Additional nucleic acid sequences can be included in such a nucleic acid sequence to aid in purification, such as a protein purification tag (e.g., his-tag sequences) or a leader sequence to promote secretion from the host cell (e.g., immunoglobulin kappa light chain leader sequences). In certain embodiments, the leader sequence is inserted in frame with each of the first, second, third, fourth, and fifth nucleic acid.

gH/gL/gO.

Figure 14:
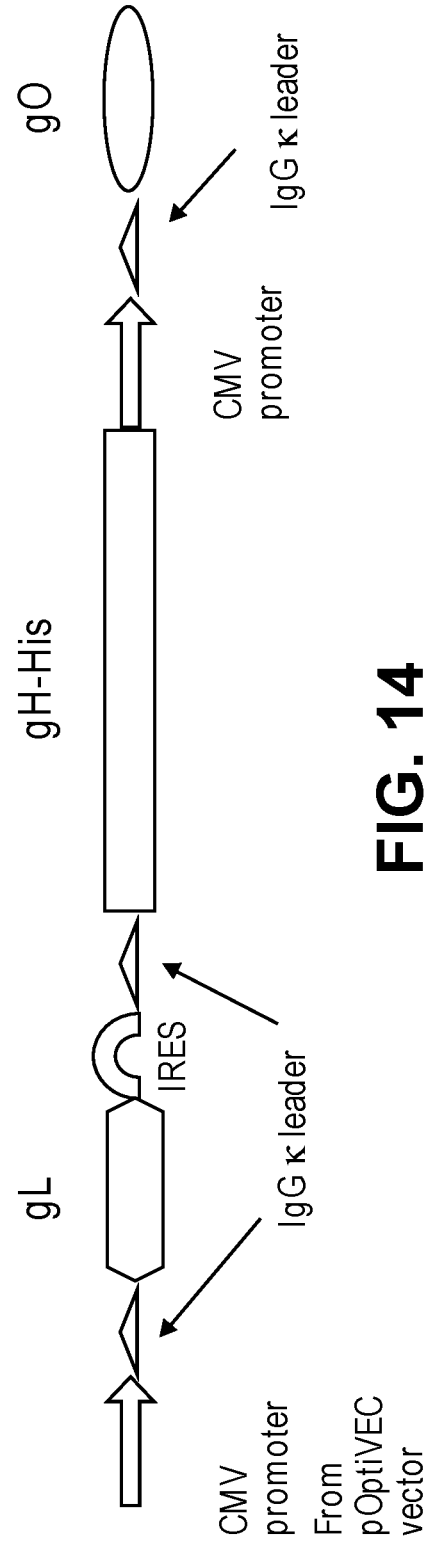

Recombinant nucleic acid constructs were designed to produce a HHV complex comprising gH, gL, and gO. In one embodiment, the recombinant nucleic acid construct comprises a first nucleic acid encoding a HHV gH polypeptide, a second nucleic acid encoding a HHV gL polypeptide, a third nucleic acid encoding a HHV gO polypeptide. In certain embodiments, a trimeric complex is formed when the recombinant nucleic acid is expressed in a host cell. In certain embodiments, none of the encoded polypeptides comprise a transmembrane domain or an intracellular domain. In certain embodiments, the recombinant nucleic acid comprises one or more internal ribosome entry cites (IRES) to facilitate expression of multiple proteins from a single transcript. In certain embodiments, the recombinant nucleic acid comprises an IRES between the first and second nucleic acids. In certain embodiments, the recombinant nucleic acid comprises one or more promoter sequences to facilitate expression of the HHV polypeptides. In certain embodiments the recombinant nucleic acid comprises a first promoter operatively linked to the first nucleic acid and a second promoter operatively linked to the third nucleic acid. In one embodiment, the promoter is a CMV promoter. In certain embodiments, the HHV is a betaherpesvirus subfamily member, including, for example, HCMV. An exemplary embodiment of such a recombinant nucleic acid is depicted in FIG. 14. Additional nucleic acid sequences can be included in such a nucleic acid sequence to aid in purification, such as a protein purification tag (e.g., his-tag sequences) or a leader sequence (e.g., immunoglobulin kappa light chain leader sequences). In certain embodiments, the leader sequence is inserted in frame with each of the first, second and third nucleic acid.

Vaccine Compositions.

The combinations of monomeric and/or multimeric HHV polypeptides and nucleic acids encoding the same that are described in this application provide an improved platform for developing a HHV vaccine.

Thus, one aspect is directed to an antigenic composition as described herein comprising two or more HHV fusion and host cell entry proteins (or nucleic acids encoding the same). In certain embodiments, the vaccine comprises virus like particles. In certain embodiments, the antigenic composition further comprises at least one pharmaceutically acceptable excipient, and optionally an adjuvant (hereinafter referred to as "vaccine composition"). In certain embodiments, the vaccine composition does not include an adjuvant.

In certain embodiments, the vaccine is a nucleic acid vaccine, comprising a nucleic acid encoding the two or more HHV fusion and host cell entry proteins. In certain embodiments, the nucleic acid vaccine is a DNA vaccine. In other embodiments, the nucleic acid vaccine is an RNA vaccine. In certain embodiments, the nucleic acid vaccine is a viral vector vaccine.

The pharmaceutically acceptable excipient can be chosen from, for example, diluents such as starch, microcrystalline cellulose, dicalcium phosphate, lactose, sorbitol, mannitol, sucrose, methyl dextrins; binders such as povidone, hydroxypropyl methylcellulose, dihydroxy propylcellulose, and sodium carboxylmethylcellulose; and disintegrants such as crospovidone, sodium starch glycolate, croscarmellose sodium, and mixtures of any of the foregoing. The pharmaceutically acceptable excipient can further be chosen from lubricants such as magnesium stearate, calcium stearate, stearic acid, glyceryl behenate, hygrogenated vegetable oil, glycerine fumerate and glidants such as colloidal silicon dioxide, and mixtures thereof. In some embodiments, the pharmaceutically acceptable excipient is chosen from microcrystalline cellulose, starch, talc, povidone, crospovidone, magnesium stearate, colloidal silicon dioxide, sodium dodecyl sulfate, and mixtures of any of the foregoing. The excipients can be intragranular, intergranular, or mixtures thereof.

The vaccine composition can be formulated as freeze-dried or liquid preparations according to any means suitable in the art. Non-limiting examples of liquid form preparations include solutions, suspensions, syrups, slurries, and emulsions. Suitable liquid carriers include any suitable organic or inorganic solvent, for example, water, alcohol, saline solution, buffered saline solution, physiological saline solution, dextrose solution, water propylene glycol solutions, and the like, preferably in sterile form. After formulation, the vaccine composition can be incorporated into a sterile container which is then sealed and stored at a low temperature (e.g., 4° C.), or it can be freeze dried.

The vaccine composition can be formulated in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccine composition can optionally comprise agents that enhance the protective efficacy of the vaccine, such as adjuvants. Adjuvants include any compound or compounds that act to increase an immune response to the two or more HHV fusion and host cell entry proteins, thereby reducing the quantity of proteins (or nucleic acid encoding the same) necessary in the vaccine, and/or the frequency of administration necessary to generate a protective immune response.

Adjuvants can include for example, emulsifiers, muramyl dipeptides, avridine, aqueous adjuvants such as aluminum hydroxide, chitosan-based adjuvants, and any of the various saponins, oils, and other substances known in the art, such as Amphigen, LPS, bacterial cell wall extracts, bacterial DNA, CpG sequences, synthetic oligonucleotides and combinations thereof (Schijns et al. (2000) *Curr. Opin. Immunol.*, 12:456), *Mycobacterial phlei* (*M. phlei*) cell wall extract (MCWE) (U.S. Pat. No. 4,744,984), *M. phlei* DNA (M-DNA), and *M. phlei* cell wall complex (MCC). Compounds which can serve as emulsifiers include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids, and organic sulfonates such as sodium lauryl sulfate. Synthetic cationic agents include, for example, cetyltrimethylammonium bromide, while synthetic nonionic agents are exemplified by glycerylesters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil can be a mineral oil, a vegetable oil, or an animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange roughy oil and shark liver oil, all of which are available commercially. Suitable vegetable oils, include, for example, canola oil, almond oil, cottonseed oil, corn oil, olive oil, peanut oil, safflower oil, sesame oil, soybean oil, and the like. Freund's Complete Adjuvant (FCA) and Freund's Incomplete Adjuvant (FIA) are two common adjuvants that are commonly used in vaccine preparations, and are also suitable for use in the present invention. Both FCA and FIA are water-in-mineral oil emulsions; however, FCA also contains a killed *Mycobacterium* sp.

Immunomodulatory cytokines can also be used in the vaccine compositions to enhance vaccine efficacy, for example, as an adjuvant. Non-limiting examples of such cytokines include interferon alpha (IFN-α), interleukin-2 (IL-2), and granulocyte macrophage-colony stimulating factor (GM-CSF), or combinations thereof.

The vaccine composition can be prepared using techniques well known to those skilled in the art including, but not limited to, mixing, sonication and microfluidation. The adjuvant can comprise from about 10% to about 80% (v/v) of the vaccine composition, more preferably about 20% to about 50% (v/v), and more preferably about 20% to about 30% (v/v), or any integer within these ranges.

The vaccine composition can be administered to any animal, and preferably is a mammal such as a human, mouse, rat, hamster, guinea pig, rabbit, cat, dog, monkey, cow, horse, pig, and the like. Humans are most preferred.

Administration of the vaccine composition can be by infusion or injection (e.g., intravenously, intramuscularly, intracutaneously, subcutaneously, intrathecal, intraduodenally, intraperitoneally, and the like). The vaccine composition can also be administered intranasally, vaginally, rectally, orally, intratonsilar, or transdermally. Additionally, the vaccine composition can be administered by "needle-free" delivery systems.

The effective amount of the vaccine composition may be dependent on any number of variables, including without limitation, the species, breed, size, height, weight, age, overall health of the patient, the type of formulation, or the mode or manner or administration. The appropriate effective amount can be routinely determined by those of skill in the art using routine optimization techniques and the skilled and informed judgment of the practitioner and other factors evident to those skilled in the art. Preferably, a therapeutically effective dose of the vaccine composition described herein will provide the therapeutic preventive benefit without causing substantial toxicity to the subject.

The vaccine composition can be administered to a patient on any schedule appropriate to induce and/or sustain an immune response against the two or more HHV fusion and host cell entry proteins. For example, patients can be administered a vaccine composition as a primary immunization as described and exemplified herein, followed by administration of a secondary immunization, or booster, to bolster and/or maintain protective immunity.

The vaccine administration schedule, including primary immunization and booster administration, can continue as long as needed for the patient, for example, over the course of several years, to over the lifetime of the patient. The frequency of primary vaccine and booster administration and dose administered can be tailored and/or adjusted to meet the particular needs of individual patients, as determined by the administering physician according to any means suitable in the art.

The vaccine composition may be administered prophylactically (before exposure to the antigen or pathogen of interest) or therapeutically (after exposure to the antigen or pathogen of interest).

Methods of Inducing an Immune Response.

In another aspect, two or more HHV fusion and host cell entry proteins (or nucleic acid encoding the same) can be used in a method of inducing an immune response or otherwise treating or preventing a HHV infection in a subject. The immune response can be induced in a naïve subject who has not previously been exposed to HHV. Alternatively, the immune response can be induced in a subject who has been previously exposed to HHV and used to enhance an existing immune response.

In one embodiment, the method of inducing an immune response comprises administering to a subject two or more HHV fusion and host cell entry proteins, as described herein, in an amount sufficient to induce an immune response against the two or more HHV fusion and host cell entry proteins in the subject. In another embodiment, the method of inducing an immune response comprises administering to a subject one or more nucleic acid constructs encoding the two or more HHV fusion and host cell entry proteins, as described herein, in an amount sufficient to induce an immune response against the two or more HHV polypeptides in the subject. In certain embodiments, the method induces an additive antibody response to the two or more HHV fusion and host cell entry proteins. In certain embodiments, the method induces a synergistic antibody response to the two or more HHV fusion and host cell entry proteins.

In these methods of inducing an immune response, the immune response can be measured using routine methods in the art, such as those disclosed in this application. These routine methods include, but are not limited to, measuring an antibody response, such as an antibody response directed against an HHV protein, and measuring cellular proliferation, including, for example, by measuring tritiated thymidine incorporation or cytokine (e.g., IFN-γ) production.

In certain embodiments, the method of treating or preventing an HHV infection comprises administering to a subject a therapeutically effective amount of two or more HHV polypeptides, as described herein, or one or more nucleic acid constructs encoding the same.

In these methods that comprise a step of administering two or more HHV fusion and host cell entry proteins, the proteins can be administered simultaneously or sequentially. In certain embodiments, the HHV proteins that make up the antigenic compositions disclosed herein are administered simultaneously (concomitantly), for example, as part of the same composition or as part of different compositions administered at the same time. In other embodiments, the HHV proteins that make up the antigenic compositions disclosed herein are administered separately (sequentially), for example, administered as individual compositions at different times. That is, the at least two HHV polypeptides in the compositions can be simultaneously or separately administered to achieve the effects disclosed herein. Further, compositions can be administered in one or more doses to achieve the desired result.

Typically, the subject is a human. In certain embodiments, the subject is at risk of developing PTLD following a transplant, such as a hematopoietic stem cell or solid organ transplant. In certain embodiments, the subject suffers from a primary immunodeficiency syndrome, including, for example, AIDS. In certain embodiments, the subject is at risk of developing nasopharynegeal carcinoma. In certain embodiments, the subject has nasopharyngeal carcinoma.

Subjects in some embodiments concurrently receive one or more of an anti-CD20 antibody, anti-viral therapy, interferon alpha, radiotherapy, and/or chemotherapy. CD-20 antibody therapy and related biologics are known in the art, as are radiotherapy and chemotherapy. Any of the known therapy regimens of these categories can be concurrently administered to the subject in need thereof.

Passive Immunotherapy and Adoptive Transfer of Cell-Mediated Immunity.

Passive immunotherapy methods for various indications are known in the art and have been employed in various forms for over 120 years. (See, Waldman, T. A., *Nature Medicine*, 9(3):269-277, 2003; and Chippeaux et al., *J. Venom. Anim. Toxins Incl. Trop. Dis.*, 21:3, 2013; see also Casadevall et al., *Clin. Infect. Dis.*, 21(1):150-61, 1995). The benefits of passively transferring antibodies for inflammation, immune deficiency, acute and chronic autoimmune diseases, and cancer is well established. (Kivity et al., *Clin. Rev. Allergy Immunol.*, 38:201-69, 2010; and Toubi et al., *Clin. Rev. Allergy Immunol.*, 29:167-72, 2005). Studies have documented multifunctional mechanisms of passively transferred antibodies, including mediation of humoral and cellular immune responses through both its Fab and Fc portions with neutralization and enhanced clearance of pathogens. Passive immunotherapy is also sometimes referred to optionally as cell transfer therapy, immunoglobulin therapy, antiserum therapy, passive transfer, or passive immunity. When immune cells are the immune components or neutralizing agent administered to the subject in need thereof, the method is often referred to as adoptive transfer, adoptive cellular therapy (ACT), or adoptive immunotherapy.

In passive immunotherapy, antibodies (or immunoglobulins) or other immune system components, i.e., agents that possess antigen neutralizing activity, such as immune cells, are made outside of the subject being administered these components, typically made in a laboratory and/or produced ex vivo by a second subject (or several other subjects). In some embodiments, the immune system component administered to the subject is a monoclonal antibody. In other embodiments, the immune component is a polyclonal antibody. In still other embodiments, the immune component is one or more immune cells. In all instances, the immune component includes antibodies or cells that specifically recognize a target antigen, such as a target antigen present on an HHV fusion and host cell entry protein.

Having shown that various combinations of HHV fusion and host cell entry proteins induce high-titer neutralizing antibodies, it was contemplated that such high-titer neutralizing antibodies could be used to passively transfer immunity against HHV. Thus, antibodies generated by a subject who was immunized with two or more HHV fusion and host cell entry proteins, as described herein, can be harvested from the subject and isolated. The donor subject can be immunized with any combination of HHV (e.g., EBV, HCMV, HSV-1 or HSV-2, VZV, HHV-6, HHV-7, or KSVH) fusion and host cell entry proteins as described herein to induce the high-titer anti-HHV antibodies.

In an EBV passive immunization or adoptive transfer embodiment, a donor subject is immunized with, for example, a tetrameric EBV gp350 protein and the induced high-titer neutralizing antibodies obtained therefrom are employed in a passive transfer of immunity to an acceptor subject who benefits therefrom. In a further EBV embodiment, a donor subject is immunized with, for example, a trimeric EBV gH/gL protein and the induced high-titer neutralizing antibodies obtained therefrom are employed in a passive transfer of immunity to an acceptor subject who benefits therefrom. In another exemplary EBV embodiment, a donor subject is immunized with, for example, a trimeric gB protein and the induced high-titer neutralizing antibodies obtained therefrom are employed in a passive transfer of immunity to an acceptor subject who benefits therefrom.

In an HCMV passive immunization or adoptive transfer embodiment, a donor subject is immunized with, for example, a trimeric HCMV gB protein and the induced high-titer neutralizing antibodies obtained therefrom are employed in a passive transfer of immunity to an acceptor subject who benefits therefrom. In a further HCMV embodiment, a donor subject is immunized with, for example, a trimeric HCMV gH/gL protein and the induced high-titer neutralizing antibodies obtained therefrom are employed in a passive transfer of immunity to an acceptor subject who benefits therefrom.

In an HSV passive immunization or adoptive transfer embodiment, a donor subject is immunized with, for example, a trimeric HSV gB protein and the induced high-titer neutralizing antibodies obtained therefrom are employed in a passive transfer of immunity to an acceptor subject who benefits therefrom. In a further HSV embodiment, a donor subject is immunized with, for example, a trimeric HSV gH/gL protein and the induced high-titer neutralizing antibodies obtained therefrom are employed in a passive transfer of immunity to an acceptor subject who benefits therefrom.

In a VZV passive immunization or adoptive transfer embodiment, a donor subject is immunized with, for example, a trimeric HSV gB protein and the induced high-titer neutralizing antibodies obtained therefrom are employed in a passive transfer of immunity to an acceptor subject who benefits therefrom. In a further VZV embodiment, a donor subject is immunized with, for example, a trimeric VZV gH/gL protein and the induced high-titer neutralizing antibodies obtained therefrom are employed in a passive transfer of immunity to an acceptor subject who benefits therefrom.

In a KSHV passive immunization or adoptive transfer embodiment, a donor subject is immunized with, for example, a trimeric KSHV gB protein and the induced high-titer neutralizing antibodies obtained therefrom are employed in a passive transfer of immunity to an acceptor subject who benefits therefrom. In a further KSHV embodiment, a donor subject is immunized with, for example, a trimeric KSHV gH/gL protein and the induced high-titer neutralizing antibodies obtained therefrom are employed in a passive transfer of immunity to an acceptor subject who benefits therefrom.

Immunization with the two or more HHV fusion and host cell entry proteins can be simultaneous, in multiple doses, or in staggered doses, as long as the desired neutralizing activity is obtained in the donor subject. These antibodies induced in the donor subject can then be administered to another subject in need thereof. Alternatively, the high-titer neutralizing antibodies against the HHV fusion and host cell entry proteins can be obtained from one or more blood, serum, or plasma samples that have been selected for the high-titer antibodies. In certain embodiments, the one or more blood, serum, or plasma samples are obtained from a human donor.

The immune components can also be obtained synthetically, as in monoclonal antibodies, produced in tissue culture or by animals, or can be obtained from another, donor, subject who is either seropositive for immune components specifically recognizing the desired antigen, or who has been exposed to the antigen and thereby has developed seropositivity. In certain embodiments, the donor subject possesses a high degree of responsiveness to the antigen, i.e., possess a high concentration, or high titer, of the antigen-neutralizing immune components (e.g., antibodies or immune cells). These immune components are then extracted from the donor subject, or obtained from tissue culture or animals, purified or otherwise manipulated in the laboratory as needed to avoid possible graft vs. host reactions or other adverse reactions, and then administered to the subject in need thereof.

Steps for implementing a passive immunotherapy or adoptive transfer protocol or methodology involve, in some embodiments, first identifying a donor subject possessing a high neutralizing activity against HHV. In certain embodiments, high titer anti-HHV antibodies or immune cells are obtained from blood, serum, and/or plasma samples collected from the donor subject. These immune components are then transferred to a second subject in need thereof, in order to induce an immunoprotective effect in the second subject, thereby preventing or treating an HHV infection. The second subject can be infected with an HHV, or susceptible to infection with HHV. The antibodies can be optionally extracted and/or purified prior to administration to the subject in need thereof. Further, in other embodiments, optionally the donor subject is histocompatible with the subject in need thereof, such that blood, serum, and/or plasma may be administered to the subject in need thereof. In some embodiments, the blood, serum, and/or plasma is obtained from a human donor.

The term "high-titer" as used herein, refers to an antibody having a titer specific for the desired HHV polypeptide in an amount that is 2-fold, 3-fold, 4-fold, 5-fold, 6-fold, 7-fold, 8-fold, 9-fold, 10-fold, 12-fold, 14-fold, 16-fold, 18-fold, 20-fold, 25-fold, or in some embodiments, as much as 30-fold higher than an average titer from unselected plasma, serum, or blood samples from a general population of donor subjects and that comprises antibodies possessing the same specificity. In certain embodiments, the donor subject has been exposed to the HHV polypeptide antigen and is not seronegative or naïve. In certain embodiments, the donor subject, or donor subjects, has/have been administered two or more of the HHV fusion and host cell entry proteins, in order to generate a high-titer antibody response in the donor subject(s). High-titer antibodies can be identified or selected using the methods described in this application (e.g., Raji B cell neutralization assay or a HeLa cell neutralization assay) or any known method in the art. Antibody titers can be determined by various art-recognized screening methods or by the methods disclosed in this application. In one embodiment, high-titer antibodies are identified or selected using a Raji B cell neutralization assay or a HeLa cell neutralization assay, as described, for example, in the examples of this application. In certain embodiments, the HeLa cell neutralization assay comprises, infecting HeLa cells with labeled EBV (e.g., EBV with a fluorescent label, such as green fluorescent protein) to yield EBV-infected HeLa cells, incubating the blood, plasma or serum sample with the EBV-infected HeLa cells, analyzing the neutralization activity of the blood, plasma, or serum sample (e.g., using flow cytometry or an ELISpot assay) and optionally calculating the $IC_{50}$ of the blood, plasma, or serum sample.

The subject in need thereof is a subject who is naïve (seronegative for HHV), immunocompromised, or otherwise susceptible to infection, or already infected with one or more HHV. In certain embodiments, the subject is administered high titer anti-EBV antibodies and is at risk of developing post-transplantation lymphoproliferative disorder (PTLD) following hematopoietic stem cell or solid organ transplantation, or has or is at risk of developing nasopharyngeal carcinoma (NPC), Burkitt lymphoma, Hodgkin's lymphoma, non-Hodgkin's lymphoma, gastric carcinoma, severe infectious mononucleosis, chronic active EBV infection, multiple sclerosis, systemic lupus erythematosus, or rheumatoid arthritis. In certain embodiments, the subject is at risk of developing PTLD, for example, following hematopietic stem cell or solid organ transplant. In certain embodiments, the subject is at risk of developing nasopharyngeal carcinoma.

In another embodiment, the subject is administered high titer anti-HCMV antibodies and is a pregnant woman, a transplantation patient, a patient who is immunosuppressed during chemotherapy or radiotherapy, or a patient infected with human immunodeficiency virus (HIV). In another embodiment, the subject is administered high titer anti-HSV-1 or HSV-2 antibodies and is at risk of developing encephalitis caused by HSV-1 or HSV-2 infection, or is a pregnant woman with active HSV-2 or HSV-1 infection and/or HSV encephalitis. In another embodiment, the subject is administered high titer anti-ZVZ antibodies and is at risk of developing Zoster (shingles) or Varicella (chickenpox). In a further embodiment, the subject is administered high titer anti-KSHV antibodies and is at risk of developing KSHV-associated Kaposi's sarcoma, primary effusion lymphoma, multicentric Cattleman's disease, KSHV-associated inflammatory cytokine syndrome, or KSHV immune reconstitution inflammatory syndrome.

In another embodiment, the subject in need thereof is concurrently receiving anti-viral therapy, anti-CD20 antibody compositions, interferon-alpha, radiotherapy, and/or chemotherapy.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

1. Epstein Bar Virus (EBV)

Example 1.1—Production of EBV gH and EBV gL Polypeptides

To recombinantly produce EBV gH and gL polypeptides, coding sequences for EBV gH and gL were downloaded from the NCBI website, reference sequence NC_009334.1, including EBV gH nucleotides 129454 through 131574, and EBV gL nucleotides 98500 through 98913. The gL sequence encoding amino acids 23-137 was used, and the signal peptide at amino acids 1-22 was replaced with an IgG κ leader sequence. The gH sequence coding corresponding to amino acids 19-678 was linked to the 3' end of the gL sequence and separated by a 15-amino acid linker $(Gly_4Ser)_3$ (SEQ ID NO: 3) sequence. (See representative schematic in FIG. 1). A foldon trimerization domain coding sequence derived from T4 phage fibritin (see e.g., U.S. Pat. Nos. 6,911,205; 8,147,843, and WO 01/19958) was linked to the 3' end of gH, followed by a $His_6$ (SEQ ID NO: 49) coding sequence. DNA coding for the trimeric gH/gL was synthesized and cloned into the vector pOptiVEV (Invitrogen, Carlsbad, Calif., USA), and the sequence verified by sequencing. The monomeric EBV gH/gL construct was made by PCR amplification of EBV gH/gL without the foldon trimerization coding sequence, and cloned into pOptiVEV. The sequence was verified by sequencing.

Chinese Hamster Ovary (CHO) cells (strain DG44, Invitrogen, Carlsbad, Calif., USA) were transfected with the resultant pOptiVEV-gH/gL constructs and positive cells were selected with gradually increased concentrations of methotrexate (MTX), up to 4 µM. Selected CHO cells were loaded into "Fibercell" cartridges (FiberCell Systems, Frederick, Md., USA) for protein production. Supernatants were concentrated and purified using cobalt affinity purification (Thermo Fisher Scientific, Waltham, Mass., USA). Recombinant proteins were further purified by size exclusion chromatography using Sephadex® G200 column or Superose® 6 Increase 10/300 GL column (GE Healthcare, Little Chalfont, UK).

Figure 2A:
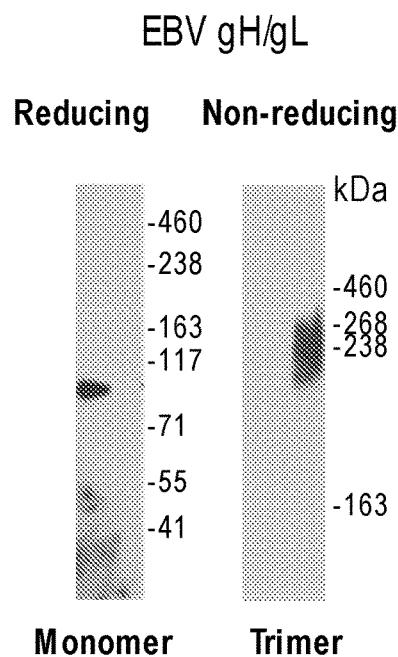

Western blot analysis of trimeric gH/gL polypeptides using an anti-$His_6$ (SEQ ID NO: 49) mAb or an anti-EBV gH/gL mAb (clone E1D1, gift from Dr. L. M. Hutt-Fletcher, La. State University Health Sciences Center, Shreveport, La., USA), under reducing conditions that disrupt the native oligomers, revealed a molecular weight (MW) band of about 90 kiloDaltons (kDa), consistent with the predicted size of monomeric gH/gL (FIG. 2A). Under non-reducing conditions, a MW band of about 270 kDa was observed, consistent with predicted size of trimeric gH/gL (FIG. 2A).

Example 1.2—Production of EBV gB Polypeptides

To recombinantly produce EBV gB polypeptides, the coding sequence for EBV gB was downloaded from the NCBI website, corresponding to reference sequence NC_009334.1, nucleotides 157775 through 160348. The sequence encoding the extracellular domain of EBV gB (amino acids 23-732 of wild type EBV) was used to design the construct for trimeric gB expression. The signal peptide, corresponding to amino acids 1-22, was replaced with an IgG κ leader sequence, and the coding sequence of the furin cleavage site (RRRRD) (SEQ ID NO: 50) between amino acids 427 (L) and 434 (A) was replaced with a 15-amino acid $(Gly_4Ser)_3$ (SEQ ID NO: 3) linker sequence (FIG. 1). A $His_6$ (SEQ ID NO: 49) sequence was linked to the 3' end for protein purification. All the following steps were as described above for EBV gH/gL.

Figure 2B:
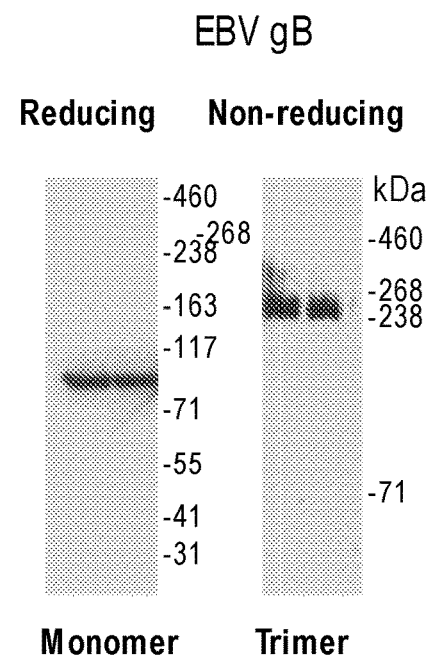

Western blot analysis under fully reducing conditions using an anti-$His_6$ (SEQ ID NO: 49) mAb or an anti-gB mAb (Virusys Corp., Taneytown, Md., USA) demonstrated that the EBV gB protein was the predicted size of the monomeric form (about 80 kDa) (FIG. 2B). Under modified non-reducing conditions that allows for detection of the native form of EBV gB protein, a uniform band with the predicted size of a trimeric EBV gB (about 240 kDa) was observed (FIG. 2B).

Example 1.3—Production of EBV Gp350 Polypeptides

EBV gp350 polypeptides were expressed as previously described (see, Cui et al., *Vaccine*, 31:3039-45, 2013; see also WO 2014/018858, which is hereby incorporated by reference in its entirety). Briefly, an EBV monomeric gp350 construct was made by PCR amplification of the gp350 cDNA, strain B95-8. A sequence encoding amino acids 1-470 was cloned with an IgG κ leader sequence added to the 5' end and $His_6$ (SEQ ID NO: 49) coding sequence added to the 3' end. The tetrameric gp350 construct was made by ligation of a second gp350 fragment (1-470) to the 3' end of the monomeric gp350 construct (without $His_6$ (SEQ ID NO: 49)). The second gp350 fragment has a $(Gly_4Ser)_3$ (SEQ ID NO: 3) linker at the 5' end and a leucine zipper sequence at the 3' end for homodimerization, followed by $His_6$ (SEQ ID NO: 49) sequence for protein purification (FIG. 1). Monomeric and tetrameric gp350 DNA were cloned into pOptiVEV, and their sequences verified by sequencing. All of the following steps were as described above for EBV gH/gL.

Figure 2C:
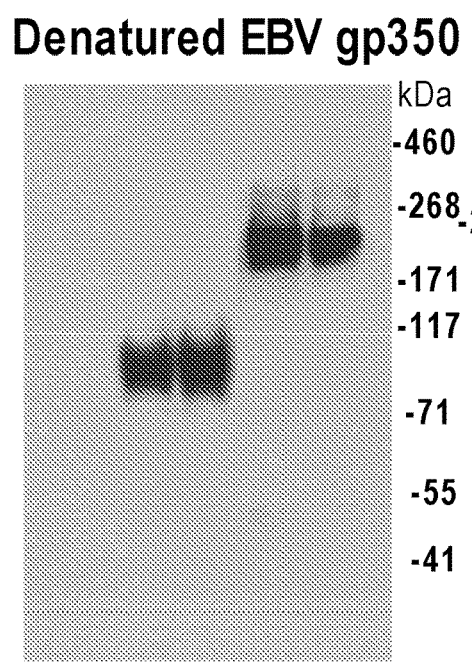
Figure 2C:
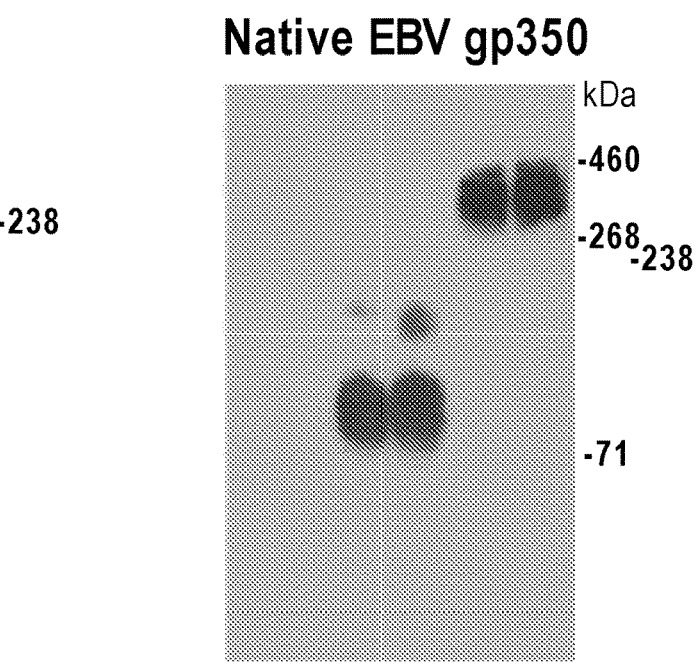

Western blot analysis using anti-gp350 mAbs, clone 2L10 (Merck Millipore, Billerica, Mass., USA), 72A1 (ATCC, Manassas, Va., USA), or an anti-$His_6$ (SEQ ID NO: 49) mAb, under denatured (reducing) condition, revealed a single ~100 kDa band corresponding to monomeric gp350, and a single band at about 200 kDa consistent with a gp350 dimer, resulting from the dissociation of the two gp350 dimers that form the tetrameric gp350 (FIG. 2C). Under native (non-reducing) condition, a single band at about 100 kDa was revealed, consistent with monomeric gp350, and a single band at about 400 kDa was observed, consistent with the tetrameric gp350 (FIG. 2C).

Example 1.4—Induction of EBV Immune Response in Rabbits

The obtained EBV polypeptides were examined in vaccine preparations for their ability to induce an immune response in rabbits. In this study and the example following this example, the level of immune response was determined by the level of EBV polypeptide-specific antibodies found in serum. In this study, groups of five male New Zealand white rabbits, 12 to 15 weeks old, were immunized subcutaneously with 25 µg of each of the EBV antigens, including tetrameric EBV gp350, trimeric EBV gH/gL, or trimeric EBV gB, versus monomeric EBV gp350, or monomeric EBV gH/gL. The antigens were adsorbed to aluminum hydroxide (alum; 0.25 µg alum/mg of protein) and mixed with 50 µg of a 12-mer phosphorothioate-modified CpG oligodeoxynucleotide (ODN) with optimization for use in rabbits (hereinafter, ODN 2007, TCGTCGTTGTCGTTTTGTCGTT (SEQ ID NO: 51)) prior to injection (see, Ioannou et al., *Vaccine*, 21:4368-72, 2003). The activity of ODN 2007 was confirmed by its ability to stimulate IgM secretion when added to rabbit splenocytes (Id.). Rabbits immunized with alum and CpG-ODN alone served as the negative control. Rabbits were immunized on day 0, day 21, and day 42. Serum samples were taken before initial immunization, and 10 days following each immunization.

Figure 3:
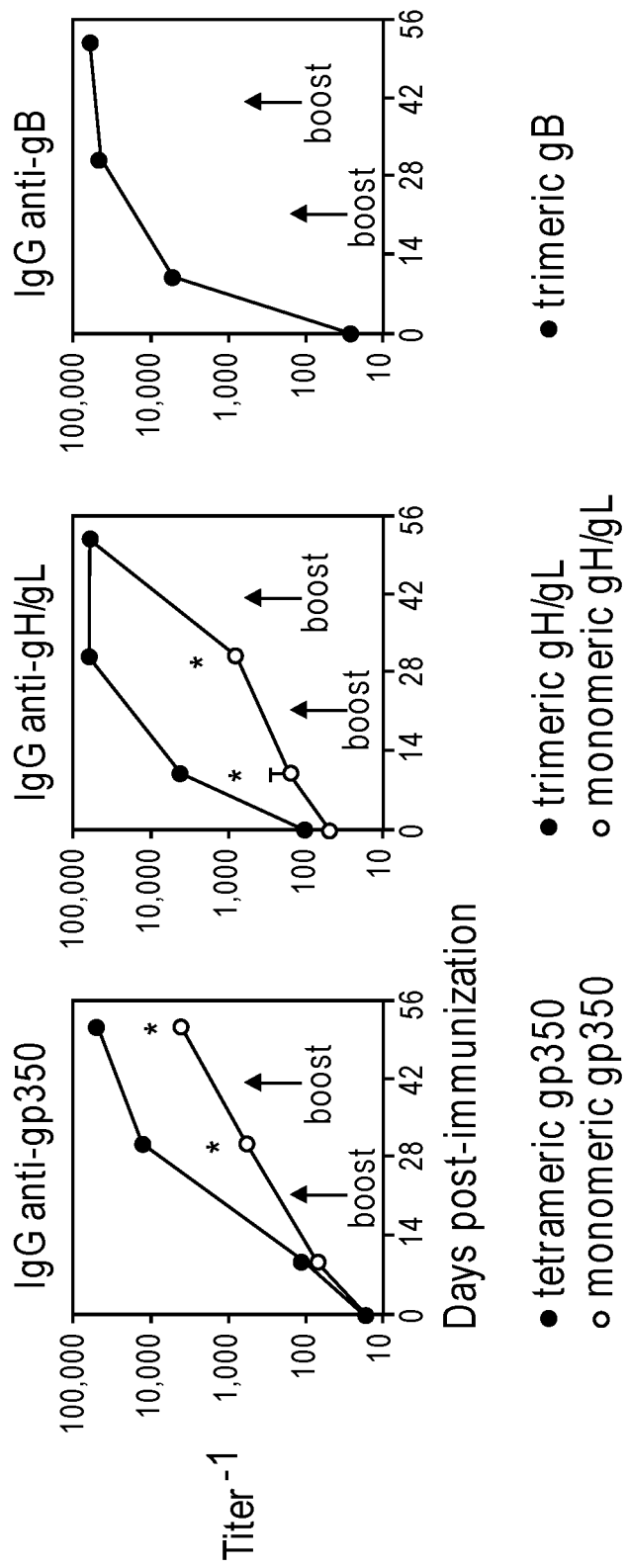

Sera were obtained 10 days after the last immunization for measurement of $IC_{50}$ neutralization titers in cultures of Raji B lymphoma cells and green fluorescent protein (GFP)-labeled EBV. $IC_{50}$ values shown in FIG. 3 represent the reciprocal serum titer that generates 50% EBV neutralization. EBV infection was measured by flow cytometry. As illustrated in FIG. 3, tetrameric gp350 and trimeric gH/gL elicited significantly (*p<0.05) higher $IC_{50}$ titers than their monomeric counterparts. Of note, significant differences (p<0.05) in $IC_{50}$ titers were also observed among the multimeric proteins with gH/gL ($IC_{50}$=506) >gB ($IC_{50}$=89) >gp350 ($IC_{50}$=22).

Thus, as illustrated in FIG. 3, each of the five EBV polypeptides induced augmented IgG responses following the first booster immunization, including monomeric gp350 (FIG. 3, left panel, open circles) and monomeric gH/gL (FIG. 3, middle panel, open circles). Further significant augmentation in serum IgG titers followed the second booster immunization. Tetrameric EBV gp350 (FIG. 3, left panel, closed circles) induced >20-fold serum gp350-specific IgG titers relative to monomeric EBV gp350 (FIG. 3, left panel, open circles) following the first and second booster immunizations. Trimeric EBV gH/gL (FIG. 3, middle panel, closed circles) induced greater than 30-fold and greater than 90-fold increases in serum gH/gL-specific IgG titers following the primary immunization and the first booster immunization, respectively, with the titers equalizing by the second booster immunization. These data are consistent with a previous study performed in mice using tetrameric and monomeric gp350 (Cui et al., *Vaccine*, 31:3039-45, 2013), that showed that multimerization of tetrameric fusion EBV gp350 polypeptides induce marked increases in immunogenicity.

Example 1.5—EBV Antibody Titers Induced by Monomeric gH/gL, Trimeric gH/gL, and Trimeric gB, as Compared to Titers Induced by Monomeric and Tetrameric Gp350

Determination of serum in vitro EBV-neutralizing titers, using Raji cells (EBV-positive human Burkitt lymphoma cell line), were performed as described (Sashihara et al., *Virology*, 391:249-56, 2009). Briefly, GFP-EBV (B95-8/F) was prepared by transfection of 293/2089 cells with plasmids p509 and p2670 expressing EBV BZLF1 and EBV BALF4, respectively (gift from Dr. Jeffrey I. Cohen, N.I.H., Bethesda, Md., USA) (Neuhierl et al., *Proc. Natl. Acad. Sci. U.S.A.*, 99:15036-41, 2002; and Delecluse et al., *Proc. Natl. Acad. Sci. U.S.A.*, 95:8245-50, 1998). Serial serum dilutions were mixed for 2 h with GFP-EBV in 96-well plates, followed by addition of Raji cells for 1 additional hour. Cells were then washed and re-cultured in medium alone for 3 days, fixed in paraformaldehyde and analyzed by flow cytometry for GFP+ Raji cells. The serum dilution that inhibited infectivity by 50% ($IC_{50}$), based on reduction of the number of GFP+ cells, was calculated by non-linear regression analysis using Prism 6 software (GraphPad Software, Inc., La Jolla, Calif., USA). An EBV-neutralizing anti-gp350 mAb (72A1) was used as a positive control. Pre-immune sera and sera from rabbits immunized with alum+CpG-ODN alone served as negative controls. For determination of serum neutralizing titers using peripheral blood naïve human B cells, naïve human B cells isolated from peripheral blood of healthy donors were incubated with GFP-EBV and cultured in RPMI 1640 medium containing 100 ng/ml IL-4 (BioLegend, San Diego, Calif., USA) and 1 µg/ml CD40 antibody (R&D Systems, Minneapolis, Minn., USA).

Figure 4A:
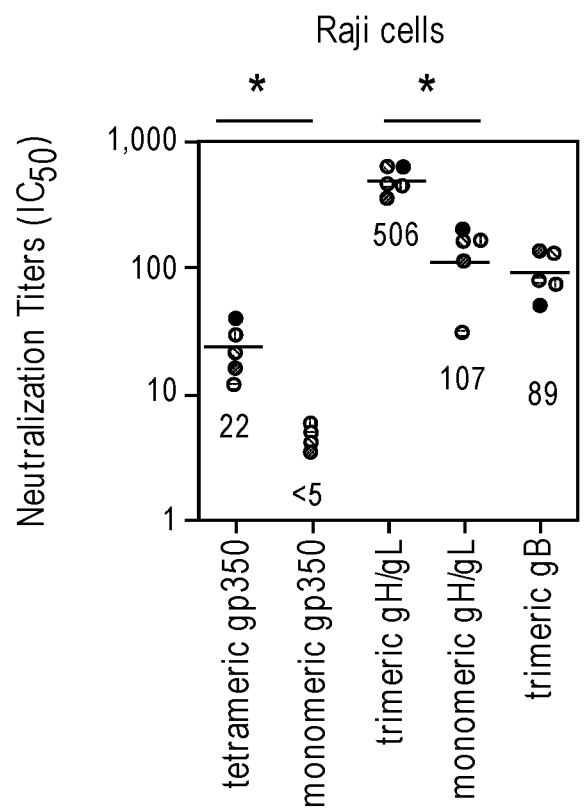
Figure 4B:
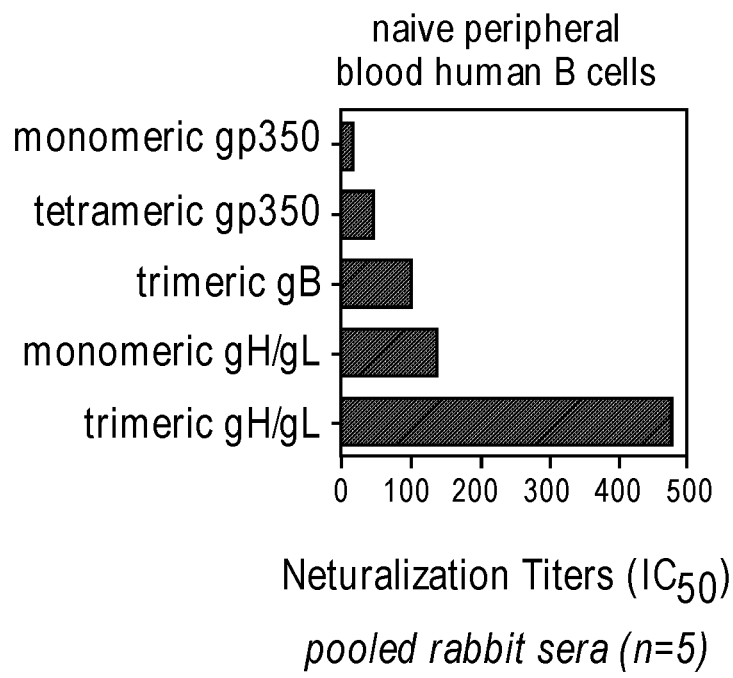

As illustrated in FIG. 4A, tetrameric EBV gp350 induced significantly higher $IC_{50}$ titers (the effective dilution of antibody that inhibited infectivity by 50%) than monomeric EBV gp350 ($IC_{50}$ 22 versus less than 5, respectively). Of note, trimeric gH/gL induced significantly higher $IC_{50}$ titers than monomeric gH/gL ($IC_{50}$ 506 versus 107, respectively), titer levels that are markedly and significantly higher than that induced by tetrameric gp350. Similarly, trimeric EBV gB induced significantly higher $IC_{50}$ titers ($IC_{50}$ 89) than tetrameric gp350 ($IC_{50}$ 22) and was comparable to that elicited by monomeric gH/gL ($IC_{50}$ 107). Compared to monomeric gp350, which has been previously tested in a phase II clinical trial, trimeric gH/gL, monomeric gH/gL, trimeric gB, and tetrameric gp350 elicited greater than 100-, 20-18-, and 4-fold higher $IC_{50}$ titers respectively. Similar data was obtained from sera that were pooled from each of the groups shown in FIG. 4A, utilizing GFP-EBV and naïve peripheral blood human B cells from healthy donors for determination of EBV neutralization titers (FIG. 4B), except that monomeric and tetrameric gp350 showed slightly higher $IC_{50}$ titers compared to those calculated using Raji cells (FIG. 4A). Thus, EBV gH/gL and EBV gB proteins, like EBV gp350, elicit antibodies in rabbits that block EBV entry into Raji Burkitt lymphoma and naïve peripheral human B cells. However, EBV gH/gL and EBV gB proteins appear to be significantly more potent on a per weight basis than EBV gp350.

Example 1.6—Immunization of Rabbits with EBV Trimeric gB and Monomeric gH/gL

Figure 5:
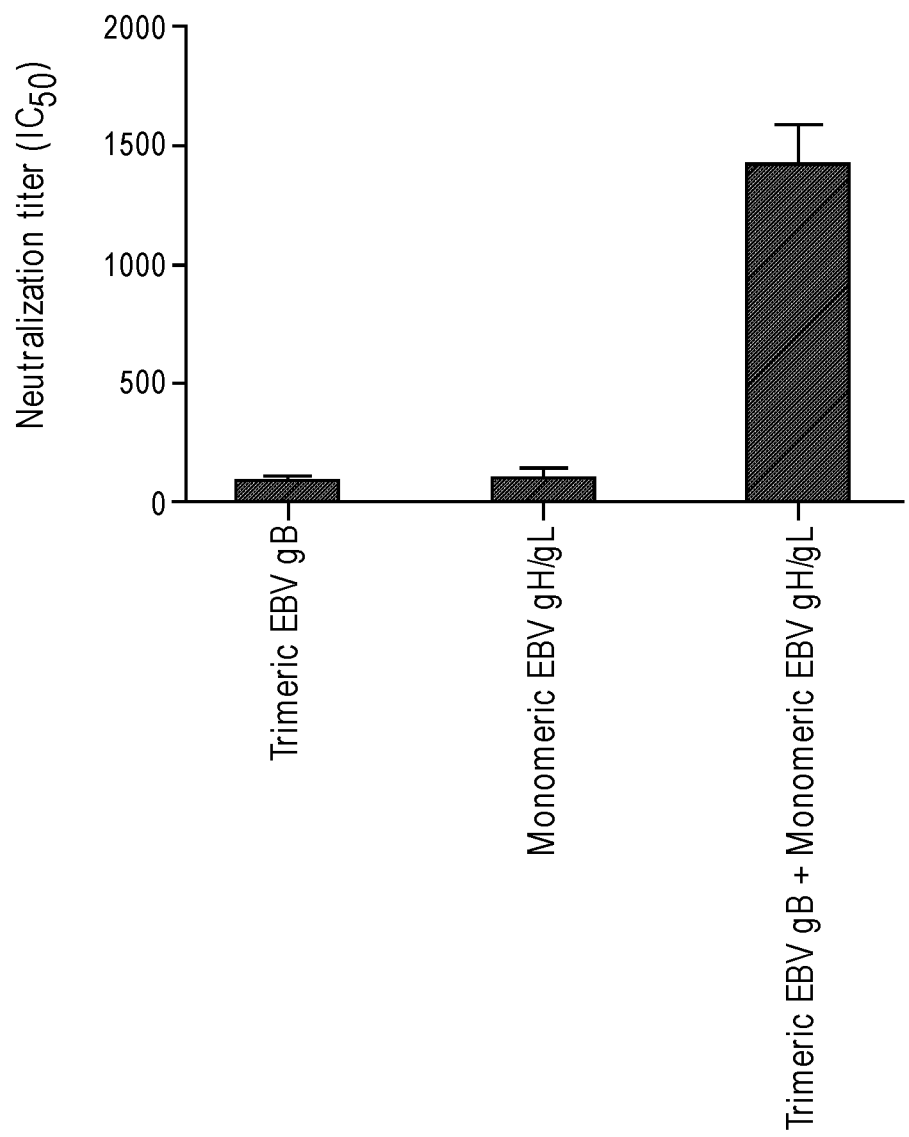

New Zealand white rabbits, 12-15 weeks old, were immunized subcutaneously with a combination of EBV trimeric gB and monomeric gH/gL, each 25 µg adsorbed to aluminum hydroxide (alum; 0.25 µg alum/mg protein) and mixed with 100 µg of a 12-mer phosphorothioate-modified CpG-ODN (TCATAACGTTCC (SEQ ID NO: 52)) optimized for rabbits (Ioannou et al., *Vaccine*, 21:4368-72, 2003). Rabbits were immunized on day 0, day 21, and day 42, and serum samples were taken before initial immunization, and 10 days following each immunization. EBV neutralization assay based on flow cytometric analysis of GFP-labeled EBV entry into Raji Burkitt lymphoma B cells was used to measure serum EBV neutralizing titers that inhibit infectivity of 50% of Raji B cells ($IC_{50}$). Administering both EBV trimeric gB and monomeric gH/gL yielded synergistic results as compared to administering the individual EBV proteins. More specifically, at day 52, rabbits immunized with the EBV trimeric gB and monomeric gH/gL demonstrated 16-fold and 14-fold higher EBV neutralization activity compared to the rabbits immunized with EBV trimeric gB or monomeric gH/gL alone, respectively (FIG. 5).

Example 1.7—EBV Neutralization In Vitro with Anti-Sera Combinations

Figure 6A:
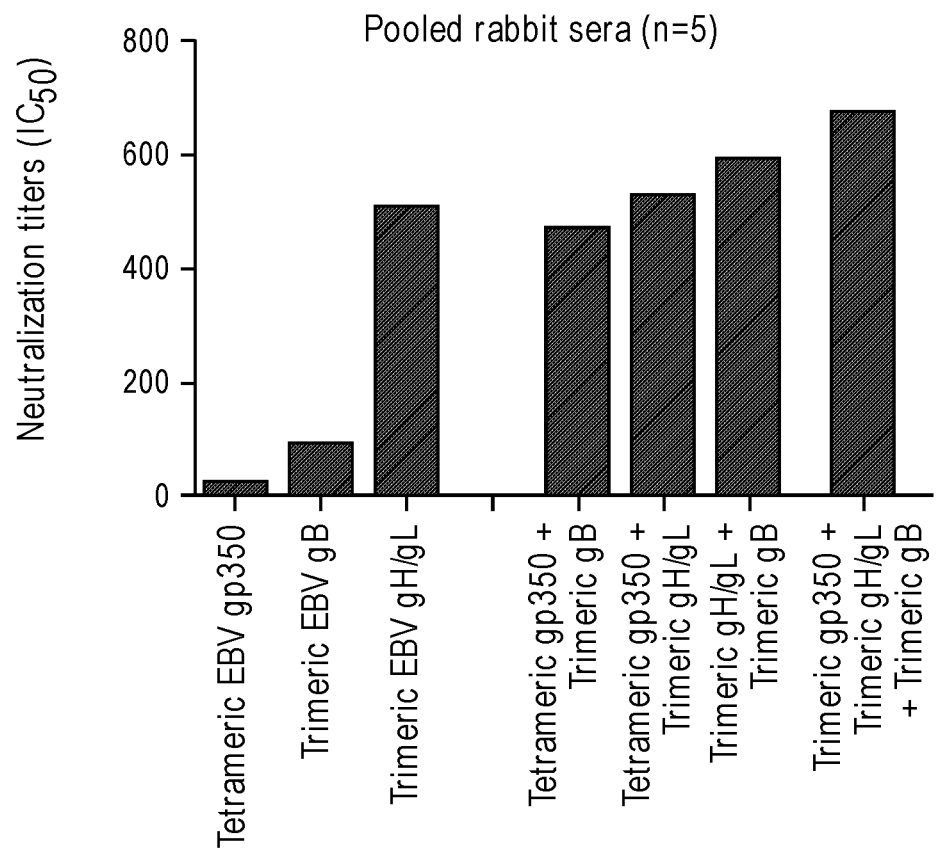
Figure 6B:
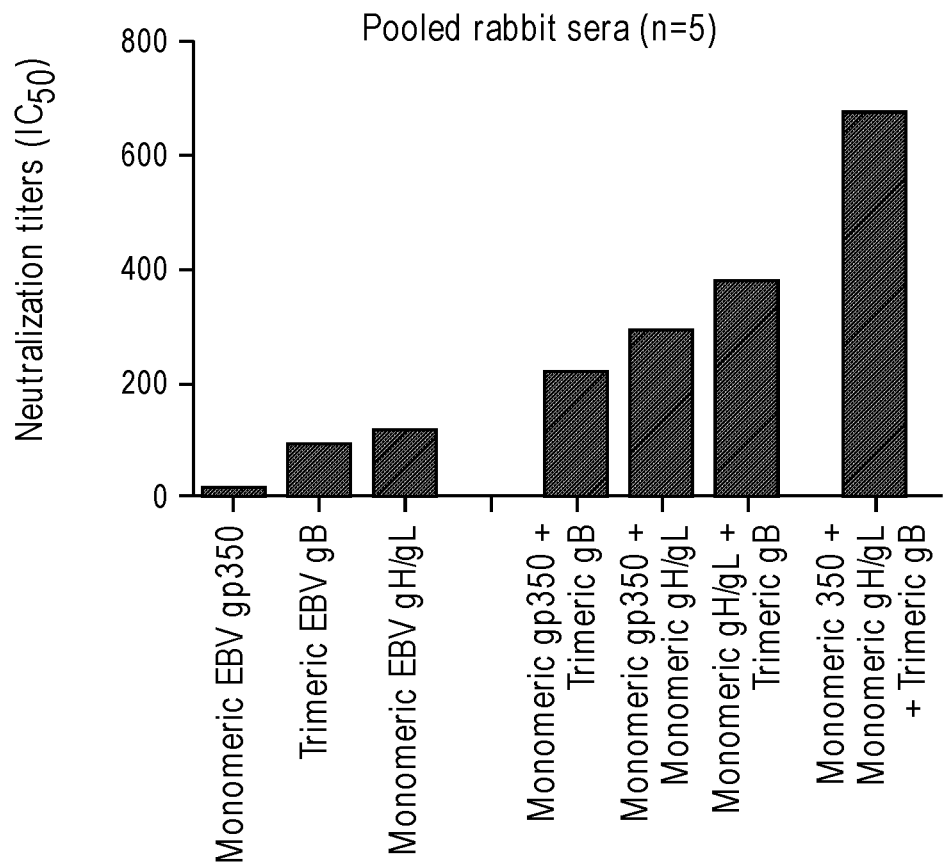

Different combinations of the sera obtained from rabbits immunized with trimeric EBV gB, monomeric EBV gH/gL, or monomeric EBV gp350, were analyzed for in vitro EBV-neutralizing titers using Raji cells. Trimeric gB+monomeric gH/gL sera, trimeric gB+monomeric gp350 sera, monomeric gH/gL+monomeric gp350 sera, and trimeric gB+monomeric gH/gL+monomeric gp350 sera, all showed more than 2-fold increased EBV neutralization activity compared to the sum of the neutralization activity of individual protein immune serum, clearly demonstrating synergistic effects in EBV neutralization activity (FIG. 6B).

Different combinations of the sera from rabbits immunized with EBV trimeric gB, trimeric gH/gL or tetrameric gp350 were also analyzed for in vitro EBV-neutralizing titers using Raji cells. Trimeric gB+trimeric gH/gL sera, trimeric gH/gL+tetrameric gp350 sera, and trimeric gB+trimeric gH/gL+tetrameric gp350 sera showed EBV neutralization activity comparable to the sum of the neutralization activity of individual protein immune serum (FIG. 6B). Trimeric gB+tetrameric gp350 sera showed more than 2-fold increased EBV neutralization activity compared to the sum of the neutralization activity of individual protein immune serum, demonstrating synergism (FIG. 6A).

The synergistic results obtained when certain EBV proteins were combined was not expected. The additive results obtained when other EBV proteins were combined were similarly unexpected given the potential for diminished antibody responses due to vaccine or immune interference.

Example 1.8—Passive Transfer of Immunity Against EBV in NOG Mice

In this study, mice were challenged with live EBV to determine whether anti-sera from the rabbits exposed to EBV polypeptides, above, can protect the mice from EBV infection, i.e. through a passive immunity transfer model. NOD/Shi-scid/IL-2Rγ$^{null}$ (NOG) mice are an art-recognized humanized mouse model of EBV infection, mirroring key aspects of EBV infection in humans (Yajima et al., *J. Infect. Dis.*, 198:673-82, 2008). NOG mice are immunodeficient, lacking mature T, B, and natural killer cells. The immune system of NOG mice can be reconstituted with a functional human immune system to generate humanized NOG (hu-NOG) mice by transplanting hematopoietic stem cell (HSC) from human cord blood (Yajima et al., *J. Infect. Dis.*, 198:673-82, 2008). Inoculation of the mice with about $1\times10^3$ TD$_{50}$ (50% transforming dose) of EBV causes B cell lymphoproliferation with histopathological findings and latent EBV gene expression similar to that observed in immunocompromised humans, and mortality by 10 weeks post-infection and are thus considered a useful model for EBV-driven PTLD in humans. (Dittmer et al., *Curr. Opin. Virol.*, 14:145-50, 2015).

Hu-NOG mice are still defective in eliciting specific human IgG responses to protein antigens and thus not appropriate for direct vaccination studies (Seung et al., *J. Infect. Dis.*, 208 Suppl 2:S155-9, 2013), necessitating passive immunization studies to determine a protective role for EBV-specific antibodies. In this regard, an earlier study reported that 85% of SCID mice injected i.p. with peripheral blood mononuclear cells (PBMCs) from an EBV-seropositive healthy blood donor developed B cell lymphomas over a 150-day period. However, tumor formation was prevented by weekly treatments with 2 different commercial IVIg preparations (not specifically selected for high EBV neutralizing activity) or by purified IgG from EBV-seropositive, but not seronegative donors. (Abedi et al., *Int. J. Cancer,* 71:624-9, 1997).

In this study, hu-NOG mice were derived by intravenous injection of human CD34(+) HSCs isolated from cord blood (about $1\times10^4$ to $1.2\times10^5$ cells/female mouse at 6-10-week-old). After the human hemato-immune system was reconstituted, four groups (n=4) of hu-NOG mice were injected with 300 μl i.p. of the day 52 pooled sera from rabbits immunized with tetrameric EBV gp350, trimeric EBV gH/gL, trimeric EBV gB, or control (adjuvant (alum+CpG-ODN) alone). Two hours following i.p. injection of rabbit sera, hu-NOG mice were infected intravenously with about $1\times10^3$ TD$_{50}$ of EBV (AKATA Burkitt lymphoma cell line), a dose that induces B cell lymphoproliferation and fatality within or at about 10 weeks. (Yajima et al., *J. Infect. Dis.,* 198:673-682, 2008).

Figure 7A:
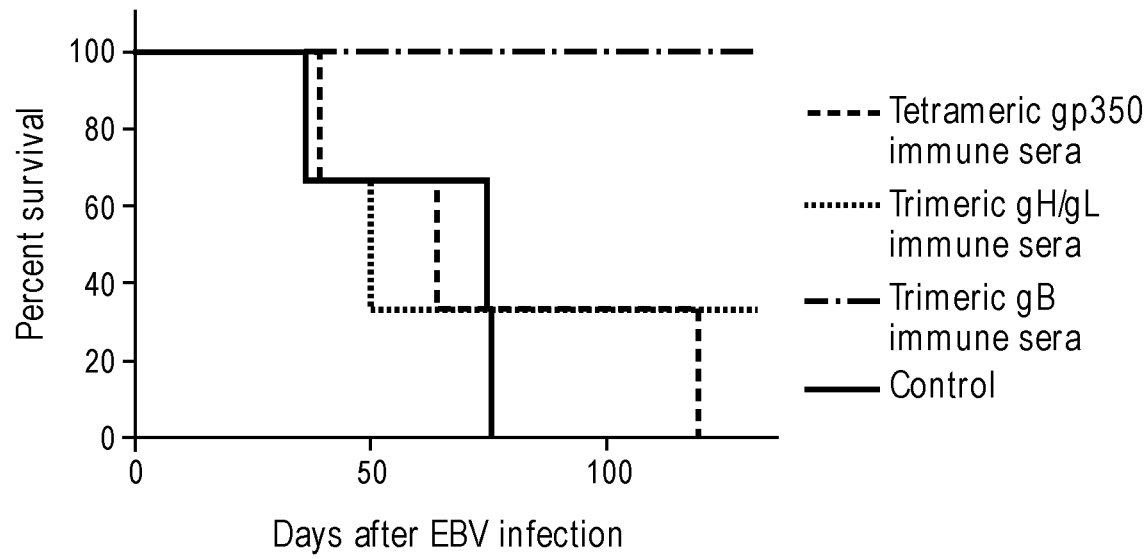
Figure 7B:
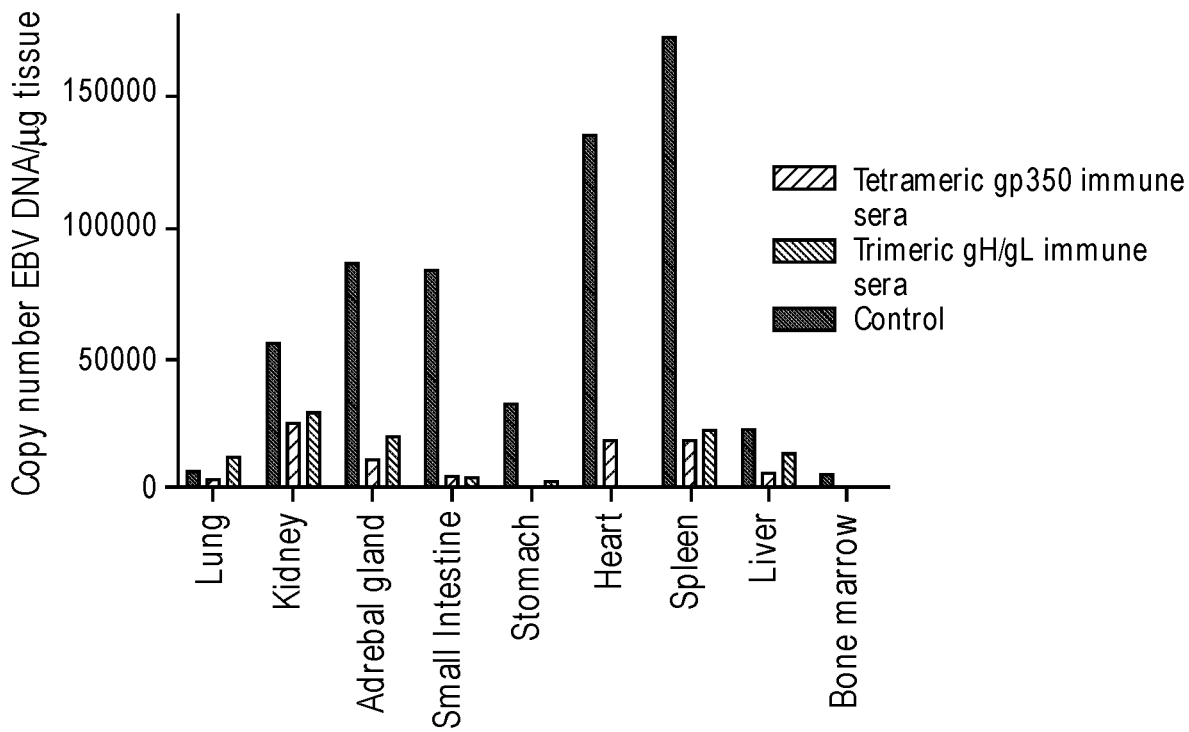
Figure 7C:
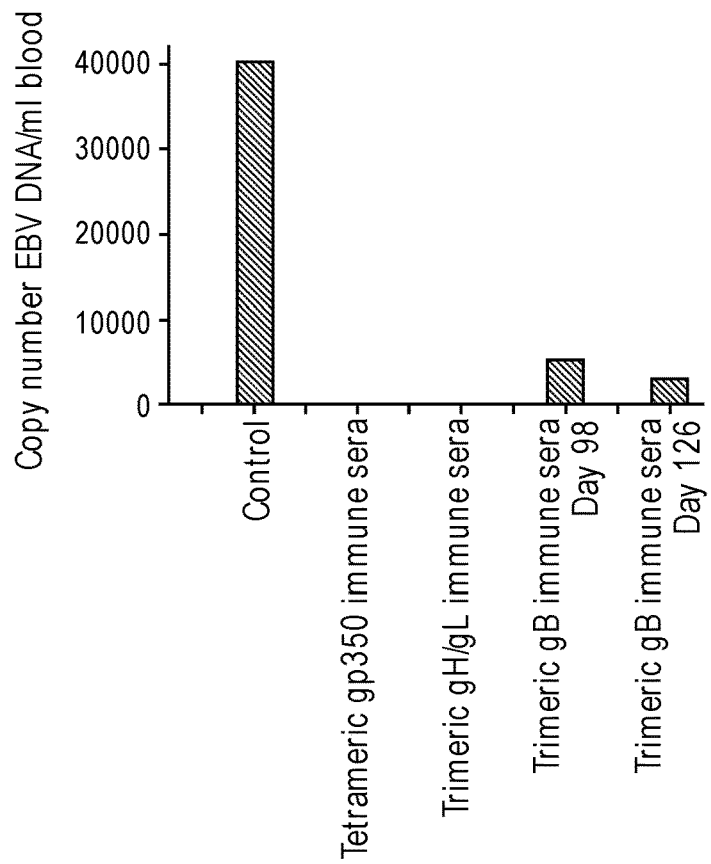

Seventy-five (75) days after EBV infection, the three hu-NOG mice receiving sera from alum+CpG-ODN-injected rabbits all died, whereas all three mice receiving trimeric gB-specific pooled antisera survived after 132 days of EBV infection (FIG. 7A). One hu-NOG mouse receiving tetrameric gp350-specific pooled antisera survived for 119 days, and one hu-NOG mouse receiving trimeric gH/gL-specific pooled antisera survived 132 days (FIG. 7A). Compared to the hu-NOG mice receiving control (alum+CpG-ODN sera), the copy number of EBV from multiple organs of the mice receiving trimeric gH/gL-specific pooled antisera or tetrameric gp350-specific pooled antisera was significantly lower relative to sera from rabbits injected with alum+CpG-ODN alone in multiple organs (FIG. 7B). The effects of gB-specific pooled antisera on EBV organ involvement were not reported as the experiment was ongoing. Hu-NOG mice receiving gB-, gH/gL-, or gp350-specific pooled antisera also showed markedly lower EBV DNA blood levels relative to the adjuvant control, though the hu-NOG mice receiving trimeric gB-specific pooled antisera had higher EBV load in peripheral blood compared to the mice receiving tetrameric gp350-specific pooled antisera or trimeric gH/gL-specific pooled antisera (FIG. 7 C).

2. Human Cytomegalovirus (HCMV)

Example 2.1—Production of Trimeric HCMV gB

The above results with EBV fusion/cell entry proteins show unexpectedly high levels of antibody induction when the EBV polypeptides were combined. Based on these novel findings, we expected to obtain similar results when combining fusion/cell entry proteins from other HHV families, such as HCMV. To this end, similar studies were designed to show that the observations made in the EBV studies can be extended to other HHV family members, like HCMV.

Figure 8:
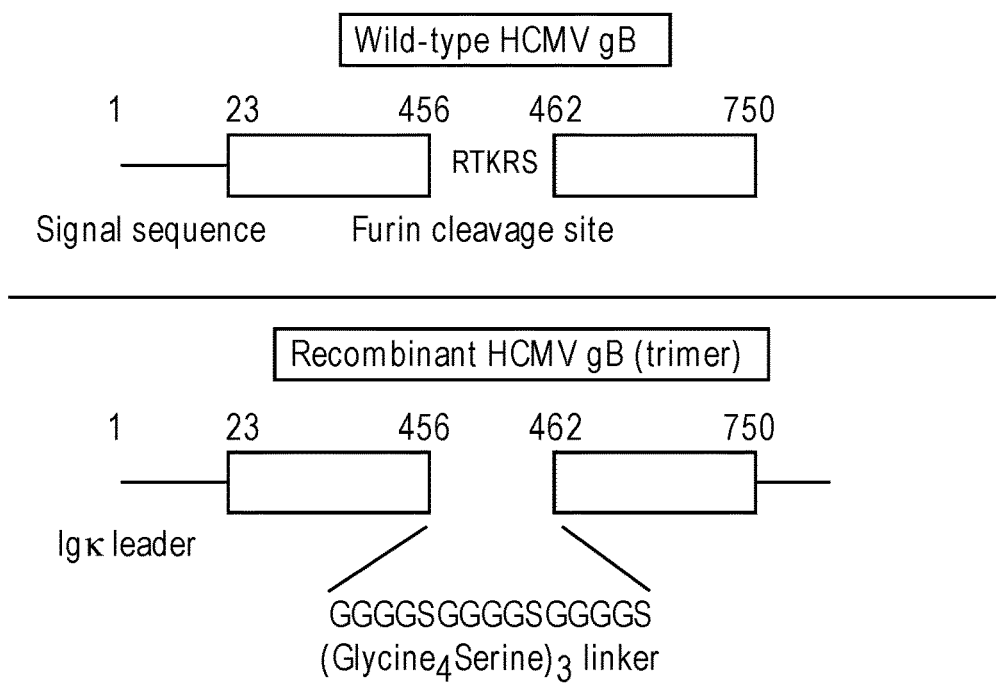

For HCMV, a coding sequence for HCMV gB was obtained from the NCBI website, reference sequence NC_006273.2, strain Merlin, nucleotides 82066 through 84789. The DNA sequence encoding for amino acids 23-750 of HCMV gB (corresponding to the extracellular domain of gB) was used, and the signal peptide (corresponding to amino acids 1-22) was replaced with an IgG κ leader sequence. To make a trimeric version of the gB polypeptide, the coding sequence for the cleavage site, RTKRS (SEQ ID NO: 53) between amino acids 456 (N) and 462 (T), was replaced with a 15-amino acid (Gly₄Ser)₃ (SEQ ID NO: 3) linker sequence (FIG. 8A). A His₆ (SEQ ID NO: 49) sequence was added to the 3' end for protein purification. The DNA coding for the gB protein was synthesized, cloned into pOptiVEV (Invitrogen, Carlsbad, Calif., USA), and the sequence verified by sequencing. CHO cells (strain DG44; Invitrogen, Carlsbad, Calif., USA) were stably transfected with pOptiVEC-gB, and positive cells selected with increasing concentrations of methotrexate up to 4 µM. Supernatants were concentrated for affinity purification using a cobalt column (Thermo Fisher Scientific, Waltham, Mass., USA).

Figures 9A, 9B:
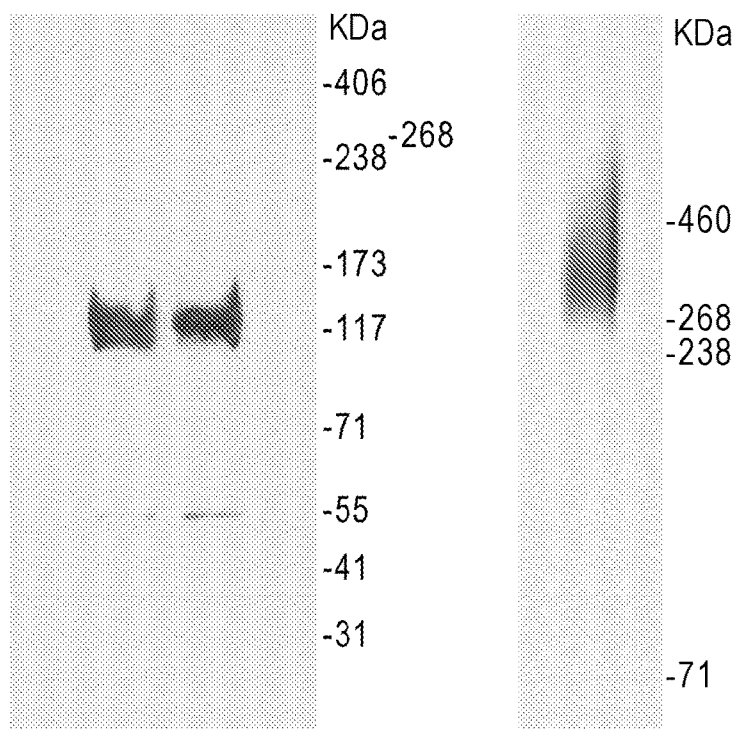

Purified proteins were analyzed by electrophoresis on 3-8% NuPAGE Tris-Acetate Mini-Gels, under reducing condition. Purified HCMV gB was boiled for 10 minutes in lithium dodecyl sulfate sample loading buffer containing 50 mM DTT, blotted with anti-gB monoclonal antibody 2F12 (Virusys Corp., Taneytown, Md., USA) or LS-C64457 (LifeSpan BioSciences, Inc., Seattle, Wash., USA), and both showed 120 kDa band corresponding to monomer (FIG. 9A). Purified HCMV gB was also analyzed by PAGE under modified non-reducing condition (mixed protein with Lithium dodecyl sulfate sample buffer without DTT, resolved on 3-8% PAGE in native running buffer), and blotted with anti-gB monoclonal antibody LS-C64457, which showed a band with molecular weight of about 360 kDa, consistent with trimeric gB (FIG. 9B).

Example 2.2—Production of Monomeric and Trimeric HCMV gH/gL Polypeptides

Likewise, the coding sequences for HCMV gH and gL were obtained from the NCBI website, reference sequence NC_006273.2, strain Merlin, gH nucleotides 109224 through 111452, gL nucleotides 165022 through 165858. The construct for trimeric HCMV gH/gL expression was synthesized using MacVector (MacVector, Inc., Apex, N.C., USA) and following the design used to express trimeric EBV gH/gL. The gL sequence encoding amino acids 31-278 was used, and the signal peptide corresponding to amino acids 1-30 was replaced with an IgG κ leader sequence. The gH sequence encoding amino acids 24-718 was linked to the 3' end of gL and separated by a 15-amino acid linker (Gly₄Ser)₃ (SEQ ID NO: 3) sequence. A foldon trimerization domain coding sequence derived from T4 phage fibritin was linked to the 3' end of gH, followed by a His₆ (SEQ ID NO: 49) coding sequence for protein purification. DNA coding for the trimeric gH/gL was synthesized, cloned into pOptiVEV (Invitrogen, Carlsbad, Calif., USA), and the sequence was verified by sequencing. The monomeric HCMV gH/gL construct was made by PCR amplification of the trimeric HCMV gH/gL without the foldon trimerization domain coding sequence, cloned into pOptiVEV, and the sequence verified by sequencing.

Figures 9C, 9D, 9E:
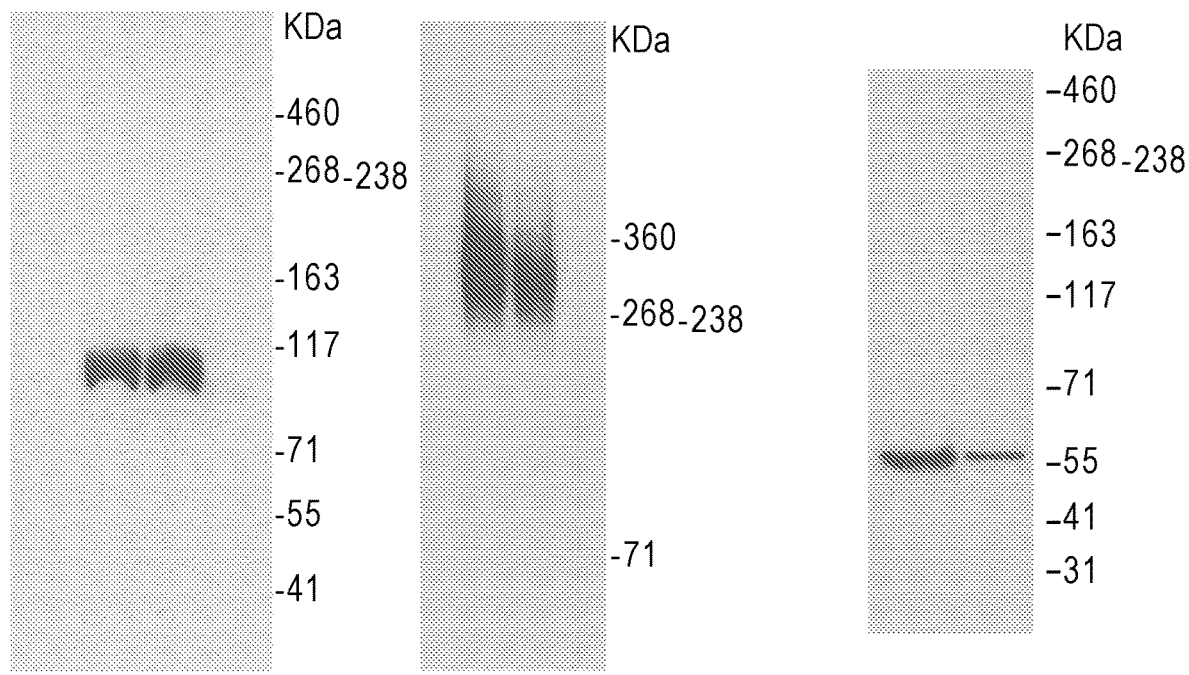

Chinese Hamster Ovary (CHO) cells (strain DG44) (Invitrogen) were stably transfected with the obtained pOptiVEC-gH/gL constructs using Free-style Max reagent (Invitrogen, Carlsbad, Calif., USA), and positive transformants were selected with gradually increased concentration of methotrexate up to 4 µM. Supernatants were concentrated and purified using Cobalt affinity purification (Thermo Fisher Scientific, Waltham, Mass., USA), and analyzed by Western blot using both an anti-His₆ (SEQ ID NO: 49) antibody and anti HCMV gH/gL antibody (Santa Cruz Biotech, Dallas, Tex., USA). Under reducing conditions, the Western blot showed monomeric gH/gL as a band of about 110 kDa (FIG. 9C), and under non-reducing conditions, the trimeric gH/gL appeared as a band of about 330 kDa (FIG. 9D).

Example 2.3—Induction of HCMV IgG with Trimeric gB and Monomeric gH/gL

Figure 11:
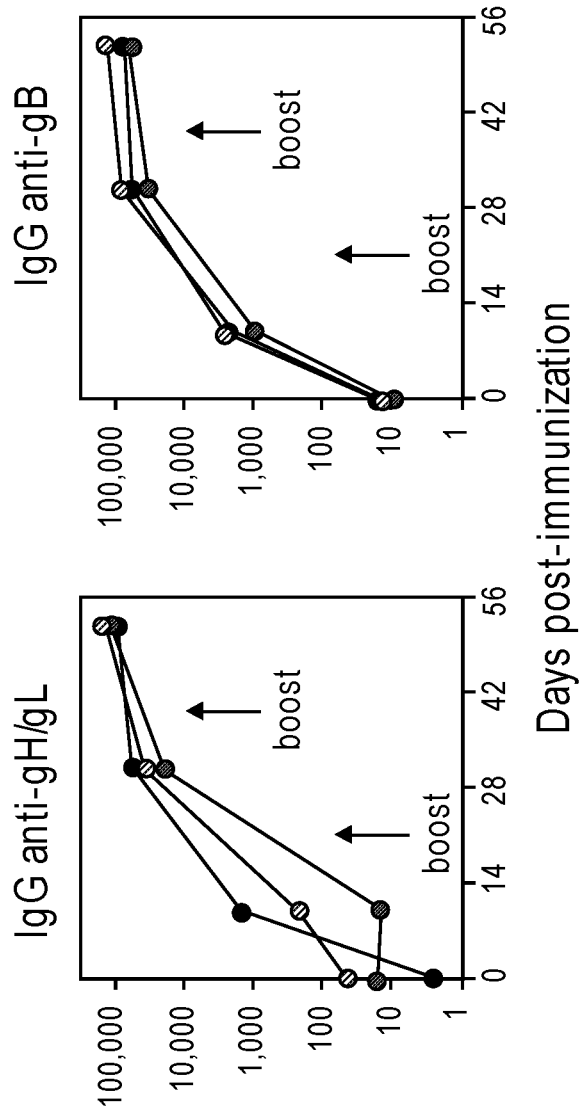

Having generated the desired HCMV polypeptide constructs, comparative studies were conducted to determine whether multimeric polypeptides and/or various polypeptide combinations generated substantially greater immune response than monomeric polypeptides. Thus, seven groups of five male New Zealand white rabbits, 12 to 15 weeks old were immunized subcutaneously with 25 µg of a single HCMV envelope protein or a combination of HCMV envelope proteins (25 µg of each protein in the combination). Twenty-five µg of each protein was adsorbed to aluminum hydroxide (alum; 0.25 µg alum/mg protein) and mixed with 25 µg of CpG-ODN with known activity in rabbits (ODN 2007 having the sequence TCGTCGTTGTCGTTTGTCGTT (SEQ ID NO: 51)). The HCMV proteins/combinations used were monomeric gH/gL, monomeric UL128/UL130/UL131A, monomeric gB (Sino gB), trimeric gB, monomeric gH/gL+monomeric UL128/UL130/UL131A, trimeric gB+monomeric gH/gL, or trimeric gB+monomeric gH/gL+monomeric UL128/UL130/UL131A. Rabbits were immunized on Day 0, Day 21, and Day 42, and serum samples were taken before initial immunization, and at days 10, 31, 52, and 72 following immunization. Serum titers of antigen-specific IgG against live HCMV were determined using fibroblasts (cell line MRC-5, ATCC, Manassas, Va., USA) and epithelial cells (cell line ARPE-19, ATCC, Manassas, Va., USA). Recombinant trimeric HCMV gB and monomeric HCMV gH/gL proteins were incubated together at room temperature of 30 minutes and were found to induce high titers of protein-specific IgG (FIG. 11).

HCMV Neutralization Assay.

Pooled Day 52 and Day 72 sera from the five rabbits in each cohort immunized with a single HCMV envelope protein or a combination of HCMV envelope proteins were either heat inactivated at 56° C. for 30 minutes to eliminate complement activity or not heat treated. Serum HCMV neutralizing antibody titers were determined using ELISpot assay. Each serum sample was prepared 1:2 serial dilutions with culture medium in in quadruplicates. Each dilution was mixed with an equal volume of culture medium containing HCMV strain AD169WT131, incubated for 4 hours at 37° C. then added to the wells of 96-well plates containing ARPE-19 (epithelial line, ATCC, Manassas, Va., USA) or MRC-5 (fibroblast line, ATCC, Manassas, Va., USA) monolayers and cultured overnight at 37° C., with 5% $CO_2$. Cells were fixed with absolute ethanol, rehydrated and blocked with 5% normal horse serum in PBS, followed by incubation with anti-IE1 monoclonal antibody MAB810 (Merck Millipore, Burlington, Mass., USA), goat anti-mouse secondary antibody (Jackson ImmunoResearch Labs, West Grove, Pa., USA) each for 1 hour, and VECTASTAIN ABC reagent (Vector Labs, Burlingame, Calif., USA) for 30 minutes. Plates were washed three times with 0.05 Tween 20 in PBS between each step, and TrueBlue (Sigma-Aldrich, St. Louis, Mo., USA) was added for color development. The plates were scanned and analyzed using a CTL-ImmunoSpot® S6 Micro Analyzer (ImmunoSpot, Cellular Technology Limited, Cleveland, Ohio, USA). Fifty percent inhibitory concentration ($IC_{50}$) values and standard errors of the means were calculated using GraphPad Prism6 software by plotting the means of triplicate values for each serum dilution against log serum concentration, calculating the best fit four-parameter equation for the data, and interpolating the serum dilution at the mid-point of the curve as the $IC_{50}$ neutralizing titer.

Figure 12A:
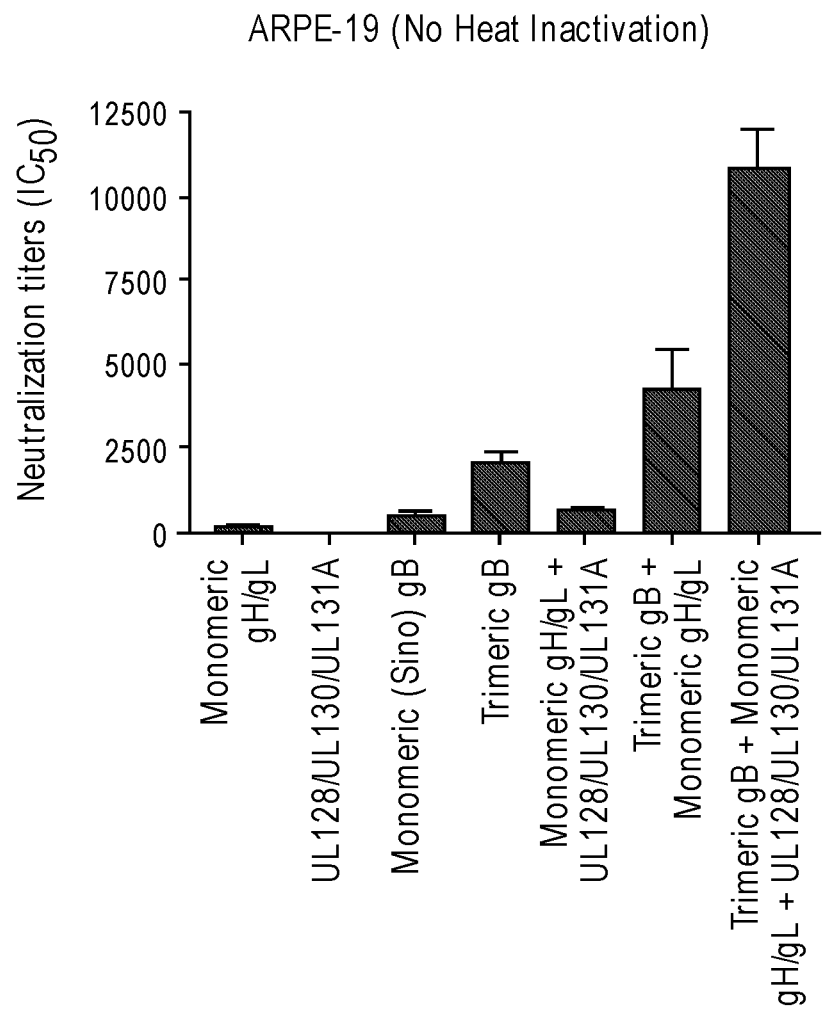

FIG. 12A shows the HCMV neutralization activity analyzed using ARPE-19 cells, where the rabbit immune sera were not heat inactivated Immunization of rabbits with monomeric UL128/UL130/UL131A elicited little HCMV neutralization activity, yielding an $IC_{50}$ titer of less than 10 (FIG. 12A) Immunization with monomeric gH/gL elicited low level complement-dependent HCMV neutralization activity ($IC_{50}$ of 190.9, FIG. 12A). Immunization of rabbits with the combination of monomeric gH/gL+monomeric UL128/UL130/UL131A elicited 3-fold higher complement-dependent HCMV neutralization activity ($IC_{50}$ of 676.9) than the sum of the HCMV neutralization elicited by monomeric gH/gL or monomeric UL128/UL130/UL131A alone (FIG. 12A) Immunization of rabbits with monomeric gB (Sino gB) elicited moderate complement-dependent HCMV neutralization activity ($IC_{50}$ 528.0), and trimeric gB elicited 4-fold higher complement-dependent HCMV neutralization activity related to monomeric gB ($IC_{50}$ of 2168.8). FIG. 12A Immunization with a combination of trimeric gB and monomeric gH/gL elicited 2-fold higher complement-dependent HCMV neutralization activity ($IC_{50}$ of 4299.2) than the sum of the HCMV neutralization elicited by trimeric gB and monomeric gH/gL individually, demonstrating a synergistic effect (FIG. 12A) Immunization of rabbits with a combination of trimeric gB, monomeric gH/gL and monomeric UL128/UL130/UL131A elicited 5-fold higher complement-dependent HCMV neutralization activity ($IC_{50}$ of 10910.8) than the sum of the HCMV neutralization elicited by trimeric gB, monomeric gH/gL and monomeric UL128/UL130/UL131A individually, demonstrating a synergistic effect (FIG. 12A). The complement-dependent HCMV neutralization activity elicited by the immunization with combination of trimeric gB, monomeric gH/gL, and monomeric UL128/UL130/UL131A is 20-fold higher than that of the monomeric gB (Sino gB), which demonstrated 50% efficacy in prevention of HCMV infection in phase II clinical trials.

Figure 12B:
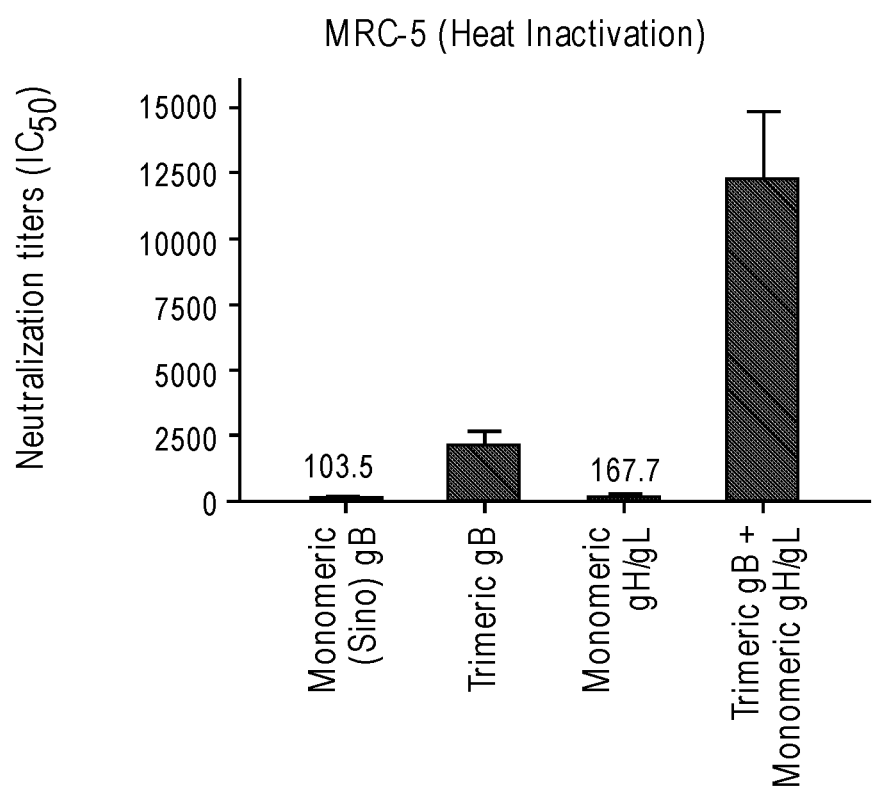

The HCMV neutralization activity analyzed using fibroblast cell line MRC-5, where the rabbit immune sera were heat inactivated at 56° C. for 30 minutes to eliminate complement activity, is shown in FIG. 12B Immunization of rabbits with monomeric gB (Sino gB) elicited low levels of complement-independent HCMV neutralization activity ($IC_{50}$ 103.5), and trimeric gB elicited 20-fold higher complement-independent HCMV neutralization activity as compared to monomeric gB ($IC_{50}$ of 2185.2, FIG. 12B). Immunization of rabbits with monomeric gH/gL also elicited low level complement-independent HCMV neutralization activity ($IC_{50}$ of 167.7). In contrast, immunization with a combination of trimeric gB and monomeric gH/gL elicited 5-fold higher complement-independent HCMV neutralization activity ($IC_{50}$ of 12299.4) than the sum of the HCMV neutralization activity elicited by trimeric gB and monomeric gH/gL individually, demonstrating a synergistic effect (FIG. 12B). The complement-independent HCMV neutralization activity elicited by the immunization with a combination of trimeric gB and monomeric gH/gL was more than 100-fold higher than monomeric gB (Sino gB), which demonstrated 50% efficacy in prevention of HCMV infection in phase II clinical trials.

Example 2.4—In Vitro Neutralization Assays Using HCMV gB and gH/gL Anti-Sera

Serum HCMV neutralizing antibody titers were determined using an ELISpot assay. Serum samples were combined, and then divided by 1:2 serial dilutions with culture medium in triplicates. Each dilution was mixed with an equal volume of culture medium containing 200 pfu of HCMV strain AD169$^{WT131}$, incubated for 3 h at 37° C., then added to the wells of 96-well plates containing MRC-5 monolayers and cultured overnight at 37° C., with 5% $CO_2$. Cells were fixed with absolute ethanol, rehydrated, and blocked with 1% BSA in PBS, followed by incubation with anti-IE1 monoclonal antibody MAB810 (Millipore), biotin-labeled goat anti-mouse secondary antibody, and ABC reagent (Vector Laboratories) each for 1 h. Plates were washed three times with 0.05% Tween® 20 in PBS between each step, and TrueBlue was added for color development. The plates were scanned and analyzed using a CTL-ImmunoSpot® S6 Micro Analyzer (Cellular Technology Limited, Cleveland, Ohio). Fifty percent inhibitory concentration ($IC_{50}$) values and standard errors of the means were calculated using GraphPad Prism7 software by plotting the means of triplicate values for each serum dilution against log serum concentration, calculating the best fit four-parameter equation for the data, and interpolating the serum dilution at the mid-point of the curve as the $IC_{50}$ neutralizing titer.

Figure 15:
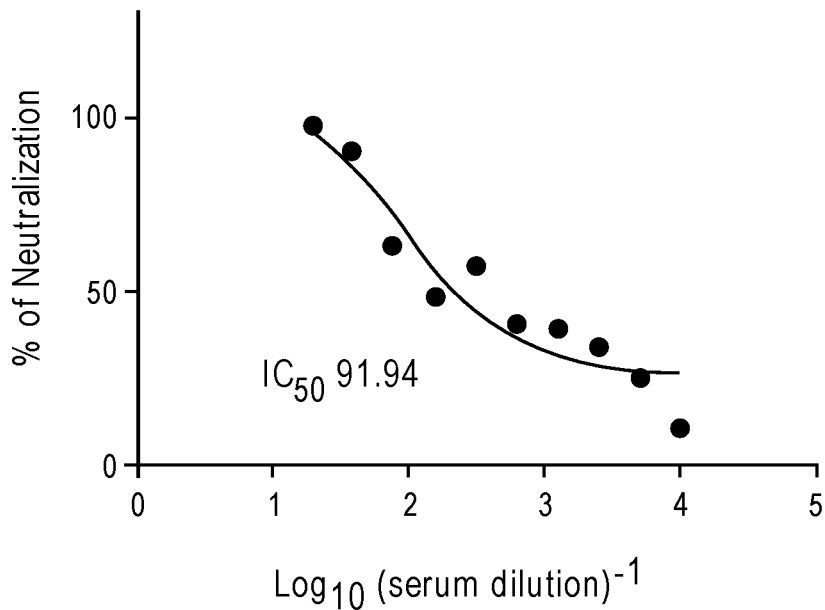
Figure 16:
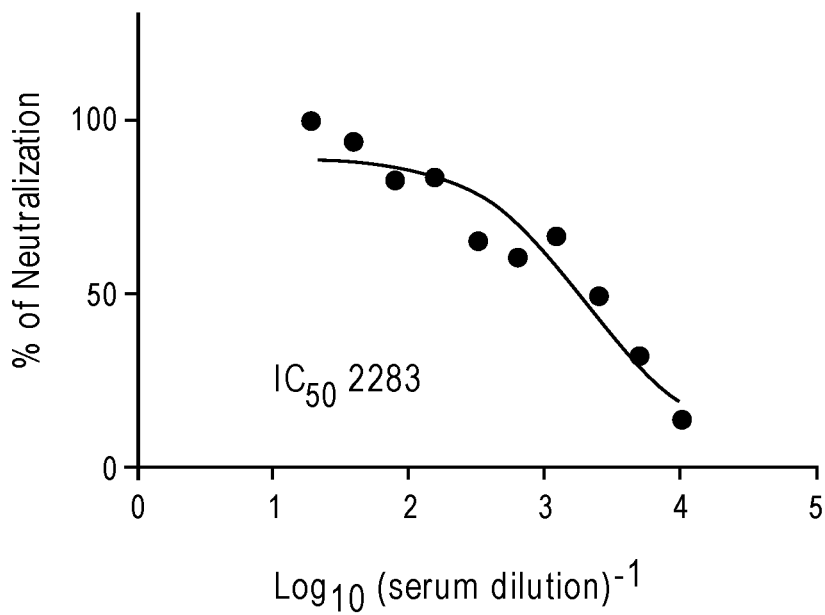
Figure 17:
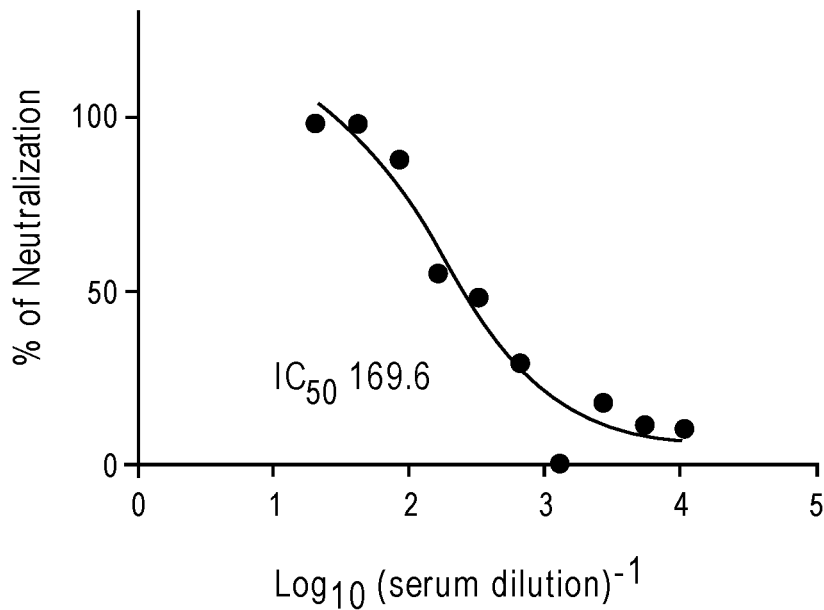
Figure 18:
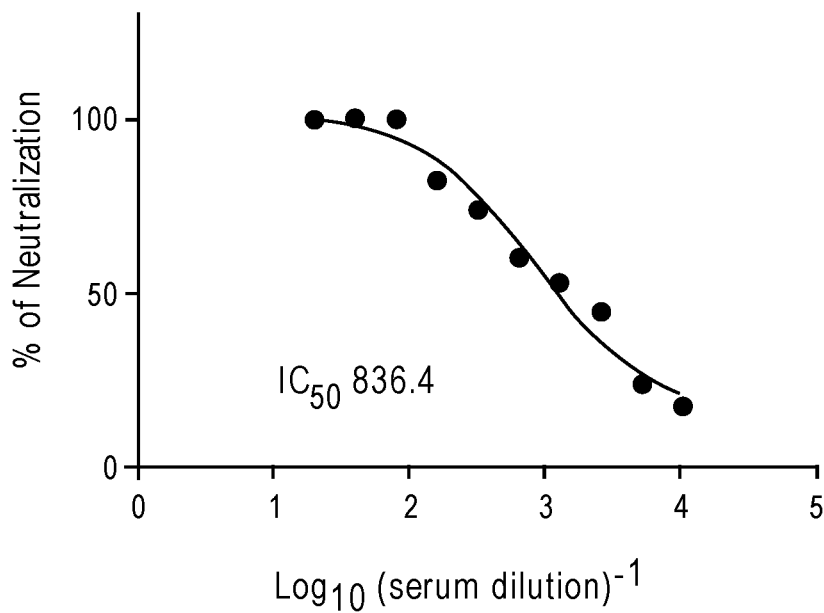
Figure 19:
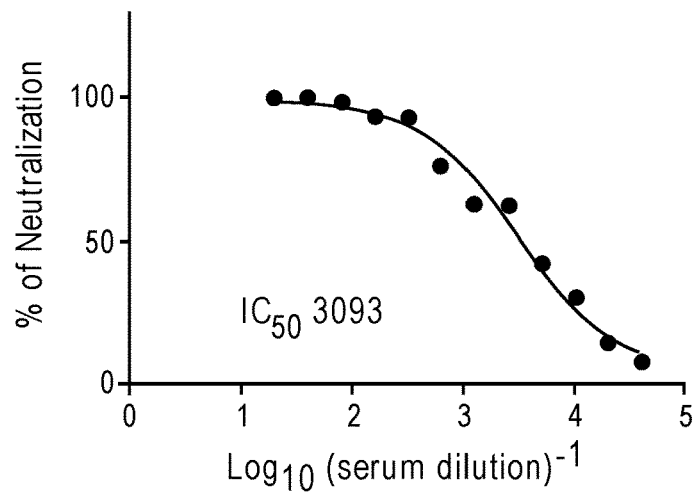
Figure 20:
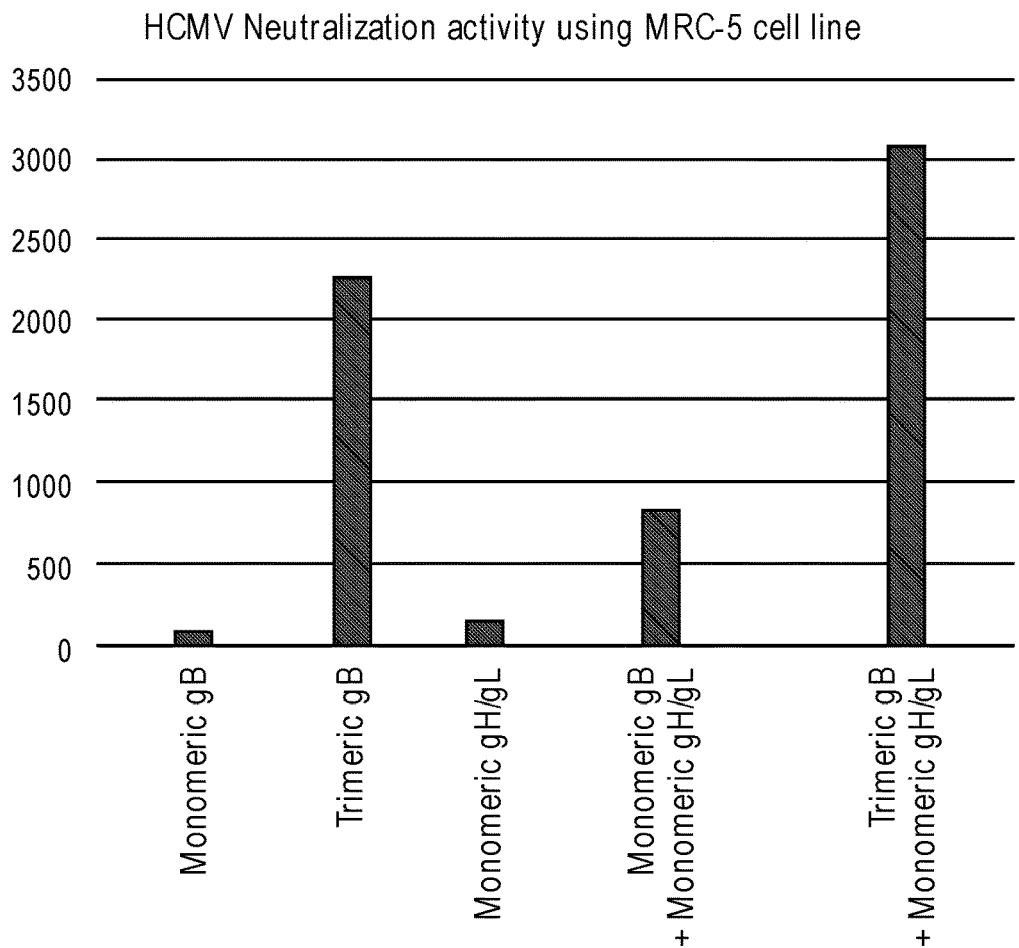

The in vitro HCMV neutralization results obtained using pooled immune sera from rabbits immunized with monomeric HCMV gB, trimeric HCMV gB, monomeric HCMV gH/gL, and in vitro combinations thereof are provided in FIGS. 15-20. Multimerizing the HCMV polypeptides significantly enhanced the neutralizing activity of antibodies generated against the multimerized polypeptides, as compared to a monomeric version of the polypeptide. For example, the $IC_{50}$ of monomeric HCMV gB was 91.94 compared to 2283 for trimeric HCMV gB (FIGS. 15 and 16). Combining HCMV gB immune sera and HCMV gH/gL immune sera unexpectedly induced higher HCMV neutralizing activity than the sum of the neutralizing activity induced by each of the proteins individually, demonstrating synergism. For example, the $IC_{50}$ of the in vitro combination of monomeric HCMV gB immune sera and monomeric gH/gL immune sera was 836.4 (FIG. 18), as compared to an $IC_{50}$ of 91.94 and 169.6, respectively for each of proteins individually (FIGS. 15 and 17). Similarly, the $IC_{50}$ of the in vitro combination of trimeric HCMV gB immune sera and monomeric gH/gL immune sera was 3093 (FIG. 19), as compared to an $IC_{50}$ of 2283 and 169.6 (FIGS. 16 and 17, respectively for each of the proteins individually. These synergistic results are summarized in FIG. 20.

Thus, as with EBV, these comparative tests demonstrate that combining HCMV fusion/cell entry proteins (e.g., gB and gH/gL) unexpectedly enhances HCMV neutralization activity in vivo Immunization of rabbits with a combination of HCMV trimeric or monomeric gB and monomeric gH/gL elicited significantly higher HCMV neutralization activity than the sum of individual proteins, demonstrating unexpected synergistic effects.

Figure 10:
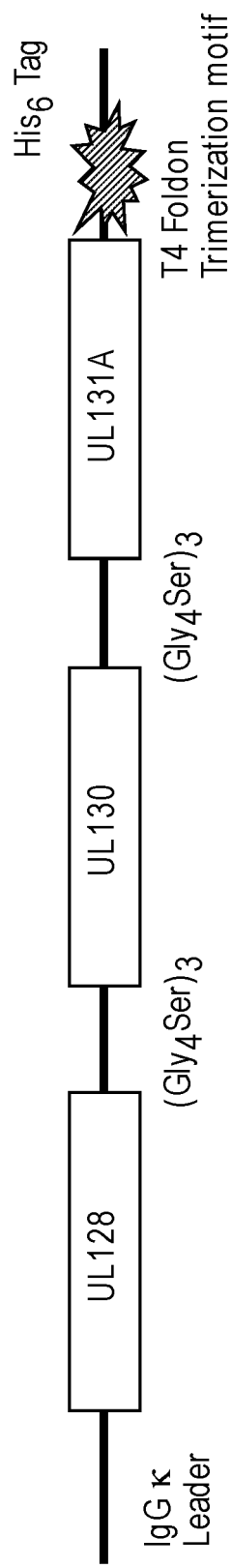

Example 2.5—Production of HCMV Monomeric and Trimeric UL128/130/131 Polypeptides In an effort to further characterize the possibilities of generating heightened antibody titers by administering antigen compositions comprising HHV polypeptides, the HCMV proteins UL128, UL130, and UL131 were recombinantly produced. Briefly, the coding sequences for HCMV UL128 were obtained from the NCBI website, reference sequence GQ121041.1, strain Towne, nucleotides 175653 through 176410. Coding sequences for HCMV UL130 and UL131A were also obtained from the NCBI website, reference sequence NC_006273.2, strain Merlin, UL130 nucleotides 176984 through 177628, and UL131A nucleotides 177649 through 177802 joined to nucleotides 177911 through 178146. UL128 from strain Towne was used because the UL128 from strain Merlin has a mutation and is not functional. The construct for trimeric UL128-UL130-UL131A expression was designed using MacVector. The UL128 sequence encoding amino acids 28-171, UL130 sequence encoding amino acids 26-214, and UL131A sequence encoding amino acids 19-129, were linked by a 15-amino acid linker $(Gly_4Ser)_3$ (SEQ ID NO: 3) between each coding sequence (FIG. 10). A foldon trimerization domain coding sequence derived from T4 phage fibritin was linked to the 3' end of UL131A, followed by a $His_6$ (SEQ ID NO: 49) coding sequence, and an IgGκ leader sequence was placed 5' to the UL128 sequence for secretion of recombinant protein (FIG. 10). DNA coding for the trimeric UL128-UL130-UL131A was synthesized, cloned into pOptiVEV (Invitrogen, Carlsbad, Calif., USA), and the sequence was verified. The monomeric UL128-UL130-UL131A construct was made by PCR amplification of trimeric UL128-UL130-UL131A without the foldon trimerization domain coding sequence, cloned into pOptiVEV, and the sequence was verified.

CHO cells (strain DG44, Invitrogen, Thermo Fisher Scientific, Carlsbad, Calif., USA) were stably transfected with the resultant pOptiVEC-UL128-UL130-UL131A construct using the Free-style Max reagent (Invitrogen, Carlsbad, Calif.), and positive transfectants were selected with gradually increased concentrations of methotrexate, up to 4 µM. Supernatants were concentrated and purified using Cobalt affinity purification (Thermo Fisher Scientific, Waltham, Mass., USA). Western blot analysis of the supernatants from CHO cells transfected with the monomeric UL128-UL130-UL131A construct using anti-$His_6$ (SEQ ID NO: 49) and anti-UL128 antibodies exhibited a band of about 57 kDa, consistent with monomeric UL128/UL130/UL131A (FIG. 9E).

Example 2.6—Production of HCMV Pentameric gH/gL/UL128/130/131 Complex

The coding sequences for HCMV gH, gL, UL128, UL130 and UL131A were obtained from the NCBI website. A construct for pentameric complex gH/gL/UL128/UL130/UL131A expression was designed using MacVector and is depicted in FIG. 13. The construct includes a gL sequence encoding amino acids 31-278, a gH sequence encoding amino acids 24-718, where the signal peptide of both sequences were replaced with an IgG κ leader sequence. The EV71 Internal Ribosome Entry Site (IRES) sequence was inserted between the sequences of gH and gL, and a $His_6$ (SEQ ID NO: 49) encoding sequence was attached to the 3' end of gH for protein purification. The signal peptides of UL128, UL130, and UL131A were also replaced with an IgG κ leader sequence, and the UL128 sequence encoding amino acids 28-171, UL130 sequence encoding amino acids 26-214, and UL131A sequence encoding amino acids 19-129, were linked together by insertion of the EV71 IRES sequence between each. The UL128, UL130, and UL131A were driven by a second CMV promoter, which was placed 5' end of UL128, and 3' end of gH-$His_6$ (SEQ ID NO: 49) coding sequence. HCMV gL and gH were driven by a first CMV promoter derived from vector pOptiVEC.

DNA coding for the pentameric complex gH/gL/UL128/UL130/UL131A will be synthesized, cloned into pOptiVEV (Invitrogen), and verified. CHO cells (strain DG44; Invitrogen) will be transfected with pOptiVEC-gH/gL/UL128/UL130/UL131A, and positive transformants can be selected with increasing concentrations of methotrexate up to 4 µM, using the procedures already outlined above for similar constructs.

Example 2.7—Production of HCMV gH/gL/gO Complex

As with the other HCMV constructs discussed above, the coding sequences for HCMV gH, gL were also obtained from the NCBI website, and the coding sequences for HCMV gO was also obtained from the NCBI website, reference sequence NC_006273.2, strain Merlin, gO nucleotides 107430 through 108848. The construct for gH/gL/gO complex expression was designed using MacVector and is depicted in FIG. 14, including the gL sequence encoding amino acids 31-278 and the gH sequence encoding amino acids 24-718. The signal peptides of both sequences were replaced with an IgGκ leader sequence. The EV71 Internal Ribosome Entry Site (IRES) sequence was inserted between the gH and gL sequences, and a $His_6$ (SEQ ID NO: 49) encoding sequence was attached to the 3' end of gH for protein purification. The signal peptide of gO was also replaced with an IgG κ leader sequence, and the gO sequence coding amino acids 31-466 was driven by the second CMV promoter, which was placed 5' end of gO, and 3' end of gH-$His_6$ (SEQ ID NO: 49) coding sequence. HCMV gH and gL were driven by the first CMV promoter derived from vector pOptiVEC.

DNA coding for the gH/gL/gO complex will be synthesized and cloned into pOptiVEV as previously described. Stable CHO transformants will be purified and analyzed with size exclusion chromatography and multi-angle light scattering (SEC-MALS).

Example 2.8—Immunization of Mice with HCMV Trimeric gB and Monomeric gB

Six groups of 7- to 10-week old Balb/c mice (n=5) were immunized by the intraperitoneal (i.p.) route with 1 µg, 5 µg, or 25 µg of HCMV trimeric gB or 1 µg, 5 µg, or 25 µg HCMV monomeric gB (Sino gB, Sino Biological Inc., China). Antigen was adsorbed to aluminum hydroxide (alum; 0.25 µg alum/mg protein) and mixed with 25 µg of a 30-mer phophorothioate-modified CpG-ODN (AAAAAAAAAAAAAAACGTTAAAAAAAAAAAA (SEQ ID NO: 54)) optimized for mice. Mice immunized with only alum+CpG-ODN served as negative controls. Mice were immunized on day 0, day 21, and day 42, and serum samples were taken before initial immunization, 10 days following each immunization, and at day 63. Individual mouse serum samples were analyzed for titers of gB-specific IgG by ELISA, and in vitro neutralizing activity using fibroblasts (MRC-5) and epithelial cells (ARPE-19).

HCMV Neutralization Assay.

Sera from mice immunized with monomeric or trimeric gB were either heat inactivated at 56° C. for 30 minutes to eliminate complement activity or not heat treated. Serum HCMV neutralizing antibody titers were determined using ELISpot assay. Each serum sample was prepared 1:2 serial dilutions with culture medium in triplicates. Each dilution was mixed with an equal volume of culture medium containing HCMV strain AD169WT131, incubated for 4 hours at 37° C. and then added to the wells of 96-well plates containing MRC-5 (fibroblast line, ATCC, Manassas, Va., USA) monolayers and cultured overnight at 37° C., with 5%

$CO_2$. Cells were fixed with absolute ethanol, rehydrated, and blocked with 5% normal horse serum in PBS, followed by incubation with anti-IE1 monoclonal antibody MAB810 (Merck Millipore, Burlington, Mass., USA), goat anti-mouse secondary antibody (Jackson ImmunoResearch Labs, West Grove, Pa., USA) each for 1 hour, and VECTASTAIN ABC reagent (Vector Labs, Burlingame, Calif., USA) for 30 minutes. Plates were washed three times with 0.1% Tween 20 in PBS between each step, and TrueBlue (Sigma-Aldrich, St. Louis, Mo., USA) was added for color development. The plates were scanned and analyzed using a CTL-Immuno-Spot® S6 Micro Analyzer (ImmunoSpot, Cellular Technology Limited, Cleveland, Ohio, USA). Fifty percent inhibitory concentration ($IC_{50}$) values and standard errors of the means were calculated using GraphPad Prism6 software by plotting the means of triplicate values for each serum dilution against log serum concentration, calculating the best fit four-parameter equation for the data, and interpolating the serum dilution at the mid-point of the curve as the $IC_{50}$ neutralizing titer.

Figure 21A:
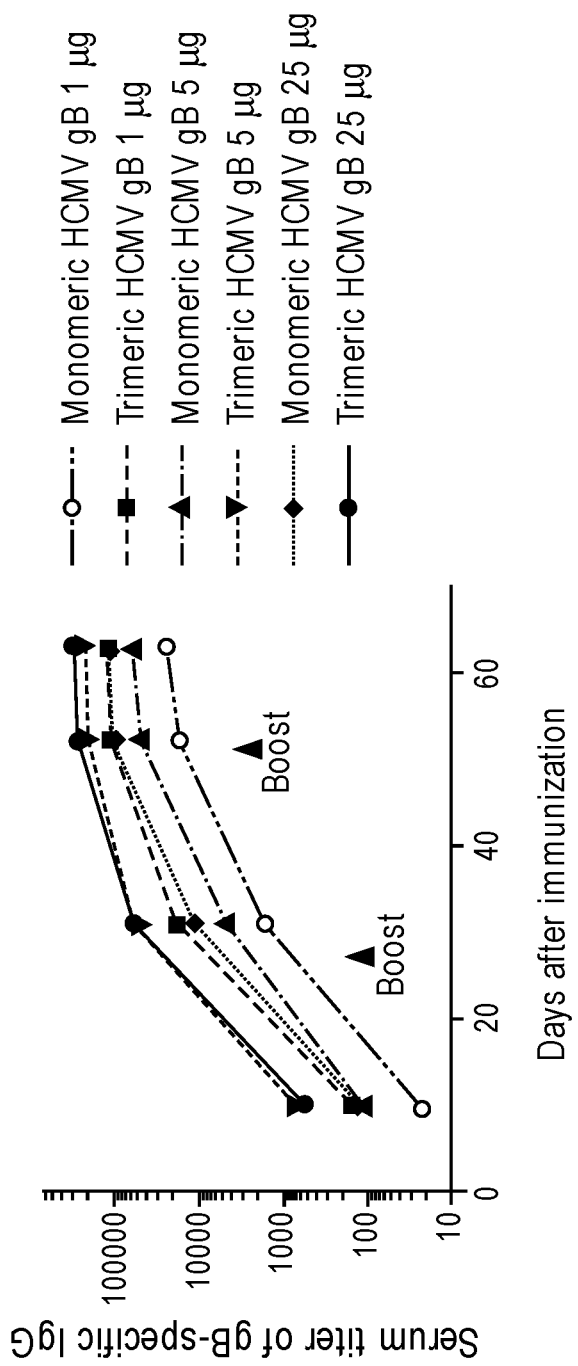

Monomeric and trimeric HCMV gB were directly compared side-by-side for elicitation of total serum titers of antigen-specific IgG. As shown in FIG. 21A, each group of the HCMV proteins induced augmented serum IgG responses following the first booster immunization, and further significant augmentation in serum IgG titers following the second booster immunization. Trimeric HCMV gB induced 5-fold to 11-fold higher serum titers of gB-specific antibody IgG titers relative to monomeric HCMV gB after the first and second immunization, with greater differences observed at the lower doses. The difference of HCMV gB specific IgG titers elicited by trimeric and monomeric HCMV gB decreased after the third immunization, with less differences observed at the higher doses. Five μg of trimeric HCMV gB elicited optimal antigen specific IgG response. 25 μg of trimeric HCMV gB elicited slightly higher gB specific IgG titers, but not significantly different compared to that of 5 μg of HCMV trimeric gB.

Figure 21B:
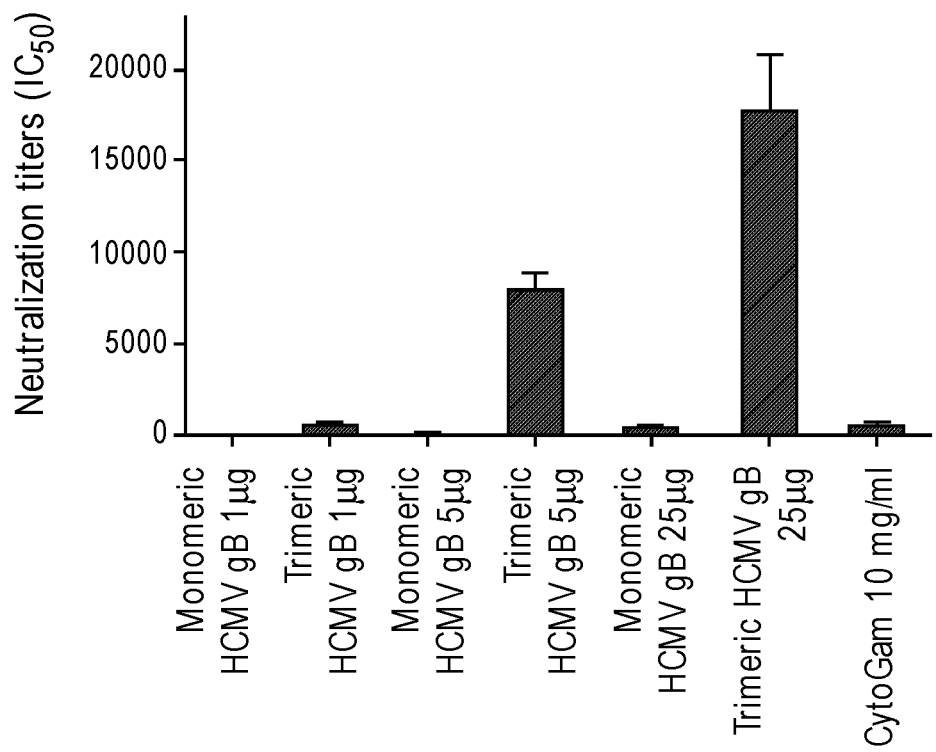
Figure 21C:
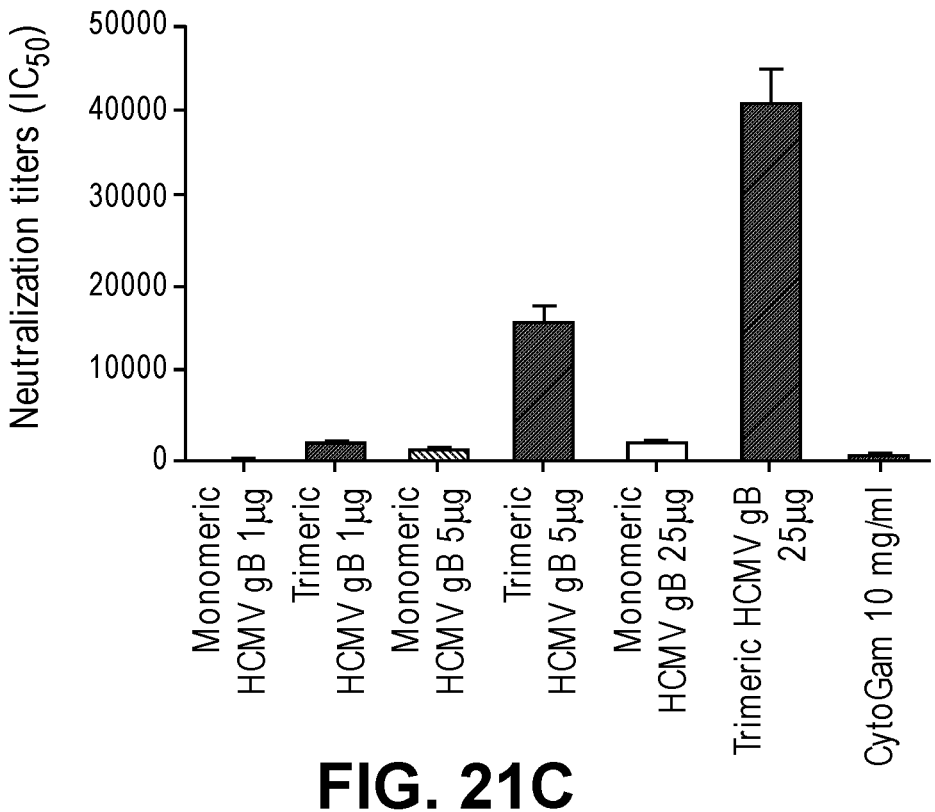

Using the MRC-5 fibroblast cell line, immune sera from mice immunized with trimeric HCMV gB that was heat inactivated at 56° C. for 30 minutes (to eliminate complement activity), demonstrated 50-fold higher HCMV neutralization activity against HCMV strain AD169wt131 compared to that of immune sera from mice immunized with monomeric HCMV gB (FIG. 21B). The non-heat inactivated sera from mice immunized with monomeric HCMV gB (FIG. 21C) demonstrated 6-fold higher HCMV neutralization activity compared to heat inactivated sera (FIG. 21B), whereas the non-heat inactivated sera from mice immunized with trimeric gB demonstrated 2 to 3-fold higher HCMV neutralization activity compared to heat inactivated sera. Without heat inactivation, the HCMV neutralization activity against HCMV strain AD169wt131 elicited by trimeric HCMV gB was 20-fold higher than that of monomeric HCMV gB, suggesting that monomeric HCMV gB induces a more complement-dependent response (FIG. 21C). Cyto-Gam®, a commercial cytomegalovirus CMV-IgIV immunoglobulin containing high titers of HCMV neutralizing antibody derived from the plasma of HCMV seropositive healthy donors (CSL Behring, King of Prussia, Pa., USA) showed much lower HCMV neutralization activity against HCMV strain AD169wt131 relative to trimeric gB. Using the MRC-5 cell line, 10 mg/ml CytoGam® demonstrated about one-thirtieth of the complement-independent HCMV neutralization activity of the sera from mice immunized with trimeric HCMV gB. Heat inactivation has no effect on CytoGam®, which made its complement-dependent HCMV neutralization activity even lower compared to non-heat inactivated sera from mice immunized with trimeric HCMV gB or monomeric HCMV gB.

What is claimed:

1. An antigenic composition comprising a combination of at least two Epstein-Barr Virus (EBV) polypeptides, the antigenic composition comprising at least a first EBV polypeptide and at least a second EBV polypeptide that are not combined to form a fusion protein, wherein:

the first EBV polypeptide comprises a monomeric EBV glycoprotein 350 (gp350) polypeptide, or multimeric EBV gp350 polypeptide(s), comprising an extracellular domain of EBV gp350; and the second EBV polypeptide comprises a monomeric EBV glycoprotein B (gB) polypeptide, or multimeric EBV gB polypeptide(s), comprising an extracellular domain of EBV gB and/or a monomeric EBV gH/glycoprotein gL (gH/gL) heterodimer, or multimeric EBV gH/gL heterodimer(s), comprising an EBV gL polypeptide and an EBV gH polypeptide comprising an extracellular domain of gH;

wherein in the second EBV polypeptide, the furin cleavage site of the monomeric or multimeric EBV gB polypeptide(s) is replaced and/or wherein the EBV qH/gL heterodimer comprises a qH/qL fusion protein; and wherein the first EBV polypeptide and the second EBV polypeptide are not fused with a polypeptide that can assemble into a nanoparticle.

2. The composition of claim 1, wherein the EBV gB polypeptide, the EBV gp350 polypeptide, and/or the EBV gH polypeptide, if present, each further comprises a corresponding EBV gB, EBV gp350, and/or EBV gH intracellular domain, respectively.

3. The composition of claim 2, wherein the extracellular domain is fused to the intracellular domain via a polypeptide linker sequence.

4. The composition of claim 3, wherein the polypeptide linker sequence is about 6 to about 70 amino acids in length, or wherein the peptide linker is about 15 amino acids in length.

5. The composition of claim 1, wherein the at least two EBV polypeptides comprise the monomeric or multimeric EBV gp350 polypeptide and the monomeric or multimeric EBV gB polypeptide.

6. The composition of claim 5, wherein the EBV gp350 polypeptide is monomeric, dimeric, trimeric, or tetrameric gp350, and wherein the EBV gB polypeptide is monomeric, dimeric, or trimeric gB.

7. The composition of claim 1, wherein the at least two EBV polypeptides comprise the monomeric or multimeric EBV gp350 polypeptide and the monomeric or multimeric EBV gH/gL heterodimer.

8. The composition of claim 7, wherein the EBV gp350 polypeptide is monomeric and the EBV gH/gL heterodimer is monomeric or the EBV gp350 polypeptide is tetrameric and the gH/gL heterodimer is trimeric.

9. The composition of claim 1, wherein the at least two EBV polypeptides comprise a monomeric EBV gp350 polypeptide, a trimeric EBV gB polypeptide, and a monomeric EBV gH/gL heterodimer.

10. The composition of claim 1, wherein the at least two EBV polypeptides comprise a tetrameric EBV gp350 polypeptide, a trimeric EBV gB polypeptide, and a EBV trimeric gH/gL heterodimer.

11. The composition of claim 1, further comprising a human EBV glycoprotein 42 (gp42) polypeptide, BDFL2 polypeptide, and/or a human EBV BMRF-2 polypeptide.

12. The composition of claim 1, further comprising a pharmaceutically acceptable excipient and/or an adjuvant.

13. A method for preventing or treating symptoms of an EBV infection in a subject comprising administering to the subject a therapeutically effective amount of the composition of claim 1.

14. A method for inducing immunity EBV in a subject comprising administering to the subject a therapeutically effective amount of the composition of claim 1.

15. The method of claim 13, wherein the subject is at risk of developing an EBV infection.

16. The method of claim 13, wherein the at least two EBV polypeptides in the composition are administered sequentially or concurrently.

17. The composition of claim 6, wherein the EBV gp350 polypeptide is monomeric or tetrameric and the EBV gB polypeptide is trimeric.

18. The composition of claim 1,
wherein the first EBV polypeptide includes at least one copy of gp350 and does not include an EBV antigen that is not gp350; and
wherein the second EBV polypeptide includes:
at least one copy of gB, and/or
at least one copy of gH and gL;
wherein the second EBV polypeptide does not include an EBV antigen that is not gB, gH or gL.

19. The composition of claim 1,
wherein the first EBV polypeptide comprises separate polypeptides bound together via oligomerization domains; and/or
wherein the second EBV polypeptide comprises separate polypeptides bound together via oligomerization domains.

20. The composition of claim 1, wherein the first EBV polypeptide and the second EBV polypeptide are not bound together via oligomerization domains.

21. A composition comprising a combination of one or more nucleic acids encoding the at least two Epstein-Barr Virus (EBV) polypeptides of claim 1.

22. The composition of claim 21, wherein the one or more nucleic acids are in a viral vector that permits expression of the at least two EBV polypeptides.

23. The antigenic composition of claim 1, wherein the antigenic composition is soluble.

24. The antigenic composition of claim 1, wherein the antigen composition is 1320 kDa or less in size.

* * * * *